US010801045B2

(12) United States Patent
Fischer et al.

(10) Patent No.: US 10,801,045 B2
(45) Date of Patent: *Oct. 13, 2020

(54) METHODS FOR MAKING CHEMOAUTOTROPHIC CELLS BY ENGINEERING AN ENERGY CONVERSION PATHWAY AND A CARBON FIXATION PATHWAY

(71) Applicant: Ginkgo BioWorks, Inc., Boston, MA (US)

(72) Inventors: Curt R. Fischer, Sunnyvale, CA (US); Austin J. Che, Cambridge, MA (US); Reshma P. Shetty, Boston, MA (US); Jason R. Kelly, Cambridge, MA (US)

(73) Assignee: Ginkgo Bioworks, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/867,209

(22) Filed: Jan. 10, 2018

(65) Prior Publication Data

US 2018/0223317 A1    Aug. 9, 2018

Related U.S. Application Data

(63) Continuation of application No. 14/354,354, filed as application No. PCT/US2012/062540 on Oct. 30, 2012, now Pat. No. 9,902,980, which is a continuation-in-part of application No. 13/285,919, filed on Oct. 31, 2011, now Pat. No. 8,349,587.

(51) Int. Cl.
| | |
|---|---|
| *C12P 7/40* | (2006.01) |
| *C12P 7/00* | (2006.01) |
| *C12P 7/16* | (2006.01) |
| *C12N 9/04* | (2006.01) |
| *C12N 15/70* | (2006.01) |
| *C12P 5/00* | (2006.01) |
| *C12N 9/02* | (2006.01) |
| *C12N 15/52* | (2006.01) |

(52) U.S. Cl.
CPC ............ *C12P 7/40* (2013.01); *C12N 9/0006* (2013.01); *C12N 9/0051* (2013.01); *C12N 15/52* (2013.01); *C12N 15/70* (2013.01); *C12P 5/00* (2013.01); *C12P 7/00* (2013.01); *C12P 7/16* (2013.01); *C12Y 101/05006* (2013.01); *C12Y 108/05004* (2013.01); *Y02E 50/10* (2013.01)

(58) Field of Classification Search
None
See application file for complete search history.

(56) References Cited

U.S. PATENT DOCUMENTS

| 1,746,464 | A | 2/1930 | Fischer |
| 5,302,525 | A | 4/1994 | Groleau et al. |
| 7,118,896 | B2 | 10/2006 | Kalscheuer et al. |
| 7,256,016 | B2 | 8/2007 | San et al. |
| 7,803,589 | B2 | 9/2010 | Burk et al. |
| 7,923,227 | B2 | 4/2011 | Hickey et al. |
| 7,981,647 | B2 | 7/2011 | Berry et al. |
| 8,349,587 | B2 * | 1/2013 | Fischer ............... C12P 5/00 435/41 |
| 9,902,980 | B2 * | 2/2018 | Fischer ............... C12P 5/00 |
| 2003/0157636 | A1 | 8/2003 | Figueira et al. |
| 2004/0142435 | A1 | 7/2004 | Gunji et al. |
| 2007/0264688 | A1 | 11/2007 | Venter et al. |
| 2007/0269862 | A1 | 11/2007 | Glass et al. |
| 2010/0086958 | A1 * | 4/2010 | Davis ............ C12N 9/0008 435/26 |
| 2010/0228067 | A1 | 9/2010 | Peterson et al. |
| 2012/0064622 | A1 | 3/2012 | Fischer et al. |
| 2015/0037853 | A1 | 2/2015 | Fischer et al. |
| 2015/0315599 | A1 | 11/2015 | Shetty et al. |

FOREIGN PATENT DOCUMENTS

| WO | WO-2007041872 A1 | 4/2007 |
| WO | WO-2007/139925 A2 | 12/2007 |
| WO | WO-2007140339 A2 | 12/2007 |
| WO | WO2009022754 | * 8/2008 |
| WO | WO-2009/022754 A1 | 2/2009 |
| WO | WO-2009154753 A2 | 12/2009 |
| WO | WO-2010028262 A1 | 3/2010 |
| WO | WO-2011028264 A1 | 3/2010 |
| WO | WO-2010042197 A1 | 4/2010 |
| WO | WO-2010070295 A1 | 6/2010 |

(Continued)

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Accession AXX60695. Jun. 10, 2010. (Year: 2010).*
Contador et al. Metab Eng. Jul.-Sep. 2009;11(4-5):221-33 (Year: 2009).*
Yurimoto et al. FEMS Microbiology Letters (2002), 214(2), 189-193 (Year: 2002).*
Abelson et al., "Carbon Isotope Fractionation in Formation of Amino Acids by Photosynthetic Organisms," Proc. Natl. Acad. Sci. USA. 47(5): 623-632 (1961).
Accession No. AXX60695, 3 pages (Jun. 10, 2010).

(Continued)

*Primary Examiner* — Christian L Fronda
(74) *Attorney, Agent, or Firm* — Wolf, Greenfield & Sacks, P.C.

(57) ABSTRACT

The present disclosure identifies pathways, mechanisms, systems and methods to confer chemoautotrophic production of carbon-based products of interest, such as sugars, alcohols, chemicals, amino acids, polymers, fatty acids and their derivatives, hydrocarbons, isoprenoids, and intermediates thereof, in organisms such that these organisms efficiently convert inorganic carbon to organic carbon-based products of interest using inorganic energy, such as formate, and in particular the use of organisms for the commercial production of various carbon-based products of interest.

15 Claims, 29 Drawing Sheets

Specification includes a Sequence Listing.

(56) References Cited

FOREIGN PATENT DOCUMENTS

| WO | WO2011088425 | * | 7/2011 |
|---|---|---|---|
| WO | WO-2011088425 A2 | | 7/2011 |
| WO | WO-2013/066848 A1 | | 5/2013 |
| WO | WO-2014/089436 A1 | | 6/2014 |

OTHER PUBLICATIONS

Agrawal, P. et al., An algorithm for operating a fed-batch fermentor at optimum specific-growth rate, Biotechnology and Bioengineering, 33: 115-125 (1989).
Aharoni et al., "Identification of the SAAT Gene Involved in Strawberry Flavor Biogenesis by Use of DNA Microarrays," The Plant Cell. 12: 647-661 (2000).
Alber et al., "Malonyl-Coenzyme A Reductase in the Modified 3-Hydroxypropionate Cycle for Autotrophic Carbon Fixation in *Archaeal metallosphaera* and *Sulfolobus* spp," Journal of Bacteriology. 188(24): 8551-8559 (2006).
Alber et al., "Propionyl-Coenzyme a Synthase from Chloroflexus aurantiacus, as Key Ensyme of the 3-Hydroxypropionate Cycle for Autotrophic $CO_2$ Fixation," The Journal of Biological Chemistry. 277(14): 12137-12143 (2002).
Andersen et al., "New Unstable Variants of Green Fluorescent Protein for Studies of Transient Gene Expression in Bacteria," Applied and Environmental Microbiology, 64(6): 2240-2246 (1998).
Anderson et al., "Environmental Signal Integration by a Modular and Gate," Molecular Systems Biology. 3:133 (2007).
Aoshima et al., "A Novel Biotin Protein Required for Reductive Carboxylation of 2-Oxoglutarate by Isocitrate Dehydrogenase in Hydrogenobacter thermophilus TK-6," Molecular Microbiology. 51(3): 791-798 (2004).
Aoshima et al., "A Novel Enzyme, Citryl-CoA Lyase, Catalysing the Second Step of the Citrate Cleavage Reaction in Hydrogenobacter thermophilus TK-6," Molecular Microbiology. 52(3): 763-770 (2004).
Aoshima et al., "A Novel Enzyme, Citryl-CoA Synthetase, Catalysing the First Step of the Citrate Cleavage Reaction in Hydrogenobacter thermophilus TK-6," Molecular Microbiology. 52(3): 751-761 (2004).
Aoshima et al., "A Novel Oxalosuccinate-Forming Enzyme Involved in the Reductive Carboxylation of 2-Oxoglutarate in Hydrogenobacter thermophilus TK-6," Molecular Microbiology. 62(3): 748-759 (2006).
Baba et al., "Construction of *Escherichia coli* K-12 In-Frame, Single-Gene Knockout Mutants: The Keio Collection," Molecular Systems Biology. 2006.2008 (2006).
Bai et al., "Ethanol Fermentation Technologies from Sugar and Starch Feedstocks," Biotechnology Advances. 26(1): 89-105 (2008).
Bailer et al., "Determination of Saponifiable Glycerol in 'Bio-Diesel,'" Fresenius' Journal of Analytical Chemistry. 340(3): 186 (1991).
Bar-Even et al., "Design and Analysis of Synthetic Carbon Fixation Pathways," Proc. Natl. Acad. Sci. USA. 107(19): 8889-8894 (2010).
Bassham et al., "The Path of Carbon in Photosynthesis. XXI. The Cyclic Regeneration of Carbon Dioxide Acceptor," Radiation Laboratory and Department of Chemistry, University of California, Berkeley. 76:1760-1770 (1954).
Bayer et al., "Synthesis of Methyl Halides from Biomass Using Engineered Microbes," JACS. 131(18): 6508-6515 (2009).
Berrios-Rivera et al., "The Effect of the NAPRTase Overexpression on the Total Levels of NAD, The NADH/NAD.sup.+ Ratio, and the Distribution of Metabolites in *Escherichia coli*," 4(3): 238-247 (2002).
Bourque, D. et al., High cell density production of poly-beta-hydroxybutyrate (PHB) from methanol by Methylobacterium extorquens: production of high-molecular-mass PHB, Appl. Microbiol. Biotechnol., 44: 367-376 (1995).
Brugna-Guiral et al., "[NiFe] Hydrogenases from the Hyperthermophilic Bacterium Aquifex aeolicus: Properties, Function, and Phylogenetics," Extremophiles. 7(2):145-157 (2003).
Buchanan et al., "A Reverse KREBS Cycle in Photosynthesis: Consensus at Last," Photosynthesis Research. 24: 47-53 (1990).

Burgdorf et al., "The Soluble NAD+-Reducing [NiFe]-Hydrogenase from Ralstonia eutropha H16 Consists of Six Subunits and can be Specifically Activated by NADPH," Journal of Bacteriology. 187(9): 3122-3132 (2005).
Camilli et al., "Bacterial Small-Molecule Signaling Pathways," Science. 311(5794): 1113-1116 (2006).
Campbell et al., "Adaptations to Submarine Hydrothermal Environments Exemplified by the Genome of Nautilia profundicola," PLoS Genetics. 5(2): e1000362 (2009).
Campbell et al., "Growth and Phylogenetic Properties of Novel Bacteria Belonging to the Epsilon Subdivision of the Preteobacteria Enriched from Alvinella pompejana and Deep-Sea Hydrothermal Vents," Applied and Environmental Microbiology. 67(10):4566-4572 (2001).
Canton et al., "Refinement and Standardization of Synthetic Biological Parts and Devices," Nature Biotechnology. 26(7): 787-793 (2008).
Cheesbrough et al., "Alkane Biosynthesis by Decarbonylation of Aldehydes Catalyzed by a Particulate Preparation from Pisum sativum," Proc. Natl. Acad. Sci. USA. 81(21): 6613-6617 (1984).
Chen et al., "Biosynthesis of Ansatrienin (Mycotrienin) and Naphthomycin Identification and Analysis of Two Separate Biosynthetic Gene Clusters in Streptomyces collinus Tu 1892," European Journal of Biochemistry. 261(1): 98-107 (1999).
Chica, R.A. et al., Semi-rational approaches to engineering enzyme activity: combining the benefits of directed evolution and rational design, Current Opinion in Biotechnology, 16: 378-384 (2005).
Chin et al., "Improved NADPH Supply for Xylitol Production by Engineered *Escherichia coli* with Glycolytic Mutations," Biotechnol. Prog. 27(2): 333-341 (2011).
Cline, Joel. "Spectrophotometric Determination of Hydrogen Sulfide in Natural Waters," Limnology and Oceanography. 14(3): 454-458 (1969).
Contador, C.A. et al., Ensemble modeling for strain development of L-lysine-producing *Escherichia coli*, Metablic Engineering, 11: 221-233 (2009).
Cropp et al., "Identification of a Cyclohexylcarbonyl CoA Biosynthetic Gene Cluster and Application in the Production of Doramectin," Nature Biotechnology. 18(9): 980-983 (2000).
Crowther, Gregory J. et al., Formate as the main branch point for methylotrophic metabolism in Methylobacterium extorquens AM1, Journal of Bacteriology, 190(14): 5057-5062 (2008).
Davis et al., "Design, Construction and Characterization of a Set of Insulated Bacterial Promoters," Nucleic Acids Research. doi:10.1093 (2010).
Dellomonaco et al., "Engineered Reversal of the .beta.-oxidation Cycle for the Synthesis of Fuels and Chemicals," Nature. 476(7360): 355-361 (2011).
Dennis et al., "Alkane Biosynthesis by Decarbonylation of Aldehyde Catalyzed by a Microsomal Preparation from Botryococcus brraunii," Archives of Biochemistry and Biophysics. 287(2): 268-275 (1991).
Denoya et al., "A Second Branched-Chain .alpha.-Keto Acid Dehydrogenase Gene Cluster (bkdFGH) from Streptomyces avermitilis: Its Relationship to Avermectin Biosynthesis and the Construction of a bkdF Mutant Suitable for the Production of Novel Antiparasitic Avermectins," Journal of Bacteriology. 177(12): 3504-3511 (1995).
Deshpande, Mukund, "Ethanol Production from Cellulose by Coupled Saccharification/Fermentation Using *Saccharomyces cerevisiae* and Cellulase Complex from *Sclerotium rolfsii* UV-8 Mutant," Applied Biochemistry and Biotechnology. 36(3): 227-234 (1992).
Dettman et al., "Controls on the Stable Isotope Composition of Seasonal Growth Bands in Aragonitic Fresh-Water Bivalves (Unionidae)," Geochimica et Cosmochimica Acta. 63(7/8): 1049-1057 (1999).
Dunham, M.J., Experimental Evolution in Yeast: A practical guide, Methods in Enxymology, 470: 487-507 (2010).
Edgar, Roger C., "MUSCLE: A Multiple Sequence Alignment Method with Reduced Time and Space Complexity," BMC Bioinformatics. 5: 113 (2004).
Edgar, Roger C., "MUSCLE: Multiple Sequence Alignment with High Accuracy and High Throughput," Nucleic Acids Research. 32(5): 1792-1797 (2004).

(56) References Cited

OTHER PUBLICATIONS

Edwards et al., "Characterizing the Metabolic Phenotype: A Phenotype Phase Plane Analysis," Biotechnology and Bioengineering. 77(1): 27-36 (2002).
Eisenreich et al., "Retrobiosynthetic Analysis of Carbon Fixation in the Phototrophic Eubacterium Chloroflexus aurantiacus," Eur. J. Biochem. 215(3): 619-632 (1993).
Evans et al., "[.sup.13C]Propionate Oxidation in Wild-Type and Citrate Synthase Mutant *Escherichia coli*: Evidence for Multiple Pathways of Propionate Utilization," Biochem. J. 291: 927-932 (1993).
Evans et al., "A New Ferredoxin-Dependent Carbon Reduction Cycle in a Photosynthetic Bacterium," Biochemistry. 55(4): 928-934 (1966).
Evdokimov, E.V. et al., Mikrobiologiya, 61(4): 652-659 (1992).
Farquhar et al., "Carbon Isotope Discrimination and Photosynthesis," Annu. Rev. Plant Physiol. Plant Mol. Biol. 40: 503-537 (1989).
Ferenci et al., "Purification and Properties of 3-Hexulose Phosphate Synthase and Phospho-3-Hexuloisomerase from Methylococcus capsulatus," Biochem. J. 144(3): 477-486 (1974).
Fischer et al., Assessment of heterologous butyrate and butanol pathway activity by measurement of intracellular pathway intermediates in recombinant *Escherichia coli*, Applied Microbial Biotechnology 88: 265-275 (2010).
Fogel et al., "Prokaryotic Genome Size and SSU rDNA Copy Number: Estimation of Microbial Relative Abundance from a Mixed Population," Microbial Ecology. 38(2): 93-113 (1999).
Fong et al., "Metabolic Gene-Deletion Strains of *Escherichia coli* Evolve to Computationally Predicted Growth Phenotypes," Nature Genetics. 36(10): 1056-1058 (2004).
Fong et al., "Predicting Specificity in bZIP Coiled-Coil Protein Interactions," Genome Biology. 5(2): R11.1-R11.10 (2004).
Friedmann et al., "Properties of R-Citramalyl-Coenzyme A Lyase and Its Rold in the Autotrophic 3-Hydroxypropionate Cycle of Chloroflexus aurantiacus," Journal of Bacteriology. 189(7): 2906-2914 (2007).
Friedmann et al., "Properties of Succinyl-Coenzyme A: L-Malate Coenzyme A Transferase and Its Role in the Autotrophic 3-Hydroxypropionate Cycle of Chloroflexus aurantiacus," Journal of Bacteriology. 188(7): 2646-2655 (2006).
Gehring and Arnon. "Purification and Properties of .alpha.-Ketoglutarate Synthase from a Photosynthetic Bacterium," The Journal of Biological Chemistry. 247(21): 6963-6969 (1972).
Gerhold et al., "DNA Chips: Promising Toys Have Become Powerful Tools," Trends in Biochemical Science. 24(5):168-173 (1999).
Grantham et al., "Codon Catalog Usage and the Genome Hypothesis," Nucleid Acids Research. 8(1): r49-r62 (1980).
Greene et al., "Artificially Evolved Synechococcus PCC6301 Rubisco Variants Exhibit Improvements in Folding and Catalytic Efficiency," Biochem. J. 404(3):571-524 (2007).
Griesbeck et al., "Biological Sulfide Oxidation: Sulfide-Quinone Reductase (SQR), the Primary Reaction," Recent Research Developments in Microbiology. 4:129-203 (2000).
Gul-Karaguler et al., "A Single Mutation in the NAD-specific Formate Dehydrogenase from Candida methylica Allows the Enzyme to Use NADP," Biotechnology Letters. 23(4):283-287 (2001).
Gutteridge et al., "Expression of Bacterial Rubisco Genes in *Escherichia coli*," Phil. Trans. R. Soc. Lond. B. 313: 433-445 (1986).
Han and Reynolds. "A Novel Alternative Anaplerotic Pathway to the Glyoxylate Cycle in Streptomycetes," Journal of Bacteriology. 179(16): 5157-5164 (1997).
Harms, N. and Van Spanning, R.J.M., C1 Metabolism in Paracoccus denitrificans: Genetics of Paracoccus denitrificans, Journal of Bioenergetics and Biomembrances, 23(2): 187-209 (1991).
Hatrongjit and Packdibamrung. "A Novel NADP.sup.+-dependent Formate Dehydrogenase from Burkholderia stabilis 15516: Screening, Purification and Characterization," Enzyme and Microbial Technology. 46(7):557-561 (2010).

Hawkley and McClure. "Compilation and Analysis of *Escherichia coli* Promoter DNA Sequences," Nucleic Acids Research. 11(8): 2237-2255 (1983).
Hayes, John M. "Fractionation of Carbon and Hydrogem Isotopes in Biosynthetic Processes," Rev. Mineral. Geochem. 43(1):225-277 (2001).
Helling and Kukora. "Nalidixic Acid-Resistant Mutants of *Escherichia coli* Deficient in Isocitrate Dehydrogenase," Journal of Bacteriology. 105(3): 1224-1226 (1971).
Henry et al., "Genome-Scale Thermodynamic Analysis of *Escherichia coli* Metabolism," Biophysical Journal. 90(4):1453-1461 (2006).
Henstra et al., "Microbiology of Synthesis Gas Fermentation for Biofuel Production," Current Opinion in Biotechnology. 18(3): 200-206 (2007).
Herter et al., "A Bicyclic Autotrophic $CO_2$ Fixation Pathway in Chloroflexus aurantiacus," Journal of Bacteriology. 277(23): 20277-20283 (2002).
Herter et al., "L-Malyl-Coenzyme A Lyases/.beta.-Methylmalyl-Coenzyme A Lyase from Chloroflexus aurantiacus, a Biofunctional Enzyme Involved in Autotrophic $CO_2$ Fixation," Journal of Bacteriology. 184(21): 5999-6006 (2002).
Hirt, W. et al., Formaldehyde incorporation by a new methylotroph (L3), Applied and Environmental Microbiology, 36(1): 56-62 (1978).
Ho et al., "Genetically Engineered *Saccharomyces* Yeast Capable of Effective Cofermentation of Glucose and Xylose," Applied and Environmental Microbiology. 64(5): 1852-1859 (1998).
Hoffmeister et al., "Mitochondrial trans-2-Enoyl-CoA Reductase of Wax Ester Fermentation from *Euglena gracilis* Defines a New Family of Enzymes Involved in Lipid Synthesis," The Journal of Biological Chemistry. 280(6): 4329-4338 (2005).
Holo, Helge. "Chloroflexus aurantiacus Secretes 3-Hydroxypropionate, A Possible Intermediate in the Assimilation of $CO_2$ and Acetate," Archives of Microbiology. 151(3): 252-256 (1989).
Hou et al., "Metabolic Impact of Increased NADH Availability in *Saccharomyces cerevisiae*," Applied and Environmental Microbiology. 76(3): 851-859 (2010).
Huan-Hsu et al., "Addition of Autotrophic Carbon Fixation Pathways to Increase the Theoretical Heterotrophic Yield of Acetate", The Fourth International Conference on Computational Systems Biology (ISB2010), Suzhou, China, Sep. 9-11, 2010, pp. 314-322.
Hugler et al., "Autotrophic $CO_2$ Fixation via the Reductive Tricarboxylic Acid Cycle in Different Lineages Within the Phylum Aquificae: Evidence for Two Ways of Citrate Cleavage," Environmental Microbiology. 9(1): 81-92 (2007).
Hugler et al., "Beyond the Calvin Cycle: Autotrophic Carbon Fixation in the Ocean," Annu. Rev. Marine. Sci. 3:261-289 (2011).
Hugler et al., "Malonyl-Coenzyme A Reductase from Chloroflexus aurantiacus, a Key Enzyme of the 3-Hydroxypropionate Cycle for Autotrophic $CO_2$ Fixation," Journal of Bacteriology. 184(9):2404-2410 (2002).
Hugler et al., "Pathways of Carbon and Energy Metabolism of the Epibiotic Community Associated with the Deep-Sea Hydrothermal Vent Shrimp Rimicaris exoculata," PLoS One. 6(1):e16018 (2011).
Huisman and Gray, "Towards Novel Processes for the Fine-Chemical and Pharmaceutical Industries," Curr. Opin. Biotechnol. 13(4):352-358 (2002).
Ikeda et al., "Two Tandemly Arranged Ferredoxin Genes in the Hydrogenobacter thermophilus Genome: Comparative Characterization of the Recombinant [4FE-4S] Ferredoxins," Biosci. Biotechnol. Biochem. 69(6):1172-1177 (2005).
Inokuma et al., "Characterization of Enzymes Involved in the Ethanol Production of *Moorella* sp. HUC22-1," Arch. Microbiol. 188(1):37-45 (2007).
International Preliminary Report on Patentability for PCT/US2012/06540, 9 pages (dated May 15, 2014).
International Search Report for PCT/U2012/062540, 5 pages (dated Apr. 10, 2013).
International Search Report for PCT/US2013/073582, 5 pages (dated Mar. 20, 2015).
Janausch et al., "$C_4$-Dicarboxylate Carriers and Sensors in Bacteria," Biochemica et Biophysica Acta. 1553(1-2): 39-56 (2002).
Jukes and Osawa. "Mini Review: Evolutionary Changes in the Genetic Code," Comp. Biochem. Physiol. 106B(3): 489-494 (1993).

(56) References Cited

OTHER PUBLICATIONS

Kalscheuer and Steinbuchel. "A Novel Bifunctional Wax Ester Synthase/Acyl- CoA:Diacylglycerol Acyltransferases Mediates Wax Ester and Triacylglycerol Biosynthesis in Acinetobactor calcoaceticus ADP1," The Journal of Biological Chemistry.278(10):8075-8082 (2003).
Kalscheuer et al., "Microdiesel: *Escherichia coli* engineered for Fuel Production," Microbiology. 152:2529-2536 (2006).
Kanao et al., "Characterization of Isocitrate Dehydrogenase from the Green Sulfur Bacterium Chlorobium limicola," Eur. J. Biochem. 269(7): 1926-1931 (2002).
Kanao et al., "Kinetic and Biochemical Analyses on the Reaction Mechanism of a Bacterial ATP-Citrate Lyase," Eur. J. Biochem. 269(14): 3409-3416 (2002).
Kaneda, T. "Iso- and Antesio-Fatty Acids in Bacteria: Biosynthesis, Function, and Taxonomic Significance," Microbiological Reviews. 55(2): 288-302 (1991).
Kapust and Waugh. "*Escherichia coli* Maltose-Binding Protein is Uncommonly Effective at Promoting the Solubility of Polypeptides to Which it is Fused," Protein Science. 8:1668-1674 (1999).
Keasling, Jay D. "Gene-Expression Tools for the Metabolic Engineering of Bacteria," Trends in Biotechnol. 17(11):452-460 (1999).
Kelly et al., "Methodology: Measuring the Activity of BioBrick Promoters Using an in vivo Reference Standard," Journal of Biological Engineering. 3(4): 1-13 (2009).
Kelly et al., Autotrophic Metabolism of Formate by Thiobacillus Strain A2, Journal of General Microbiology. 144:1-13 (1979).
Kelly, D.P. et al., Proposal for the reclassification of Thiobaccillus novellus as *Starkeya novella* gen. nov., comb. nov., in the a-subclass of the Proteobacteria, International Journal of Systematic and Evolutionary Microbiology, 50: 1797-1802 (2000).
Kemp, M.B. "Hexose Phosphate Synthetase from Methylococcus capsulatus Makes a D-arabino-3-Hexulose Phosphate," Biochem J. 139(1):129-134 (1974).
Kemp, M.B. "The Hexose Phosphate Synthetase of Methylococcus capsulatus," Biochem J. 127(3):64P-65P (1972).
Kiely, P.D. et al., Anodic biofilms in microbial fuel cells harbor low numbers of higher-power-producing bacteria than abundant genera, Appl. Microbiol. Biotechnol., 88: 371-380 (2010).
Kim and Unden, "The I-Tartrate/Succinate AntiporterTtdT (YgjE) of I-Tartrate Fermentation in *Escherichia coli*," Journal of Bacteriology. 189(5): 1597-1603 (2007).
Kim et al., "Production of Biohydrogen by Heterologous Expression of Oxygen-Tolerant Hydrogenovibrio marinus [NiFe]-Hydrogenase in *Escherichia coli*," Journal of Biotechnology. 1155(3):312-319 (2011).
Klimke et al., "The National Center for Biotechnology Information's Protein Clusters Database," Nucleic Acids Research. 37:D216-D223 (2009).
Knight, T., "Draft Standard for Biobrick Biological Parts," http://hdl.handle.net/1721.1/45138 (2007).
Knight, T., "Idempotent Vector Design for Standard Assembly of Biobricks," http://hdl.handle.net/1721.1/21168 (2003).
Knothe et al., "Biodiesel: The Use of Vegetable Oils and Their Derivatives as Alternative Diesel Fuels," Am. Chem. Soc. Symp. Series, vol. 666, Fuels and Chemicals from Biomass, Chapter 10, pp. 172-208 (1997).
Knothe, Gerhard. "Dependence of Biodiesel Fuel Properties on the Structure of Fatty Acid Alkyl Esters," Fuel Processing Technology. 86:1059-1070 (2005).
Knothe, Gerhard. "Rapid Monitoring of Transesterification and Assessing Biodiesel Fuel Quality by Near-Infrared Spectroscopy Using a Fiber-Optic Probe," J. Am. Oil Chem. Soc. 76(7): 795-800 (1999).
Kolkman et al., "Directed Evolution of Proteins by Exon Shuffling," Nat. Biotechnol. 19(5):423-428 (2001).
Larkum, AWD. "Limitation and Prospects of Natural Photosynthesis for Bioenergy Production," Current Opinion in Biotechnology. 21(3):271-276 (2010).
LaRue and Kurz. "Estimation of Nitrogenase Using a Colorimetric Determination for Ethylene," Plant Physiol. 51(6):1074-1075 (1973).
Li et al., "Alteration of the Fatty Acid Profile of Streptomyces coelicolor by Replacement of the Initial Enzyme 3-Ketoacyl Carrier Protein Synthase III (FabH)," Journal of Bacteriology. 187(11): 3795-3799 (2005).
Liu et al., "Formate Dehydrogenase of Clostridium pasteurianum," Journal of Bacteriology. 159(1):375-380 (1984).
Marcia et al., "A New Structure-Based Classification of Sulfide: Quinone Oxidoreductases," Proteins. 78(5):1073-1083 (2010).
Marrakchi et al., "A New Mechanism for Anaerobic Unsaturated Fatty Acid Formation in *Streptococcus pneumoniae*," The Journal of Biological Chemistry. 277(47):44809-44816 (2002).
Marrakchi et al., "Mechanistic Diversity and Regulation of Type II Fatty Acids Synthesis," Biochem. Soc. Trans. 30(6): 1050-1055 (2002).
Martin et al., "Redesigning Cells for Production of Complex Organic Molecules," ASM News. 68(7): 336-343 (2002).
Martinez-Alonso et al., "Rehosting of Bacterial Chaperones for High-Quality Protein Production," Applied and Environmental Microbiology, 75(24): 7850-7854 (2009).
Martinez-Alonso et al., "Side Effects of Chaperone Gene Co-Expression in Recombinant Protein Production," Microbial Cell Factories. 9(64):1-6 (2010).
Marty and Planas. "A Comparison of Methods to Determine Algal .delta..sup.13C in Freshwater," Limnol Oceanogr Methods. 6:51-63 (2008).
Mendoza et al., "Thermal Regulation of Membrane Fluidity in *Escherichia coli*," The Journal of Biological Chemistry. 258(4):2098-2101 (1983).
Menendez et al., "Presences of Acetyl Coenzyme A (CoA) Carboxylase and Propionyl-COA Carboxylase in Autotrophic Crenarchaeota and Indication for Operation of a 3-Hydroxypropionate Cycle in Autotrophic Carbon Fixation," Journal of Bacteriology.181(4):1088-1098 (1999).
Minshull and Stemmer. "Protein Evolution by Molecular Breeding," Curr. Opin. Chem. Biol. 3(3):284-290 (1999).
Miroshnichenko et al., "*Nautilia lithotrophica* gen. nov., sp. nov., a Thermophilic Sulfuro-Reducing .epsilon.-Proteobacterium Isolated from a Deep-Sea Hydrothermal Vent," International Journal of Systematic and Evolutionary Microbiology.52:1299-1304 (2002).
Mitsui et al., "A Novel Operon Encoding Formaldehyde Fixation: the Ribulose Monophosphate Pathway in the Gram-Positive Facultative Methylotrophic Bacterium Mycobacterium gastri MB19," Journal of Bacteriology. 182(4):944-948 (2000).
Monson and Hayes. "Biosynthetic Control of the Natural Abundance of Carbon 13 at Specific Positions within Fatty Acids in *Escherichia coli*," The Journal of Biological Chemistry. 255(23):11435-11441 (1980).
Moriya et al., "KAAS: An Automatic Genome Annotation and Pathway Reconstruction Server," Nucleic Acids Research. 35:W182-W185 (2007).
Morweiser et al., "Developments and Perspectives of Photobioreactors for Biofuel Production," Appl. Microbiol. Biotechnol. 87:1291-1301 (2010).
Murli et al., "A Role for the umuDC Gene Products of *Escherichia coli* in Increasing Resistance to DNA Damage in Stationary Phase by Inhibiting the Transition to Exponential Growth," Journal of Bacteriology. 182(4):1127-1135 (2000).
Murtagh, F. "Complexities of Hierarchic Clustering Algorithms: State of the Art," Computational Statistics Quarterly. 1(2):101-113 (1984).
Ober, Joyce A. "Sulfur," U.S. Geological Survey Minerals Yearbook. U.S. Department of the Interior U.S. Geological Survey. 74.1-74.17 (2010).
Orita et al., "Bifunctional Enzyme Fusion of 3-Hexulose-6-Phosphate Synthase and 6-Phospho-3-Hexuloisomerase," Appl. Microbiol. Biotechnol. 76:439-445 (2007).
Orita et al., "The Archaeon Pyrococcus horikoshii Possesses a Bifunctional Enzyme for Formaldehyde Fixation via the Ribulose Monophosphate Pathway," Journal of Bacteriology. 187(11):3636-3642 (2005).

(56) References Cited

OTHER PUBLICATIONS

Orita et al., "The Ribulose Monophosphate Pathway Subsititues for the Missing Pentose Phosphate Pathway in the Archaeon Thermococcus kodakaraensis," Journal of Bacteriology. 188(13):4698-4704 (2006).
Palaniappan et al., "Enhancement and Selective Production of Phoslactomycin B, a Protein Phosphatase IIa Inhibitor, Through Identification and Engineering of the Corresponding Biosynthetic Gene Cluster," The Journal of Biological Chemistry. 278(37):35552-35557 (2003).
Pant, D. et al., A review of the substrates used in microbial fuel cells (MFCs) for substainable energy production, Bioresource Technology, 101: 1533-1543 (2010).
Parikh et al., "Directed Evolution of RuBisCO Hypermorphs Through Genetic Selection in Engineered *E. coli*," Protein Engineering, Design & Selection. 19(3): 113-119 (2006).
Park, Myong-Ok. "New Pathway for Long-Chain n-Alkane Synthesis via 1-Alcohol in Vibrio furnissii M1," Journal of Bacteriology. 187(4):1426-1429 (2005).
Patton et al., "A Novel .DELTA..sup.3, .DELTA..sup.2-Enoyl-CoA Isomerase Involved in the Biosynthesis of the Cyclohexanecarboxylic Acid-Derived Moiety of the Polyketide Anastrienin A," Biochemistry. 39:7595-7604 (2000).
Pinske et al., "Metabolic Deficiences Revealed in the Biotechnologically Important Model Bacterium *Escherichia coli* BL21 (DE3)," PLoS One. 6(8): e22830 (2011).
Portis and Parry. "Discoveries in Rubisco (Ribulose 1,5-Biophosphate Carboxylase/Oxygenase): A Historical Perspective," Photosynth Res. 94:121-143 (2007).
Pramanik and Keasling. "Effect of *Escherichia coli* Biomass Composition on Central Metabolic Fluxes Predicted by a Stoichiometric Model," Biotechnol. Bioeng. 60(2): 230-238 (1998).
Pramanik and Keasling. "Stoichiometric Model of *Escherichia coli* Metabolism: Incorporation of Growth-Rate Dependent Biomass Composition and Mechanistic Energy Requirements," Biotechnol. Bioeng. 56(4): 398-421 (1997).
Rathnasingh et al., "Production of 3-Hydroxypropionic Acid via Malonyl-CoA Pathway Using Recombinant *Escherichia coli* Strains," Journal of Biotechnology. 157(4):633-640 (2012).
Reading and Sperandio. "Quorum Sensing: The Many Languages of Bacteria," FEMS Microbiol. Left. 254(1):1-11 (2006).
Rock et al., "Increased Unsaturated Fatty Acid Production Associated with a Suppressor of the fabA6(Ts) Mutation in *Escherichia coli*," Journal of Bacteriology. 178(18):5382-5387 (1996).
Roessner et al., "Overexpression in *Escherichia coli* of 12 Vitamin B.sub.12 Biosynthetic Enzymes," Protein Expression and Purification. 6(2):155-163 (1995).
Sachdev and Chirgwin. "Fusions to Maltose-Binding Protein: Control of Folding and Solubility in Protein Purification," Methods Enzymol. 326:312-321 (2000).
Sachdev and Chirgwin. "Solubility of Proteins Isolated from Inclusion Bodies is Enhanced by Fusion to Maltose-Binding Protein or Theoredoxin," Protein Expression and Purification. 12(1):122-132 (1998).
Saitou and Nei. "The Neighbor-joining Method: A New Method for Reconstructing Phylogenetic Trees," Mol. Biol. Evol. 4(4):406-425 (1987).
Sakata et al., "Carbon Isotopic Fractionation Associated with Lipid Biosynthesis by a Cyanobacterium: Relevance for Interpretation of Biomarker Records," Geochim. Cosmochim Acta. 61(24):5379-5389 (1997).
San et al., "Metabolic Engineering Through Cofactor Manipulation and its Effects on Metabolic Flux Redistribution in *Escherichia coli*," Metabolic Engineering. 4(2):182-192 (2002).
Sauer et al., "The Soluble and Membrane-Bound Transhydrogenases UdhA and PntAB Have Divergent Functions in NADPH Metabolism of *Escherichia coli*," The Journal of Biological Chemistry. 279(8):6613-6619 (2004).

Schendel, F.J. et al., L-lysine production at 50 degrees C by mutants of a newly isolated and characterized methylotrophic *Bacillus* sp, Applied and Environmental Microbiology, 56(4):963-970 (1990).
Schrader, Jens et al., Methanol-based industrial biotechnology: current status and future perspectives of methylotrophic bacteria, Trends in Biotechnology, 27(2): 107-115 (2009).
Schutz et al., "Sulfide-Quinone Reductase from Rhodobacter capsulates," The Journal of Biological Chemistry. 272(15):9890-9894 (1997).
Self et al., "Expression and Regulation of a Silent Operon, hyf, Coding for Hydrogenase 4 Isoenzyme in *Escherichia coli*," Journal of Bacteriology. 186(2):580-587 (2004).
Sen, S. et al., Developments in Directed Evolution for Improving Enzyme Functions, Appl. Biochem. Biotechnol., 143: 212-223 (2007).
Serov et al., "Engineering of Coenzyme Specificity of Formate Dehydrogenase from *Saccharomyces cerevisiae*," Biochem. J. 367:841-847 (2002).
Shetty et al., "Assembly of BioBrick Standard Biological Parts Using Three Antibiotic Assembly," Methods in Enzymology. 498: 311-326 (2011).
Shetty et al., "Methodology: Engineering BioBrick Vectors from BioBrick Parts," Journal of Biological Engineering. 2(5):1-12 (2008).
Shibata and Kobayashi. "Sulfide Oxidation in Gram-Negative Bacteria by Expression of the Sulfide-Quinone Reductase Gene of Rhodobacter capsulates and by Electron Transport to Ubiquinone," Can. J. Microbiol. 47(9):855-860 (2001).
Shpaer, Eugene G. "GeneAssist: Smith-Waterman and Other Database Similarity Searches and Identification of Motifs," Methods Mol. Biol. 70:173-187 (1997).
Smith et al., "*Nautilia profundicola* sp. nov., a Thermophilic Sulfur-Reducing Epsilonproteobacterium from Deep-Sea Hydrothermal Vents," Int. j. Syst. Evol. Microbiol. 58:1598-1602 (2008).
Smolke and Keasling. "Effect of Copy Number and mRNA Processing and Stabilization on Transcript and Protein Levels from an Engineered Dual-Gene Operon," Biotechnol. Bioeng. 78(4):412-424 (2002).
Smolke and Keasling. "Effect of Gene Location, mRNA Secondary Structures, and RNase Sites of Expression of Two Genes in an Engineered Operon," Biotechnol. Bioeng. 80(7): 762-776 (2002).
Smolke et al., "Controlling the Metabolic Flux Through the Carotenoid Pathway Using Directed mRNA Processing and Stabilization," Metabolic Engineering. 3(4):313-321 (2001).
Smolke et al., "Coordinated, Differential Expression of Two Genes Through Directed mRNA Cleavage and Stabilization by Secondary Structures," Appl. Environ. Microbiol. 66(12):5399-5405 (2000).
Sokal and Michener. "A Statistical method for Evaluating Systematic Relationships," The University of Kansas Science Bulletin. 38(22):1409-1438 (1958).
Strauss and Fuchs. "Enzymes of a Novel Autotrophic CO2 Fixation Pathway in the Phototrophic Bacterium Chloroflexus aurantiacus, the 3-Hydroxypropionate Cycle," Eur. J. Biochem. 215(3):633-643 (1993).
Strom et al., "The Carbon Assimilation Pathways of Methylococcus capsulatus, Pseudomonas methanica and Methylosinus trichosporium (OB3B) During Growth on Methane," Biochem. J. 144(3):465-476 (1974).
Sun et al., "Heterologous Expression and Maturation of an NADP-Dependent [NiFe]-Hydrogenase: A Key Enzyme in Biofuel Production," PLoS One. 5(5): e10526 (2010).
Tabita et al., "Expression and Assembly of Active Cyanobacterial Ribulose-1,5-Bisphosphate Carboxylase/Oxygenase in *Escherichia coli* Containing Stiochiometric Amounts of Large and Small Subunits," Proc. Natl. Acad. Sci. 82(18):6100-6103 (1985).
Tatusov et al., "A Genomic Perspective on Protein Families," Science. 248(5338):631-637 (1997).
Tatusov et al., "The COG Database: An Updated Version Includes Eukaryotes," BMC Bioinformatics. 4:1-14 (2003).
Theissen et al., Sulfide: quinone oxidoreductase (SQR) from the lugworm *Arenicola marina* shows cyanide and thioredoxin-dependent activity, FEBS Journal 275: 1131-1139 (2008).

(56) References Cited

OTHER PUBLICATIONS

Van Wezel et al., "GlcP Constitutes the Major Glucose Uptake System of *Streptomyces Coelicolor* A3(2)," Molecular Microbiology. 55(2):624-636 (2005).

Venturi, Vittorio. "Regulation of Quorum Sensing in Pseudomonas," FEMS Microbiol. Rev. 30(2):274-291 (2006).

Vignais and Billoud. "Occurrence, Classification, and Biological Function of Hydrogenases: An Overview," Chem. Rev. 107(10):4206-4272 (2007).

Vignais and Colbeau. "Molecular Biology of Microbial Hydrogenases," Curr. Issues Mol. Biol. 6(2):159-188 (2004).

Wells et al., "Engineering a Non-Native Hydrogen Production Pathway into *Escherichia coli* via a Cyanobacterial [NiFe] Hydrogenase," Metabolic Engineering. 13(4):445-453 (2011).

Whisstock, J.C. et al., Prediction of protein function from protein sequence and structure, Quarterly Reviews of Biophysics, 36(3): 307-340 (2003).

Written Opinion for PCT/U2012/062540, 13 pages (dated Apr. 10, 2013).

Written Opinion for PCT/US2013/073582 9 pages, (dated Mar. 20, 2015).

Wubbolts et al., "Variation of Cofactor Levels in *Escherichia coli* : Sequence Analysis and Expression of the pncB Gene Encoding Nicotinic Acid Phosphoribosyktrabsferase," The Journal of Biological Chemistry. 265(29): 17665-17672 (1990).

Yamamoto et al., "Carboxylation Reaction Catalyzed by 2-Oxoglutarate:Ferredoxin Oxidoreductases from Hydrogenobacter thremophilus," Extremeophiles. 14(1):79-85 (2010).

Yamane et al., Annals New York Academy of Science, 364-381 (1986).

Yoon et al., "Purification and Characterization of Pyruvate:Ferredoxin Oxidoreductase from Hydrogenobacter thermophilus TK-6," Arch. Microbiol. 167(5):275-279 (1997).

Yurimoto, H. et al., The ribulose monophosphate pathway operon encoding formaldehyde fixation in a thermotolerant methylotroph, Bacillus brevis 51, FEMS Microbiology, Letters, 214: 189-193 (2002).

Zarzycki and Fuchs. "Co-Assimilation of Organic Substrates via the Autotrophic 3-Hydroxypropionate Bi-Cycle in Chloroflexus aurantiacus," Appl. Environ. Microbio. 77(17):6181-6188 (2011).

Zarzycki et al., "Identifying the Missing Steps of the Autotrophic 3-Hydroxypropionate $CO_2$ Fixation Cycle in Chloroflexus aurantiacus," Proc. Natl. Acad. Sci. USA. 106(50):21317-21322 (2009).

Zdobnov and Apweiler. "InterProScan—An Integration Platform for the Signature-Recognition Methods in InterPro," Bioinformatics. 17(9):847-848 (2001).

Zhang et al., "Molecular and Genetical Analysis of the Fructose-Glucose Transport System in the Cyanobacterium Synechocystis PCC6803," Molecular Microbiology. 3(9):1221-1229 (1989).

Zhang et al., "The FabR (YijC) Transcription Factor Regulates Unsaturated Fatty Acid Biosynthesis in *Escherichia coli*," The Journal of Biological Chemistry. 277(18):15558-15565 (2002).

Zhu et al., "Production of Ubiquinone in *Escherichia coli* by Expression of Various Genes Responsible for Ubiquinone Biosynthesis," Journal of Fermentation and Bioengineering. 79(5):493-495 (1995).

Zweiger, Gary. "Knowledge Discovery in Gene-Expression-Microarray Data: Mining the Information Output of the Genome," Trends Biotechnol. 17(11):429-436 (1999).

\* cited by examiner

SEQUENCE LISTING

```
<160> NUMBER OF SEQ ID NOS: 66

<210> SEQ ID NO 1
<211> LENGTH: 1161
<212> TYPE: DNA
<213> ORGANISM: Burkholderia stabilis

<400> SEQUENCE: 1
atggccactg ttctatgcgt gctatatcct gatccggttg atggttatcc accgcactat      60
gttcgtgata ccatcccggt gatcacccga tatgcagatg gccaaacagc ccccactccc     120
gcggggccgc caggatttcg tcccggtgaa ctggtgggca gtgtttctgg tgcgctggga     180
cttcgcggtt accttgaagc ccatggtcac actctcatcg tcacatcgga taaagatggt     240
ccggatagtg agtttgaaag acggctgcct gatgccgatg ttgtcatcag ccagccgttt     300
tggcccgcat atcttacggc tgaacgtatc gcgagggcgc cgaagttacg tctggctctg     360
actgctggta taggctcaga ccacgttgac ctcgatgccg cggcgcgtgc tcacattacg     420
gtcgccgaag tgactggaag taacagtatt tcagtggctg aacacgttgt tatgacaacg     480
ctggccttag tgcggaacta tttacctagc cacgcaattg cgcagcaagg tggttggaac     540
atcgccgact gtgtttcacg ctcttatgac gtcgaaggaa tgcatttcgg cacagtaggg     600
gcgggtagga ttggattggc tgttctgcgc cggcttaaac cgtttggtct gcatttgcat     660
tacacccaaa gacatcgctt ggatgcagcc atcgaacaag aactcggtct tacttaccat     720
gccgatccag ccagtcttgc ggcggcagta gacattgtta atttgcagat tccgctgtat     780
ccttccactg aacacctttt tgatgctgca atgattgcac gcatgaaaag aggtgcgtac     840
ctgattaata ctgcccgtgc gaagttagtg gaccgcgatg ccgtcgtcag ggctgtcaca     900
agcggacatc tggctggtta tggcggggac gtctggtttc cccagcctgc tccggctgat     960
catccgtggc gggcgatgcc ttttaatggc atgacacctc atattagcgg tacttcactt    1020
tctgctcagg cgcggtacgc agcggggacc cttgaaatcc tccagtgttg gtttgatggc    1080
agaccgatca ggaacgagta cctgatagtg gatggaggaa cattggccgg tacaggtgcc    1140
caatcatatc ggctgaagta a                                               1161

<210> SEQ ID NO 2
<211> LENGTH: 1095
<212> TYPE: DNA
```

<213> ORGANISM: Candida methylica

<400> SEQUENCE: 2

```
atgaaaattg tactggtgct ctatgatgca ggaaaacacg ccgcagacga ggaaaagctg      60
tatggctgca ctgagaacaa gctaggaatc gccaattggc tgaaggatca gggccatgaa     120
ttaatcacta cctccgataa agaaggtgaa acctcagagt tagataagca cattcccgat     180
gccgatataa tcattacgac gccttttcac ccagcttaca ttacaaaaga gcgtctggat     240
aaagcgaaaa acctcaaatc ggttgtagtc gccggcgtcg gttccgacca cattgacctg     300
gattatatta tcagactgg taagaagatc agcgtcctgg aagtcaccgg ctctaatgtg      360
gtatctgttg ctgagcatgt tgtaatgact atgctggttt tagtgcgcaa ttttgtgccc     420
gcacacgagc agatcataaa ccatgactgg gaagtagcag caatagctaa agatgcgtat     480
gatattgaag gcaaaactat cgctacgatc ggcgcgggcc ggatcggtta ccgggttctg     540
gagcggctgc tgccgttcaa tcctaaagag ctcctatact atgattatca ggcactgccc     600
aaggaagcag aggaaaaagt tggtgcgcgg agagtggaaa acattgaaga acttgtggct     660
caggccgaca ttgtaacggt aaatgctcca cttcacgcag gcaccaaagg ccttatcaat     720
aaagagttgc tttcaaagtt taagaaaggt gcctggttgg taaatacggc ccgtggagca     780
atttgcgttg cggaggatgt cgccgccgct ctggaatcgg acagctccg gggatacggt      840
ggggatgttt ggtttcccca gccggcgcca aaggatcacc cgtggcgtga tatgcgaaac     900
aaatatggcg cagggaacgc catgacaccg cattactccg gacgaccttt agatgcacaa     960
actcgatacg ctgaaggtac caagaacatc ctggaaagtt tctttacggg caagtttgat    1020
tatcgccctc aggatattat tctgcttaat ggagaatatg taacaaaagc ttacggcaaa    1080
catgacaaaa agtaa                                                     1095
```

<210> SEQ ID NO 3
<211> LENGTH: 1095
<212> TYPE: DNA
<213> ORGANISM: Candida boidinii

<400> SEQUENCE: 3

```
atgaaaatcg tgttggtact gtatgacgct gggaaacatg ctgctgatga ggagaaattg      60
tatggctgta ccgagaataa actgggcatt gcgaactggt tgaaagatca agggcatgag     120
cttattacca cgagcgataa ggagggcgaa accagcgagc tggacaaaca tattcctgac     180
gcggatatta ttatcactac acccttcac cctgcgtaca ttactaaaga gcgtcttgat      240
aaggctaaga atctaaaact cgttgtcgtc gctggcgttg gatctgatca tatcgatttg     300
gattacataa accagacagg aaagaagatc agcgtgctgg aagttacggg ctcgaacgtt     360
gttagcgtcg cagaacacgt ggttatgacc atgctagtcc tggtccgtaa cttcgtgccg     420
gcgcatgaac agatcattaa ccatgattgg gaagttgcgg ctattgcaaa ggatgcttat     480
gatatcgaag gtaaaaccat cgccaccatt ggcgctgggc gtattggcta tcgcgtcttg     540
gagcgcctgc tgccatttaa cccgaaagaa ctgttgtatt acgactatca agccttacca     600
aaagaagcgg aagaaaaagt gggtgcacgt cgtgtagaaa atattgaaga attggtagcg     660
caggcagata tagttaccgt taatgctccc ctccacgccg gaacgaaagg tcttattaac     720
aaagaattac tgtctaagtt taaaaaaggg gcctggcttg tgaacacagc ccgaggcgct     780
atatgtgttg cagaagatgt tgcagctgcg ctggagagtg gtcaactgcg tgggtacgga    840
ggtgatgtgt ggtttcctca gccggcccca aaggatcacc cctggcgaga tatgcgcaat     900
```

```
aaatatgggg ccggaaatgc aatgacgcca cattatagtg gtacaaccct ggacgctcag      960
accagatatg cagaaggtac taagaatata cttgagtcgt tttttaccgg aaagtttgac     1020
tacagaccgc aagatatcat tttattgaat ggggagtatg tcaccaaagc atatggaaag     1080
catgataaaa agtaa                                                      1095
```

<210> SEQ ID NO 4
<211> LENGTH: 1131
<212> TYPE: DNA
<213> ORGANISM: Saccharomyces cerevisiae

<400> SEQUENCE: 4

```
atgtcgaaag gcaaagtgct tctcgtcctg tatgaaggtg ggaagcatgc agaagaacag       60
gagaaattac tgggctgtat cgaaaatgaa ttaggaatac gaaattttat cgaagaacaa      120
ggttatgaac tcgttactac gatcgataaa gatccggaac ctaccagtac tgtcgatcgc      180
gaattaaaag atgcggaaat cgttatcacc acacctttct ttcctgccta catatctagg      240
aaccgtattg ccgaagcccc gaacctcaaa ctatgcgtga ccgccggagt tgggtctgat      300
cacgtggatc tggaggcagc caatgaacgt aaaataacag taaccgaggt tactgggagt      360
aacgtggtca gcgtagctga gcacgttatg gcgacaatcc tggtacttat ccgtaactac      420
aacgggggtc atcagcaagc gatcaatggt gaatgggata tcgctggcgt agcaaagaac      480
gaatatgatt tggaggataa gattattagt accgtgggag ccgggcggat cgggtatcgt      540
gtactggaac gtcttgtagc tttcaatccg aaaaagcttc tgtattacga ctatcaagaa      600
ttgccggccg aagccatcaa tcggcttaat gaagcctcta gctgttcaa cggccgcggg       660 gacatcgttc agcgcgttga aagctggag acatggtgg cgcagtcaga tgtcgttaca        720
atcaattgtc cgctacataa agactccaga ggcttgttta caaaaaaact tatatcccat      780
atgaaagatg gagcctatct tgtaaatact gcacgcggcg ctatttgcgt agcagaggac      840
gttgccgagg ctgtaaaatc gggcaagctg gctggctatg gaggcgacgt gtgggacaaa      900
caacctgcgc ccaaggacca tccttggcgt acaatggata acaaggacca cgtaggaaat      960
gcgatgacgg ttcatatcag cggcacgagt ctggatgcac agaagcgtta tgcgcagggg     1020
gtcaagaata tccttaattc ctattttca aagaaatttg actatagacc ccaggatatc      1080
atagtgcaaa atggttcata cgccactaga gcttacggac aaaaaagta a               1131
```

<210> SEQ ID NO 5
<211> LENGTH: 731
<212> TYPE: PRT
<213> ORGANISM: Clostridium pasteurianum

<400> SEQUENCE: 5

| Met | Tyr | Lys | Ile | Lys | Met | His | Cys | Thr | Gly | Leu | Leu | Phe | Cys | Leu | Ile |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Gln Arg Ser Val Asn Met Glu Lys Lys Val Leu Thr Val Cys Pro Tyr
            20                  25                  30

Cys Gly Ser Gly Cys Asn Leu Tyr Leu Val Val Glu Gly Gly Lys Val
        35                  40                  45

Val Arg Ala Glu Pro Ala Lys Gly Arg Asn Asn Glu Gly Lys Leu Cys
    50                  55                  60

Leu Lys Gly Tyr Tyr Gly Trp Asp Phe Leu Asn Asp Pro Lys Leu Leu
65                  70                  75                  80

Thr Ser Arg Leu Lys Lys Pro Met Ile Arg Lys Asn Gly Val Leu Glu

```
            85                  90                  95
Glu Val Ser Trp Asp Glu Ala Ile Lys Phe Thr Ala Glu Asn Leu Met
            100                 105                 110

Lys Ile Lys Ala Gln Tyr Gly Pro Asp Ala Ile Met Gly Thr Gly Ser
            115                 120                 125

Ala Arg Gly Pro Gly Asn Glu Pro Asn Tyr Ile Met Gln Lys Phe Met
            130                 135                 140

Arg Ala Ala Ile Gly Thr Asn Asn Ile Asp His Cys Ala Arg Val Cys
145                 150                 155                 160

His Gly Pro Ser Val Ala Gly Leu Asp Tyr Ser Leu Gly Gly Ala Ala
                    165                 170                 175

Met Ser Asn Ser Ile Pro Glu Ile Glu Asp Thr Asp Val Val Phe Val
                    180                 185                 190

Phe Gly Tyr Asn Pro Ser Glu Thr His Pro Ile Val Ala Arg Arg Ile
                    195                 200                 205

Val Lys Ala Arg Glu Lys Gly Ala Lys Ile Ile Val Ala Asp Pro Arg
            210                 215                 220

Lys Ile Glu Thr Val Lys Ile Ser Asp Leu Trp Leu Gln Leu Lys Gly
225                 230                 235                 240

Gly Thr Asn Met Ala Leu Val Asn Ala Leu Gly Asn Val Leu Ile Asn
                    245                 250                 255

Glu Glu Leu Tyr Asp Glu Lys Phe Val Glu Asn Cys Thr Glu Gly Phe
                    260                 265                 270

Glu Glu Tyr Lys Glu Ala Val Lys Lys Tyr Thr Pro Glu Tyr Ala Glu
                    275                 280                 285

Lys Ile Thr Gly Val Ser Ala Glu Tyr Ile Arg Lys Ala Met Arg Ile
            290                 295                 300

Tyr Ala Lys Ala Lys Lys Ala Thr Ile Leu Tyr Gly Met Gly Val Cys
305                 310                 315                 320

Gln Phe Ser Gln Ala Val Asp Val Val Lys Gly Leu Ala Ser Leu Ala
                    325                 330                 335

Leu Leu Thr Gly Asn Leu Gly Arg Pro Asn Val Gly Ile Gly Pro Val
                    340                 345                 350

Arg Gly Gln Asn Asn Val Gln Gly Thr Cys Asp Met Gly Val Leu Pro
            355                 360                 365

Asn Arg Phe Pro Gly Tyr Gln Ser Val Thr Asp Glu Lys Ala Arg Glu
            370                 375                 380

Lys Phe Glu Lys Ala Trp Gly Val Lys Leu Ser Asp Arg Val Gly Tyr
385                 390                 395                 400

Phe Leu Thr Glu Val Pro Lys His Val Leu Lys Glu Asp Lys Ile Lys
                    405                 410                 415

Ala Tyr Tyr Ile Phe Gly Glu Asp Pro Ala Gln Ser Asp Pro Asn Ala
                    420                 425                 430

Ala Glu Val Arg Glu Ala Leu Asp Lys Ile Asp Phe Val Ile Val Gln
            435                 440                 445

Asp Ile Phe Met Asn Lys Thr Ala Leu His Ala Asp Val Val Leu Pro
            450                 455                 460

Ala Thr Ser Trp Gly Glu His Asp Gly Val Tyr Ser Ala Ala Asp Arg
465                 470                 475                 480

Ser Phe Gln Arg Ile Arg Lys Ala Val Glu Pro Met Gly Glu Ala Lys
                    485                 490                 495

Asp Asp Trp Glu Ile Ile Cys Glu Ile Ser Thr Ala Met Gly Tyr Pro
            500                 505                 510
```

Met His Tyr Asn Asn Thr Glu Glu Ile Trp Asn Glu Met Arg Ser Leu
            515                 520                 525

Cys Pro Lys Phe Ala Gly Ala Ser Tyr Glu Lys Met Glu Lys Gln Gly
        530                 535                 540

Ala Val Pro Trp Pro Cys Thr Ser Glu Glu Asp Pro Gly Thr Asp Tyr
545                 550                 555                 560

Leu Tyr Asp Asp Gly Lys Phe Met Thr Glu Asn Gly Arg Gly Lys Leu
                565                 570                 575

Phe Ala Cys Glu Trp Arg His Pro Phe Glu Leu Thr Asp Glu Lys Tyr
            580                 585                 590

Pro Leu Val Leu Ser Thr Val Arg Glu Ile Gly His Tyr Ser Val Arg
        595                 600                 605

Thr Met Thr Gly Asn Cys Arg Thr Leu Gln Lys Leu Ala Asp Glu Pro
    610                 615                 620

Gly Tyr Ile Glu Ile Ser Val Glu Asp Ala Lys Glu Leu Asn Ile Lys
625                 630                 635                 640

Asp Gln Glu Leu Val Thr Val Ser Ser Arg Gly Lys Ile Ile Thr
                645                 650                 655

Arg Ala Ala Val Ala Glu Arg Val Lys Lys Gly Ala Thr Tyr Met Thr
            660                 665                 670

Tyr Gln Trp Trp Val Gly Ala Cys Asn Glu Leu Thr Ile Asp Ser Leu
        675                 680                 685

Asp Pro Ile Ser Lys Thr Pro Glu Phe Lys Tyr Cys Ala Val Lys Val
    690                 695                 700

Glu Arg Ile Lys Asp Gln Gln Lys Ala Glu Gln Ile Glu Glu Arg
705                 710                 715                 720

Tyr Ser Ser Leu Lys Lys Gln Met Lys Ala Glu
                725                 730

<210> SEQ ID NO 6
<211> LENGTH: 211
<212> TYPE: PRT
<213> ORGANISM: Clostridium pasteurianum

<400> SEQUENCE: 6

Met Asp Arg Phe Lys Thr Ala Val Ile Leu Ala Gly Gly Lys Ser Ser
1               5                   10                  15

Arg Met Gly Phe Asp Lys Gln Phe Leu Lys Ile Gly Glu Lys Arg Leu
            20                  25                  30

Met Asp Ile Leu Ile Asn Glu Ile Lys Glu Glu Phe Gln Asp Ile Ile
        35                  40                  45

Ile Val Thr Asn Lys Pro Lys Glu Tyr Lys Ser Leu Tyr Lys Ser Cys
    50                  55                  60

Arg Ile Val Ser Asp Glu Ile Glu Ser Gln Gly Pro Leu Ser Gly Ile
65                  70                  75                  80

His Ile Gly Leu Lys Glu Ser Lys Ser Lys Tyr Ala Tyr Phe Ile Ala
                85                  90                  95

Cys Asp Met Pro Lys Val Asn Ile Pro Tyr Ile Arg Tyr Met Lys Glu
            100                 105                 110

Glu Leu Ile Lys Thr Asp Ala Asp Ala Cys Val Thr Glu Ala Gly Cys
        115                 120                 125

Arg Met Gln Pro Phe Asn Ala Phe Tyr Ser Lys Glu Val Phe Tyr Lys
    130                 135                 140

Ile Glu Asp Leu Leu Arg Glu Gly Lys Arg Ser Met Phe Ser Phe Ile

```
                145                 150                 155                 160
Asn Ile Ile Asn Thr His Phe Ile Asp Glu Asp Thr Ala Lys Lys Tyr
                    165                 170                 175

Asn Lys Asp Phe Asn Met Phe Phe Asn Leu Asn Thr Pro Glu Asp Leu
                180                 185                 190

Lys Asp Phe Gln Val Lys Leu Tyr Asn Pro Lys Asn Met Asp Lys Asn
            195                 200                 205

Ile Glu Lys
    210

<210> SEQ ID NO 7
<211> LENGTH: 191
<212> TYPE: PRT
<213> ORGANISM: Clostridium pasteurianum

<400> SEQUENCE: 7

Met Arg Asn Phe Ile Lys Leu Phe Leu Tyr Arg Leu Ser Gly Lys Val
1               5                   10                  15

Gly Lys Ala Met Ser Arg Glu Val Asn Ser Phe Val Ile Gly Asp Ala
            20                  25                  30

Ser Lys Cys Val Gly Cys Arg Ala Cys Glu Val Ala Cys Phe Lys Ala
        35                  40                  45

His Ser Asn Arg Glu Glu Ser Ser Lys Pro Ile Phe Val Lys Gly Lys
    50                  55                  60

Arg Arg Asp Ile Ile Thr Arg Ile His Val Val Lys Asn Glu Lys Phe
65                  70                  75                  80

Ser Val Pro Val Gln Cys Arg Gln Cys Glu Asp Ala Pro Cys Ala Asn
                85                  90                  95

Ala Cys Pro Val Gly Ala Ile Lys Glu Lys Glu His Val Leu Val Val
            100                 105                 110

Glu Glu Glu Leu Cys Ile Gly Cys Lys Ala Cys Val Met Ala Cys Pro
        115                 120                 125

Phe Gly Ala Ile Glu Val Lys Arg Lys Ser Glu Glu Val Arg Lys Val
    130                 135                 140

Ala Tyr Lys Cys Asp Leu Cys Arg Asn Arg Asp Thr Lys Ala Cys Val
145                 150                 155                 160

Glu Ile Cys Ser Lys Lys Ala Leu Lys Leu Phe Asp Pro Val Lys Glu
                165                 170                 175

Arg Lys Gln Arg Asn Ile Asp Thr Val Asn Asn Leu Ile Asp Asp
            180                 185                 190

<210> SEQ ID NO 8
<211> LENGTH: 206
<212> TYPE: PRT
<213> ORGANISM: Clostridium pasteurianum

<400> SEQUENCE: 8

Met Thr Asn Leu Cys His Phe Arg Gln Arg Glu Glu Arg Ile Ile
1               5                   10                  15

Met Asn Ser Phe Val Ile Ala Asn Pro Lys Lys Cys Ile Gly Cys Lys
            20                  25                  30

Thr Cys Glu Ala Gly Cys Ala Met Ala His Ser Glu Lys Asn Ile Leu
        35                  40                  45

Asn Arg Lys Ser Asp Glu Leu Lys Phe Asn Pro Arg Leu Lys Val Ile
    50                  55                  60

Lys Thr Trp Asp Val Thr Ala Pro Val Met Cys Arg His Cys Glu Asn
```

```
            65                  70                  75                  80
Ser Pro Cys Ala Ser Val Cys Pro Asn Gly Ser Ile Thr Asn Lys Glu
                    85                  90                  95

Gly Val Val Leu Ile Asn Gln Asp Thr Cys Ile Gly Cys Lys Ser Cys
            100                 105                 110

Met Val Ala Cys Pro Phe Gly Ala Ile Asn Leu Ile Val Gln Gln Asp
            115                 120                 125

Gly Glu Gly Lys Ala Ile Thr Gln Ser Gly Leu Lys Lys Thr Asp Gly
130                 135                 140

Lys Glu Ile Ile His Lys Glu Lys Ile Val Ala Asn Lys Cys Asp Leu
145                 150                 155                 160

Cys Ile Glu Arg Asp Lys Gly Pro Ala Cys Val Glu Val Cys Pro Thr
                165                 170                 175

Glu Ala Leu Arg Leu Val Ser Gly Glu Asp Ile Glu Glu Ser Ile Lys
            180                 185                 190

Glu Lys Arg Glu Ala Ala Ala Leu Gly Leu Ser Arg Ile Gly
            195                 200                 205

<210> SEQ ID NO 9
<211> LENGTH: 1293
<212> TYPE: DNA
<213> ORGANISM: Aquifex aeolicus

<400> SEQUENCE: 9
atggccaaac atgtggttgt tattggcggc ggcgttggag gtattgcgac ggcctataac      60
ctgcgcaact tgatgccgga tttaaaaata acgttgatca cgatcgccc atatttcggc     120 tttacgccag cattcccgca tctggcgatg ggctggcgca aatttgaaga tatcagcgtt     180
cccctggcgc ctttgttacc gaaattcaac atagagttta ttaacgaaaa ggctgaaagc     240
atcgatccag atgcgaacac ggttaccacg cagagcggaa aaaaaatcga gtatgattat     300
ctggttattg ccacaggccc gaaactggtg ttcggagcag aaggccagga ggagaactcg     360
acgagcattt gtaccgccga acatgcgcta gaaactcaga aaaactgca agaattatat     420 gcgaatccgg ccctgtagt tattggtgcc ataccgggcg tgagttgttt cggccctgcc     480
tatgagttcg ccttgatgtt acattatgaa ctgaagaaac gtgggattcg ctataaagtg     540
ccgatgacgt tcatcacgag cgaaccgtat ttaggccatt ttggcgtggg tggtattggt     600
gcctctaaac gtctcgttga ggatttattc gccgaacgca acattgactg gatcgcgaac     660
gttgcggtaa aagccattga accagataaa gtgatttatg aagatctcaa cggcaacacg     720
catgaagtac cggctaaatt tacgatgttc atgccgagtt ccaaggcccc agaggttgtg     780
gccagcgcag gcgataaggt cgcgaacccg gcgaacaaaa tggtgattgt gaaccgctgc     840
ttccagaacc cgacttataa aaacattttc ggcgttggtg tggttaccgc cattccgcca     900
attgaaaaaa ccccaattcc gacgggagtt cccaaaaccg gtatgatgat cgagcaaatg     960
gccatggccg ttgcccataa cattgttaac gatattcgca caacccggga taaatatgcc    1020
cctcgtttaa gcgctatttg tattgccgat tcggcgaag atgccggctt tttcttcgcg    1080
gatccggtta ttccacctcg cgaacgtgtt attacgaaaa tgggaaaatg ggcgcattat    1140
ttcaaaacgg catttgaaaa atatttcctg tggaaagtac gcaacggcaa catagcgccg    1200
agctttgaag aaaaagttct ggaaattttt ctgaaagtgc atccgattga attatgtaaa    1260
gattgcgaag gcgcgccggg ctcccgctgc taa                                 1293
```

<210> SEQ ID NO 10
<211> LENGTH: 1302
<212> TYPE: DNA
<213> ORGANISM: Nostoc sp.

<400> SEQUENCE: 10

| | | |
|---|---|---|
| atggcccaca ttgtgatcgt aggcgccgga ttaggcggcc tgcctactgc gtatgaactg | 60 |
| agacatatcc ttcctaaaca acatcaggtg actgtaatta gtgaaactcc atactttacg | 120 |
| tttattccaa gtttaccatg ggttgccatg ggcctgacct ctttggagag tattcaagtg | 180 |
| agcctccagc agagattgaa gcagaagggg attaactgga tattgggacg agttgattac | 240 |
| ttaaacccac agaatcagaa gatatcacta ggtgagcaga gcattagcta cgattacctg | 300 |
| attattgcaa cgggcgctga actcgccctg gatgcagttg cgggcctggg gcctgatggt | 360 |
| tatacccaga gtgtttgtaa ccccatcat gccatcaagg cttttcaagc gtggcagaat | 420 |
| tttcttctgg ccccgggacc gctggttgtt ggagccctgc cgaaaacaag ctgcctgggg | 480 |
| ccagcatacg agtttacatt gctggcggac tacgttctta ggaaacaagg tctgcgggag | 540 |
| caggttagta ttacctttgt cacccggaa ccatacgccg gtcacttagg cataggcgga | 600 |
| atggcgaact cggcagagct ggtcacgaaa ttcatggccg aacgaggagt tgaggtgatt | 660 |
| gaaaatgttg ccgtgacggc cattgaggcc aaccaaattc atctcggtaa cgggcgggtt | 720 |
| ctgccgtttg cgtacagtat gttgcttccg cctttcagag gaccccgttt tgtaagacag | 780 |
| gttccgggtc tgagcaacca agatggcttt attccggttt taccaacgta ccggcatcca | 840 |
| gaatatgcaa gtatttatgc tgtcggtgtg gttgttgaaa ttaaaccgag tgaggttacg | 900 |
| ccacttcctt taggtgttcc taaaaccggt cagatgacgg aagccatggg gatggccgtt | 960 |
| gcacataaca ttgcaattga attaggtgtt ttttcggcgc ccccagtcac cccgacgcta | 1020 |
| gatgcaattt gttttgcgga ctttggcaac agtggtattc tgtttcttgc gaatcctgtc | 1080 |
| ctgccggatc tggcaacggg taaacgcaga cgagcggttg ctttaagcgg cgcgtgggtt | 1140 |
| acctgggcga aagcagcctt tgaaaggtat tttttggcga aaatgcgttt cgggaccgcg | 1200 |
| gttccatggt ttgaaaaatt ggcgttaaaa ctgttaggtc tctcgctggt ggctccactc | 1260 |
| gccgttaaga gcagccggaa catctcccag gagaactatt aa | 1302 |

<210> SEQ ID NO 11
<211> LENGTH: 1458
<212> TYPE: DNA
<213> ORGANISM: Chlorobium tepidum

<400> SEQUENCE: 11

| | | |
|---|---|---|
| atggccaaag tcgtcgtcct cggggctggc gtcagcggac acacctgcgc aagtttcctg | 60 |
| aaaaagaagt tggggaaaca gcacgaagtc gtggtcatta gcccaaactc gtactatcag | 120 |
| tggatcccga gcaatatatg ggttggcgtg ggccacatga ccattgatga cgtgcgcttt | 180 |
| aaactgaaaa aagtctacga tcgctggggc attgactata acaggccaa ggcggtcagc | 240 |
| atccacccag aaggcgatgc gaacatttcg aaagggtatg ttaccattga atataccgat | 300 |
| gaagaacatg cgggatatac cgaaacggtt gactatgatt attttggttaa cgcgaccggt | 360 |
| cctaaattaa actttgaagc taccgaagga ttgggacccg ataagaacag cttatcagtt | 420 |
| tgcacctatt cgcatgccgc tcacgcctgg gaagaactcc aaaagtcgat tgagaaaatg | 480 |
| aaaaatggtc agaaacagcg gtttctgatc ggcaccggcc acgccatggc tacctgtcag | 540 |
| ggcgcagctt ttgaatacat tttaaacgtt gctcatgaga ttagtcggcg cggcttatcg | 600 |

```
catatggccg aattaacctg gatctccaac gaatatgaat taggtgactt tggtatgggc    660
ggcgccttta ttaaacgcgg cggttatatc acgccgacca aagttttcac cgagagctta    720
ctggctgaat atggcattaa atggattcgc cgtgccggtg tttataaagt ggaaccgggc    780
gtggcgcatt atgagacgct ggatggcgag atgttgagcc aggaatttga tttcgccatg    840
ttgatcccga gctttagtgg cgtcggctta accgcgtttg ataagtcggg caacgatatt    900
accgataaaa tgttcttacc gaacaaattt atgaaagttg acgccgatta taccgcgaaa    960
ccgtttggcg aatgggcgc taacgattgg ccgaccattt atcagacgcc gatgtattcg   1020
aatatttatg cggccggcat tgcgtttgcc ccgccgcaca gcattagcaa accaatgacg   1080
tcggtgaatg gccgccagat ctttccgacg ccgccgcgca ccggcatgcc gagcggcgtc   1140
attggcaaaa ttatcgccct gaatattagt gaacagatta aaggcaacca taaagaacat   1200
caccataagg cgagcatggc gcgcatgggc gcagcgtgca tcgtgagcgc gggctttggt   1260
agcttcgatg gctgggcgc cagcatgacc gtgtttccaa ttgtgccaga ctgggaaaaa   1320
tacccggaat ggggccgcga tatgacctat agcgttggcg aggtgggatt ggcgggtcat   1380
tggttaaaat ttatgttaca ttatctgttt tttcataaag ccaagggcta cccgttttgg   1440
tatttaatcc cggaataa                                                1458

<210> SEQ ID NO 12
<211> LENGTH: 1305
<212> TYPE: DNA
<213> ORGANISM: Acidithiobacillus ferrooxidans

<400> SEQUENCE: 12 atgcccatg tggtaatctt gggtgccggc acaggcggaa tgccggccgc gtacgaaatg     60
aaagaagctc tgggttctgg gcatgaggtg acgctgatta gcgcgaatga ttattttcag    120
tttgtcccgt cgaacccgtg ggtgggggtg ggctggaaag agcgcgatga tattgctttt    180
cccattcgtc actatgtgga acggaaggga atacatttca ttgcccagtc ggcggaacag    240
attgatgcgg aagcccagaa tattaccctc gcggacggca acacggtaca ttacgactac    300
ctgatgatta ccacaggtcc gaaactggct tttgagaatg taccgggttc ggatccacat    360
gaaggcccgg tgcagtcgat ctgtacggtg gaccatgccg aacgtgcgtt cgcggaatac    420 caggcttttgt tgcgcgagcc aggcccaatc gttattggtg cgatggcggg cgcatcctgc    480
tttggaccgg cttacgaata tgcgatgatt gttgcttcgg acttaaagaa gcgtggcatg    540
cgcgacaaaa tcccgtcgtt taccttcatt acctccgagc catacattgg tcatctgggc    600
atccagggcg tgggcgattc gaaaggcatc ctgacgaaag gcttaaaaga agaaggtatt    660
gaagcctaca cgaactgtaa agttaccaaa gttgaagaca acaaaatgta tgtaacccag    720
gtggacgaga aaggtgaaac cattaaagag atggtcctgc cggttaaatt tgggatgatg    780
attccggctt ttaaaggcgt gcccgccgtg ccggtgtttg aaggattgtg caatccaggt    840
ggctttgtgc tggtggatga gcaccagcgc agcaaaaagt acgcaaatat tttcgccgcc    900
ggtattgcga ttgcgatccc gccggtagag acgaccccgg tgccgaccgg cgccccaaaa    960
accggttata tgattgaatc gatggtgagt gccgccgtgc acaacattaa agccgatctg   1020
gaaggccgca aaggcgagca gaccatgggc acctggaatg ccgtgtgttt cgcggatatg   1080
ggtgatcgcg cgccgcatt cattgcgttg ccacagttga aaccacggaa ggtggacgtt   1140
ttcgcgtacg ggcgctgggt gcatctgccc aaagtgcgt tcgaaaagta cttcattcgc   1200
aagatgaaaa tgggtgtttc ggagccattt tatgagaaag tgctgtttaa aatgatgggc   1260
```

```
atcacccggc tgaaagaaga agatacccat cggaaagcgt cgtaa              1305
```

<210> SEQ ID NO 13
<211> LENGTH: 1458
<212> TYPE: DNA
<213> ORGANISM: Allochromatium vinosum

<400> SEQUENCE: 13

```
atggcccgca ttctgatatt aggagcgggt attagtggcc acacgaccgc gcggtatctg    60
ggcaaatggg ttggcaaaca gcaccagatt accgttgtga gcccaaatag taagtggaac   120
tggatcccta gtaacatttg ggttggcgta ggtgagatga ccgaacgcca agtgacccttt  180
gaactggcac cagtgtacaa aaaaattaac gtgggttttc gtcaggcacg cgcggtgagc   240
attcacccag acgcggtgc gggacatgaa tcgccatttg tgaccattga atacacggat    300
ccgacacgtg cgggtcagtc ggatgaaatt gagtacgatt atctggtgaa tgcgaccggc   360
ccaaaattaa actttgatgc gacgccgggt ctggggccgg aaacgggcta caccatgagc   420
gtgtgcaccc cgagtcacgc cctggaagcg aacgaacagt tacagaaatg cgtgcaggaa   480
atgaaagcgt gtcccgcaa aacctttgtg attggcaccg gcacggcat gtgcacctgc    540
cagggcgccg cgtttgaata catttacaac gtggaccatg tgctgcgggg agcgggcgtt   600
cgccacctgg cccgcgttgt gtggattttcg aacgaatacg agttaggcga ttttggcatg  660
ggaggcgttc atattacccg aggcggctat ctgaccaacg gcaaagtgtt tgcggaaagc   720
ctgatggtgg aacgcggcct ggaatggatt cccgcgccg ctgtgaccaa agtggaaccg    780
ggcaaaattc actacgaaca gttagatggc tccgtgcatg aactggaatt tgactttagt   840
atgttaattc cgccatttag cggcgttgga ttaaaggcgt atgataagag tgggtcggat   900
attaccgaac aattatttgc cccaaacggc tttatgaaag tggatgcgga ttacaatcca   960
aaaccatttg aggagtggtc gaaagcgat tggccgaaaa cctatcagac cccgaaatac    1020
aaaaacattt ttgcgattgg cattgcgttt gcgccgccgc acccgattct gaaagttatg   1080
aaatccccgt cgggtctgca aatttcgccc actccgccgc gcaccggcat gccaagcgcc   1140
accatcggga aagctgttgc ggaaaacatt cgcgacctgt taaatggcgc caccacgttg   1200
agccataccg cgagcatggg cgaaatgggc gccgcttgcg ttgcgagcac cggcatggac   1260
ttatttaaag gcacggccgc caccatgacc gtatttccgg ttgttccgga ttacgaaacc   1320
tatccagaat acggacgcga tatggacctg acctttggtg aaattggcct ggcgggacat   1380
tggatgaagt acctcctgca ccacgtgttt atttaccagg cgaaactgcg cccgggctgg   1440
agcgttctgc cagactaa                                                  1458
```

<210> SEQ ID NO 14
<211> LENGTH: 1284
<212> TYPE: DNA
<213> ORGANISM: Rhodobacter capsulatus

<400> SEQUENCE: 14

```
atggcccata ttgtggtcct gggggccggg ctcgcggcg ccattatggc atatgagctc      60
cgcgagcagg tgcgcaaaga ggataaagtt accgttatta ccaaagatcc gatgtatcat   120
tttgtgccaa gcaacccatg ggtggcggtg ggctggcgcg atcgcaaaga aattaccgtg   180
gatttagcgc cgacgatggc gcgcaaaaac attgattta ttccggtggc agcgaaacgc    240
ctgcatccgg cggagaaccg tgttgaactg gagaacggcc agagcgtttc gtacgatcag   300
```

```
attgttattg ccaccggccc ggagctggcc tttgatgaaa ttgaaggctt cggcccagaa      360
ggccacacgc aaagcatttg ccatattgat catgccgaag aagcgcggct ggccttcgat      420
cgcttctgcg agaacccagg cccgattttg attggtgcgg cgcagggcgc ctcgtgcttt      480
ggcccggctt acgagtttac ctttatttta gacaccgcgc tgcgcaaacg caaaattcgc      540
gataaagtgc cgatgacctt tgttaccagc gaaccatatg ttggtcatct gggtctggat      600
ggtgtgggcg ataccaaagg cctgttggag ggcaacctgc gcgataaaca cattaagtgg      660
atgaccagca cccgtattaa gcgcgttgag aaaggcaaaa tggtggttga agaagtgacc      720
gaagatggca cggttaaacc agaaaaggaa ctgccatttg ctatgcgat gatgctgcca       780 gcgtttcgcg gcattaaagc gctgatgggt attgaaggtc tggttaatcc gcgcggcttt      840
gttattgttg accagcacca gcagaacccg acctttaaaa acgttttgc ggttggcgtt       900 tgcgtggcga ttccgccgat tggtccgacg ccggtgccat gcggcgtgcc gaaaaccggc      960
tttatgattg agtcgatggt taccgccacc gcccacaaca ttggccgtat tgtgcgcggt     1020
ttcgaagccg atgaagttgg ctcgtggaac gccgtttgtc tggccgactt tggcgaccag     1080
ggcattgcct tcgttgcgca gccgcagatt ccgccgcgca acgtgaactg gagctcgcag     1140
ggcaagtggg tgcattgggc caagaaggt tttgaacgct attttatgca caaactgcgc      1200
cgcggtacca gtgaaacctt ttatgagaaa gccgcgatga aattcctggg cattgataaa     1260
ctgaaagccg ttaagaaagg gtaa                                            1284

<210> SEQ ID NO 15
<211> LENGTH: 1269
<212> TYPE: DNA
<213> ORGANISM: Thiobacillus denitrificans

<400> SEQUENCE: 15
atggcccata ttgtaatatt aggcgccggc gtgggcggca tgaccatggc gtacgagatg       60
cgcgaaagcg cacgtgccga agataaagtg accgtgatca gtaacaatag ctatttcag      120 tttacgccga gtaaccttg ggttggtgtt aactggcgca acgggatga tgtgacgtta       180 gaagccgcgc cttatttaaa caaaaagaac attgatttta tcccggtggg cgccgcgcgc     240
gttcacccag atagaaacca gattgattta accgatggca gaaccgtgga ttacgatttt      300
ttagtgattg cgacgggtcc aaaattagcg tttgatgagg tgccgggctt aggcccagaa      360
gggtataccc agagcgtatg cacggtggat cacgcccagg ccgcgggccg cgcgtgggat      420
gacttcgtta aaaacccggg tccgattgtt gtgggcgcgg ttcagggtgc tagttgctat      480
ggcccggcgt atgaatatgc cgatgattat gataccgatc tgcgcaaacg caaaatccgg      540
gatcgtgttc cgatgaccta tgtgacggcc gaaccgtaca ttggccacct gggactgggc      600
ggcgtgggcg acagtaaagg catgttagag agcgtgttac gcgaacgcca tattaaatgg      660
atttgcaacg ccaaagtgac caaagtgaaa gctggcaaaa tgtttgtggc cgaacataac      720
gataaaggcg aggttattaa agaacatgag ctgccgtttg ctatagcat gatgctgccg       780 gcgtttaaag gcattgacgc tgtttttggc attgaaggtc tgaccaatcc gcgcggcttt      840
attacgattg atccatatca gcgcaacgcg aaatatccga acgtgtatag tgtgggcgtt      900
tgcgtggcga ttccccccagt ggaagtgaca ccagttccga ccggcacgcc gaaaaccggc     960
tatatgattg agagcatggt tacggcgacc gcgcataaca ttcgcgccgt tttagatggc     1020
cgcgaacctg ccgaaaaagc gacctggaac gcgatttgct tagccgattt tggcgatacc     1080
ggcgccgcct tgttgccct gccgcagatc ccgccgcgca atgtgaactg gtttaaagag      1140
```

```
ggcaaatggg ttcacctggc caaagtggcc tttgaaaaat attttattcg caaaatgaag    1200
aagggcagca ccgaaccgct gtatgaaaaa tatgttttag cttaatggg cattaaaaag     1260 ttaaagtaa                                                             1269
```

<210> SEQ ID NO 16
<211> LENGTH: 1284
<212> TYPE: DNA
<213> ORGANISM: Magnetococcus sp.

<400> SEQUENCE: 16

```
atggcccata ttgtggtgtt aggtggtggt gtaggggat ggccggctgc ctatgaatta      60
cgtggcgcct taggtaaaga acataaggtc actgtggtgc acaatagcac ccatttttct    120
tttaccccct ctaatccttg ggtagccgtc ggttggcgca aggcagagga gattcagctt    180
ccgatggagg gttatttaag caaaaagggc atccattta tttccgtcgc gtgcgaggaa    240
attaagcccg acgacaataa attagtgctg gcggatgggc agatcgtgga ttatgactat    300
ctggttatct gtaccggtcc tgaactggca tttgatgaag tcgagggatt aggtccgcat    360
ggtggttaca cgcagtccgt ttgctcaacg ccgcatgcgg aaaccgcatg cgagggatgg    420
gaggcgttct taaagatccc aggcccgatc gtggtgggtg ccgtgcaggg cgcgtcatgt    480
tttggacccg cctatgaatt tgcatttatc atggatgcag acctgcgcaa gcgtcgtata    540
cgtgatcagg tgccgatgac ctatgtgacc tctgaacctt acattggcca tttagggctg    600
gcaggggtgg gtgactcgcg caccatgatg gaatctgagc tgcgtggcca ccacattaac    660
tggatctgta acgcgaaggt aacccgtgtc gaacctggta aaatgtttgt ggatgaacat    720
gatatgtcgg gtaatgtggt taagcagcac gaactgccgc acaaatactc tatgatgcta    780
ccagcattcc gtggggtgcc tgccgtggcc aaggtagggg ataagctgtg caatccacgt    840
ggttttgtga aggtggataa acatcagcgc aacaccgtgt ggccaaacat ttattcagcc    900
ggtgtgtgcg tggccattcc tcctgtcgaa gccacacctg tgccgaccgg taccccgaag    960
acgggttata tgatcgaatc catggtgacg gcgattgtgc acaatattga actggacctg   1020
caaggcaagc cgttaaccca cgagggcacc tggaacgcga tctgtttagc cgatatgggg   1080
gatacagggg tggcctttgt ggccatgcca cagattggcc gcgtaacgt cgcatggatg   1140 cgcaaaggta agtgggtgca tttagccaaa gtgggctttg aaaaatattt tatgcgcaag   1200
atgaagaccg ttcttctga accaatgttt gaaaagttta tgctgcgcat ggtgggtatt   1260
acccgcctga agaaggattc gtaa                                           1284
```

<210> SEQ ID NO 17
<211> LENGTH: 171
<212> TYPE: DNA
<213> ORGANISM: Clostridium pasteurianum

<400> SEQUENCE: 17

```
atggcctata aaatagcgga tagctgcgtg tcctgcgggg cgtgcgcgag cgaatgcccg     60
gttaacgcga ttagtcaggg cgattcgatt ttcgttattg atgcagatac ctgcatagac   120
tgcggtaatt gcgcgaatgt ttgcccggtt ggcgccccgg tgcaggaata a             171
```

<210> SEQ ID NO 18
<211> LENGTH: 219
<212> TYPE: DNA
<213> ORGANISM: Hydrogenobacter thermophilus

```
<400> SEQUENCE: 18
atggccttgc gtaccatggt cgaccctgat acgtgtacct cttgcgaatt atgttatgat    60
cgcgtcccag aggtttataa gaaccgcggc gatggcattg cggaagtggt ttcccccggt   120
ccagatggtt ggatgatggt tcctcctgaa ttggaacaag aagtcaaaga ggtcaccgac   180
gaatgtccat ccgggtcgat aattacgag gaggtataa                           219

<210> SEQ ID NO 19
<211> LENGTH: 204
<212> TYPE: DNA
<213> ORGANISM: Hydrogenobacter thermophilus

<400> SEQUENCE: 19
atgcgcattt tgatcgacat tgatacgtgc acgacctgcc gtttatgcta tgatacactg    60
ccgactgttt ttgtggaccg cggcgatggg attccaatta cgttaccaat gaaaagcttc   120
ccggaccgta acctggttga ggcgattaag gaagtgatgg aaagctgccc aagcaattcg   180
attcagatgg aggaggtcgg gtaa                                          204

<210> SEQ ID NO 20
<211> LENGTH: 183
<212> TYPE: DNA
<213> ORGANISM: Methanosarcina barkeri

<400> SEQUENCE: 20
atgccagcga tcgtgaacgc ggatgaatgc tccggctgcg gcacttgcgt cgatgaatgt    60
cctaacgatg cgattacgct ggatgaggag aagggcatag cggttgtcga caacgacgaa   120
tgtgttgaat gtggtgcgtg tgaagaagcg tgtcccaatc aggcgattaa agttgaagaa   180
taa                                                                 183

<210> SEQ ID NO 21
<211> LENGTH: 243
<212> TYPE: DNA
<213> ORGANISM: Aquifex aeolicus

<400> SEQUENCE: 21
atggccaagt tgaaaacgat ggtggatcag gaaacgtgta ccgcctgcga gctctgttat    60
gaccgtgtgc cggaggtgta taaaaaccgc ggcgatggca ttgcagacgt ggtaaaatgt   120
gatattaagg atgaggaaga ccattgctgg atgattgtac ctgaaggcct cgaagatgaa   180
gtacgtgaag ttgaggagga gtgcccgagt ggttcgatca gtggaagga actggaagaa   240 taa                                                                 243

<210> SEQ ID NO 22
<211> LENGTH: 80
<212> TYPE: PRT
<213> ORGANISM: Aquifex aeolicus

<400> SEQUENCE: 22

Met Ala Lys Leu Lys Thr Met Val Asp Gln Glu Thr Cys Thr Ala Cys
1               5                   10                  15

Glu Leu Cys Tyr Asp Arg Val Pro Glu Val Tyr Lys Asn Arg Gly Asp
            20                  25                  30

Gly Ile Ala Asp Val Val Lys Cys Asp Ile Lys Asp Glu Glu Asp His
        35                  40                  45

Cys Trp Met Ile Val Pro Glu Gly Leu Glu Asp Glu Val Arg Glu Val
    50                  55                  60
```

Glu Glu Glu Cys Pro Ser Gly Ser Ile Ile Val Glu Leu Glu Glu
65                  70                  75                  80

<210> SEQ ID NO 23
<211> LENGTH: 231
<212> TYPE: DNA
<213> ORGANISM: Aquifex aeolicus

<400> SEQUENCE: 23
atggggttaa aggtgcgtgt tgaccaggat acgtgcacgg cctgcgagct gtgctatgac      60
cgtataccgg aagtattcaa aaacgcaggc gatggcattg cagatgttgt aaaatgcgat    120
atagaagatg atgaaggctg ctggatgata gtgccggaag gcctggagga ggaagttcag    180
gaagtggcgg atgagtgccc gagtggcagc attatagttg aggaagaata a             231

<210> SEQ ID NO 24
<211> LENGTH: 76
<212> TYPE: PRT
<213> ORGANISM: Aquifex aeolicus

<400> SEQUENCE: 24

Met Gly Leu Lys Val Arg Val Asp Gln Asp Thr Cys Thr Ala Cys Glu
1               5                   10                  15

Leu Cys Tyr Asp Arg Ile Pro Glu Val Phe Lys Asn Ala Gly Asp Gly
            20                  25                  30

Ile Ala Asp Val Val Lys Cys Asp Ile Glu Asp Asp Glu Gly Cys Trp
        35                  40                  45

Met Ile Val Pro Glu Gly Leu Glu Glu Val Gln Val Ala Asp
    50                  55                  60

Glu Cys Pro Ser Gly Ser Ile Ile Val Glu Glu Glu
65                  70                  75

<210> SEQ ID NO 25
<211> LENGTH: 3633
<212> TYPE: DNA
<213> ORGANISM: Unknown
<220> FEATURE:
<223> OTHER INFORMATION: gamma-proteobacterium

<400> SEQUENCE: 25
atgaacacag aaactcgcac caccagcggc ggacggttgc atgacaaggt ggttatcttg      60
accggcgcgg ccggaaacat tggcagctac attagccggt ccttgctgcg cgaaggggcg    120
aatttggtaa tgaccgggcg gaatgaaccg aaattacagg cgtttgtgga aggtttagtt    180
gaggagggtt ttgatcgtga caatatatta attgccatcg gtgactccgc gaaggcggat    240
atatgtcgcg aaatcgttaa ggcgactgtt aatcatttcg gcaacattga tgtcctggtt    300
aataacgccg gaggcgcggg gcctcgtcgc acgctgcggg acattccgtt ttctgagagt    360
gaacgcttag cccgcggcga cgatgagacc atgttagatg ccgccatgaa tctattagct    420
ggcgcgtgga acatgacccg gccgccgttc cacacatga gcgagggcgg cagtattgtt    480
aatgttagta ccatctttag tcgcacccat tactatggac gcataccgta cgtggtgccc    540
aaaagtggat tgaatgccct gagtataggc ttagcgaaag aactcggtga agaacatggg    600
atccgcgtta atacgctgtt tccgggcccg atcgagtcgg aacgcattga caccgttttt    660
ggcaatatgg atgccctgca agcgcacca gcaggtgcca cttcgcagga gttccgtgac    720
ctgatgatca cccgtcgaga aaacccggat ggtgaatatg agtaccgcta cccaacgccc    780

```
aacgatgtgg cgtcaacggt gacctggctg gcatcggagg agagtgcggc cctaagtgga    840
catcatattg aagttaccaa tggcatgcag gtgccggccc aaagccgctc aaagttagta    900
agttggccgg acaaacgact ggaggacctg tccgggcagg tcgtattttt gttagctggc    960
agcgactacg aggacgcact ggcatttgct gagcgccaca tggtttccgg tgcgaaagtc   1020
gtcctcgcgt tccgctccct ggagtcgtta gggttagctc gctctttatg cgcgtcgcgc   1080
gatttagaga gcatccacct actgcacctg gagccactgc gacgtgagtc ggcagaccgg   1140
tgtttcgatt acattcgcga tcatttcggc cgacttgacg gcatcgtcgt gcttccacgc   1200
tcgggcaacg gagaacatgg ctattcgtta tccaccgcgg gtgatgacga tgtcgaggcg   1260
tttgtccgcg atgagatcat atcaccggta gcatttgctg ctgcattggc cattaacctc   1320
gatcgctggg gcattttaga ggaggcacca gcgctgacct atgtcaccaa tccgaccgat   1380
ggccacgggg actacttaaa cgaggtaaag cgtgcagcta ttgaggccct gattcgcatc   1440
tggcggcatg aggaccgcca gatgcgcaag aagggcgaac gcgaatgggc aatgctgcct   1500
aaccagctgg tccgctatga caacaacgag gaggacaatt taacttttac cgcagactgg   1560
gcggccacgc taaccaaccg tgttcgacgc atggatccaa taaacttatg ggtgcctgag   1620
agcattatgc gcgcaaccgg caaaagcggt atgccacaaa gtatccagcg cgtgttgcca   1680
ggcctgcata aaggccggac cgccgtgatc accggtggct ccctcggcat cggcctgcaa   1740
ttgggccggt tcctggctat tgccggtgcg cgggtattgt tatcggctcg ctccaaagag   1800
aaattagaag aagcacgcca cgagatcgtt gaggagttac gcggcgtcgg ctacccgaac   1860
gcgcaccagc gtgttcatat tttaccagac attgatgttg gcgatgagga ggccctcgaa   1920
cggttgtaca atcactctat agaattattc ggaaatgtgg acttcttaat taacaacgcg   1980
ggcatcagtg gcgctgagga gatggtcgtt gatatgtcgc tcgaagcatg gaatcgcacc   2040
atgtatgcga acttaatcag taactattct ttgatccgca aatatgcgcc caagatgaaa   2100
gcgaatggct acgcgttgt actcaatgtt agtagttatt tcggcggcga gaaatatgtt   2160
gccgtggctt acccgaatcg tgccgactat gcggtctcta aggcaggtca gcgagtactg   2220
gcagagatcc tctctcggca ccttggccca gagatccgaa tcaacgcatt agcaccaggg   2280
ccagtggatg gcgcccgcct gcgcggcctt ggcggcgcac cgggattatt tgaacgacgc   2340
ggtcgactgg ttctcgagaa caaacgatta acagcgtgc ataaagcggt gttggcggcg   2400
ttgcgggagg gcgcaacccc cgaggttatc atggcgctgt cgagaaacgc cctgggcgac   2460
gcaaaaccga ccgccggaca gtccaaagca ttggacaaac tctttgccca ggtcgaagac   2520
tcccctgaag gcggtaatag taccgcattc ttattaaacc gagatttagc agagaaactg   2580
atgaaccggc tggttaccgg cgggttattt actcccgagt ccgctacaca attcatggaa   2640
ggctttgtcg atgcgccggc tatcttcttt gacgaaaagt cggtaaacaa ggcggcggca   2700
ggaattgagg ccggtatctt aaatcgactg cacttacata agatgccgac cgatgagcag   2760
atcggcctgt ctacggtgtt tcatctcgcg gacgatatcg cgagcggcga aacctttcat   2820
ccgagtggcg gcttaaaatt tgaccgctcg gtaaccgaag gggagttgct gctaccccca   2880
gaccgtgaca gcttagcgaa gttaaaaggc aaacgtgtcg tgttaattgg tgattcgatg   2940
cgcgaggagc tgtcggccat cggcaatggc ttcattaatc agggcgtcgc ttctctgacg   3000
gtcttaacac gcagcccaga agcctgtgag gaggtgcagc atagcctcca gaaaagcaat   3060
tcggttacat tggatgtccg atgcattgaa gataatatcg aggacgcttt agatgatctg   3120
ttgcaaaacc agggtggctt tgatgtagtg gttagcgccc cgttcagtcg actgccgtat   3180
```

```
aacccattag cggccgagcg tgagggtagt tggaatcgtg tgttgtctca tacggacttt    3240
gcccgcctga ttgatgaaca gttaacccac catttccgcg tggcaagacg cgcggccctg    3300
gtaccgaact gccagattgt cttgttaaca ccagatacat ctttcgtatc gtctcgtgag    3360
gagttcgcgc tcgccctgtt cgttaaaaac tcgctgcacg cgtttacggt aaccctgggg    3420
gtcgagaccg aacgcttacc gaccgtaccg gccgttaatc aggtgcagct tacccgtcgg    3480
gctcgcgctg aagaaccagc gaccgaaagc gagttgcagg aggagatgga gcgcctggtc    3540
tcggccgtac tgcaatgcgc cgttcctgca ccgtccccgt ctgaaagccg gtacctggcg    3600
cgcattttca gaggtaatgc ggtcaccgta tga                                 3633

<210> SEQ ID NO 26
<211> LENGTH: 3690
<212> TYPE: DNA
<213> ORGANISM: Roseiflexus castenholzii

<400> SEQUENCE: 26
atgtcgactg tgcgacgact ggaaggaaag gtggcgctga ttaccggcgg cgctggcaac      60
atcggcgagg ttattacgcg ccgattcctg gcggaaggcg cgaccgttgt catcaccggt     120
cgcaatgcgg aaaagcttgc ggtgtaccgc cgtcgtctga ttgatgagga gcgcgtcgct     180
ccagagcgcg ttgtcgcgct gcggatggac ggcagtgata tcgctcaggt gcgcgcagga     240
gtcgcgcaga ttgttcatgg cggcactgac gtcccaatac cgctgcaccg gattgatatt     300
ctggttaaca acgccggcag tgccggacca cgccggcgcc tggtcgatat cccgttagaa     360
ccaagcgaag tgcaaccgcc tgactcggaa accctggcgc aggcggttgg taatctggtc     420
ggaatcacct ggaatctgac tcgcgcagcg gcgccgcaca tgccgtcagg ctcgtcggtg     480
attaatatca gcaccatttt ctcacgcacg gattattatg gtcggatcgc gtacgtcgcg     540
cccaaagcgg cgttaaatgc gctgtcggac ggttttggcg cgcgaattgg ggtgcgcggc     600
atccgcgtta atacgattta tccaggtccg attgagtcgg aacgcatcta caccatgttc     660
caggcgatgg acgcgttaaa ggggcaacca gagggcgaca cagcctccgg cttcctgaga     720
atgatgcgct tgtcgcgcat tgatcagaat ggcgaagtgg ttaagcgctt tccctcaccc     780
gtcgatgttg ccaataccgc ggtgtttttta gcctcggatg agagcgcagc gtttacgggt     840
catgcctttg aggtgactca tggcatggag gtgcctacgg agagtcgcac taccttcgtg     900
agccgcccag gtctgcgctc ggttgatgcc acgggcaaag tcatcctgat ttgcgctggc     960
gatcaggtcg atgatgcggt cgcgctggcc gacaccttac gcagttgccg cgcgaccgtt    1020
gtgattggtt tcgggatccg cgcgcgcgctt gaaaaagcgt ctgtgttact gcgcgaacct    1080
cgccatgcgc ttgctgccga tatgtacggc cgcccgacca tgaccgcgga agcgcgcctg    1140
gtgcgcttag atccattaga cccgcgtgct gcggcacaga ccttagagca gatccacgcc    1200
gaattaggcg ccatccatca tgctgttgtc ctgcccggtc agagtcgtca cgcgcccagt    1260
gcatcgctga ttgaagtgga cgatcaggtt gttgagcgct ttctgcatca ggagctagta    1320
ggcaccatcg cgctggcgcg cgaactggcg cgcttttggg aggaataccc cagtggctcc    1380
tctatgcacc gcgtgctgtt cgtgtcgaat ccagacgatc agcaggggaa tcagtactcc    1440
catattctgc gcgctgcggt tgagcaattg gtgcgcgttt ggcgccacga gtcggagtat    1500
gacagcgtta atcctgcgca ccagcaggaa gggcagagct cggccgctgt gtgggcgaac    1560
caattgattc gctacgtgaa caatgagatg gccaacttag atttcacgtg cgcatgggtg    1620
```

```
gcaaagttat taggttcgga ccgtcgcatc gccgaaatta atttatactt accagaagaa    1680
attgtgggca ccatcggcgt gcacaatccg ggttttgggt gggcggaaag tctgttcggg    1740
ttacacatgg gtaaagtggc gttaattacg ggcggcagtg cgggcattgg cgggcagatt    1800
ggtcggttac tggcgttaag tggcgcgcat gtgatgctgg cggcgcggaa cgccgatcag    1860
ttagagcaga tgcgcgcgag cattgtgcgg gaggtgcgtg atgccagtta ccccgatgcc    1920
gagagccgcg tggcgatttt tccaggctcg gatgttagtg acattgacgg tctcgaacgc    1980
ctggttaacc acaccgtgcg cgtgttcggc aaagtggatt atctgattaa caatgcgggc    2040
attgccggcg ccgaggagat ggtgattgat atgccggtgg acgcctggcg ccacactctg    2100
cgcgccaatc tgatttcgaa ttacgcgctg ctgcgccgct tagcgccgca aatgaaagcg    2160
gcgggcggtg cgtacgtgct gaatgtgagc agttattttg gcggcgaaaa atacgtggcg    2220
attccttatc cgaaccgcag tgattacgcg gttagtaaag cggggcagcg cgccatggtt    2280
gaaagtctgg cgcgctttct tgggcccgag atccagatta acgcaattgc gccagggccg    2340
gtggaagggg aacgtctgaa gggcgccggt agtcggcccg ggctgtttat gcgccgggcg    2400
cgtttaatcc tggaaaacaa gcgcttaaat gaggttttg ctgcgctgct ggcagcgcgc    2460
catgagggcg cgacgattgc cgatctgtta ccagatctgt ttgccaatga catccagagt    2520
attgccaatt cggctgcgat gccggcgccg ctgcgccgcc tggcgaccat gctgcgcgag    2580
acctcggatg ctggcggttc ggcgcagagc tatctgatga atgcgactat cgcgcgcaag    2640
ttgttaaatc gtctggagaa tggcggttat atcaccttac atgaccgacg cgcgctgacg    2700
gtcgaaccgc cggagccgtt tttcacgaaa gcgcagattg agcgcgaagc gattaaagtg    2760
cgggatggca tcctgggaat gttacatctg caacgaatgc cgacggagtt tgatgtggcg    2820
ctggcgaccg tttttacct ggcggaccgt aatgtgaccg gcgagacctt tcacccgagc    2880
ggcggtctgc gcttcgagcg caccgttacg gaaggcgaac tgttcggcaa accgggacag    2940
cagccgctga aacgactgaa gggctcggtt gtttacctga ttggggagca tctgcgccaa    3000
cacctggtgc tgctggcgcg cacgttttta gatgagatcc acgttgcgcg cgttgtcctg    3060
ctgactgaaa cgacccaggc ggcaacggac ctggcagccg aactgagtga ttacgaagcc    3120
gccggacgat tgtcgttat tccgacctgt ggcgacatcg aaggcgggat cgatcgagcg    3180
atggcagaat atgccgccc agggccggtc attagcaccc cgtttcgccc gctgccggat    3240
cgcgccctga gtgcccgaaa cggggattgg agtagtgtgt taacgacggc cgaatttgag    3300
gaattggttg aacagcagat tacgcaccat tttcgcgtcg cgcgcaaagc gggtctgatt    3360
gagggcgcga acgttacgct ggtgacccg ccgacgagcg cgcgcagcac cagtgaggag    3420
tttgcgctgg caaactttgt taaaaccacc ttacatgcat taaccgcgac ggctggcgcc    3480
gaaagtgaac gcaccgtgcc gcacgtgccg gttaatcagg tggacctgac ccgtcgtgcc    3540
cgtagtgagg agccccgtac ccctagtgag gaggaggagg aattacagcg gttcgtgaat    3600
gccgtgctgc tgacgagtgc gccgctgcct accccgttag aaagtcgtta ccgtgcgcgt    3660
atttaccggg gaaatgcgat cacggtatga                                     3690
```

<210> SEQ ID NO 27
<211> LENGTH: 3651
<212> TYPE: DNA
<213> ORGANISM: Unknown
<220> FEATURE:
<223> OTHER INFORMATION: marine gamma proteobacterium

<400> SEQUENCE: 27

```
atgaacgatt tcgtgcaatt caccgatgac atgaccagtc agtcaaagtc cggaaaaaga    60
ctggacaaca aatctattat ccttacgggc gccgcgggat ctattggccg atttattacc   120
cggcaattac tctgcgaagg tgcgagagtg atgatgacag ggcgtgatat cagcaagttg   180
gaagaatttg tagattccct ctgcgatgac ggttttgaca gggagaatat ggtggttact   240
gtgggcgatt gcgcggaccc agaggtttgt cggcggatcg ttgcagacac cgtggaagcg   300
ttcggcacca ttgacgtgct ggtcaacaac gcgggtgctg ctggcccgaa atatacgcta   360
agagatattc cgttttccga tgtagagatg aagaccgcgg gatcagatca aacgatgttc   420
gattcagcga tgaatctatt aggcgctccc tggaatatgg cacgtgcagc ggcccctcac   480
atgtccgtgg gtgcttcaat catcaatgta tctacaatct tttctcggac gcattacttt   540
ggtcgcatac cgtatgtggt tccgaagtcg ggcctaaatg cgctatcaaa gggactcgca   600
ttggaattgg gggaggaaca aggcattcgt gtcaacactg tatttccggg acccattgaa   660
tcggaacgta tcgacacggt gtttgcgcgc atggacgaat gcagaatctg gaacccggc    720
agcacgggcc gcgagttccg cgacctcatg attacgactc gcgagggtga ggaggggttg   780
gagtatcgct atcctacacc gaccgatgtg gcgtcgtcca ttacttggct cgcgtccggg   840
gagtcggccg cagtttctgg tcacgcagtt gaagtcacta atggtatgca ggtgccagcc   900
cagagtcggt cgcagttggt gtcatggccg gataagcgac tagaggatct ttccgatcac   960
attgtgctga tattaggcgg ctcagactat gaggaggcgg tgaccttcgc cgaacggcat  1020
actgaaagtg gcgctcgggt gttactagct tttagaaact tggaatccgt aggccatgct  1080
cgatctatta tccaagctcg ggaattggag tcagttcaat tgtctcattt ggacccgtta  1140
cgccgagagt cggtagacag aaccatgcaa ttcatagacg accatttcgg ccggttggat  1200
ggcgttattg ttttgcccca agagaaaaac ggtcaatacg gttattccat ctgttccgct  1260
accgacgacg atgtagaaaa cttcgtcaag gacgaagtcg tggctccggt agcctttgcg  1320
tcaaccctcg cgaccaatct tagccgctgg tttggaaaat gtgatccgcc ggcgattacc  1380
tacgtcacca atgcgagtga tggacacggt aaccttctga cgaggtcat tcgcgcgtcg   1440
aacgaggcgc taattcgcgg ttggcgccac gaggatgaga cactaaaagc tgctggagag  1500
ttgtcgtggt ccgtgcaacc gaatcagtta gtgcgctatg acactgaaga tagagatgcg  1560
ctcccgtttg cagctgattg ggccgctacc ctcactaatc gcgtgcgaca gatggatccc  1620
attaatctct ggattcctaa ggatattaaa cgcgcgacag gtaaaggcgc gatgccgaca  1680
tctctgatgc gtgttcttcc gggcttacat aaaggaaaaa ccgcggtcat cacaggtggc  1740
agcttgggca taggcctaca attaggacgc tatctcgcca tcgcgggagc gcgagtgcta  1800
cttagtgccc gcagtgaggc gaaattgata gaagctaagg ccgagattgt tgcagaattg  1860
agtggcattg gctatccgaa cgccgacaac cggattcacg tgttggcgaa catcgacgtt  1920
ggagatcccg cagcactaga gacattacac cagcacgcgg tagacctttt cggtcaagtc  1980
gattttctta ttaataatgc aggcatttca ggtgcggagg agatggttgt tgatatgacc  2040
ctaaaagact gggatcgcac catggaggca aatctaatct caaattactc gctaatacgt  2100
aagtttggcc cctaatgaa agataaaggg cgaggctcta tattgaatgt ttccagttac   2160
tttggtggtg aaaaatatgt ggcggtggcg tatccgaatc gcgccgacta tgcggtgtca  2220
aaggcaggac aacgtgtgct cgcggaaatc ctgtcgcgcc acttgggacc tgagattcag  2280
atcaacgcgc tggctccagg cccagttgat ggagctcggt tgcggggatt aggcgatgcg  2340
```

```
cccggtctttt tgatcgtcg cgggagactt gttctcgaga ataaacgctt gaaccaggtc    2400
cacgcggcga tcatatcggc cgtcgcggat ggctacccca ttgaggaaat caggaaactc    2460
tcagccaacg cggttgaagt tttgccgacc cataatctac catccgtact aagccgtttg    2520
tattcccaag taaagactc cggggggaaca ggaagctcta gtaaatgcct gctgcatatg    2580
ggcatggctg tcaagctcgt cgaacggtta gtcaatgctg gtattttac gactgaggac    2640 aaagacgaat ttttaggctc gttcgtcgac gcaccgtcgc cgttctttga caaggaggcg    2700
tgcaaaagat ctgcaaccca gatcgaatct ggaatcctta accggctgca tttgcacaaa    2760
atgcctacag atgaacaagt cggcttatct accgtatttc atctcgcgga tgagatcgtc    2820
agtggtgaaa ctttccatcc atcaggcggc ctgaaatttg accgctctgt aaccgagggc    2880
gagcttctct tgtcccctag tgagaaagat ttagcccgat tgagtggcaa gcgcgttgtg    2940
atacttggcg actgcatgcg taacgaaatc acagagattg caaaggggtt taaatctaac    3000
ggtgttgaga agctctggat ccttacgcgc tcggaggaga ccaaaaccac gctataccat    3060
gctctcgaat gtgacagtgt ggagaacatc gacgtgcgct gcatcggtga cgatatcgaa    3120
ggtgcgctag ataatttact gcgccacgac ggcggattcg acgttgttgt cagcagcccg    3180
tttgaacgcc ttccgctaaa cgcactgca ggagaccgcg gtggtgactg ggatcgcgtg    3240
ctatcagatg agcagttccg acaactcgtt catcagcagt tgacccacca cttccgcagt    3300
gctcgaattg ctgccttaat accgagctgc caaatcgtat tattgacacc ggaaacctcg    3360
cttgcatcca cccgtgagga atttgcactt gcactgttcg tcaaaaatag tctgcacgct    3420
tttacggtga cgctaggtgt ggagggtgag cgtcttccca ccgttccagc tgtcaaccag    3480
gtgcagctta ctcgcagggc gcataccgag gagccaagta atgatcagga attaagtgag    3540
gagatggagc ggctggttgc tgctgtcatg caatgctcgg tcccagcccc ctctcctaaa    3600
gagagtcgtt acctgagtaa gatcttccgg ggaaacgccg tgacggtatg a             3651

<210> SEQ ID NO 28
<211> LENGTH: 3654
<212> TYPE: DNA
<213> ORGANISM: Erythrobacter sp.

<400> SEQUENCE: 28
atgtcgaagg aaggaaacgc cgccaaaggt cggttagaag gtaaagtggc gctgattacg      60
ggggcggcag gcaatttagg caacgagata tcgcgggcct tcgcccgcga aggcgccttc     120
gttgttatga cggggcgcac cgaggagcgg atctctgcgg cgcgtgaaca gttaattgcg     180
gataccggcg tggcgcctga gcgaattgat accgccgtgt tagacggcgg caatcccgac     240
tcgattcgcg cagcgatggc aaaattgcgc aaggaatacg gccgtattga cattttaatt     300
aacaatgcag gttctgctgg cccaaaacag ccgttacata acgtaccgtt aagccctcag     360
gagatggaag cgtgcggcga caccgagacc gtgcgcgacg cgatgttaaa tattttgggc     420
gttacctgga acatggcgcg cattgtcgcg ccaatgatgc cggttggcgg cgctatggtt     480
aatatttcga cgatctttag ccatacgcgc tactatggac gcacggctta cgtggttcca     540
aaagctcgcg tgaacgcgct ttcgaaccag ttggccagcg agttaggacc gcgcggcatt     600
cgcgttaaca cagtgtttcc aggcccgatc gaaagcgatc gcattcgcac cgtcttcgcc     660
gcgatggatg aggttcagag ccagccaaaa gatacgaccg caaactattt taccggtcgc     720
atggcgttaa cccgcagcgt gaacggaaaa gtagatggca aacctctgcc aaaccccaaa     780
gacattgcgg ggacgtgcct gttttttggcc tcagaggaag ccgcaggaat cgcgggcgag     840
```

```
gaagttgatg ttacccatgg tcttagtgcc aaccgcacct cggcatcgac ctacatgacc    900
cgtcccagta tgcgctcgtt agatggggcg ggtttaaata tttttattgt gtcgggagag    960
aactgggatg acgcgctggt ggccgctcat acgctgattg gaagtggcgc aaaagttcgc   1020
ttaggcttag ctcgcaatgc cgatgtcgcg caggccaatg cgcgtctgaa ggcgcaaggg   1080
atcggcgagg agctgaccgt gacccgtttt aaccgtgcag agccagacgc gatggaagat   1140
gcgttagccg cgttcagtgg cgacgtggat ggggcgatta ccggcgcgat tattctgccg   1200
gtgaaaccct cgggccattt taccggatcg ctgttagccg ccgatgacga caccgtcacg   1260
aaatttatgg ataccgagtt ggttggcgcg atcgcagtgt cgcgaagctt ggcgcgttac   1320
tggcacgggc gagaggactt acagagtcct ccacgctgcg tttttatgac caatccgggc   1380
gacccactcg gcaatagttt tgcctcggtg ttaagtgccg gcattaccca gctgattcgc   1440
atttggcgcg acgaggaacg cgttcaggcg ggcaatggct cgaccgagca tgccgtttgg   1500
tcgaaccaga ttgttcgcca taccaacacc gaagatgaga cacccgcttc gcctcgggc    1560 cacgccaccc gcgtcttatt tcgcgaacag catattgccg agattgattt aaaactgcca   1620
gcgaatatta gcgaggaaac cggatcgcgc aaagccatgg tgggcttcgc cgagaacatt   1680
accgggcttc atttgggcaa agtcgctttt attaccggcg gctctgccgg gattggcggc   1740
caggttgcgc gcctcttagc gttagcaggc gcaaaagtta tgatggtggc aagacgcgaa   1800
agcgagttgg tggccgcccg ggatcgtatt gttggtgagt tgcaggacat ggctttgcg    1860 ggcgtcgaac gccgtgtgaa gtatatggcc gatattgatg tgagcgattt tgcctcgtta   1920
gataaagcgg tcgatgcgac gttagaggag tttgggcgta tcgactattt aattaataac   1980
gcaggcgtcg cgggcgccga ggatatggtt attgatatgg agccagaggc atggcgcttt   2040
acgttagacg cgaacttaat tagtaattat cacctgatgc agcgcgtggt tccgctgatg   2100
aaagaacagg gcagtggcta tgtgttaaat gtgagtagtt actttggcgg tgaaaaattt   2160
ttagcggtgg cctatccaaa ccgtgccgac tacggactga gtaaggcggg ccagcgggcg   2220
atggtggagg cgtttagtcc gttttaggg cccgaggtac agtgcaacgc catcgcgccg    2280
ggccctgtgg acggcgatcg gcttagtggt accggtggaa agccaggtct gtttcagcgc   2340
cgtgccaaac tgattttgga gaacaaacga ctgaatgcgg tgtacagtgc agtgattcat   2400
gcgattcgcg agggcggcga cgcggcgaag attctgacgc gactctcgcg caattcgacc   2460
tcgaccttaa gccacgatgc agaagcacca gaggaactgc gcaaattagc attagatttt   2520
gcatcgcagg gtgacgggct gtgcacgtgg gaccagtact tactgaccga tgcgatggcg   2580
cagcggctct tagtgcggtt gcagttgggc ggctttctgt taggctcgaa cgaatgggcg   2640
agcctgtcga gcagcgagca gacgtggtta aagttatcgc ctccagacga taaaccattt   2700
ttaccagctg cgcaggtgga taaagtggca acggcgtgg gcaaaggcgt tatttcgcag    2760
ttgcatttgg gtgcgatgcc gaccgaggcg gaggttgcgc aagcgaccgt gttttttta    2820 gccgatcgcg ctgttagcgg ggaaaccttt atgccgtccg gcggcttacg tgtggaacgc   2880
agtaacaccg agcgcgagat gtttggcagc ccaaaacaag agcgcattga taaaatgaaa   2940
gggaagaccg tgtggattat tggcgagcat ctgagtgact acgtggctgc gacaattgag   3000
gagttagtct ccggctgcgg cgtggccaaa gtggttctga ttgccaaaga taaaagtggc   3060
gaaaaagcgg ttcgcgatca gctcccaaac gatttgtcga aggatgcgtt agaagttctg   3120
attgcgggtg acgggttgga ggaagcgatg gatgaggcgt tgggccactg gggcaaacca   3180
```

| | |
|---|---|
| accacggtgc tgagtatgcc gggtgaacca ctcccagacc atctgtttga aggcggcaac | 3240 |
| ccgttgtcga ccaaagactt tgcgcacatg gtggaggcga acattacccg ccattaccgc | 3300 |
| gttacgcgca aagcgtcgtt gtacgatgga tgccaagtgg ttctcgtttc gccggatgtt | 3360 |
| ccgtatggca gtgacggccc aggagttgcg ttagccaatt tgttaaaaac gagcctgcat | 3420 |
| gcttttaccg cgacggtcgc ggttgagaat gagagactcg tgcatgacgt tccggtgaac | 3480 |
| cagattaact taacccgccg ggtgtcgagc gaggagccgc gcgacgctga tgaacacgcc | 3540 |
| gaggagttaa gacgctttac ccgcgctgtc ctgcttgtgg gcgcaccgct gccagacgcg | 3600 |
| caggatagtc gctatcgctc gaaaatttac cgcggcacgt cgatgacggt atga | 3654 |

<210> SEQ ID NO 29
<211> LENGTH: 3660
<212> TYPE: DNA
<213> ORGANISM: Chloroflexus aurantiacus

<400> SEQUENCE: 29

| | |
|---|---|
| atgtcgggaa ctggacgact ggcaggaaaa atcgcccctta tcaccggcgg tgcgggtaac | 60 |
| attggttcgg aattgactcg tcgcttttta gcagagggag ccacggttat catctcggga | 120 |
| cggaaccggg ccaaattgac cgcactggcg gaacggatgc aggcagaggc aggagtgccg | 180 |
| gcaaaacgca ttgatttaga agttatggat gggtcggatc cggttgccgt acgtgcgggc | 240 |
| attgaagcca tcgtgcgcg tcatggtcag attgacatcc tggttaataa cgcaggatcg | 300 |
| gcgggcgcgc agcgtcgtct ggcggagatc ccattaacag aagctgaact tggtcccggt | 360 |
| gcggaggaga cgctccacgc gagcattgcg aaccttctcg gcatgggatg gcacctgatg | 420 |
| cgtatcgccg caccccacat gccggtagga tcggccgtta ttaacgttag taccattttt | 480 |
| tcccgggctg agtattatgg gcggatcccg tacgttaccc caaggctgc tctcaacgct | 540 |
| ctatcacaac tcgctgcccg tgagcttggc gcacgtggta ttcgcgtcaa cacgattttt | 600 |
| cctggtccga tcgaatcgga tcgcattcgt actgtgttcc agcgtatgga tcagttaaaa | 660 |
| gggcggcctg aaggtgacac tgcccatcac ttttttgaata ccatgcgatt gtgccgtgcg | 720 |
| aatgaccagg tgccctcga acgtcggttc ccttctgttg gcgatgtggc agacgcggct | 780 |
| gttttttctgg cgtcggcgga atctgcggct ttatctggcg agacgatcga ggtcacgcat | 840 |
| ggaatggagt tgccggcgtg ttcggagacc agcctgctgg cgcgtacaga tctgcgcacg | 900 |
| atcgatgcgt cgggtcgcac gacgttaatt tgtgcgggtg accagatcga ggaggtgatg | 960 |
| gccttaaccg gcatgttgcg tacctgcggg tcggaagtga ttattggttt ccgtagtgct | 1020 |
| gccgccctgg cgcagttcga gcaggcagtt aacgagtcgc ggcggctggc gggtgcagac | 1080 |
| tttacgcccc ctatcgcgtt gccattagat ccacgcgatc cggcaactat cgacgctgtt | 1140 |
| ttcgattggg cgggtgagaa caccggtggg atccacgcag ccgtgatcct gcccgctacc | 1200 |
| tcgcatgaac cggcaccgtg tgtgatcgag gtcgatgatg agcgggtgct gaactttctg | 1260 |
| gcggatgaaa ttaccgggac tatcgtgatc gcgtcgcgcc tggcgcgtta ttggcagagt | 1320 |
| caacggctca cccctggtgc acgtgcccgt gggccgcgtg ttatcttttt aagtaatggc | 1380 |
| gcggatcaaa acgggaacgt ctatggacgc atccaatcgg cggctattgg ccagttaatc | 1440 |
| cgtgtgtggc gtcatgaggc tgaactcgac taccagcgtg cgagcgcggc gggcgatcac | 1500 |
| gtgctgccgc cggtatgggc gaaccagatc gtgcgcttcg ctaatcgcag cctcgaaggg | 1560 |
| cttgaatttg cgtgcgcgtg gactgctcaa ttgttacact cgcaacgcca cattaacgag | 1620 |
| atcacccttaa atattcccgc gaatatcagc gcgaccaccg gtgcacgctc ggccagtgtt | 1680 |

```
ggatgggccg aaagcctgat tgggttacac ttggggaagg tcgcgttgat caccggcggt    1740
agcgcgggca tcggcgggca gattgggcgc ttactggctt tatcgggtgc ccgcgtgatg    1800
ctggcagcgc gtgatcggca caaattagaa cagatgcagg ccatgattca atcagagctg    1860
gctgaggtgg ggtacaccga tgttgaagat cgcgttcata tcgcaccggg ttgtgatgtg    1920
tcgagcgaag cccagctcgc cgatctcgtc gaacgtaccc tgtccgcttt tggtaccgtt    1980
gattacctga ttaataatgc ggggattgcg ggcgttgagg agatggtcat tgatatgcca    2040
gtcgagggat ggcgccacac cttattgcgc aacctgatta gcaattatag tttgatgcgc    2100
aagctggccc cgttgatgaa gaagcagggc agcggctata ttctcaatgt ttcctcctat    2160
tttggtggcg aaaaggatgc cgcgatccct tatcctaatc gtgcggatta tgcggttagt    2220
aaagctggcc agcgggcaat ggcggaagtt tttgcccgct tcctcggtcc ggagatacag    2280
attaacgcga tcgccccggg cccggttgaa ggcgatcgct tacgcggcac cggcgaacgt    2340
cctggtttat ttgcgcgtcg ggcccggctg atcttggaga ataaacggct gaacgagctc    2400
catgctgctc tcattgccgc tgcccgcacc gatgagcgat caatgcatga actggtcgaa    2460
ctgttacttc ctaacgatgt ggcggcacta gagcagaacc cagcagcacc caccgccttg    2520
cgtgaactgg cacgacgttt tcgcagcgaa ggtgatccgg ccgcatcctc cagctcggcc    2580
ctgctgaatc gttccatcgc ggctaagttg ctggctcgtt tgcacaacgg cggttacgtg    2640
ttgcccgcgg acatttttgc aaatctgcca atccgcctg atcctttctt cacccgagcg    2700
cagatcgatc gcgaggctcg caaagtccgt gacggtatta tggggatgtt atatctgcaa    2760
cggatgccga cagagtttga tgttgcaatg gcgaccgttt actatctcgc ggaccgcaac    2820
gtttcgggcg agactttcca tccatccggc ggcttgcgtt atgaacgcac ccccaccggc    2880
ggtgaattat tcggtttgcc ttccccggaa cggctggccg agctggttgg aagcacggtt    2940
tacctgatag gcgaacacct gacagaacat ctcaatctgc tcgcgcgtgc ctatttagaa    3000
cgttatgggg cacgtcaggt agtgatgatc gtcgagactg aaaccggggc agagactatg    3060
cgtcgcttgt tacatgatca tgttgaggct ggccggctga tgacaatcgt ggcgggcgat    3120
cagattgaag cggctattga ccaggctatt acacgctatg ccgcccagg gccggttgtt    3180 tgcacccctt tccggccact gccgacggta ccactggttg ggcgtaagga ctcggactgg    3240
agcactgtgt tgtcggaggc tgaatttgcg gagttgtgtg aacatcagtt aacccatcac    3300
ttccgggtag cccgcaaaat cgcgctgtcg gatggcgcgt cgttagccct ggttacacct    3360
gaaacaacgg ctacctccac aaccgagcaa tttgctctgg ctaatttcat taagacgacc    3420
ctccatgctt ttacggctac gatcggcgtt gagagcgaaa ggacagctca gcgcatcctg    3480
attaaccaag ttgatctgac ccggcgtgcc cgtgcgaggg agccgcgtga tccgcatgag    3540
cgtcaacaag aactggaacg ttttattgag gcagttttac tggttacagc accattaccg    3600
cccgaagcgg atacccgtta tgcggggcgg atccaccgcg gacgggccat caccgtatga    3660
```

<210> SEQ ID NO 30
<211> LENGTH: 5469
<212> TYPE: DNA
<213> ORGANISM: Chloroflexus aurantiacus

<400> SEQUENCE: 30

```
atgatcgaca ctgcgcccct tgccccacca cgggcgcccc gctctaatcc gattcgggat      60
cgagttgatt gggaagctca gcgtgctgct gcgctggcag atcccggtgc ctttcatggc     120
```

```
gcgattgccc ggacagttat ccactggtac gacccacaac accattgctg gattcgcttc      180
aacgagtcta gtcagcgttg ggaagggctg gatgccgcta ccggtgcccc tgtaacggta      240
gactatcccg ccgattatca gccctggcaa caggcgtttg atgatagtga agcgccgttt      300
taccgctggt ttagtggtgg gttgacaaat gcctgcttta atgaagtaga ccggcatgtc      360
acgatgggct atggcgacga ggtggcctac tactttgaag gtgaccgctg ggataactcg      420
ctcaacaatg gtcgtggtgg tccggttgtc caggagacaa tcacgcgacg gcgtctgttg      480
gtggaggtgg tgaaggctgc gcaggtgttg cgcgatctgg gcctgaagaa gggtgatcgg      540
attgctctga atatgccgaa tattatgccg cagatttatt atacggaagc ggcaaaacga      600
ctgggtattc tgtacacgcc ggtcttcggt ggcttctcgg acaagactct ttccgaccgt      660
attcacaatg ccggtgcacg agtggtgatt acctctgatg gcgcgtatcg caacgcgcag      720
gtggtgccct acaaagaagc gtataccgat caggcgctcg ataagtatat tccggttgag      780
actgcgcagg cgattgttgc gcagaccctg gccaccttgc ccctgactga gtcgcagcgc      840
cagacgatca tcaccgaagt ggaggccgcc ctggcaggtg agattacggt tgagcgttcg      900
gacgtgatgc gtggggttgg ttctgccctc gcaaagctcc gcgatcttga tgcaagcgtg      960
caggcaaagg tgcgcacagt actggcgcag gcgctggtcg agtcgccgcc gcgggttgaa     1020
gctgtggtgg ttgtgcgtca taccggtcag gagattttgt ggaacgaggg gcgagatcgc     1080
tggagtcacg acttgctgga tgctgcgctg gcgaagattc tggccaatgc gcgtgctgca     1140
ggctttgatg tgcacagtga gaatgatctg ctcaatctcc ccgatgacca gcttatccgt     1200
gcgctctacg ccagtattcc ctgtgaaccg gttgatgctg aatatccgat gtttatcatt     1260
tacacatcgg gtagcaccgg taagcccaag ggtgtgatcc acgttcacgg cggttatgtc     1320
gccggtgtgg tgcacacctt gagggtcagt tttgacgccg agccgggtga tacgatatat     1380
gtgatcgccg atccgggctg gatcaccggc cagagctata tgctcacagc cacaatggcc     1440
ggtagactga ccgggtgat tgccgaggga tcaccgcttt tcccctcagc cgggcgttat     1500
gccagcatca tcgagcgcta tggggtgcag atctttaagg cgggtgtgac cttcctcaag     1560
acagtgatgt ccaatccgca gaatgttgaa gatgtgcgac tctatgatat gcactcgctg     1620
agagttgcaa ccttctgcgc cgagccggta agtccggcgg tgcagcagtt tggtatgcag     1680
atcatgaccc cgcagtatat caattcgtac tgggcgaccg agcacggtgg aattgtctgg     1740
acgcatttct acggtaatca ggactttccg cttcgtcccg atgcccatac ctatcccttg     1800
ccctgggtga tgggtgatgt ctgggtggcc gaaactgatg agagcgggac gacgcgctat     1860
cgggtcgctg atttcgatga agagggcgag attgtgatta ccgccccgta tccctacctg     1920
acccgcacac tctggggtga tgtgcccggt ttcgaggcgt acctgcgcgg tgagattccg     1980
ctgcgagcct ggaagggtga tgccgagcgt ttcgtcaaga cctactggcg acgtgggcca     2040
aacggtgaat ggggctatat ccagggtgat tttgccatca agtaccccga tggtagcttc     2100
acgctccacg gacgctctga cgatgtgatc aatgtgtcgg gccaccgtat gggcaccgag     2160
gagattgagg gtgccatttt gcgtgaccgc cagatcacgc ccgactcgcc tgtcggtaat     2220
tgtattgtgg tcggtgcgcc gcatcgtgag aagggtctga ccccggttgc cttcattcaa     2280
cctgcgcctg gccgtcatct gaccggtgca gacaggcgcc gtctcgatga gctggtgcgc     2340
accgagaagg gggcggtcag tgtcccagag gattacatcg aggtcagtgc ctttcccgaa     2400
acccgcagcg ggaagtatat gaggcgcttt ttgcgcaata tgatgctcga tgaaccactg     2460
ggtgatacga cgacgttgcg caatcctgaa gtgctcgaag aaattgcagc caagatcgct     2520
```

-continued

```
gagtggaaac gccgtcagcg tatggccgaa gaacagcaga tcatcgaacg ctatcgctac    2580
ttccggatcg agtatcatcc accaacggcc agtgcgggta aactcgcggt agtgacggtg    2640
acaaatccgc cggtgaacgc actgaatgag cgtgcgttag atgagttgaa cacaattgtt    2700
gaccacctgg cccgtcgtca ggatgttgcc gcaattgtct tcaccggaca gggcgccagg    2760
agttttgtcg ccggtgctga tattcgccag ttgctcgaag aaattcatac ggttgaagaa    2820
gcaatggccc tgccgaataa cgcccatctt gctttccgca agattgagcg tatgaataag    2880
ccgtgtatcg cggcgatcaa cggtgtggcg ctcggtggtg gtctggaatt tgccatggcc    2940
tgccattacc gggttgccga tgtctatgcc gaatttggtc agccagagat taatctgcgc    3000
ttgctacctg gttatggtgg cacgcagcgc ttgccgcgtc tgttgtacaa gcgcaacaac    3060
ggcaccggtc tgctccgagc gctggagatg attctgggtg ggcgtagcgt accggctgat    3120
gaggcgctgg agctgggtct gatcgatgcc attgctaccg gcgatcagga ctcactgtcg    3180
ctggcatgcg cgttagcccg tgccgcaatc ggtgccgatg tcagttgat cgagtcggct    3240 gcggtgaccc aggctttccg ccatcgccac gagcagcttg acgagtggcg caaaccagac    3300
ccgcgctttg ccgatgacga actgcgctcg attatcgccc atccacgtat cgagcggatt    3360
atccggcagg cccataccgt tgggcgcgat gcggcagtgc accgggcact ggatgcaatc    3420
cgctatggca ttatccacgg cttcgaggcc ggtctggagc acgaggcgaa gctctttgcc    3480
gaggcagtgg ttgacccgaa cggtggcaag cgtggtattc gcgagttcct cgaccgccag    3540
agtgcgccgt tgccaacccg ccgaccattg attacacctg aacaggagca actcttgcgc    3600
gatcagaaag aactgttgcc ggttggttca cccttcttcc ccggtgttga ccggattccg    3660
aagtggcagt acgcgcaggc ggttattcgt gatccggaca ccggtgcggc ggctcacggc    3720
gatcccatcg tggctgaaaa gcagattatt gtgccggtgg aacgcccccg cgccaatcag    3780
gcgctgattt atgttctggc ctcggaggtg aacttcaacg atatctgggc gattaccggt    3840
attccggtgt cacggtttga tgagcacgac cgcgactggc acgttaccgg ttcaggtggc    3900
atcggcctga tcgttgcgct gggtgaagaa gcgcgacgcg aaggccggct gaaggtgggt    3960
gatctggtgg cgatctactc cgggcagtcg gatctgctct caccgctgat gggccttgat    4020
ccgatggccg ccgatttcgt catccagggg aacgacacgc cagatggatc gcatcagcaa    4080
tttatgctgg cccaggcccc gcagtgtctg cccatcccaa ccgatatgtc tatcgaggca    4140
gccggcagct acatcctcaa tctcggtacg atctatcgcg ccctctttac gacgttgcaa    4200
atcaaggccg gacgcaccat ctttatcgag ggtgcggcga ccggcaccgg tctggacgca    4260
gcgcgctcgg cggccggaa tggtctgcgc gtaattggaa tggtcagttc gtcgtcacgt    4320
gcgtctacgc tgctggctgc gggtgcccac ggtgcgatta accgtaaaga cccggaggtt    4380
gccgattgtt tcacgcgcgt gcccgaagat ccatcagcct gggcagcctg ggaagccgcc    4440
ggtcagccgt tgctggcgat gttccgggcg cagaacgacg ggcgactggc cgattatgtg    4500
gtctcgcacg cgggcgagac ggccttcccg cgcagtttcc agcttctcgg cgagccacgc    4560
gatggtcaca ttccgacgct cacattctac ggtgccacca gtggctacca cttcaccttc    4620
ctgggtaagc cagggtcagc ttcgccgacc gagatgctgc ggcgggccaa tctccgcgcc    4680
ggtgaggcgg tgttgatcta ctacggggtt gggagcgatg acctggtaga taccggcggt    4740
ctggaggcta tcgaggcggc gcggcaaatg ggagcgcgga tcgtcgtcgt taccgtcagc    4800
gatgcgcaac gcgagtttgt cctctcgttg ggcttcgggg ctgccctacg tggtgtcgtc    4860
```

-continued

```
agcctggcgg aactcaaacg acgcttcggc gatgagtttg agtggccgcg cacgatgccg    4920
ccgttgccga acgcccgcca ggacccgcag ggtctgaaag aggctgtccg ccgcttcaac    4980
gatctggtct tcaagccgct aggaagcgcg gtcggtgtct tcttgcggag tgccgacaat    5040
ccgcgtggct accccgatct gatcatcgag cgggctgccc acgatgcact ggcggtgagc    5100
gcgatgctga tcaagccctt caccggacgg attgtctact tcgaggacat tggtgggcgg    5160
cgttactcct tcttcgcacc gcaaatctgg gtgcgccagc gccgcatcta catgccgacg    5220
gcacagatct ttggtacgca cctctcaaat gcgtatgaaa ttctgcgtct gaatgatgag    5280
atcagcgccg tctgctgac gattaccgag ccggcagtgg tgccgtggga tgaactaccc    5340
gaagcacatc aggcgatgtg ggaaaatcgc cacacggcgg ccacttatgt ggtgaatcat    5400
gccttaccac gtctcggcct aaagaacagg gacgagctgt acgaggcgtg gacggccggc    5460
gagcgctaa                                                             5469
```

<210> SEQ ID NO 31
<211> LENGTH: 1822
<212> TYPE: PRT
<213> ORGANISM: Chloroflexus aurantiacus

<400> SEQUENCE: 31

```
Met Ile Asp Thr Ala Pro Leu Ala Pro Arg Ala Pro Arg Ser Asn
1               5                   10                  15

Pro Ile Arg Asp Arg Val Asp Trp Glu Ala Gln Arg Ala Ala Leu
                20                  25                  30

Ala Asp Pro Gly Ala Phe His Gly Ala Ile Ala Arg Thr Val Ile His
                35                  40                  45

Trp Tyr Asp Pro Gln His His Cys Trp Ile Arg Phe Asn Glu Ser Ser
    50                  55                  60

Gln Arg Trp Glu Gly Leu Asp Ala Ala Thr Gly Ala Pro Val Thr Val
65                  70                  75                  80

Asp Tyr Pro Ala Asp Tyr Gln Pro Trp Gln Ala Phe Asp Asp Ser
                85                  90                  95

Glu Ala Pro Phe Tyr Arg Trp Phe Ser Gly Gly Leu Thr Asn Ala Cys
                100                 105                 110

Phe Asn Glu Val Asp Arg His Val Thr Met Gly Tyr Gly Asp Glu Val
                115                 120                 125

Ala Tyr Tyr Phe Glu Gly Asp Arg Trp Asp Asn Ser Leu Asn Asn Gly
            130                 135                 140

Arg Gly Gly Pro Val Val Gln Glu Thr Ile Thr Arg Arg Leu Leu
145                 150                 155                 160

Val Glu Val Val Lys Ala Ala Gln Val Leu Arg Asp Leu Gly Leu Lys
                165                 170                 175

Lys Gly Asp Arg Ile Ala Leu Asn Met Pro Asn Ile Met Pro Gln Ile
                180                 185                 190

Tyr Tyr Thr Glu Ala Ala Lys Arg Leu Gly Ile Leu Tyr Thr Pro Val
            195                 200                 205

Phe Gly Gly Phe Ser Asp Lys Thr Leu Ser Asp Arg Ile His Asn Ala
    210                 215                 220

Gly Ala Arg Val Val Ile Thr Ser Asp Gly Ala Tyr Arg Asn Ala Gln
225                 230                 235                 240

Val Val Pro Tyr Lys Glu Ala Tyr Thr Asp Gln Ala Leu Asp Lys Tyr
                245                 250                 255

Ile Pro Val Glu Thr Ala Gln Ala Ile Val Ala Gln Thr Leu Ala Thr
```

```
              260                 265                 270
Leu Pro Leu Thr Glu Ser Gln Arg Gln Thr Ile Ile Thr Glu Val Glu
            275                 280                 285

Ala Ala Leu Ala Gly Glu Ile Thr Val Glu Arg Ser Asp Val Met Arg
        290                 295                 300

Gly Val Gly Ser Ala Leu Ala Lys Leu Arg Asp Leu Asp Ala Ser Val
305                 310                 315                 320

Gln Ala Lys Val Arg Thr Val Leu Ala Gln Ala Leu Val Glu Ser Pro
                325                 330                 335

Pro Arg Val Glu Ala Val Val Val Arg His Thr Gly Gln Glu Ile
            340                 345                 350

Leu Trp Asn Glu Gly Arg Asp Arg Trp Ser His Asp Leu Leu Asp Ala
        355                 360                 365

Ala Leu Ala Lys Ile Leu Ala Asn Ala Arg Ala Ala Gly Phe Asp Val
        370                 375                 380

His Ser Glu Asn Asp Leu Leu Asn Leu Pro Asp Asp Gln Leu Ile Arg
385                 390                 395                 400

Ala Leu Tyr Ala Ser Ile Pro Cys Glu Pro Val Asp Ala Glu Tyr Pro
                405                 410                 415

Met Phe Ile Ile Tyr Thr Ser Gly Ser Thr Gly Lys Pro Lys Gly Val
            420                 425                 430

Ile His Val His Gly Gly Tyr Val Ala Gly Val His Thr Leu Arg
        435                 440                 445

Val Ser Phe Asp Ala Glu Pro Gly Asp Thr Ile Tyr Val Ile Ala Asp
        450                 455                 460

Pro Gly Trp Ile Thr Gly Gln Ser Tyr Met Leu Thr Ala Thr Met Ala
465                 470                 475                 480

Gly Arg Leu Thr Gly Val Ile Ala Glu Gly Ser Pro Leu Phe Pro Ser
                485                 490                 495

Ala Gly Arg Tyr Ala Ser Ile Ile Glu Arg Tyr Gly Val Gln Ile Phe
            500                 505                 510

Lys Ala Gly Val Thr Phe Leu Lys Thr Val Met Ser Asn Pro Gln Asn
        515                 520                 525

Val Glu Asp Val Arg Leu Tyr Asp Met His Ser Leu Arg Val Ala Thr
        530                 535                 540

Phe Cys Ala Glu Pro Val Ser Pro Ala Val Gln Gln Phe Gly Met Gln
545                 550                 555                 560

Ile Met Thr Pro Gln Tyr Ile Asn Ser Tyr Trp Ala Thr Glu His Gly
                565                 570                 575

Gly Ile Val Trp Thr His Phe Tyr Gly Asn Gln Asp Phe Pro Leu Arg
            580                 585                 590

Pro Asp Ala His Thr Tyr Pro Leu Pro Trp Val Met Gly Asp Val Trp
        595                 600                 605

Val Ala Glu Thr Asp Glu Ser Gly Thr Thr Arg Tyr Arg Val Ala Asp
        610                 615                 620

Phe Asp Glu Lys Gly Glu Ile Val Ile Thr Ala Pro Tyr Pro Tyr Leu
625                 630                 635                 640

Thr Arg Thr Leu Trp Gly Asp Val Pro Gly Phe Glu Ala Tyr Leu Arg
                645                 650                 655

Gly Glu Ile Pro Leu Arg Ala Trp Lys Gly Asp Ala Glu Arg Phe Val
            660                 665                 670

Lys Thr Tyr Trp Arg Arg Gly Pro Asn Gly Glu Trp Gly Tyr Ile Gln
        675                 680                 685
```

```
Gly Asp Phe Ala Ile Lys Tyr Pro Asp Gly Ser Phe Thr Leu His Gly
690                 695                 700

Arg Ser Asp Asp Val Ile Asn Val Ser Gly His Arg Met Gly Thr Glu
705                 710                 715                 720

Glu Ile Glu Gly Ala Ile Leu Arg Asp Arg Gln Ile Thr Pro Asp Ser
                725                 730                 735

Pro Val Gly Asn Cys Ile Val Val Gly Ala Pro His Arg Glu Lys Gly
                740                 745                 750

Leu Thr Pro Val Ala Phe Ile Gln Pro Ala Pro Gly Arg His Leu Thr
                755                 760                 765

Gly Ala Asp Arg Arg Leu Asp Glu Leu Val Arg Thr Glu Lys Gly
770                 775                 780

Ala Val Ser Val Pro Glu Asp Tyr Ile Glu Val Ser Ala Phe Pro Glu
785                 790                 795                 800

Thr Arg Ser Gly Lys Tyr Met Arg Arg Phe Leu Arg Asn Met Met Leu
                805                 810                 815

Asp Glu Pro Leu Gly Asp Thr Thr Leu Arg Asn Pro Glu Val Leu
                820                 825                 830

Glu Glu Ile Ala Ala Lys Ile Ala Glu Trp Lys Arg Arg Gln Arg Met
                835                 840                 845

Ala Glu Glu Gln Gln Ile Ile Glu Arg Tyr Arg Tyr Phe Arg Ile Glu
850                 855                 860

Tyr His Pro Pro Thr Ala Ser Ala Gly Lys Leu Ala Val Val Thr Val
865                 870                 875                 880

Thr Asn Pro Pro Val Asn Ala Leu Asn Glu Arg Ala Leu Asp Glu Leu
                885                 890                 895

Asn Thr Ile Val Asp His Leu Ala Arg Arg Gln Asp Val Ala Ala Ile
                900                 905                 910

Val Phe Thr Gly Gln Gly Ala Arg Ser Phe Val Ala Gly Ala Asp Ile
                915                 920                 925

Arg Gln Leu Leu Glu Glu Ile His Thr Val Glu Glu Ala Met Ala Leu
930                 935                 940

Pro Asn Asn Ala His Leu Ala Phe Arg Lys Ile Glu Arg Met Asn Lys
945                 950                 955                 960

Pro Cys Ile Ala Ala Ile Asn Gly Val Ala Leu Gly Gly Gly Leu Glu
                965                 970                 975

Phe Ala Met Ala Cys His Tyr Arg Val Ala Asp Val Tyr Ala Glu Phe
                980                 985                 990

Gly Gln Pro Glu Ile Asn Leu Arg  Leu Leu Pro Gly Tyr  Gly Gly Thr
                995                 1000                1005

Gln Arg Leu Pro Arg Leu Leu  Tyr Lys Arg Asn Asn  Gly Thr Gly
1010                1015                1020

Leu Leu Arg Ala Leu Glu Met  Ile Leu Gly Gly Arg  Ser Val Pro
1025                1030                1035

Ala Asp Glu Ala Leu Glu Leu  Gly Leu Ile Asp Ala  Ile Ala Thr
1040                1045                1050

Gly Asp Gln Asp Ser Leu Ser  Leu Ala Cys Ala Leu  Ala Arg Ala
1055                1060                1065

Ala Ile Gly Ala Asp Gly Gln  Leu Ile Glu Ser Ala  Ala Val Thr
1070                1075                1080

Gln Ala Phe Arg His Arg His  Glu Gln Leu Asp Glu  Trp Arg Lys
1085                1090                1095
```

```
Pro Asp Pro Arg Phe Ala Asp Asp Glu Leu Arg Ser Ile Ile Ala
    1100            1105                1110

His Pro Arg Ile Glu Arg Ile Ile Arg Gln Ala His Thr Val Gly
    1115            1120                1125

Arg Asp Ala Ala Val His Arg Ala Leu Asp Ala Ile Arg Tyr Gly
    1130            1135                1140

Ile Ile His Gly Phe Glu Ala Gly Leu Glu His Glu Ala Lys Leu
    1145            1150                1155

Phe Ala Glu Ala Val Val Asp Pro Asn Gly Gly Lys Arg Gly Ile
    1160            1165                1170

Arg Glu Phe Leu Asp Arg Gln Ser Ala Pro Leu Pro Thr Arg Arg
    1175            1180                1185

Pro Leu Ile Thr Pro Glu Gln Gln Leu Leu Arg Asp Gln Lys
    1190            1195                1200

Glu Leu Leu Pro Val Gly Ser Pro Phe Phe Pro Gly Val Asp Arg
    1205            1210                1215

Ile Pro Lys Trp Gln Tyr Ala Gln Ala Val Ile Arg Asp Pro Asp
    1220            1225                1230

Thr Gly Ala Ala Ala His Gly Asp Pro Ile Val Ala Glu Lys Gln
    1235            1240                1245

Ile Ile Val Pro Val Glu Arg Pro Arg Ala Asn Gln Ala Leu Ile
    1250            1255                1260

Tyr Val Leu Ala Ser Glu Val Asn Phe Asn Asp Ile Trp Ala Ile
    1265            1270                1275

Thr Gly Ile Pro Val Ser Arg Phe Asp Glu His Asp Arg Asp Trp
    1280            1285                1290

His Val Thr Gly Ser Gly Gly Ile Gly Leu Ile Val Ala Leu Gly
    1295            1300                1305

Glu Glu Ala Arg Arg Glu Gly Arg Leu Lys Val Gly Asp Leu Val
    1310            1315                1320

Ala Ile Tyr Ser Gly Gln Ser Asp Leu Leu Ser Pro Leu Met Gly
    1325            1330                1335

Leu Asp Pro Met Ala Ala Asp Phe Val Ile Gln Gly Asn Asp Thr
    1340            1345                1350

Pro Asp Gly Ser His Gln Gln Phe Met Leu Ala Gln Ala Pro Gln
    1355            1360                1365

Cys Leu Pro Ile Pro Thr Asp Met Ser Ile Glu Ala Ala Gly Ser
    1370            1375                1380

Tyr Ile Leu Asn Leu Gly Thr Ile Tyr Arg Ala Leu Phe Thr Thr
    1385            1390                1395

Leu Gln Ile Lys Ala Gly Arg Thr Ile Phe Ile Glu Gly Ala Ala
    1400            1405                1410

Thr Gly Thr Gly Leu Asp Ala Ala Arg Ser Ala Ala Arg Asn Gly
    1415            1420                1425

Leu Arg Val Ile Gly Met Val Ser Ser Ser Ser Arg Ala Ser Thr
    1430            1435                1440

Leu Leu Ala Ala Gly Ala His Gly Ala Ile Asn Arg Lys Asp Pro
    1445            1450                1455

Glu Val Ala Asp Cys Phe Thr Arg Val Pro Glu Asp Pro Ser Ala
    1460            1465                1470

Trp Ala Ala Trp Glu Ala Ala Gly Gln Pro Leu Leu Ala Met Phe
    1475            1480                1485

Arg Ala Gln Asn Asp Gly Arg Leu Ala Asp Tyr Val Val Ser His
```

Ala Gly Glu Thr Ala Phe Pro Arg Ser Phe Gln Leu Leu Gly Glu
1505                1510                1515

Pro Arg Asp Gly His Ile Pro Thr Leu Thr Phe Tyr Gly Ala Thr
1520                1525                1530

Ser Gly Tyr His Phe Thr Phe Leu Gly Lys Pro Gly Ser Ala Ser
1535                1540                1545

Pro Thr Glu Met Leu Arg Arg Ala Asn Leu Arg Ala Gly Glu Ala
1550                1555                1560

Val Leu Ile Tyr Tyr Gly Val Gly Ser Asp Asp Leu Val Asp Thr
1565                1570                1575

Gly Gly Leu Glu Ala Ile Glu Ala Ala Arg Gln Met Gly Ala Arg
1580                1585                1590

Ile Val Val Val Thr Val Ser Asp Ala Gln Arg Glu Phe Val Leu
1595                1600                1605

Ser Leu Gly Phe Gly Ala Ala Leu Arg Gly Val Val Ser Leu Ala
1610                1615                1620

Glu Leu Lys Arg Arg Phe Gly Asp Glu Phe Glu Trp Pro Arg Thr
1625                1630                1635

Met Pro Pro Leu Pro Asn Ala Arg Gln Asp Pro Gln Gly Leu Lys
1640                1645                1650

Glu Ala Val Arg Arg Phe Asn Asp Leu Val Phe Lys Pro Leu Gly
1655                1660                1665

Ser Ala Val Gly Val Phe Leu Arg Ser Ala Asp Asn Pro Arg Gly
1670                1675                1680

Tyr Pro Asp Leu Ile Ile Glu Arg Ala Ala His Asp Ala Leu Ala
1685                1690                1695

Val Ser Ala Met Leu Ile Lys Pro Phe Thr Gly Arg Ile Val Tyr
1700                1705                1710

Phe Glu Asp Ile Gly Gly Arg Arg Tyr Ser Phe Phe Ala Pro Gln
1715                1720                1725

Ile Trp Val Arg Gln Arg Arg Ile Tyr Met Pro Thr Ala Gln Ile
1730                1735                1740

Phe Gly Thr His Leu Ser Asn Ala Tyr Glu Ile Leu Arg Leu Asn
1745                1750                1755

Asp Glu Ile Ser Ala Gly Leu Leu Thr Ile Thr Glu Pro Ala Val
1760                1765                1770

Val Pro Trp Asp Glu Leu Pro Glu Ala His Gln Ala Met Trp Glu
1775                1780                1785

Asn Arg His Thr Ala Ala Thr Tyr Val Val Asn His Ala Leu Pro
1790                1795                1800

Arg Leu Gly Leu Lys Asn Arg Asp Glu Leu Tyr Glu Ala Trp Thr
1805                1810                1815

Ala Gly Glu Arg
1820

<210> SEQ ID NO 32
<211> LENGTH: 1575
<212> TYPE: DNA
<213> ORGANISM: Metallosphaera sedula

<400> SEQUENCE: 32
atgaccgcca cgttcgagaa gcccgatatg tcgaagttgg ttgaggagct tcgtgcgttg      60
aaagcgaaag catatatggg tggcggcgaa gaacgtgtcc aggcacaaca cgcaaaagga     120

```
aaactcactg ctcgcgaacg cctaaattta ttgtttgatg aagggacctt caacgaagta    180
atgaccttcg cgacaactaa agcaacggaa tttggccttg ataagtccaa agtatatggc    240
gacggagtcg tcacgggctg gggccaggta gaaggccgca cggtcttcgc cttcgcgcag    300
gactttacaa gtattggcgg aacattgggg gaaacgcatg ctagtaagat tgcaaaagtt    360
tacgaattag ccctaaaagt tggcgcccct gtcgttggga ttaatgatag tggcggcgcg    420
cgtattcaag aaggagccgt agccttggaa ggttatggta cagtattcaa agcgaacgtg    480
atggccagtg gagtcgttcc gcagattacc attatggcag gtccagcagc tggcggtgcc    540
gtttattcgc cagcgttaac ggactttatt ataatgatta aaggagacgc gtattatatg    600
ttcgtgaccg gtccagaaat aactaaagtg gtgcttggtg aagacgtttc gtttcaagac    660
ttgggtggcg cggtcatcca tgccacgaag tcgggagtgg ttcatttat cgctgaaaac    720 gagcaagata gcatcaacat taccaaacgc cttttaagtt atttgccgag taacaacatg    780
gaagaaccac cgtttatgga cacaggcgac cctgctgacc gcgagatgaa agacgtggaa    840
tccgttgttc aacggacac cgtaaaaccg ttcgatatgc gtgaagtcat ttatcgcacg    900
gtggacaacg gagaatttat ggaagtgcag aaacactggg cacagaacat ggtggttggc    960
ttcggccgcg tcgcggggaa cgtggtcggt attgtcgcca ataacagcgc gcacctcggg   1020
gccgcgattg atattgacgc gtcggacaaa gctgcgcgct ttattcgctt ttgcgacgca   1080
ttcaatatcc cgcttatctc ccttgtggac acgcctggtt atatgccgg cactgaccag   1140 gagtacaaag gaataatccg ccatggcgcc aaaatgcttt atgcgttcgc agaagccact   1200
gttccgaaag taacggtggt ggttcgtcgc agctatggtg gagcacatat agcgatgtcc   1260
attaaatccc tgggcgctga tttaatttac gcatggccga gtgccgaaat tgctgtgacg   1320
gggcctgaag gggcggtgcg catactctat cgccgtgaga tccagaactc caaaagtcct   1380
gacgatttaa taaagaacg tattgcagaa tataaaaaac ttttgcgaa cccgtactgg   1440 gccgcagaaa aaggccttat cgacgacgtc attgaaccga agatacacg caaagtcatt   1500 gcttcggcgc ttaaaatgct aaaaaacaaa cgcgaatttc gctatccgaa aaaacacggc   1560
aatattccgc tctaa                                                    1575
```

<210> SEQ ID NO 33
<211> LENGTH: 1533
<212> TYPE: DNA
<213> ORGANISM: Metallosphaera sedula

<400> SEQUENCE: 33

```
atgccaccgt tctctcgtgt tcttgttgcc aaccgcggcg agatcgccgt ccgcgtcatg     60
aaagccatta agagatggg catgactgcc attgcagttt atagtgaagc agacaaatat    120
gccgtacatg ttaaatacgc ggatgaggca tactacatcg gcccgtcacc cgcgcttgag    180
tcttatttaa acattccgca tataatcgac gccgctgaaa aagcacatgc agacgcagtt    240
caccctggct acggctttct ttcagaaaat gcagactttg tggaagccgt tgagaaagcc    300
ggcatgacgt atattggtcc gagtgcagaa gtaatgcgta aaattaaaga taaactcgat    360
gggaagcgca ttgcgcagct aagtggtgta ccgatcgcgc tggatcaga tggaccggtc    420 gagagcatcg acgaagcact gaaacttgca gaaaaaattg gctatccgat aatggttaaa    480
gcggcatccg ggggtggtgg cgtcggtatt actaaaattg atactcctga ccagttaatc    540
gacgcctggg agcgtaacaa acgcctagca actcaagcgt ttggccgaag tgatttgtat    600
```

```
attgagaagg cggcggtcaa ccctcgccat atcgaatttc agctaatcgg agataaatat      660
ggaaactacg tagttgcatg ggaacgcgag tgcacgatcc agcgtcgtaa ccagaaactt      720
attgaagaag ccccaagtcc agccataact atggaggagc gctcgcgaat gtttgaacct      780
atttataagt acgggaaact aatcaattat ttcaccctcg gtacgtttga aactgttttt      840
agtgatgcga ctcgcgaatt ttattttctg gaactcaaca agcgcctgca agtcgagcat      900
ccagttacgg aactaatttt tcgtatcgat ctcgtcaaat tgcagattcg cttggcagcc      960
ggcgagcacc ttccatttac acaggaggag ttaaacaaac gcgctcgtgg tgccgccatt     1020
gaatttcgca ttaatgcgga agatccaatt aataattttt ccggctcctc gggttttatc     1080
acatattatc gcgaaccgac aggtcctggc gtgcgtatgg attccggtgt cacagaaggc     1140
tcctgggtcc ctccttttta tgacagtttg gtctcaaaac ttatcgtgta cggcgaggac     1200
cgccaatatg ccattcaaac ggcgatgcgc gccttggacg attataaaat cggaggcgta     1260
aagacaacga ttcccttgta taattaata atgcgcgatc cggacttcca ggagggccgc     1320
ttttctacgg cgtacatcag ccagaaaatc gactcgatgg ttaaaaagct caaagcggag     1380
gaagaaatga tggcatcggt ggcggccgtt ctgcaatccc gcggcttact gcgtaaaaaa     1440
gcatcggcac tcaggaaca ggctaagcca ggatcgggct ggaaatctta tggtataatg     1500
atgcagtcca cgcctcgcgt gatgtggggg taa                                 1533

<210> SEQ ID NO 34
<211> LENGTH: 504
<212> TYPE: DNA
<213> ORGANISM: Metallosphaera sedula

<400> SEQUENCE: 34
atgaaactct accgcgttca cgctgatact ggcgatacct ttatcgtggc gcatgatcaa       60
aaagagaaca agaccgtttt gaaaacagag aataacgaat ttgaaattga atacgtaggt      120
cagggtactc gcgagggcga gattatactc aaaatcaacg gtgaaatgca tcgcgtattt      180
attgacaacg gctggattat cctggacaat gcccgcattt ttcgcgccga acgtgttact      240
gaactgccga cgcaggaggg ccagactctc gacgaaatga taagggtaa agaaggcgag      300
gtgttgtcgc ccctgcaagg acgtgtcgtt caggtacgcg ttaaagaggg agatgctgtg      360
aataaaggcc agccgctttt gtcaatcgaa gcgatgaagt ccgaaaccat tgtgtcagcc      420
ccaatttccg ggttggtgga aaaagtccta gttaaagccg gtcaaggcgt caaaaaaggc      480
gatatattgg tggtgattaa gtaa                                            504

<210> SEQ ID NO 35
<211> LENGTH: 1548
<212> TYPE: DNA
<213> ORGANISM: Nitrosopumilus maritimus

<400> SEQUENCE: 35
atgcactcgg aaaaacttga aactataat aataaacaca aacgtcgca gcagggaggt        60
ggtcaagatc gaataaaagc acaacatgat aaagggaaac tgacggcacg ggaacgcata      120
gatttactcc tggatgaggg tagttttact gaaatagacc cgatggttac gcatcattat      180
catgaatatg atatgcaaaa aaagaagttc tttacggatg gtgttgtggg tggttatggc      240
aacgtcaatg gtcgccagat attcgttttt gcctatgatt tcacggtgtt aggtggcacg      300
ctcagtcaga tgggtgcaaa aaaaattacg aaactgatgg atcatgcggt gcgcacgggc      360
tgcccggtga taggcataat ggattcgggt ggtgcgcgca ttcaggaagg catcatgagt      420
```

```
ttagatggct tgcggatat tttttatcat aaccagctgg ccagcggcgt ggtgccacag      480
attaccgcga gtattggtcc atcggcgggt gggagcgtat atagcccggc catgaccgac      540
tttgtcgtta tggtagaaaa ggcgggcagc atgtttgtga cgggtccaga tgtggttaag      600
accgtgttgg gtgaagaaat tagcatggat gatttaggtg gcgccatgac ccatggtagc      660
aaaagtggcg tggcgcattt tgtggcgcag aatgaatacg aatgcatgga ttacataaaa      720
aaactgatat cgtacatccc gcagacaac tcggaagaac cgccgaaaat caaaactgat      780
gatgatccga atcgcctgga taacaacctt attaacgtga taccggaaaa cccgctgcaa      840
ccatatgata tgaaagaaat tataaactcg attgttgata accatgagtt ctttgaagtg      900
catgaactgt ttgcgccgaa cattgtcgtt ggttatgccc gcatggatgg tcaggttgtg      960
ggcatcattg cgaataaccc gatgcatctg gcgggcgcgt tagacattga tagcagcaac     1020
aaatcggcgc gtttcattcg cttctgcgat gcgtttaata ttcctattat aacgctggtt     1080
gatacccggg ttacatgcc gggttcgaac caggaacaca atggtataat cgccatggt      1140 agtaaattgc tttatgcgta ctgcgaagcg actgtgccgc gcattacctt agttattggc     1200
aaggcgtatg gtggggcgta cattgcgatg ggcagtaaga atttacggac ggacattaac     1260
tatgcgtggc cgacggcgcg ttgcgccgtt ctcggtggtg aagccgccgt taaaataatg     1320
aatcgcaaag atttggcgga cgcggataac ccagaagaat taagaagaa attgattgat     1380 gagtttaccg aaaaattcga aaatccgtac gtggcggcga ccacggcac cgtggataac     1440 gttattgatc ctgcggaaac ccgcccaatg ttgattaaag cacttaaaat gttagcgaat     1500
aaacgcgaaa acagttacc acgcaaacat ggcaacataa acctctaa                  1548

<210> SEQ ID NO 36
<211> LENGTH: 1488
<212> TYPE: DNA
<213> ORGANISM: Nitrosopumilus maritimus

<400> SEQUENCE: 36
atgatcgaga aagttttaat tgcgaatcgc ggcgaaattg cccttcgcgt tattcgcacc       60
tgcaacgcgc tgggtataaa gacggtggcg gtttactcgg atgaggatta caactcgctg      120
catgttaaga aagccgatga atcgtatcac attggagaag cggccccagc gaaatcgtat      180
ttaaaccagg aaaaaatttt agaagtaatg ctaagctcgg gtgcggatgc cgttcatccg      240
ggttatggtt tcttatcgga aaacgatgac tttgcgcgcc tgtgcgaaaa aaacaaaatt      300
aacttcattg gtccgtcggc cgactccatg aacctctgcg gtgataagat ggaatgcaaa      360
gcggcgatgc tgaaagccca ggtgccgacc gttccaggca gtccgggcct ggttgatact      420
gcggaagaag cggaaaaaat tgcgaacgaa attggttatc cagttctttt gaaaagcgtg      480
tatggtggtg gcggtcgtgg catacgcctg gtgactacgg atcaggaact ccgggaaggt      540
tttgaaaccg ttacgtcgga atcgattgcc gccgttggca atcggcgat aattgtggaa      600 aaattcctcg aaaaaacccg ccacattgaa tatcagatgt gccgcgatca tcatggtaac      660
gccgttcacc tttttgagcg cgaatgctcg attcagcgcc gcaaccagaa actcattgaa      720
cagacgccat cccagtggt tgatgaagcg aaacgggagg agattggtga actggtggtg      780
aaagcggcgg aagccgtcaa ctatacgaat ttaggtacgg cggaattttt acgcgcggat      840
aacggtgagt tttactttat tgagattaac gcgcgcctc aggttgaaca tccgataagt      900
gaaatggtga gcggcctgga ctttgttaaa ctgcaaattg atattgcgaa tggtgaaacc      960
```

```
ttaccgttca acagaaaga tctcaagatg aacggttatg cgattgaatg ccgcataaac    1020
gccgaagaca ccttttttgga ctttgcgcca agcacgggcc cagtgccgga tgttacaatt    1080
ccagcgggcc cgaacgtccg ctgcgacacg tatctctatc caggctgcac cgtttcgccg    1140
ttttacgata gcttgatggc gaaactttgc acctggggcc cgacctttga gaatcgcgc    1200 acgcgcatgt taacggcgct gaacgatatg tatgtgcagg gtgtggaaac cagcattccg    1260
ttatacaaaa ccattctcaa ttcggaagaa tacaaaaatg gtgaactcag cacggacttt    1320
ttgaaacgtt atgggatgat tgataaactc tcggaagact aaagaaaga aaagaagac    1380 aagagtgaag ccgccttagc cgcggcaatt attcattcgg aatactttaa gaatcgcgtg    1440
cagaacgata atgcgtctag tgcgacgtgg aaaaacaaat tggactga                1488

<210> SEQ ID NO 37
<211> LENGTH: 513
<212> TYPE: DNA
<213> ORGANISM: Nitrosopumilus maritimus

<400> SEQUENCE: 37
atggactata agatcgccga tgtggaaaaa agctttgaag gcaaaattac ggaaaatctg      60
ggtaacaacg attatgtaat taagataaac gacaaagaac atcagttgaa aatattatct    120
atgaacgcga aggtatcga atttattctg gatcagcagt atcataaagc gaaatattta    180
gagacggcga cgaacgaaat gaacttagtt attgataacg tgccggtgac cctgaatatg    240
aacacgcact tgacgaaat cgtgtacaaa aatagtgggg gtggtggggc gggtggtgcc    300
caggttgcgc ttaaaagtca gataccaggt aaagtggtaa gcattgcggt ggccgaaggt    360
gactcggtca agaaaggtga tgttgtgtgc acgctggaaa gcatgaagat gcaggtgggc    420
atcaaggcgc acaaagatgg tgaagtgaaa aaccttaaaa ttaagaagg tgcgacggtc    480 gcgaaagggg acgtgattgc ggatctggaa taa                                513

<210> SEQ ID NO 38
<211> LENGTH: 1548
<212> TYPE: DNA
<213> ORGANISM: Cenarchaeum symbiosum

<400> SEQUENCE: 38
atgcactctg agaaattgga taaacgtagc gcgaacaacc gctcggcgtt aatgggtggc      60
ggtgaagcgc gaatcgaagc gcagcatggc aaaggcaaat taaccgcgcg cgaacgcatt    120
gcgatcatgt tagatgaagg tagttttacg gaagtggata gcctggccac ccatcattat    180
catgaatttg atatgcagaa aaagaaattc tttggtgatg gtgtagttgg cggttatggc    240
cgcattgatg gccgcaaagt ttttgttttc gcctatgatt ttaccgtgat gggcggcacg    300
ttaagtcaga tgggcgcaaa gaaaatcact aaactgatgg atcacgcagt ccgcactggc    360
tgcccggtga ttggtgttat ggactccggt ggtgcgagaa tccaggaagg tattatgagt    420
ttagatggtt ttgccgatat tttctatcat aaccagttgg catcgggtgt ggtgccgcag    480
atcactgcta gtattggtcc aagcgccggt ggctcggtgt atagcccggc gatgacggat    540
tttgtgatta tggttgagaa aagcgcgacc atgttcgtta cgggtccgga tgtggtgcag    600
acggttttag gcgaatcgat cagctttgaa gatttaggcg cgcgatgac ccatggttcg    660 aaaagtggcg tggcgcattt tgttgcaaaa acgaatatg actgcatgga ttacatccgc    720
aaactgttaa gctttatccc gcagaacaac cgcgaagaac caccagtcgt caaaacagcg    780
gatgatccgg atcgcttaga tcatggcttg atcgggatga tcccggaaaa cccactgcaa    840
```

```
acctatgata tgaagaatgt gattcatagc attgtggatg atcgtacgtt cttggaggtg      900
catgagaact ttgcgacgaa tatcattgtc ggtttcggcc ggttcaacgg ccgcgcggca      960
gggattgtgg cgaaccagcc agcgagtttg gccggcgcct tagatattga tgcctcgagt     1020
aaagcggcac gcttcatccg gttctgcgat gccttcaaca ttccagtgat caccttggta     1080 gatacccag gttatatgcc gggctcggat caggaacatg gcggtattat ccggcatggc     1140
agtaaattat tatttgcata ttgcgaagcg accatcccga aaattacgct ggtcattggc     1200
aaagcgtatg gtggtgcgta tattgcgatg gcgagtaaaa acctggggac ggacatcaac     1260
tacgcctggc ccaccgcgcg ttgcgcggtg ttaggcgcag aggctgcggt caaaattatg     1320
aacaggaaag atctggctgc cgcatcggat ccggaaggtt aaagaaaga actgattggc     1380 aactttgcgg agaaattcga taacccatat gtagcggcct cgcatggtac tgtggatgcg     1440
gtcattgatc cggcagaaac ccgtccgatg ctgattaaag ccttagaaat gttaagctcg     1500
aaacgtgaag gccgtatatc gcgaaaacat gggaacatta acctctaa                  1548

<210> SEQ ID NO 39
<211> LENGTH: 1431
<212> TYPE: DNA
<213> ORGANISM: Cenarchaeum symbiosum

<400> SEQUENCE: 39
atgatccgca cctgccgcgc cttaggcttg ggtagcgtgg cagtctattc ggatgaagat       60
tacaacgccc tgcatgttaa gaaagcatcg gaatcctatc atattggcgg tgccgcgcca      120
gctgagtcgt atttaaacca gcagcgcatc attgaagccg ccttatcgtc gggcgccgac      180
gcgatacatc cagggtatgg ctttttaagc gaaaacggcg aatttgcggc cctgtgcgag      240
aaaaaccgca ttaactttat cggcccctcg gccaagagca tgaacctgtg cggcgataaa      300
atggaatgca aagcggcaat gttaaaagcg gacgtgccga cggtaccggg cagtccaggc      360
cttgtgggct ccgcggatga agccgcgggc attgcctcca aaattggcta ccccgtactg      420
ttaaaaagcg ttttttggcgg tggcggccgt ggcatccgtc tggctgagga tgaaggcggt      480
ttacgcggcg ggtacgactc tgcgacagca gagagcattg ccgctgtcgg caaaagcgcg      540
attctggtgg agaaattctt aaaacgcacc cgtcacattg agtatcagat ggcccgtgat      600
aaacatggga acgcagttca tattttcgag cgcgaatgca gcattcagcg acgaaaccag      660
aaattaatcg aacagacccc gagccccgtc atggatgaag acaccccgtaa acgcattggc      720 gacctggtgg ttaaagcagc ggaagcggtt gattacacca acctggggac ggcagaattt      780
cttcgtgccg actcgggcga attttacttc attgaaatca acgcccgcct gcaagtggaa      840
catccgatta cggaactggt tagcggtctg gatctcgtta aactgcaaat tgatattgca      900
aacggcgaac cgctgccgtt caaacagaat gatctgcgca tgaacggcta tgcgattgaa      960
tgccgcatta acgcagagga cacgttttttg gattttgccc caagcgttgg tccagttcca     1020
gatgttaaac tgccttcggg tccaggcgtg cggtgcgata cttatctgta tcccgggtgc     1080
actgttagcc cattctacga ctctctgatg gcaaaactgt gcacctgggg tgccactttc     1140
gaagaatccc gcttacgcat gctgggcgcg ttaggcgatt tttatgtgga gggggtggaa     1200
acttcgatcc cgttatataa aacgattatg gcatcggatg aatataagaa cggcgaatta     1260
tcgacggatt ttttatcgcg ctataatatc attgatcgcc tggataagga tatcaagaaa     1320
gaacgcgcgg caaacggcga agctgccgca gcggcggcga ttatgcatag cgaatttctc     1380
```
agcagtcgcg ccggcggtaa cagtgggacc gcatggaaag ggggcgcctg a    1431

<210> SEQ ID NO 40
<211> LENGTH: 510
<212> TYPE: DNA
<213> ORGANISM: Cenarchaeum symbiosum

<400> SEQUENCE: 40
atgaaatatg aaattgagga tgccggctcg ttcgaaggcc gcatggccgc aaacccgggg    60
aacggggagt atactctgga aattaacggg aaggaagtgc ggttaaaagt cattagcatg    120
ggcccgcgtg gtatggaatt tctgctggat caaaaatatc atagcgcacg atatctggaa    180
cgcagtactt cgggcataga tatgattatc gatgggacgc cggttcgcgc aggcatgcac    240
gcagacctag ataaaattgt ttataagaat agcggcggcg gtggggcgg cggcccgggc    300
atagcgctgc ggagtcagat tcctggcaaa gttgtctccc ttgaagtctc ggaaggtgat    360
gaaattaaaa aaggcgatcc ggtggccgtt ttggaatcca tgaaaatgca ggtggcggtt    420
aaagcccata aggatggcac ggtcaagtcg gttagtatta agaaggcgg cagtgttgca    480
aaaaacgatg ttatcgcgga aattgaataa    510

<210> SEQ ID NO 41
<211> LENGTH: 1551
<212> TYPE: DNA
<213> ORGANISM: Halobacterium sp.

<400> SEQUENCE: 41
atgaccatgg aggaacgcat tgaagatttg cgcgaacaga ccgaacgcgc actgctgggc    60
ggcggagaag ctcgcattga agtcaacat gaaaaggta aattaacggc tcgcgaacgc    120
attgattatt ttctggatga tggcacgttt aacgaattgg accagttacg cacgcatcgc    180
agtacgaact tgatatgga tgagacgaaa ctgccaggcg atggcgtggt gaccggctat    240
ggcgatgtga acgccgtac gacgtttgtt tttgcccatg atttaccgt gtttggtggt    300
tcgctggggg aagttttgc ggaaaaggtt acgaaggtta tggaccgcgc gatggaagtg    360
ggcgcgccag tggttggtct gaacgatagc gcgggcgcac gcattcagga aggcgtggat    420
gcgttaggcg gttttgcgga aatttttacc cgcaacgaaa aagcctcggg cgtggtgcca    480
cagattagcg cgattatggg tccgtgtgcg ggcggggccg tgtatagccc ggcgattacg    540
gactttaccg tgatggttaa agatacgtcg catatgttta ttaccggtcc ggatgtgatt    600
gaaacggtta ccggcgaaca ggtgggcttt gaagaactgg gcggcgcgac cacccatgcc    660
gccgagagcg gtgtggcaca cttttgcctgc gattcggaag aagcggcctt agataacatt    720
aaacgcttac tgagctacct gccacagaac aacgtggaag atccgcctcg tgtgaaccca    780
tatgatgatc cagaacgccg cgatgatgcc ctggagacca ttgtgccgga tgaacctcgt    840
aaaccatatg atatgaccga tgtggtggat tcggtggtgg atgaacagag cttctttgaa    900
gttcaggcgg attatgcgaa aaacattgtg gtgggttttg cgcggctgga tggccgtagc    960
gtgggcattg tggcgaacca gccacgcgtt aacgccggca ccctggatat tgatgcctcc    1020
gaaaaaggct cgcgttttgt tcgtttttgt gatagcttta cgtgccgat ttaacgctg    1080
gttgatgttc caggttttttt accgggcacc gatcaagaac atggcggcat tattcgtcat    1140
ggcgcgaaac tgttatatgc gttttcggaa gcgtcggtc cattaatgac ggtgattacg    1200
cgtaaagcct atggcggcgc ctatgatgtt atggcgtcga acatattgg cggcgatgtg    1260
aactatgcgt ggccgaccgc cgaaattgcc gttatgggtc cgaaaggcgc ggttaacgtg    1320

```
ctgtattccg acgagctgga ggcggccgat gataccgcgg cgcgtcgcca agaactgatt   1380
gatgaatatc gcgaagaatt tgccaaccct tatacgccg ccgatcgcgg ctatctggat   1440
gccgtgattg aaccgaccga aacccggccg cgtctgattg atgatctgga tatgttggcg   1500
tcgaaacgcg aagaaacgcc ggataaaaag catggcaaca ttccgctctg a             1551

<210> SEQ ID NO 42
<211> LENGTH: 1776
<212> TYPE: DNA
<213> ORGANISM: Halobacterium sp.

<400> SEQUENCE: 42
atgatcatga aggtacggat tggcgtgggg gcgacggatg cggaagccag tgcggtggcg    60
gcagcactgg cggcacatgt gagtgatgat gtcgcggttt acttaggcga tgccgatgaa   120
ccggcagcag tgcatgaacc agaaccaccc gccgatgatt cggccgatgc cgatgatctg   180
ggtccgaccg aacgcgaaga agttctgcgc gaagaaattg cggatattct ggatggcggc   240
ccagaaaaat ataagcagcg cttaccagaa caggataagt tatttgtgcg cgatcgcctg   300
gccctgtggt ttggcgatga tgatgatggc gatgatgacc tgctgtttga agatggcaga   360
tttgcgcact tgatggctg cacccaaac tcgccagacg tggatgaagc agatgatggc     420
acacgtgtgc cggccgatgg tctgattacg ggcgcggcgg actttgatgg ccgtgatctg   480
cattttatgg ccaacgattt taccgttaag gcgggtagca tggccgaacg cggcgtggaa   540
aaatttctgc gcatgcagca gcgcgcgctg aaaaccggca agccagttttt gtatttaatg   600 gatagtagcg gtggtcgcat tgatcagcag agcggttttt ttgcgaaccg cgagggcatt   660
ggcaagtatt attttaatca tagtcgtctg agtggccgcg tgccacagat ttgcgttta    720 tatgccccat gtattgccgg tgcagcgtat acgccggttt ttgcggattt tacgattatg   780
gtggaaggta tgagtgcgat ggccattgcc tcgccacgta tggttgaaat ggttaccggc   840
gaacagattg aaatgcagga tctgggcggc ccgcaggttc atgccgaaca gagtggctcg   900
gccgatttag tggcccgcga tgaagatcat gcccgcgaat tagtggcgga tctggttcag   960
tatctgccag ataactcgga tgaaaagccg ccatcccagc cggcgaaacc gcctgcgaaa  1020
ccgccaaaag gcattgatgg cttaattccg gaagcaccga accgcgccta tgatatgcat  1080
gatctgattg gccgcgttgt ggaccaggat agtttctttg aattacgtcc agaatatggg  1140
gccgaaattt taacgggtta tgcgcgcatt gatggccgta cggtgggcat tgtggcgaac  1200
cagccagccc agcgtgccgg cgccattttt ccggatgccg ccgaaaaagc gcggaatttt  1260
gtgtggaaaa gtgatgccta taacattccg ttgttatatc tgtgtgatac gccaggcttt  1320
atgccgggta gcagtgtgga aaaggatgcc attttagaaa agggcaaaaa atgattgat    1380 gccacctcgg aagccaccgt gccgaaacag agtgtggttg ttcgtaaagc ctatggcgcc  1440
ggcatttatg cgatgagtgg tccagcctat gatccagaaa gtaccattgc actgcctagt  1500
ggcgaaattg gtattatggg tccagaggcc gcgattaacg ccgtgtatgc gaacaaactg  1560
gatgccattg atgatccaga gaacgcaag cagcgcgaac aggaactgcg cgaagcgtat  1620
cgcgaagata ttgatgccca tcgtatgccc agtgaaacgg tgattgatga aattgttccg  1680
ccaagtgagc tgcgtacaga gctgagcaac cgttttcgt tttatgaaga tgttgaaaag  1740
gatcgcccga gcaaaaagca tggcaccatt ctttga                             1776

<210> SEQ ID NO 43
```

<211> LENGTH: 1833
<212> TYPE: DNA
<213> ORGANISM: Halobacterium sp.

<400> SEQUENCE: 43

```
atgtttgaaa aagtactggt cgccaaccgc ggcgaaattg cggttcgagt tatgcgtgcg      60
tgtgatgatc tgggtgtgga tacggtggct gtttattcgg acgccgatgc gcatgccgga     120
catgttcgtt atgccgatga agcgtataac gtgggtccgg cgcgcgcggc ggatagttac     180
ctggatcatg atgccattat tgatgcggcc acgcgtgccg gtgccgatgc cattcatcca     240
ggctatggct ttctggccga aaacgccgaa tttgcgggca aggtggaaga taccgatggc     300
gtgacgtggg tgggcccgag tgcggatagc atgcgccagc tgggcgaaaa aacctcggcc     360
cgtaaaacga tgcgtgaagc cgatgttcca attgtgccag gaccaccga tccagttgaa      420
agtgtggccg atattcatga atttggcgag gagcatggct atccaattgc tattaaagcc     480
gaaggcggag gggcggccg tgcatgaaa attgttcgct cggccgatga agccgaggat       540
caattagaaa gcgcggaacg agaaggggaa gcgtattttg ataacgcgaa cgtgtactta     600
gaacgctatt tggaaaaccc acgccatatt gaagtgcaga ttctcgcgga tcatcatggt     660
aacgtgcgtc atctgggcga acgtgattgt agcttacagc gccgccatca gaaggtgatt     720
gaggagggcc cgtcgccagc gctgacggat gaacttcgcg aagaaattgg tacggcggcc     780
cgtcgaggag ccgatgccgc gggctattat aacgcaggca cctttgaatt tctggtggag     840
gaggataccg aacgtgaacc aggggatctg ctgggtccgg aaacggaatt ttattttctg     900
gaggttaaca cccgtatcca ggtggaacat accgtgacgg aagcgctgac gggcgtggat     960
atcgttaaat ggcagctgaa aattgcaagt gatgatgaac tgacctttga acaggatgat    1020
gttgcattag atggccatgc cgtggaatat cgcattaacg cggaaaacgc ggccgatgat    1080
tttgcgccag ccacgggcgg cgaattagaa acctatgatc cgccgggcgg cattggcgtt    1140
cgtgtggatg atggcctgcg tcagggcgat gacctggtga ccgattatga tagcatggtg    1200
gcgaaactga ttgttcatgg ctcggatcgc gaagaatgtt tagcgcgtag tcgtcgcgcg    1260
ctggccgaat atgatattga aggcattccg acgattattc cgtttcaccg tttaatgtta    1320
accgatgatg cgtttgtggg tggcacgcat acgacgaaat acctggatcg cgatattgaa    1380
gaaagccgta ttagtgatgc ccaggcgaa tgggggtacga cgacggccag tgaaagtagt    1440
gccgacgaaa acgttgttga acgtgacttt acggttgagg tgaacggcaa acgttttgaa    1500
gtgaacttag aagaacgtgg tgcggcgcag tttgctgccc cagaggcgga taccggtggt    1560
ggtggtccgc cggaaccagc gggtggagca gatgatggtg aaacggtggt tgaaggtgat    1620
ggcgaaacgg tgacggcgga aatgcagggt acgattttag atgttgccgt tagtgaaggc    1680
gacgcggtgg atgcaggaga tgtttttagtc gttttagagg cgatgaagat ggaaaacgat    1740
gtggttgcga tcatgggggg cacggtgacg caggtggccg tgtcggaaga tgattcggtg    1800
gatatggatg atgtttttagt tgtgattgac tga                                1833
```

<210> SEQ ID NO 44
<211> LENGTH: 3129
<212> TYPE: DNA
<213> ORGANISM: Halobacterium sp.

<400> SEQUENCE: 44

```
atgaccgaag attcgcgtac gatattactg attggttcgg gcccaattca gattggccag      60
gcagcggaat ttgattatag cggcgcgcag gcttgtcgcg cgctgcaaga agaaggcgcg     120
```

```
cgtgtcgttc tggttaacag taaccctgcg accattatga ccgatccaga aatggccgat      180
gcggtgtata ttgaaccaat tgaaccagat gccattgccg aagtgattga acaggaagat      240
ccagatggcg tgattgccgg tttaggcggc cagaccggct aaacgtgac ggcagcgtta       300 gccgaacagg gcgtgctgga tgagcatgat gtggatgtta tgggtacgcc gttggatacc      360
atttatgcga ccgaagatcg cgatttattt cgccagcgca tggcggatct gggccagccg      420
gttccggcca gcacgaccat tgcgctgggc gatgatgaaa cggcaacgga tattgatgaa      480
ggtgcgttac gggaacgcgt ggatgatgcg gtggaagcgg tgggcggttt accggttatt      540
gcgcgtacga cgtatacgtt aggcggctcg ggcagtgggg tggtgcatga ttttgaagcg      600
ctggttgatc gtgttcgcac gggcttacgt ctgagccgta acgccgaagt tttagtgacg      660
gaaagtatta ccggttgggt ggagttagaa tatgaagtta tgcgtgatgc cggcgatagt      720
tgcattattg tgtgcaacat ggaaaacatt gatccgatgg gcattcatac cggcgaaagt      780
acggtggtga cgccatcgca gattattccg gatgatggcc atcaggaaat gcgcaacgcc      840
gccgtggcgg tgattcgcga attgggcatt cagggcggct gcaacattca gtttgcgtgg      900
cgcgatgatg gcacgccagg cggcgaatat cgtgtggtgg aagtgaaccc gcgcgtgagc      960
cgtagtagcg cgttagcgag caaagcgacc ggctatccaa ttgcgcgtgt gaccgcgaaa     1020
gtggcgctgg gcaaacgcct gcatgaaatt gataacgaaa ttaccggcca gaccacggcg     1080
gcctttgaac cggccattga ttatgttgtt acgaaggttc cacgttggcc taacgataaa     1140
tttccagaag ttgattttga attaagcacg gcgatgaaaa gtacgggtga agcgatggcc     1200
attggtcgca cctttgaaga atcgttatta aaagcgttac gcagttcgga atatgacccg     1260
tcggtggatt gggcgaccgt gtcggatgat gagctggccg ccgattatct gcaacgcccg     1320
agtccagatc gtccatatgc cgtgtttgaa gcgtttgaac gtggttttac agtgggcgat     1380
gttaacgatc atacgggctt tcgtgaatgg tacttacagc gttttcagaa tgtggcagcg     1440
gccagtgcgg cagcaagtga aggtgatgtt gcgacgccgg cagcgctggg ttatacgaat     1500
agtgcggtgg cggcgttagc gagcgacggt ggagatgttg ccgtggatga tgttgcggcg     1560
actgccccag aacgtacgtt taaacaggtg gatacctgtg cgggcgaatt tgcggccagc     1620
acgccgtatt attatagcgc gcgcagccag ggaagcacgg gatcggatgt tcgtgccgat     1680
cgtgatgccc attcggttgt gattgtgggt ggcggcccaa ttcgcattgg tcagggcgtt     1740
gaatttgatt attgtacggt tcatgccgtt cgcgcgctgc gcgaagcggg cattgatgcc     1800
catgttgtta caacaacccc ggaaacggtt agcacggatt atgataccag tgatggttta     1860 tttttttgaac cgattacggc ggaagaagtg gcggatgtgg ttgaagcgac gaacgccgat     1920
ggcgttatgg ttcagtttgg cggccagacc tcggttgatg ttggcgcgcc actgcgaggcc     1980 gaattagaac gccgcggcct ggattgtgaa attatgggta cggatgttga tgcgatggac     2040
ctggcggaag atcgcgatcg ctttaatcgt ttactggatg aacgcgatat ttcgcagcca     2100
gatggtggtt cagcgacctc cgttgcgggc gcgttagaac tggccgccga agtgggatac     2160
ccggttttgg tccgcccgtc gtatgttctg ggaggtcgcg cgatggaaat tgttcatgat     2220
gatgatgaac tgcgccgcta tgtggaagaa gccgtgcgtg tgtcgccaga aaaaccggtc     2280
ctggtggatg aatttctggc cgatgccgtg aactggatgt tgatgccgt gtcggatggc     2340 gaagatgttt tagttggcgg cgttatgaa catattgaat cggcggggt gcatagtggt     2400 gatagcgcgt gcgttatccc gcctcggggt ctgggcgatg atattctggc gcgtgtccgt     2460
```

```
gaagtgacca ccgaaattgc gcgtgcgtta gatacggttg gattattaaa cgtgcaactg    2520
gccgtgcagg atggcgaggt ttatgtgctg gaggcgaacc cgcgtagtag ccgcaccgtc    2580
ccgtttgtga gcaaagcgac cggcgtgccg attgcgaaac tggcggcgaa agttatggcc    2640
ggcgaaagct tagccgatct ggatgcatcg aaggcgtac cagaacagta ttcggtgaag     2700
gaagttgttt tgccgtttga tcgtctcccg ggtagcgacc cgcgcctggg cccggaaatg    2760
aaaagtacgg gcgaagttat gggcaccgcc tcggacccgg gtatggccta ttggaaagcc    2820
caggttgcgg cgagtaacgc accagtacca ggtagcacgg cggtggtgga tctcttagtg    2880
gaaggtctcg gcgaacgttt tgaagtggtt acggtgaagg atgttccggc ggcgattcga    2940
cgcggcgaag tggaatttct ggtgtcggat gatcgcgatg cgttaaccgc ggctgtggaa    3000
gccgaaattc cgtatgtgag tacggttgcg gcagcggaag cgatgcgaga aggtattgcg    3060
gcggccgatg gggcacgaga agcaatgccg gtggccgatc gtccggtgaa tgatgaaacg    3120
tggggatga                                                            3129

<210> SEQ ID NO 45
<211> LENGTH: 1437
<212> TYPE: DNA
<213> ORGANISM: Halobacterium sp.

<400> SEQUENCE: 45
atggcccgcg agtttacgct tcccgatgtg ggagaaggcg tggcggaagg cgagctggtt      60
cgttggctgg tggatgaagg cgataccgtg accgaagacc agccggtggc ggaagtggag     120
acggataagg cacaggtgga agttccagcg ccggtggatg gtacggtgca ggagctgcat     180
tgggcggagg gcgatgttgt tccggtgggc gatctgtttg ttacgtttga tgtcgatggc     240
gaagcgagcg ccaccgcgga tgatggtgat gagagtggtc atgaagccgc gagcgcgacc     300
agtgaagcca gtggtcgtac gtttgcgccg ccgagtgtcc gtacgctggc ccgtgaatta     360
ggcgtggatc tggatagtgt ggaaggtagt ggtccgagcg gtcgtattac cgatggcgat     420
gttcgtgccg ccgcggaagg tggtgaagat accacggaac cggccaccga agccacgagt     480
gcgacggagc gtgtggatga agatgatacc gcggcgagtg caggcagtca agaaccggcg     540
ggccgtgaaa aaacgcttgc ggcaccagcg acccgtggtg tggcccgaga attaggcgtg     600
gatattaacg atgttccggc ggtggagcag cgtgatggtg aagcgtttgt gaccgcggaa     660
gcggtgcagg cgtatgcaga aggtggtcag gcagcacagg gtgaagcggg tggtgcagcc     720
acccgtgaat ttgtggccgg cggtgaaacc accgaaccat atcgtggcat cgccgcacc     780 attggcgaac agatggccga aagcaaatat acggcgcctc atgtgaccca tcatgatacc     840
gccgtgattg attcgctggt tgaaacgcga agcaaattaa aggcgcgcgc cgaagccgaa     900
gatgtttaaa taacgtatat gccgtttgtt atgaaagcgg tggtggcggc gctgaaagaa     960
tttccagttt tgaacagtga actgcgcgaa gatgatgaag aaattgcgct gaaacaggac    1020
tataacattg gcgttgcggt ggcgaccgat gccggtttaa tggttccggt ggtggaacat    1080
gtggatcaga aaagcatgct cgaaattagt acggaaatga acgatctggt ggaacaggcc    1140
cgcgaacgca gcattgcgcc agcggatatg atggcggaa cttttacgat tacgaacttt     1200
ggcgcgattg gcggcgaata tgcgaccccg attattaact atccagaaac ggcgatttta    1260
ggtttaggcg cgattgatga acgcccggtg gccgaagatg gcgatgttcg tgcggcccag    1320
acgttaccgt tgagcttaag cattgatcat cgcgtgattg atggcgcgga agccgcgcag    1380
tttacgaacc gcgttatgga atacttaaca gatccagagc ttcttcttct ggaataa       1437
```

<210> SEQ ID NO 46
<211> LENGTH: 1170
<212> TYPE: DNA
<213> ORGANISM: Methylcoccus capsulatus

<400> SEQUENCE: 46

| | | | | | |
|---|---|---|---|---|---|
| atggcaaggc | ccttaatcca | gctggctctg | gacagtttgg | atcgggatcg | tacgttagag | 60 |
| ttagcgcgcg | tgacggcccc | ttacgtggat | attttgaaa | ttggcacgcc | atgtattaag | 120 |
| tataacggca | ttgagattgt | gcgcgaatta | aaacgccgtc | atccggaccg | tttagtgctg | 180 |
| gtggatttaa | aaaccatgga | cgcgggcgag | tatgaagcgg | ccccgttcta | cgcggcgggc | 240 |
| gctgatattt | gcaccgtttt | aggtgtttcg | ggtccggcca | ccattgcggg | tgtggtcaag | 300 |
| gccgcgcagg | cccataatgc | ggaggtgcag | gttgacctga | ttaacgttcc | ggataaagct | 360 |
| gcgtgcgccc | gcgaagccgc | gcgtttaggc | gcgcagatta | ttggggttca | taccgggctg | 420 |
| gacgcgcagg | cgcaggggca | gacgccgttt | cggacttag | agagcattgc | gcgcctgaaa | 480 |
| ctgccggtga | aatttctgt | tgctggtggt | attaaccaga | caccgcgtc | tcgtgtggcg | 540 |
| aaagccggtg | cggatattgt | ggtggtgggg | ccgccatttt | atggcgcccc | atgtccagcg | 600 |
| accgccgcgc | gcacgatccg | cgaactgctg | gagggtgctc | accataaatt | tattgttagt | 660 |
| aaaattggcg | gcgttcttgc | ggcgactgat | aaaagctatg | aagcccggct | gaccgggtta | 720 |
| ttagagcggg | cgcgccggat | cttgtggcg | ggcgcgggtc | ggagtggcct | ggtgggccgc | 780 |
| ttctttgcga | tgcgtctgat | gcatggcggc | taccaggctt | acatcgttgg | cgaaattgtt | 840 |
| acgccaagca | ttcggcaagg | cgacctcctg | attgttatca | gtgggtcggg | cgagaccgag | 900 |
| accatgattg | cttatgcgaa | aaaggcgaaa | gagcagggtg | cgagcattgc | cctgattacc | 960 |
| acccgcgata | aaagtacgat | tgggatatg | gcagatgttg | tttttcgtat | tggcactcca | 1020 |
| gaacagtatg | gcaaagttgt | ggggatgccg | atgggcacca | cctttgaact | gagtaccctg | 1080 |
| gttctgttag | aggcgacgat | cagtcatatt | attcacacca | aaaaaattcc | agaagaacag | 1140 |
| atgcgtaccc | gccatgcgaa | tctggagtaa | | | | 1170 |

<210> SEQ ID NO 47
<211> LENGTH: 648
<212> TYPE: DNA
<213> ORGANISM: Methylcoccus capsulatus

<400> SEQUENCE: 47

| | | | | | |
|---|---|---|---|---|---|
| atggcaaggc | ccttgatcca | gttagcgctg | gatacgctgg | atattccgca | gaccctgaaa | 60 |
| ttagcaagct | taaccgcccc | atacgtggac | attttgaga | ttggcacccc | aagcattaaa | 120 |
| cataacggca | ttgcgctggt | taaagaattt | aagaagcgct | ttccaaacaa | actgttactg | 180 |
| gtggatttaa | agaccatgga | tgcggggag | tatgaggcga | ccccattttt | tgcggcgggc | 240 |
| gcggatatta | ccaccgtgtt | aggcgtggca | ggactggcga | ccattaaagg | cgtgattaac | 300 |
| gcggcgaaca | acataacgc | ggaagtgcag | gtggatctga | ttaacgtgcc | agataaagcg | 360 |
| gcgtgcgcgc | gggaaagtgc | gaaagcgggc | gcgcagattg | tggcattca | taccggctta | 420 |
| gatgcgcagg | cggcgggcca | gaccccattt | gcggatttac | aggcgattgc | gaaattaggc | 480 |
| ttaccagtgc | gcattagtgt | ggcggcggc | attaaagcga | gtaccgcgca | acaggtggtg | 540 |
| aagaccgggg | cgaacattat | tgtggtggga | gcggcgattt | atggcgcggc | gagtccagcg | 600 |
| gacgcggccc | gcgagattta | tgagcaggtg | gtggcggcta | gtgcgtaa | | 648 |

<210> SEQ ID NO 48
<211> LENGTH: 534
<212> TYPE: DNA
<213> ORGANISM: Methylcoccus capsulatus

<400> SEQUENCE: 48

| | |
|---|---|
| atgcaccaga agctgattat agataagatt agtggcattt tagcggcgac cgacgcgggc | 60 |
| tacgacgcaa agctgactgc gatgttagat caggcgagtc gcattttgt ggccggtgcg | 120 |
| ggccgttcgg gtctggtggc gaaattttt gcgatgcgct taatgcatgg cggctacgat | 180 |
| gtgtttgtgg tgggcgagat tgtgaccccca agcattcgca aggcgattt gctgattgtt | 240 |
| attagtggca gtggggagac cgagaccatg ttagcgttta ccaagaaggc gaaagaacag | 300 |
| ggcgcgagta ttgcgttaat tagtacccgc gatagcagta gtttaggcga tttagcggat | 360 |
| agtgtgtttc gcattggcag tcccgaatta tttggaaagg tggtgggcat gccaatgggc | 420 |
| accgtgtttg aattaagtac cttattattt ttagaagcga ccatttcaca tattattcat | 480 |
| gaaaagggca ttccagagga ggagatgagg actcggcatg cgaacctgga gtaa | 534 |

<210> SEQ ID NO 49
<211> LENGTH: 1221
<212> TYPE: DNA
<213> ORGANISM: Mycobacterium gastri

<400> SEQUENCE: 49

| | |
|---|---|
| atgaaattac aagttgcgat tgatctgctg agtaccgagg cggcgttaga actggcgggc | 60 |
| aaagtcgcgg aatatgttga tattattgag ctgggcaccc cactgattga agcggaaggc | 120 |
| ctgagcgtta ttaccgcggt taaaaaagct catccggata aaattgtttt tgcggatatg | 180 |
| aaaaccatgg atgcgggcga attagaggcg atattgcct ttaaagcggg cgctgatctg | 240 |
| gttacggttt taggcagcgc ggatgatagt accattgccg gggcggttaa agcggcgcag | 300 |
| gctcataaca aaggcgttgt tgttgatctg attggcattg aagataaagc gacccgggca | 360 |
| caggaggtcc gcgcgctggg ggcgaaattt gttgaaatgc atgctgggct ggatgaacag | 420 |
| gcgaaaccag gctttgatct gaacgggctg ttagcggcgg cgaaaaagc tcgtgtcccg | 480 |
| tttagtgtgg cggaggcgt gaaggtcgcc accattccag cagttcagaa agcgggtgca | 540 |
| gaggttgcgg ttgcgggagg tgcgatttat ggggcagcgg atccggcggc ggcggcaaaa | 600 |
| gagctgcgtg cggcaattgc gatgacgcaa gcggcagagg cggatggtgc ggtgaaagtt | 660 |
| gttggagatg atattaccaa caacctcagt cttgtccgtg atgaagttgc cgataccgcc | 720 |
| gccaaggttg atccggaaca ggtggctgtt ttagctcgcc aaaattgttca gcccggacgt | 780 |
| gtctttgtgg ccggcgcggg cgcagtggt ttagttctgc gcatggcggc gatgcgtctg | 840 |
| atgcattttg gcttaaccgt gcatgttgcc ggcgatacca ccaccccggc aatttctgcg | 900 |
| ggcgacctgc tgctggtggc tagtggcagc ggcaccacca gtgggtggt taaaagtgcg | 960 |
| gaaacggcga aaaagcggg tgcacgtatt gcggcgttta ccaccaatcc ggactcaccg | 1020 |
| ctggcgggc tggcggatgc ggtggtgatt attccagcgg cccagaaaac cgaccatggc | 1080 |
| agccatatca gccgtcagta tgcgggatcc ctctttgaac aggtgctgtt tgttgttacc | 1140 |
| gaggcggtgt ttcagagcct gtgggaccat accgaagttg aagcggagga gttatggacg | 1200 |
| cgccatgcga acttagaatg a | 1221 |

<210> SEQ ID NO 50
<211> LENGTH: 406

```
<212> TYPE: PRT
<213> ORGANISM: Mycobacterium gastri

<400> SEQUENCE: 50

Met Lys Leu Gln Val Ala Ile Asp Leu Leu Ser Thr Glu Ala Ala Leu
1               5                   10                  15

Glu Leu Ala Gly Lys Val Ala Glu Tyr Val Asp Ile Ile Glu Leu Gly
                20                  25                  30

Thr Pro Leu Ile Glu Ala Glu Gly Leu Ser Val Ile Thr Ala Val Lys
            35                  40                  45

Lys Ala His Pro Asp Lys Ile Val Phe Ala Asp Met Lys Thr Met Asp
        50                  55                  60

Ala Gly Glu Leu Glu Ala Asp Ile Ala Phe Lys Ala Gly Ala Asp Leu
65                  70                  75                  80

Val Thr Val Leu Gly Ser Ala Asp Asp Ser Thr Ile Ala Gly Ala Val
                85                  90                  95

Lys Ala Ala Gln Ala His Asn Lys Gly Val Val Asp Leu Ile Gly
                100                 105                 110

Ile Glu Asp Lys Ala Thr Arg Ala Gln Glu Val Arg Ala Leu Gly Ala
            115                 120                 125

Lys Phe Val Glu Met His Ala Gly Leu Asp Glu Gln Ala Lys Pro Gly
        130                 135                 140

Phe Asp Leu Asn Gly Leu Leu Ala Ala Gly Glu Lys Ala Arg Val Pro
145                 150                 155                 160

Phe Ser Val Ala Gly Gly Val Lys Val Ala Thr Ile Pro Ala Val Gln
                165                 170                 175

Lys Ala Gly Ala Glu Val Ala Val Gly Gly Ala Ile Tyr Gly Ala
                180                 185                 190

Ala Asp Pro Ala Ala Ala Lys Glu Leu Arg Ala Ala Ile Ala Met
            195                 200                 205

Thr Gln Ala Ala Glu Ala Asp Gly Ala Val Lys Val Val Gly Asp Asp
        210                 215                 220

Ile Thr Asn Asn Leu Ser Leu Val Arg Asp Glu Val Ala Asp Thr Ala
225                 230                 235                 240

Ala Lys Val Asp Pro Glu Gln Val Ala Val Leu Ala Arg Gln Ile Val
                245                 250                 255

Gln Pro Gly Arg Val Phe Val Ala Gly Ala Gly Arg Ser Gly Leu Val
                260                 265                 270

Leu Arg Met Ala Ala Met Arg Leu Met His Phe Gly Leu Thr Val His
            275                 280                 285

Val Ala Gly Asp Thr Thr Pro Ala Ile Ser Ala Gly Asp Leu Leu
290                 295                 300

Leu Val Ala Ser Gly Ser Gly Thr Thr Ser Gly Val Val Lys Ser Ala
305                 310                 315                 320

Glu Thr Ala Lys Lys Ala Gly Ala Arg Ile Ala Ala Phe Thr Asn
                325                 330                 335

Pro Asp Ser Pro Leu Ala Gly Leu Ala Asp Ala Val Ile Ile Pro
            340                 345                 350

Ala Ala Gln Lys Thr Asp His Gly Ser His Ile Ser Arg Gln Tyr Ala
        355                 360                 365

Gly Ser Leu Phe Glu Gln Val Leu Phe Val Thr Glu Ala Val Phe
            370                 375                 380

Gln Ser Leu Trp Asp His Thr Glu Val Glu Ala Glu Glu Leu Trp Thr
385                 390                 395                 400
```

Arg His Ala Asn Leu Glu
            405

<210> SEQ ID NO 51
<211> LENGTH: 1020
<212> TYPE: DNA
<213> ORGANISM: Synechococcus elongatus

<400> SEQUENCE: 51

| atgaccattc gagttgcgat caatggcttt ggccgtattg ccggaatttt ctctccgttgc | 60 |
| tggtttggac ggcagaacac cgatcttgag gttgtggcca ttaacaacac ctcggatgca | 120 |
| cggacggctg ctcacctgct ggagtacgac tctgttctcg gccggttcaa cgccgacatc | 180 |
| agctacgacg aaaattcgat caccgtcaac ggcaagacga tgaaaatcgt ctgcgatcgc | 240 |
| aaccccctca acctgccttg aaagagtgg gatatcgatc tcgtcattga atctacaggt | 300 |
| gtgttcgtca ccgctgaagg cgcatccaag cacatccaag ccggggccaa gaaagttctg | 360 |
| atcacggctc ctggtaaagg cgaaggtgtc ggcacctacg tcatcggtgt caacgattcg | 420 |
| gaataccgcc acgaagactt cgcagtcatc agcaatgcaa gctgcaccac caactgctta | 480 |
| gcaccggtcg ccaaagttct gcatgacaac tttggcatca tcaaaggcac gatgaccacc | 540 |
| acccacagct acacgctgga ccagcgcatc ttggacgcca gccaccgtga tctacgtcgg | 600 |
| gctcgggctg ccgccgttaa catcgttccc accacgaccg cgctgctaa agccgttgct | 660 |
| ttggtgatcc ccgagctgaa aggcaaacta acgggattg cgctgcgcgt tcctacgcca | 720 |
| aacgtgtctg tcgttgactt ggtggttcaa gtcgagaaac cgacgatcac tgagcaggtc | 780 |
| aatgaagtcc tgcaaaaagc ttctcaaacg acgatgaagg gcatcatcaa gtactcggat | 840 |
| ctgcccttgg tatcttccga cttccgggt actgacgagt cttcgatcgt tgactccagc | 900 |
| ctgaccttgg taatggatgg cgatctcgtc aaagtaattg cttggtacga caacgagtgg | 960 |
| ggctacagcc aacagttgt cgacttggct gaactggccg ctcgcaaatg gccgcctaa | 1020 |

<210> SEQ ID NO 52
<211> LENGTH: 1038
<212> TYPE: DNA
<213> ORGANISM: Synechococcus elongatus

<400> SEQUENCE: 52

| atggaaaaga cgatcggtct cgagattatt gaagttgtcg agcaggcagc gatcgcctcg | 60 |
| gcccgcctga tgggcaaagg cgaaaagaat gaagccgatc gcgtcgcagt agaagcgatg | 120 |
| cgggtgcgga tgaaccaagt ggaaatgctg gccgcatcg tcatcggtga aggcgagcgc | 180 |
| gacgaagctc cgatgctcta tatcggtgaa gaagtgggca tctaccgcga tgcagacaag | 240 |
| cgggctggcg taccggctgg caagctggtg gaaatcgaca tcgccgttga ccctgcgaa | 300 |
| ggcaccaacc tctgcgccta cggtcagccc ggctcgatgg cagttttggc catctccgag | 360 |
| aaaggcggcc tgtttgcagc tcccgacttc tacatgaaga aactggctgc accccccagct | 420 |
| gccaaaggca agtagacat caataagtcc gcgaccgaaa acctgaaaat tctctcggaa | 480 |
| tgtctcgatc gcgccatcga tgaattgtg gtcgtgtca tggatcgtcc ccgccacaaa | 540 |
| gagctaatcc aagagatccg ccaagcgggt gcccgcgtcc gtctgatcag cgatggtgac | 600 |
| gtttcggccg cgatctcctg cggttttgct ggcaccaaca cccacgccct gatgggcatc | 660 |
| ggtgcagctc ccgagggtgt gatttcggca gcagcaatgc gttgcctcgg cggtcacttc | 720 |
| caaggccagc tgatctacga cccagaagtg gtcaaaaccg gcctgatcgg tgaaagccgt | 780 |

```
gagagcaaca tcgctcgcct gcaagaaatg ggcatcaccg atcccgatcg cgtctacgac      840
gccaacgaac tggcttcggg tcaagaagtg ctgtttgcgg cttgcggtat caccccgggc      900
ttgctgatgg aaggcgtgcg cttcttcaaa ggcggcgctc gcacccagag cttggtgatc      960
tccagccagt cacggacggc tcgcttcgtt gacaccgttc acatgttcga cgatgtcaaa     1020
acggttagcc tccgctaa                                                  1038
```

<210> SEQ ID NO 53
<211> LENGTH: 1002
<212> TYPE: DNA
<213> ORGANISM: Synechococcus elongatus

<400> SEQUENCE: 53

```
atgtcgaagc cagatcgtgt tgttttgatc ggcgttgccg gtgactccgg ttgcggcaaa       60
tcaaccttcc taaatcgcct tgccgacttg tttggtacgg aattgatgac ggtcatctgc      120
ttggatgact atcacagtct cgatcgcaag ggccggaagg aagcaggcgt aacggctttg      180
gatccccgcg ccaacaactt tgacttgatg tatgaacagg tcaaggcgtt gaagaacggc      240
gaaacgatca tgaagccgat ctacaaccat gaaaccggct tgatcgatcc gcccgaaaaa      300
atcgaaccca atcgcatcat tgtgatcgag ggtctgcatc cgctttacga cgagcgcgtg      360
cgtgaactgc tcgatttcag cgtttacctc gacatcgatg acgaagtcaa aatcgcttgg      420
aagatccaac gcgatatggc agaacgcggc cactcctacg aagatgtcct cgcctcgatc      480
gaagcgcgcc gccctgactt caaggcctac attgagcccc agcgtggcca tgcggacatc      540
gtcatccgcg tcatgccgac ccagctaatc cccaatgaca ccgagcgcaa ggtgctgcgg      600
gtgcagttga tccaacggga aggccgcgat ggttttgagc cggcttacct gttcgacgaa      660
ggttcgacca tccagtggac gccctgcggt cgtaagctga cctgctccta tccgggcatt      720
cgcttagcct acggccctga cacctactac ggtcacgaag tctcagtgct gaggtcgac       780 ggtcagttcg agaacctcga ggagatgatc tacgtcgagg gccacctcag caagaccgac      840
acgcagtact acggtgagtt gacccacctg ctgctgcaac acaaagatta cccgggttcg      900
aacaacggca cgggtctgtt ccaagtgctg accggcctga aaatgcgggc ggcctatgag      960 cgtttgaccct cccaagcagc acccgtcgcc gcaagcgtat aa                       1002
```

<210> SEQ ID NO 54
<211> LENGTH: 858
<212> TYPE: DNA
<213> ORGANISM: Escherichia coli

<400> SEQUENCE: 54

```
atgaaagctg acaacccttt tgatctttta cttcctgctg caatggccaa agtggccgag       60
gaggcgggtg tctataaagc aacgaaacat ccgcttaaga cttttctatct ggcgattacc     120 gccggtgttt tcatctcaat cgcattcgtc ttctatatca cagcaaccac tggcacaggc      180
acaatgccct tcggcatggc aaaactggtt ggcggcattt gcttctctct ggggctgatt      240
ctttgtgttg tctgcggagc cgatctcttt acttccaccg tgttgattgt tgttgctaag      300
gcgagtgggc gcatcacctg gggtcagttg gcgaaaaact ggctaaatgt ctattttggc      360
aacctggtcg gcgcactgct gtttgtactt ttaatgtggc tttccggcga gtatatgacc      420
gcaaatggtc aatgggggact aaacgtccta caaaccgccg accacaaagt gcaccatact      480
tttattgagg ccgtctgtct tggtatcctg gcaaacctga tggtatgtct ggcagtatgg      540
```

| | |
|---|---|
| atgagttatt ctggccgcag cctgatggac aaagcgttca ttatggtgct gccggtcgcg | 600 |
| atgtttgttg ccagcggttt tgagcacagt atcgcaaaca tgtttatgat cccgatgggt | 660 |
| attgtaatcc gcgacttcgc atccccggaa ttttggaccg cagtcggttc tgcaccggaa | 720 |
| aattttctc acctgaccgt gatgaatttc atcactgata acctgattcc ggttacgatc | 780 |
| ggcaacatta tcggtggtgg tttgttggtt gggttgacat actgggtcat ttacctgcgt | 840 |
| gaaaacgacc accactaa | 858 |

<210> SEQ ID NO 55
<211> LENGTH: 849
<212> TYPE: DNA
<213> ORGANISM: Escherichia coli

<400> SEQUENCE: 55

| | |
|---|---|
| atgcgcaaca aactctcttt cgacttgcag ttgagcgcca gaaaagcggc aatcgctgaa | 60 |
| cggattgccg cccataaaat tgcccgcagt aaagtgtcgg tcttttaat ggcgatgtcc | 120 |
| gctggcgtgt ttatggcgat cggatttact ttttaccttt ccgttatcgc cgatgccccg | 180 |
| tcttcacagg cattaaccca tctggtgggc ggccttttgct ttacactcgg ctttattttg | 240 |
| ctggcggttt gcgcaccag cctgttcacc tcgtcggtaa tgacggtgat ggcaaaaagt | 300 |
| cggggcgtta ttagttggcg aacttggctg attaacgcac ttctggtggc ctgcggtaat | 360 |
| ctggcaggta ttgcctgttt cagtttgtta atctggtttt ccgggctggt gatgagtgaa | 420 |
| aacgcgatgt ggggagtcgc ggttttacac tgcgccgagg gcaaaatgca tcatacattt | 480 |
| actgaatctg tcagcctcgg cattatgtgc aatctgatgg tttgcctggc gctgtggatg | 540 |
| agttattgcg ggcgttcgtt atgcgacaaa atcgtcgcca tgattttgcc catcaccctg | 600 |
| tttgtcgcca gtggctttga gcactgtatc gccaatttgt ttgtgattcc gttcgccatt | 660 |
| gccattcgcc atttcgcccc tccccctttc tggcagctgg cgcacagtag cgcagacaat | 720 |
| tttccggcac tgacggtcag ccatttatt accgccaatc tgctcccggt gatgctgggt | 780 |
| aatattatcg gcggtgcggt gctggtgagt atgtgttatc gggctattta tttacgtcag | 840 |
| gaaccataa | 849 |

<210> SEQ ID NO 56
<211> LENGTH: 3461
<212> TYPE: DNA
<213> ORGANISM: Artificial Sequence
<220> FEATURE:
<223> OTHER INFORMATION: Synthetic DNA

<400> SEQUENCE: 56

| | |
|---|---|
| aaaaaaaatc cttagctttc gctaaggatg atttctggaa ttcgcggccg cttctagagc | 60 |
| ccacagctaa caccacgtcg tccctatctg ctgccctagg tctatgagtg gttgctggat | 120 |
| aactttacgg gcatgcataa ggctcgtatg atatattcag ggagaccaca acggtttccc | 180 |
| tctacaaata attttgttta actttgcccg cgctctcccc cagtgtgaga gtgttcacac | 240 |
| aggaaagtac tagatggcca ctgttctatg cgtgctatat cctgatccgg ttgatggtta | 300 |
| tccaccgcac tatgttcgtg ataccatccc ggtgatcacc cgatatgcag atggccaaac | 360 |
| agcccccact cccgcggggc cgccaggatt tcgtcccggt gaactggtgg gcagtgtttc | 420 |
| tggtgcgctg gacttcgcg gttaccttga agcccatggt cacactctca tcgtcacatc | 480 |
| ggataaagat ggtccggata tgagtttga agacggctg cctgatgccg atgttgtcat | 540 |
| cagccagccg ttttggcccg catatcttac ggctgaacgt atcgcgaggg cgccgaagtt | 600 |

```
acgtctggct ctgactgctg gtataggctc agaccacgtt gacctcgatg ccgcggcgcg     660
tgctcacatt acggtcgccg aagtgactgg aagtaacagt atttcagtgg ctgaacacgt     720
tgttatgaca acgctggcct tagtgcggaa ctatttacct agccacgcaa ttgcgcagca     780
aggtggttgg aacatcgccg actgtgtttc acgctcttat gacgtcgaag gaatgcattt     840
cggcacagta ggggcgggta ggattggatt ggctgttctg cgccggctta accgtttgg      900 tctgcatttg cattcacccc aaagacatcg cttggatgca gccatcgaac aagaactcgg     960
tcttacttac catgccgatc cagccagtct tgcggcggca gtagacattg ttaatttgca    1020
gattccgctg tatccttcca ctgaacacct ttttgatgct gcaatgattg cacgcatgaa    1080
aagaggtgcg tacctgatta atactgcccg tgcgaagtta gtggaccgcg atgccgtcgt    1140
cagggctgtc acaagcggac atctggctgg ttatggcggg gacgtctggt ttccccagcc    1200
tgctccggct gatcatccgt ggcgggcgat gccttttaat ggcatgacac ctcatattag    1260
cggtacttca ctttctgctc aggcgcgta cgcagcgggg acccttgaaa tcctccagtg     1320
ttggtttgat ggcagaccga tcaggaacga gtacctgata gtggatggag gaacattggc    1380
cggtacaggt gcccaatcat atcggctgaa gtaagccaca cgcgctctcc cccctccggt    1440
gtaatcgggg gagagcgcgt gtccgctgca gtccggcaaa aaagggcaag gtgtcaccac    1500
cctgcccttt ttcttttaaaa ccgaaaagat tacttcgcgt tatgcaggct tcctcgctca    1560
ctgactcgct gcgctcggtc gttcggctgc ggcgagcggt atcagctcac tcaaaggcgg    1620
taatacggtt atccacagaa tcaggggata acgcaggaaa gaacatgtga gcaaaaggcc    1680
agcaaaaggc caggaaccgt aaaaaggccg cgttgctggc gttttccac aggctccgcc     1740 ccctgacga gcatcacaaa aatcgacgct caagtcagag gtggcgaaac ccgacaggac     1800
tataaagata ccaggcgttt ccccctggaa gctccctcgt gcgctctcct gttccgaccc    1860
tgccgcttac cggatacctg tccgcctttc tcccttcggg aagcgtggcg ctttctcata    1920
gctcacgctg taggtatctc agttcggtgt aggtcgttcg ctccaagctg ggctgtgtgc    1980 acgaacccc cgttcagccc gaccgctgcg ccttatccgg taactatcgt cttgagtcca     2040
acccggtaag acacgactta tcgccactgg cagcagccac tggtaacagg attagcagag    2100
cgaggtatgt aggcggtgct acagagttct tgaagtggtg gcctaactac ggctacacta    2160
gaagaacagt atttggtatc tgcgctctgc tgaagccagt taccttcgga aaaagagttg    2220
gtagctcttg atccggcaaa caaaccaccg ctggtagcgg tggttttttt gtttgcaagc    2280
agcagattac gcgcagaaaa aaggatctca agaagatcc tttgatcttt tctacggggt      2340
ctgacgctca gtggaacgaa aactcacgtt aagggatttt ggtcatgaga ttatcaaaaa    2400
ggatcttcac ctagatcctt ttaaattaaa aatgaagttt taaatcaatc taagtatat     2460 atgagtaaac ttggtctgac agctcgaggc ttggattctc accaataaaa acgcccggc      2520 ggcaaccgag cgttctgaac aaatccagat ggagttctga ggtcattact ggatctatca    2580
acaggagtcc aagcgagctc gatatcaaat tacgccccgc cctgccactc atcgcagtac    2640
tgttgtaatt cattaagcat tctgccgaca tggaagccat cacaaacggc atgatgaacc    2700
tgaatcgcca gcggcatcag caccttgtcg ccttgcgtat aatatttgcc catggtgaaa    2760 acggggggcga agaagttgtc catattggcc acgtttaaat caaaactggt gaaactcacc    2820
cagggattgg ctgagacgaa aaacatattc tcaataaacc ctttagggaa ataggccagg    2880
ttttcaccgt aacacgccac atcttgcgaa tatatgtgta gaaactgccg gaaatcgtcg    2940
```

| | |
|---|---:|
| tggtattcac tccagagcga tgaaaacgtt tcagtttgct catggaaaac ggtgtaacaa | 3000 |
| gggtgaacac tatcccatat caccagctca ccgtctttca ttgccatacg aaattccgga | 3060 |
| tgagcattca tcaggcgggc aagaatgtga ataaaggccg ataaaacttt gtgcttattt | 3120 |
| ttctttacgg tctttaaaaa ggccgtaata tccagctgaa cggtctggtt ataggtacat | 3180 |
| tgagcaactg actgaaatgc ctcaaaatgt tctttacgat gccattggga tatatcaacg | 3240 |
| gtggtatatc cagtgatttt tttctccatt ttagcttcct tagctcctga aaatctcgat | 3300 |
| aactcaaaaa atacgcccgg tagtgatctt atttcattat ggtgaaagtt ggaacctctt | 3360 |
| acgtgcccga tcaactcgag tgccacttga cgtctaagaa accattatta tcatgacatt | 3420 |
| aacctataaa aataggcgta tcacgaggca gaatttcaga t | 3461 |

<210> SEQ ID NO 57
<211> LENGTH: 3395
<212> TYPE: DNA
<213> ORGANISM: Artificial Sequence
<220> FEATURE:
<223> OTHER INFORMATION: Synthetic DNA

<400> SEQUENCE: 57

| | |
|---|---:|
| aaaaaaaatc cttagctttc gctaaggatg atttctggaa ttcgcggccg cttctagagc | 60 |
| ccacagctaa caccacgtcg tccctatctg ctgccctagg tctatgagtg gttgctggat | 120 |
| aactttacgg gcatgcataa ggctcgtatg atatattcag ggagaccaca acggtttccc | 180 |
| tctacaaata attttgttta actttgcccg cgctctcccc cagtgtgaga gtgttcacac | 240 |
| aggaaagtac tagatgaaaa ttgtactggt gctctatgat gcaggaaaac acgccgcaga | 300 |
| cgaggaaaag ctgtatggct gcactgagaa caagctagga atcgccaatt ggctgaagga | 360 |
| tcagggccat gaattaatca ctacctccga taaagaaggt gaaacctcag agttagataa | 420 |
| gcacattccc gatgccgata taatcattac gacgcctttt cacccagctt acattacaaa | 480 |
| agagcgtctg gataaagcga aaaacctcaa atcggttgta gtcgccggcg tcggttccga | 540 |
| ccacattgac ctggattata ttaatcagac tggtaagaag atcagcgtcc tggaagtcac | 600 |
| cggctctaat gtggtatctg ttgctgagca tgttgtaatg actatgctgg ttttagtgcg | 660 |
| caattttgtg cccgcacacg agcagatcat aaaccatgac tgggaagtag cagcaatagc | 720 |
| taaagatgcg tatgatattg aaggcaaaac tatcgctacg atcggcgcgg gccggatcgg | 780 |
| ttaccgggtt ctggagcggc tgctgccgtt caatcctaaa gagctcctat actatgatta | 840 |
| tcaggcactg cccaaggaag cagaggaaaa agttggtgcg cggagagtgg aaaacattga | 900 |
| agaacttgtg gctcaggccg acattgtaac ggtaaatgct ccacttcacg caggcaccaa | 960 |
| aggcctatc aataaagagt tgctttcaaa gtttaagaaa ggtgcctggt tggtaaatac | 1020 |
| ggcccgtgga gcaatttgcg ttgcggagga tgtcgccgcc gctctggaat cgggacagct | 1080 |
| ccggggatac ggtggggatg tttggtttcc ccagccggcg ccaaaggatc acccgtggcg | 1140 |
| tgatatgcga aacaaatatg cgcagggaa cgccatgaca ccgcattact ccgggacgac | 1200 |
| cttagatgca caaactcgat acgctgaagg taccaagaac atcctggaaa gtttctttac | 1260 |
| gggcaagttt gattatcgcc tcaggatat tattctgctt aatggagaat atgtaacaaa | 1320 |
| agcttacggc aaacatgaca aaagtaagc cacacgcgct ctcccccctc cggtgtaatc | 1380 |
| gggggagagc gcgtgtccgc tgcagtccgg caaaaaggg caaggtgtca ccaccctgcc | 1440 |
| cttttctctt aaaaccgaaa agattacttc gcgttatgca ggcttcctcg ctcactgact | 1500 |
| cgctgcgctc ggtcgttcgg ctgcggcgag cggtatcagc tcactcaaag gcggtaatac | 1560 |

```
ggttatccac agaatcaggg gataacgcag gaaagaacat gtgagcaaaa ggccagcaaa      1620
aggccaggaa ccgtaaaaag gccgcgttgc tggcgttttt ccacaggctc cgccccctg       1680 acgagcatca caaaatcga cgctcaagtc agaggtggcg aaacccgaca ggactataaa       1740
gataccaggc gtttccccct ggaagctccc tcgtgcgctc tcctgttccg accctgccgc      1800
ttaccggata cctgtccgcc tttctccctt cgggaagcgt ggcgctttct catagctcac      1860
gctgtaggta tctcagttcg gtgtaggtcg ttcgctccaa gctgggctgt gtgcacgaac      1920
cccccgttca gcccgaccgc tgcgccttat ccggtaacta tcgtcttgag tccaacccgg      1980
taagacacga cttatcgcca ctggcagcag ccactggtaa caggattagc agagcgaggt      2040
atgtaggcgg tgctacagag ttcttgaagt ggtggcctaa ctacggctac actagaagaa      2100
cagtatttgg tatctgcgct ctgctgaagc cagttacctt cggaaaaaga gttggtagct      2160
cttgatccgg caaacaaacc accgctggta gcggtggttt ttttgtttgc aagcagcaga      2220
ttacgcgcag aaaaaaagga tctcaagaag atcctttgat cttttctacg ggtctgacg       2280 ctcagtggaa cgaaaactca cgttaaggga ttttggtcat gagattatca aaaaggatct      2340
tcacctagat ccttttaaat taaaatgaa gttttaaatc aatctaaagt atatatgagt       2400
aaacttggtc tgacagctcg aggcttggat tctcaccaat aaaaaacgcc cggcggcaac      2460
cgagcgttct gaacaaatcc agatggagtt ctgaggtcat tactggatct atcaacagga      2520
gtccaagcga gctcgatatc aaattacgcc ccgccctgcc actcatcgca gtactgttgt      2580
aattcattaa gcattctgcc gacatggaag ccatcacaaa cggcatgatg aacctgaatc      2640
gccagcggca tcagcacctt gtcgccttgc gtataatatt tgcccatggt gaaaacgggg      2700
gcgaagaagt tgtccatatt ggccacgttt aaatcaaaac tggtgaaact cacccaggga      2760
ttggctgaga cgaaaaacat attctcaata aaccctttag ggaaataggc caggttttca      2820
ccgtaacacg ccacatcttg cgaatatatg tgtagaaact gccggaaatc gtcgtggtat      2880
tcactccaga gcgatgaaaa cgtttcagtt tgctcatgga aaacggtgta acaagggtga      2940
acactatccc atatcaccag ctcaccgtct tcattgcca tacgaaattc cggatgagca       3000
ttcatcaggc gggcaagaat gtgaataaag gccggataaa acttgtgctt attttttcttt     3060 acggtcttta aaaggccgt aatatccagc tgaacggtct ggttataggt acattgagca      3120
actgactgaa atgcctcaaa atgttcttta cgatgccatt gggatatatc aacggtggta      3180
tatccagtga ttttttctc cattttagct tccttagctc ctgaaaatct cgataactca      3240
aaaaatacgc ccggtagtga tcttatttca ttatggtgaa agttggaacc tcttacgtgc      3300
ccgatcaact cgagtgccac ttgacgtcta agaaaccatt attatcatga cattaaccta      3360
taaaaatagg cgtatcacga ggcagaattt cagat                                 3395
```

<210> SEQ ID NO 58
<211> LENGTH: 3556
<212> TYPE: DNA
<213> ORGANISM: Artificial Sequence
<220> FEATURE:
<223> OTHER INFORMATION: Synthetic DNA

<400> SEQUENCE: 58

```
aaaaaaaatc cttagctttc gctaaggatg atttctggaa ttcgcggccg cttctagagc        60
ccacagctaa caccacgtcg tccctatctg ctgccctagg tctatgagtg gttgctggat       120
aactttacgg gcatgcataa ggctcgtagg ctatattcag ggagaccaca acggtttccc       180
```

```
tctacaaata attttgttta acttttcaca caggaaacct actagatggc ccatattgtg    240
gtcctggggg ccgggctcgg cggcgccatt atggcatatg agctccgcga gcaggtgcgc    300
aaagaggata aagttaccgt tattaccaaa gatccgatgt atcattttgt gccaagcaac    360
ccatgggtgg cggtgggctg cgcgatcgc aaagaaatta ccgtggattt agcgccgacg    420
atggcgcgca aaacattga ttttattccg gtggcagcga aacgcctgca tccggcggag    480
aaccgtgttg aactggagaa cggccagagc gtttcgtacg atcagattgt tattgccacc    540
ggcccggagc tggcctttga tgaaattgaa ggcttcggcc agaaggcca cacgcaaagc    600
atttgccata ttgatcatgc cgaagaagcg cggctggcct tcgatcgctt ctgcgagaac    660
ccaggcccga ttttgattgg tgcggcgcag ggcgcctcgt gctttggccc ggcttacgag    720
tttaccttta ttttagacac cgcgctcgcg aaacgcaaaa ttcgcgataa agtgccgatg    780
acctttgtta ccagcgaacc atatgttggt catctgggtc tggatggtgt gggcgatacc    840
aaaggcctgt tggagggcaa cctgcgcgat aaacacatta agtggatgac cagcacccgt    900
attaagcgcg ttgagaaagg caaaatggtg gttgaagaag tgaccgaaga tggcacggtt    960
aaaccagaaa aggaactgcc atttggctat gcgatgatgc tgccagcgtt tcgcggcatt   1020
aaagcgctga tgggtattga aggtctggtt aatccgcgcg gctttgttat tgttgaccag   1080
caccagcaga acccgacctt taaaaacgtt tttgcggttg gcgtttgcgt ggcgattccg   1140
ccgattggtc cgacgccggt gccatgcggc gtgccgaaaa ccggctttat gattgagtcg   1200
atggttaccg ccaccgccca caacattggc cgtattgtgc gcggtttcga agccgatgaa   1260
gttggctcgt ggaacgccgt ttgtctggcc gactttggcg accagggcat tgccttcgtt   1320
gcgcagccgc agattccgcc gcgcaacgtg aactggagct cgcagggcaa gtgggtgcat   1380
tgggccaaag aaggttttga cgctatttt atgcacaaac tgcgccgcgg taccagtgaa   1440
accttttatg agaaagccgc gatgaaattc ctgggcattg ataaactgaa agccgttaag   1500
aaagggtaag ccacacgcgc tctccccct ccggtgtaat cggggagag cgcgtgtccg   1560
ctgcagtccg gcaaaaaagg gcaaggtgtc accaccctgc cctttttctt taaaaccgaa   1620
aagattactt cgcgttatgc aggcttcctc gctcactgac tcgctgcgct cggtcgttcg   1680
gctgcggcga gcggtatcag ctcactcaaa ggcggtaata cggttatcca cagaatcagg   1740
ggataacgca ggaaagaaca tgtgagcaaa aggccagcaa aaggccagga accgtaaaaa   1800
ggccgcgttg ctggcgtttt tccacaggct ccgcccccct gacgagcatc acaaaaatcg   1860
acgctcaagt cagaggtggc gaaacccgac aggactataa agataccagg cgtttccccc   1920
tggaagctcc ctcgtgcgct ctcctgttcc gaccctgccg cttaccggat acctgtccgc   1980
ctttctccct tcgggaagcg tggcgctttc tcatagctca cgctgtaggt atctcagttc   2040
ggtgtaggtc gttcgctcca agctgggctg tgtgcacgaa ccccccgttc agcccgaccg   2100
ctgcgcctta tccggtaact atcgtcttga gtccaacccg gtaagacacg acttatcgcc   2160
actggcagca gccactggta acaggattag cagagcgagg tatgtaggcg gtgctacaga   2220
gttcttgaag tggtggccta actacggcta cactagaaga acagtatttg gtatctgcgc   2280
tctgctgaag ccagttacct tcggaaaaag agttggtagc tcttgatccg gcaaacaaac   2340
caccgctggt agcggtggtt ttttgtttg caagcagcag attacgcgca gaaaaaaagg   2400
atctcaagaa gatcctttga tcttttctac ggggtctgac gctcagtgga acgaaaactc   2460
acgttaaggg attttggtca tgagattatc aaaaaggatc ttcacctaga tccttttaaa   2520
ttaaaaatga agttttaaat caatctaaag tatatatgag taaacttggt ctgacagctc   2580
```

```
gaggcttgga ttctcaccaa taaaaaacgc ccggcggcaa ccgagcgttc tgaacaaatc      2640
cagatggagt tctgaggtca ttactggatc tatcaacagg agtccaagcg agctcgatat      2700
caaattacgc cccgccctgc cactcatcgc agtactgttg taattcatta agcattctgc      2760
cgacatggaa gccatcacaa acggcatgat gaacctgaat cgccagcggc atcagcacct      2820
tgtcgccttg cgtataatat ttgcccatgg tgaaaacggg ggcgaagaag ttgtccatat      2880
tggccacgtt taaatcaaaa ctggtgaaac tcacccaggg attggctgag acgaaaaaca      2940
tattctcaat aaacccttta gggaaatagg ccaggttttc accgtaacac gccacatctt      3000
gcgaatatat gtgtagaaac tgccggaaat cgtcgtggta ttcactccag agcgatgaaa      3060
acgtttcagt ttgctcatgg aaaacggtgt aacaagggtg aacactatcc catatcacca      3120
gctcaccgtc tttcattgcc atacgaaatt ccggatgagc attcatcagg cgggcaagaa      3180
tgtgaataaa ggccggataa aacttgtgct tattttttctt tacggtcttt aaaaaggccg      3240
taatatccag ctgaacggtc tggttatagg tacattgagc aactgactga atgcctcaa      3300 aatgttcttt acgatgccat gggatatat caacggtggt atatccagtg attttttttct      3360 ccattttagc ttccttagct cctgaaaatc tcgataactc aaaaaatacg cccggtagtg      3420
atcttatttc attatggtga agttggaac ctcttacgtg cccgatcaac tcgagtgcca      3480
cttgacgtct aagaaaccat tattatcatg acattaacct ataaaaatag gcgtatcacg      3540
aggcagaatt tcagat                                                     3556

<210> SEQ ID NO 59
<211> LENGTH: 3555
<212> TYPE: DNA
<213> ORGANISM: Artificial Sequence
<220> FEATURE:
<223> OTHER INFORMATION: Synthetic DNA

<400> SEQUENCE: 59
aaaaaaaatc cttagctttc gctaaggatg atttctggaa ttcgcggccg cttctagagc       60
ccacagctaa caccacgtcg tccctatctg ctgccctagg tctatgagtg gttgctggat      120
aactttacgg gcatgcataa ggctcgtatg atatattcag ggagaccaca acggtttccc      180
tctacaaata atttttgttta acttttcaca caggaaagta ctagatggcc catattgtgg      240 tcctggggc cgggctcggc ggcgccatta tggcatatga gctccgcgag caggtgcgca      300
aagaggataa agttaccgtt attaccaaag atccgatgta tcattttgtg ccaagcaacc      360
catgggtggc ggtgggctgg cgcgatcgca aagaaattac cgtggattta gcgccgacga      420
tggcgcgcaa aaacattgat tttattccgg tggcagcgaa acgcctgcat ccggcggaga      480
accgtgttga actggagaac ggccagagcg tttcgtacga tcagattgtt attgccaccg      540
gcccggagct ggcctttgat gaaattgaag cttcggccc agaaggccac acgcaaagca      600
tttgccatat tgatcatgcc gaagaagcgc ggctggcctt cgatcgcttc tgcgagaacc      660
caggcccgat tttgattggt gcggcgcagg gcgcctcgtg ctttggcccg gcttacgagt      720
ttacctttat tttagacacc gcgctgcgca acgcaaaaat tcgcgataaa gtgccgatga      780
cctttgttac cagcgaacca tatgttggtc atctgggtct ggatggtgtg ggcgatacca      840
aaggcctgtt ggagggcaac ctgcgcgata acacattaa gtggatgacc agcacccgta      900
ttaagcgcgt tgaaaaggc aaaatggtgg ttgaagaagt gaccgaagat ggcacggtta      960
aaccagaaaa ggaactgcca tttggctatg cgatgatgct gccagcgttt cgcggcatta     1020
```

```
aagcgctgat gggtattgaa ggtctggtta atccgcgcgg ctttgttatt gttgaccagc    1080
accagcagaa cccgaccttt aaaaacgttt ttgcggttgg cgtttgcgtg gcgattccgc    1140
cgattggtcc gacgccggtg ccatgcggcg tgccgaaaac cggctttatg attgagtcga    1200
tggttaccgc caccgcccac aacattggcc gtattgtgcg cggtttcgaa gccgatgaag    1260
ttggctcgtg gaacgccgtt tgtctggccg actttggcga ccagggcatt gccttcgttg    1320
cgcagccgca gattccgccg cgcaacgtga actggagctc gcagggcaag tgggtgcatt    1380
gggccaaaga aggttttgaa cgctatttta tgcacaaact gcgccgcggt accagtgaaa    1440 cctttttatga gaaagccgcg atgaaattcc tgggcattga taaactgaaa gccgttaaga    1500
aagggtaagc cacacgcgct ctcccccctc cggtgtaatc gggggagagc gcgtgtccgc    1560
tgcagtccgg caaaaaggg caaggtgtca ccaccctgcc cttttctttt aaaaccgaaa    1620
agattacttc gcgttatgca ggcttcctcg ctcactgact cgctgcgctc ggtcgttcgg    1680
ctgcggcgag cggtatcagc tcactcaaag gcggtaatac ggttatccac agaatcaggg    1740
gataacgcag gaaagaacat gtgagcaaaa ggccagcaaa aggccaggaa ccgtaaaaag    1800
gccgcgttgc tggcgttttt ccacaggctc cgcccccctg acgagcatca caaaaatcga    1860
cgctcaagtc agaggtggcg aaacccgaca ggactataaa gataccaggc gtttccccct    1920
ggaagctccc tcgtgcgctc tcctgttccg accctgccgc ttaccggata cctgtccgcc    1980
tttctccctt cgggaagcgt ggcgctttct catagctcac gctgtaggta tctcagttcg    2040
gtgtaggtcg ttcgctccaa gctgggctgt gtgcacgaac cccccgttca gcccgaccgc    2100
tgcgccttat ccggtaacta tcgtcttgag tccaacccgg taagacacga cttatcgcca    2160
ctggcagcag ccactggtaa caggattagc agagcgaggt atgtaggcgg tgctacagag    2220
ttcttgaagt ggtggcctaa ctacggctac actagaagaa cagtatttgg tatctgcgct    2280
ctgctgaagc cagttacctt cggaaaaaga gttggtagct cttgatccgg caaacaaacc    2340
accgctggta gcgtggtttt ttttgtttgc aagcagcaga ttacgcgcag aaaaaaagga    2400
tctcaagaag atcctttgat cttttctacg gggtctgacg ctcagtggaa cgaaaactca    2460
cgttaaggga ttttggtcat gagattatca aaaaggatct tcacctagat ccttttaaat    2520
taaaaatgaa gttttaaatc aatctaaagt atatatgagt aaacttggtc tgacagctcg    2580
aggcttggat tctcaccaat aaaaaacgcc cggcggcaac cgagcgttct gaacaaatcc    2640
agatggagtt ctgaggtcat tactggatct atcaacagga gtccaagcga gctcgatatc    2700
aaattacgcc ccgccctgcc actcatcgca gtactgttgt aattcattaa gcattctgcc    2760
gacatggaag ccatcacaaa cggcatgatg aacctgaatc gccagcggca tcagcacctt    2820
gtcgccttgc gtataatatt tgcccatggt gaaaacgggg gcgaagaagt tgtccatatt    2880
ggccacgttt aaatcaaaac tggtgaaact cacccaggga ttggctgaga cgaaaaacat    2940
attctcaata aaccctttag ggaaataggc caggttttca ccgtaacacg ccacatcttg    3000
cgaatatatg tgtagaaact gccggaaatc gtcgtggtat tcactccaga gcgatgaaaa    3060
cgtttcagtt tgctcatgga aaacggtgta acaagggtga acactatccc atatcaccag    3120
ctcaccgtct tcattgccta tacgaaattc cggatgagca ttcatcaggc gggcaagaat    3180
gtgaataaag gccggataaa acttgtgctt attttttctt acggtctttaa aaaggccgt    3240 aatatccagc tgaacggtct ggttataggt acattgagca actgactgaa atgcctcaaa    3300 atgttctttta cgatgccatt gggatatatc aacggtggta tatccagtga ttttttttctc    3360 cattttagct tccttagctc ctgaaaatct cgataactca aaaaatacgc ccggtagtga    3420
```

```
tcttatttca ttatggtgaa agttggaacc tcttacgtgc ccgatcaact cgagtgccac    3480
ttgacgtcta agaaaccatt attatcatga cattaaccta taaaaatagg cgtatcacga    3540
ggcagaattt cagat                                                    3555
```

<210> SEQ ID NO 60
<211> LENGTH: 7740
<212> TYPE: DNA
<213> ORGANISM: Artificial Sequence
<220> FEATURE:
<223> OTHER INFORMATION: Synthetic DNA

<400> SEQUENCE: 60

```
aaaaaaaatc cttagctttc gctaaggatg atttctggaa ttcgcggccg cttctagagc      60
ccacagctaa caccacgtcg tccctatctg ctgccctagg tctatgagtg gttgctggat     120
aactttacgg gcatgcataa ggctcgtatg atatattcag ggagaccaca acggtttccc     180
tctacaaata attttgttta acttttcaca caggaaagta ctagatgatc gacactgcgc     240
cccttgcccc accacgggcg ccccgctcta atccgattcg ggatcgagtt gattgggaag     300
ctcagcgtgc tgctgcgctg gcagatcccg gtgccttcca tggcgcgatt gcccggacag     360
ttatccactg gtacgaccca caacaccatt gctggattcg cttcaacgag tctagtcagc     420
gttgggaagg gctggatgcc gctaccggtg cccctgtaac ggtagactat cccgccgatt     480
atcagccctg caacaggcg tttgatgata gtgaagcgcc gttttaccgc tggtttagtg      540
gtgggttgac aaatgcctgc tttaatgaag tagaccggca tgtcacgatg gctatggcg     600 acgaggtggc ctactacttt gaaggtgacc gctgggataa ctcgctcaac aatggtcgtg     660
gtggtccggt tgtccaggag acaatcacgc gacggcgtct gttggtggag gtggtgaagg     720
ctgcgcaggt gttgcgcgat ctgggcctga agaagggtga tcggattgct ctgaatatgc     780
cgaatattat gccgcagatt tattatacgg aagcggcaaa acgactgggt attctgtaca     840
cgccggtctt cggtggcttc tcggacaaga ctctttccga ccgtattcac aatgccggtg     900
cacgagtggt gattacctct gatggcgcgt atcgcaacgc gcaggtggtg ccctacaaag     960
aagcgtatac cgatcaggcg ctcgataagt atattccggt tgagactgcg caggcgattg    1020
ttgcgcagac cctggccacc ttgccctga ctgagtcgca gcgccagacg atcatcaccg      1080
aagtggaggc cgccctggca ggtgagatta cggttgagcg ttcggacgtg atgcgtgggg    1140
ttggttctgc cctcgcaaag ctccgcgatc ttgatgcaag cgtgcaggca aggtgcgca     1200 cagtactggc gcaggcgctg gtcgagtcgc cgccgcgggt tgaagctgtg gtggttgtgc    1260
gtcataccgg tcaggagatt ttgtggaacg aggggcgaga tcgctggagt cacgacttgc    1320
tggatgctgc gctggcgaag attctggcca atgcgcgtgc tgcaggcttt gatgtgcaca    1380
gtgagaatga tctgctcaat ctccccgatg accagcttat ccgtgcgctc tacgccagta    1440
ttccctgtga accggttgat gctgaatatc cgatgtttat catttacaca tcgggtagca    1500
ccggtaagcc caagggtgtg atccacgttc acggcggtta tgtcgccggt gtggtgcaca    1560
ccttgagggt cagttttgac gccgagccgg tgatacgat atatgtgatc gccgatccgg     1620
gctggatcac cggccagagc tatatgctca cagccacaat ggccggtaga ctgaccgggg    1680
tgattgccga gggatcaccg cttttcccct cagccgggcg ttatgccagc atcatcgagc    1740 gctatgggt gcagatcttt aaggcgggtg tgaccttcct caagacagtg atgtccaatc     1800
cgcagaatgt tgaagatgtg cgactctatg atatgcactc gctgagagtt gcaaccttct    1860
```

-continued

```
gcgccgagcc ggtaagtccg gcggtgcagc agtttggtat gcagatcatg accccgcagt    1920
atatcaattc gtactgggcg accgagcacg gtggaattgt ctggacgcat ttctacggta    1980
atcaggactt tccgcttcgt cccgatgccc atacctatcc cttgccctgg gtgatgggtg    2040
atgtctgggt ggccgaaact gatgagagcg ggacgacgcg ctatcgggtc gctgatttcg    2100
atgagaaggg cgagattgtg attaccgccc cgtatcccta cctgacccgc acactctggg    2160
gtgatgtgcc cggtttcgag gcgtacctgc gcggtgagat tccgctgcga gcctggaagg    2220
gtgatgccga gcgtttcgtc aagacctact ggcgacgtgg gccaaacggt gaatggggct    2280
atatccaggg tgattttgcc atcaagtacc ccgatggtag cttcacgctc cacggacgct    2340
ctgacgatgt gatcaatgtg tcgggccacc gtatgggcac cgaggagatt gagggtgcca    2400
ttttgcgtga ccgccagatc acgcccgact cgcctgtcgg taattgtatt gtggtcggtg    2460
cgccgcatcg tgagaagggt ctgaccccgg ttgccttcat tcaacctgcg cctggccgtc    2520
atctgaccgg tgcagacagg cgccgtctcg atgagctggt gcgcaccgag aaggggggcgg    2580 tcagtgtccc agaggattac atcgaggtca gtgccttttcc cgaaacccgc agcgggaagt    2640
atatgaggcg cttttttgcgc aatatgatgc tcgatgaacc actgggtgat acgacgacgt    2700
tgcgcaatcc tgaagtgctc gaagaaattg cagccaagat cgctgagtgg aaacgccgtc    2760
agcgtatggc cgaagaacag cagatcatcg aacgctatcg ctacttccgg atcgagtatc    2820
atccaccaac ggccagtgcg ggtaaactcg cggtagtgac ggtgacaaat ccgccggtga    2880
acgcactgaa tgagcgtgcg ttagatgagt tgaacacaat tgttgaccac ctggcccgtc    2940
gtcaggatgt tgccgcaatt gtcttcaccg gacagggcgc caggagtttt gtcgccggtg    3000
ctgatattcg ccagttgctc gaagaaattc atacggttga agaagcaatg gccctgccga    3060
ataacgccca tcttgctttc cgcaagattg agcgtatgaa taagccgtgt atcgcggcga    3120
tcaacggtgt ggcgctcggt ggtggtctgg aatttgccat ggcctgccat taccgggttg    3180
ccgatgtcta tgccgaattt ggtcagccag agattaatct gcgcttgcta cctggttatg    3240
gtggcacgca gcgcttgccg cgtctgttgt acaagcgcaa caacggcacc ggtctgctcc    3300
gagcgctgga gatgattctg gtgggcgta gcgtaccggc tgatgaggcg ctggagctgg    3360
gtctgatcga tgccattgct accggcgatc aggactcact gtcgctggca tgcgcgttag    3420
cccgtgccgc aatcggtgcc gatggtcagt tgatcgagtc ggctgcggtg acccaggctt    3480
tccgccatcg ccacgagcag cttgacgagt ggcgcaaacc agacccgcgc tttgccgatg    3540
acgaactgcg ctcgattatc gcccatccac gtatcgagcg gattatccgg caggcccata    3600
ccgttgggcg cgatgcggca gtgcaccggg cactggatgc aatccgctat ggcattatcc    3660
acggcttcga ggccggtctg gagcacgagg cgaagctctt tgccgaggca gtggttgacc    3720
cgaacggtgg caagcgtggt attcgcgagt tcctcgaccg ccagagtgcg ccgttgccaa    3780
cccgccgacc attgattaca cctgaacagg agcaactctt gcgcgatcag aaagaactgt    3840
tgccggttgg ttcaccctttc ttccccggtg ttgaccggat tccgaagtgg cagtacgcgc    3900
aggcggttat tcgtgatccg gacaccggtg cggcggctca cggcgatccc atcgtggctg    3960
aaaagcagat tattgtgccg gtggaacgcc ccgcgccaa tcaggcgctg atttatgttc    4020
tggcctcgga ggtgaacttc aacgatatct gggcgattac cggtattccg gtgtcacggt    4080
ttgatgagca cgaccgcgac tggcacgtta ccggttcagg tggcatcggc ctgatcgttg    4140
cgctgggtga agaagcgcga cgcgaaggcc ggctgaaggt gggtgatctg gtggcgatct    4200
actccgggca gtcggatctg ctctcaccgc tgatgggcct tgatccgatg gccgccgatt    4260
```

```
tcgtcatcca ggggaacgac acgccagatg gatcgcatca gcaatttatg ctggcccagg    4320
ccccgcagtg tctgcccatc ccaaccgata tgtctatcga ggcagccggc agctacatcc    4380
tcaatctcgg tacgatctat cgcgccctct ttacgacgtt gcaaatcaag gccggacgca    4440
ccatctttat cgagggtgcg gcgaccggca ccggtctgga cgcagcgcgc tcggcggccc    4500
ggaatggtct gcgcgtaatt ggaatggtca gttcgtcgtc acgtgcgtct acgctgctgg    4560
ctgcgggtgc ccacggtgcg attaaccgta aagacccgga ggttgccgat tgtttcacgc    4620
gcgtgcccga agatccatca gcctgggcag cctgggaagc cgccggtcag ccgttgctgg    4680
cgatgttccg ggcgcagaac gacgggcgac tggccgatta tgtggtctcg cacgcgggcg    4740
agacggcctt cccgcgcagt ttccagcttc tcggcgagcc acgcgatggt cacattccga    4800
cgctcacatt ctacggtgcc accagtggct accacttcac cttcctgggt aagccagggt    4860
cagcttcgcc gaccgagatg ctgcggcggg ccaatctccg cgccggtgag gcggtgttga    4920
tctactacgg ggttgggagc gatgacctgg tagataccgg cggtctggag gctatcgagg    4980
cggcgcggca aatgggagcg cggatcgtcg tcgttaccgt cagcgatgcg caacgcgagt    5040
ttgtcctctc gttgggcttc ggggctgccc tacgtggtgt cgtcagcctg gcggaactca    5100
aacgacgctt cggcgatgag tttgagtggc gcgcacgat gccgccgttg ccgaacgccc    5160
gccaggaccc gcagggtctg aaagaggctg tccgccgctt caacgatctg gtcttcaagc    5220
cgctaggaag cgcggtcggt gtcttcttgc ggagtgccga caatccgcgt ggctaccccg    5280
atctgatcat cgagcgggct gcccacgatg cactggcggt gagcgcgatg ctgatcaagc    5340
ccttcaccgg acggattgtc tacttcgagg acattggtgg gcggcgttac tccttcttcg    5400
caccgcaaat ctgggtgcgc cagcgccgca tctacatgcc gacggcacag atctttggta    5460
cgcacctctc aaatgcgtat gaaattctgc gtctgaatga tgagatcagc gccggtctgc    5520
tgacgattac cgagccggca gtggtgccgt gggatgaact acccgaagca catcaggcga    5580
tgtgggaaaa tcgccacacg gcggccactt atgtggtgaa tcatgcctta ccacgtctcg    5640
gcctaaagaa cagggacgag ctgtacgagg cgtggacggc cggcgagcgc taagccacac    5700
gcgctctccc ccctccggtg taatcggggg agagcgcgtg tccgctgcag tccggcaaaa    5760
aagggcaagg tgtcaccacc ctgccctttt tctttaaaac cgaaaagatt acttcgcgtt    5820
atgcaggctt cctcgctcac tgactcgctg cgctcggtcg ttcggctgcg gcgagcggta    5880
tcagctcact caaaggcggt aatacggtta tccacagaat caggggataa cgcaggaaag    5940
aacatgtgag caaaaggcca gcaaaaggcc aggaaccgta aaaaggccgc gttgctggcg    6000 ttttccaca ggctccgccc ccctgacgag catcacaaaa atcgacgctc aagtcagagg    6060
tggcgaaacc cgacaggact ataaagatac caggcgtttc ccctggaag ctccctcgtg    6120 cgctctcctg ttccgaccct gccgcttacc ggatacctgt ccgcctttct cccttcggga    6180
agcgtggcgc tttctcatag ctcacgctgt aggtatctca gttcggtgta ggtcgttcgc    6240
tccaagctgg gctgtgtgca cgaaccccc gttcagcccg accgctgcgc cttatccggt    6300
aactatcgtc ttgagtccaa cccggtaaga cacgacttat cgccactggc agcagccact    6360
ggtaacagga ttagcagagc gaggtatgta ggcggtgcta cagagttctt gaagtggtgg    6420
cctaactacg gctacactag aagaacagta tttggtatct gcgctctgct gaagccagtt    6480
accttcggaa aaagagttgg tagctcttga tccggcaaac aaaccaccgc tggtagcggt    6540 ggttttttg tttgcaagca gcagattacg cgcagaaaaa aaggatctca agaagatcct    6600
```

```
ttgatctttt ctacggggtc tgacgctcag tggaacgaaa actcacgtta agggattttg    6660
gtcatgagat tatcaaaaag gatcttcacc tagatccttt taaattaaaa atgaagtttt    6720
aaatcaatct aaagtatata tgagtaaact tggtctgaca gctcgaggct tggattctca    6780
ccaataaaaa acgcccggcg gcaaccgagc gttctgaaca atccagatg gagttctgag     6840 gtcattactg gatctatcaa caggagtcca agcgagctcg atatcaaatt acgccccgcc    6900
ctgccactca tcgcagtact gttgtaattc attaagcatt ctgccgacat ggaagccatc    6960
acaaacggca tgatgaacct gaatcgccag cggcatcagc accttgtcgc cttgcgtata    7020
atatttgccc atggtgaaaa cggggggcgaa gaagttgtcc atattggcca cgtttaaatc    7080
aaaactggtg aaactcaccc agggattggc tgagacgaaa acatattct caataaaccc     7140 tttaggaaaa taggccaggt tttcaccgta acacgccaca tcttgcgaat atatgtgtag    7200
aaactgccgg aaatcgtcgt ggtattcact ccagagcgat gaaaacgttt cagtttgctc    7260
atggaaaacg gtgtaacaag ggtgaacact atcccatatc accagctcac cgtctttcat    7320
tgccatacga aattccggat gagcattcat caggcgggca agaatgtgaa taaaggccgg    7380
ataaaacttg tgcttatttt tctttacggt ctttaaaaag gccgtaatat ccagctgaac    7440
ggtctggtta taggtacatt gagcaactga ctgaaatgcc tcaaaatgtt ctttacgatg    7500
ccattgggat atatcaacgg tggtatatcc agtgattttt ttctccattt tagcttcctt    7560
agctcctgaa aatctcgata actcaaaaaa tacgcccggt agtgatctta tttcattatg    7620
gtgaaagttg gaacctctta cgtgcccgat caactcgagt gccacttgac gtctaagaaa    7680
ccattattat catgacatta acctataaaa ataggcgtat cacgaggcag aatttcagat    7740
```

<210> SEQ ID NO 61
<211> LENGTH: 1959
<212> TYPE: DNA
<213> ORGANISM: Escherichia coli

<400> SEQUENCE: 61

```
atgtcgcaaa ttcacaaaca caccattcct gccaacatcg cagaccgttg cctgataaac      60
cctcagcagt acgaggcgat gtatcaacaa tctattaacg tacctgatac cttctggggc    120
gaacagggaa aaattcttga ctggatcaaa ccttaccaga aggtgaaaaa cacctccttt    180
gcccccggta atgtgtccat taaatggtac gaggacggca cgctgaatct ggcggcaaac    240
tgccttgacc gccatctgca agaaaacggc gatcgtaccg ccatcatctg ggaaggcgac    300
gacgccagcc agagcaaaca tatcagctat aaagagctgc accgcgacgt ctgccgcttc    360
gccaataccc tgctcgagct gggcattaaa aaaggtgatg tggtggcgat ttatatgccg    420
atggtgccgg aagccgcggt tgcgatgctg gcctgcgccc gcattggcgc ggtgcattcg    480 gtgatttttcg gcggcttctc gccggaagcc gttgccgggc gcattattga ttccaactca    540
cgactggtga tcacttccga cgaaggtgtg cgtgccgggc gctccattcc gctgaagaaa    600
aacgttgatg acgcgctgaa aaacccgaac gtcaccagcg tagagcatgt ggtggtactg    660
aagcgtactg gcggaaaat tgactggcag gaagggcgcg acctgtggtg gcacgacctg    720
gttgagcaag cgagcgatca gcaccaggcg gaggagatga acgccgaaga tccgctgttt    780
attctctaca cctccggttc taccggtaag ccaaaaggtg tgctgcatac taccggcggt    840
tatctggtgt acgcggcgct gacctttaaa tatgtctttg attatcatcc gggtgatatc    900
tactggtgca ccgccgatgt gggctgggtg accggacaca gttacttgct gtacggcccg    960
ctggcctgcg gtgcgaccac gctgatgttt gaaggcgtac ccaactggcc gacgcctgcc   1020
```

-continued

```
cgtatggcgc aggtggtgga caagcatcag gtcaatattc tctataccgc acccacggcg    1080
atccgcgcgc tgatggcgga aggcgataaa gcgatcgaag gcaccgaccg ttcgtcgctg    1140
cgcattctcg gttccgtggg cgagccaatt aacccggaag cgtgggagtg gtactggaaa    1200
aaaatcggca acgagaaatg tccggtggtc gatacctggt ggcagaccga aaccggcggt    1260
ttcatgatca ccccgctgcc tggcgctacc gagctgaaag ccggtagtgc aacacgtccg    1320
ttcttcggcg tgcaaccggc gctggtcgat aacgaaggta acccgctgga gggggccacc    1380
gaaggtagcc tggtaatcac cgacagttgg ccgggtcagg cgcgtacgct gtttggcgat    1440
cacgaacgtt ttgaacagac ctacttctcc accttcaaaa atatgtattt cagcggcgac    1500
ggcgcgcgtc gcgatgaaga tggctattac tggataaccg gcgtgtggga cgacgtgctg    1560
aacgtctccg gtcaccgtct ggggacggca gagattgagt cggcgctggt ggcgcatccg    1620
aagattgccg aagccgccgt agtaggtatt ccgcacaata ttaaaggtca ggcgatctac    1680
gcctacgtca cgcttaatca cggggaggaa ccgtcaccag aactgtacgc agaagtccgc    1740
aactgggtgc gtaaagagat tggcccgctg gcgacgccag acgtgctgca ctggaccgac    1800
tccctgccta aaacccgctc cggcaaaatt atgcgccgta ttctgcgcaa aattgcggcg    1860
ggcgatacca gcaacctggg cgatacctcg acgcttgccg atcctggcgt agtcgagaag    1920
ctgcttgagg agaagcaggc tatcgcgatg ccatcgtga                          1959
```

<210> SEQ ID NO 62
<211> LENGTH: 1461
<212> TYPE: DNA
<213> ORGANISM: Listeria monocytogenes

<400> SEQUENCE: 62

```
atgggccttg aggacaaaga cctgcggagc atccaagagg taaggaactt aatagagagc     60
gcgaacaaag cccaaaaaga gctcgcggcc atgagtcaac aacaaataga cactatagtc    120
aaagctatag cggacgcagg gtatgggcg agggagaaat tagccaaaat ggcccacgag    180
gagacagggt tcggcatatg gcaagataaa gtcataaaaa acgttttgc gtccaagcat    240 gtttacaatt acatcaaaga catgaaaacg atagggatgc tgaaagagga caacgagaag    300
aaagtcatgg aagtagccgt accgcttggg gtcgtagccg gcctgatacc atcgactaac    360
ccaacttcca cagtaatata caaaactctt atatctataa aagccggcaa ttcaatcgtc    420
ttctcgccgc acccgaacgc ccttaaagcc atactcgaga ctgtccgtat aatatcagag    480
gcggccgaga aagcgggatg tccgaaaggt gcgatcagtt gtatgacagt accgactatc    540
caaggcactg accaattgat gaaacataaa gacactgccg taatcctcgc cactggaggg    600
tcggccatgg tcaaagctgc gtatagctcg ggacaccgg ccataggcgt aggtccgggg    660
aatggtccgg ccttcatcga gcggtcagca acataccac gggccgtgaa acacatactc    720
gactccaaaa cttttgacaa cggcactata tgcgcctcgg aacaatcggt tgtagtagag    780
agggtgaata aagaggcggt tatagcggag ttccgtaaac aaggcgccca ttttctgagc    840
gacgccgagg cggtacaact cgggaaattt atcctgaggc cgaatgggag catgaatccg    900
gccatcgtcg ggaaaagtgt gcaacacatc gcgaacctcg cggggcttac tgtaccggcg    960
gatgcccgtg tcctcatcgc ggaggagact aaagtagggg cgaaaatccc atatagccgt   1020
gagaaactgg cgccgatcct agcgttttat actgccgaga catggcaaga ggcgtgcgag   1080
ctcagtatgg acatactcta tcacgagggc gcgggccaca cactgatcat ccattcggag   1140
```

| gacaaagaga tcatccggga gtttgccttg aaaaaaccgg tatccaggct cctggtaaat | 1200 |
| actccgggcg ctctcggtgg cataggtgcc actactaatc tcgtcccagc gctgactctc | 1260 |
| gggtgtggag ccgtaggcgg ctcaagcagc tcggacaata tcggcccaga gaatctcttt | 1320 |
| aacatacggc ggatcgcgac tggcgtactg gaactggagg acataaggaa agaggagaac | 1380 |
| caagccactt cggagctccc tgtagacgcc gatgccttga tccaatcact ggtcgagaaa | 1440 |
| gtactggccg agctgaagta a | 1461 |

<210> SEQ ID NO 63
<211> LENGTH: 2919
<212> TYPE: DNA
<213> ORGANISM: Artificial Sequence
<220> FEATURE:
<223> OTHER INFORMATION: Synthetic DNA

<400> SEQUENCE: 63

| aaaaaaaatc cttagctttc gctaaggatg atttctggaa ttcgcggccg cttctagagc | 60 |
| ccacagctaa caccacgtcg tccctatctg ctgccctagg tctatgagtg gttgctggat | 120 |
| aactttacgg gcatgcataa ggctcgtatg atatattcag ggagaccaca acggtttccc | 180 |
| tctacaaata atttttgttta acttttcaca caggaaagta ctagatggca aggcccttga | 240 |
| tccagttagc gctggatacg ctggatattc cgcagaccct gaaattagca agcttaaccg | 300 |
| ccccatacgt ggacattttt gagattggca ccccaagcat taaacataac ggcattgcgc | 360 |
| tggttaaaga atttaagaag cgcttttcca acaaactgtt actggtggat ttaaagacca | 420 |
| tggatgcggg ggagtatgag gcgacccat tttttgcggc gggcgcggat attaccaccg | 480 |
| tgttaggcgt ggcaggactg gcgaccatta aaggcgtgat taacgcggcg aacaaacata | 540 |
| acgcggaagt gcaggtggat ctgattaacg tgccagataa agcggcgtgc gcgcgggaaa | 600 |
| gtgcgaaagc gggcgcgcag attgtgggca ttcataccgg cttagatgcg caggcggcgg | 660 |
| gccagacccc atttgcggat ttacaggcga ttgcgaaatt aggcttacca gtgcgcatta | 720 |
| gtgtggcggg cggcattaaa gcgagtaccg cgcaacaggt ggtgaagacc ggggcgaaca | 780 |
| ttattgtggt gggagcggcg atttatgcgc ggcgagtcc agcggacgcg gcccgcgaga | 840 |
| tttatgagca ggtggtggcg gctagtgcgt aagccacacg cgctctcccc cctccggtgt | 900 |
| aatcggggga gagcgcgtgt ccgctgcagt ccggcaaaaa agggcaaggt gtcaccaccc | 960 |
| tgccctttt ctttaaaacc gaaaagatta cttcgcgtta tgcaggcttc ctcgctcact | 1020 |
| gactcgctgc gctcggtcgt tcggctgcgg cgagcggtat cagctcactc aaaggcggta | 1080 |
| atacggttat ccacagaatc aggggataac gcaggaaaga acatgtgagc aaaaggccag | 1140 |
| caaaaggcca ggaaccgtaa aaaggccgcg ttgctggcgt ttttccacag gctccgcccc | 1200 |
| cctgacgagc atcacaaaaa tcgacgctca agtcagaggt ggcgaaaccc gacaggacta | 1260 |
| taaagatacc aggcgtttcc ccctggaagc tccctcgtgc gctctcctgt tccgaccctg | 1320 |
| ccgcttaccg gatacctgtc cgcctttctc ccttcgggaa gcgtggcgct ttctcatagc | 1380 |
| tcacgctgta ggtatctcag ttcggtgtag gtcgttcgct ccaagctggg ctgtgtgcac | 1440 |
| gaaccccccg ttcagcccga ccgctgcgcc ttatccggta actatcgtct tgagtccaac | 1500 |
| ccggtaagac acgacttatc gccactggca gcagccactg gtaacaggat tagcagagcg | 1560 |
| aggtatgtag gcggtgctac agagttcttg aagtggtggc ctaactacgg ctacactaga | 1620 |
| agaacagtat ttggtatctg cgctctgctg aagccagtta ccttcggaaa aagagttggt | 1680 |
| agctcttgat ccggcaaaca aaccaccgct ggtagcggtg gtttttttgt ttgcaagcag | 1740 |

```
cagattacgc gcagaaaaaa aggatctcaa gaagatcctt tgatcttttc tacgggtct    1800 gacgctcagt ggaacgaaaa ctcacgttaa gggattttgg tcatgagatt atcaaaaagg   1860
atcttcacct agatcctttt aaattaaaaa tgaagtttta aatcaatcta agtatatat    1920 gagtaaactt ggtctgacag ctcgaggctt ggattctcac caataaaaaa cgcccggcgg   1980
caaccgagcg ttctgaacaa atccagatgg agttctgagg tcattactgg atctatcaac   2040
aggagtccaa gcgagctcga tatcaaatta cgccccgccc tgccactcat cgcagtactg   2100
ttgtaattca ttaagcattc tgccgacatg gaagccatca caaacggcat gatgaacctg   2160
aatcgccagc ggcatcagca ccttgtcgcc ttgcgtataa tatttgccca tggtgaaaac   2220
gggggcgaag aagttgtcca tattggccac gtttaaatca aaactggtga actcacccca   2280
gggattggct gagacgaaaa acatattctc aataaaccct ttagggaaat aggccaggtt   2340
ttcaccgtaa cacgccacat cttgcgaata tatgtgtaga aactgccgga atcgtcgtg   2400 gtattcactc cagagcgatg aaaacgtttc agtttgctca tggaaaacgg tgtaacaagg   2460
gtgaacacta tcccatatca ccagctcacc gtctttcatt gccatacgaa attccggatg   2520
agcattcatc aggcgggcaa gaatgtgaat aaaggccgga taaaacttgt gcttattttt   2580
ctttacggtc tttaaaaagg ccgtaatatc cagctgaacg gtctggttat aggtacattg   2640
agcaactgac tgaaatgcct caaaatgttc tttacgatgc cattgggata tatcaacggt   2700
ggtatatcca gtgattttt  tctccatttt agcttcctta gctcctgaaa atctcgataa   2760
ctcaaaaaat acgcccggta gtgatcttat ttcattatgg tgaaagttgg aacctcttac   2820
gtgcccgatc aactcgagtg ccacttgacg tctaagaaac cattattatc atgacattaa   2880
cctataaaaa taggcgtatc acgaggcaga atttcagat                          2919
```

<210> SEQ ID NO 64
<211> LENGTH: 2805
<212> TYPE: DNA
<213> ORGANISM: Artificial Sequence
<220> FEATURE:
<223> OTHER INFORMATION: Synthetic DNA

<400> SEQUENCE: 64

```
aaaaaaaatc cttagctttc gctaaggatg atttctggaa ttcgcggccg cttctagagc     60
ccacagctaa caccacgtcg tccctatctg ctgccctagg tctatgagtg gttgctggat    120
aactttacgg gcatgcataa ggctcgtatg atatattcag ggagaccaca acggtttccc    180
tctacaaata attttgttta acttttcaca caggaaagta ctagatgcac cagaagctga    240
ttatagataa gattagtggc attttagcgg cgaccgacgc gggctacgac gcaaagctga    300
ctgcgatgtt agatcaggcg agtcgcattt tgtggccgg tgcggccgt tcgggtctgg    360 tggcgaaatt ttttgcgatg cgcttaatgc atggcggcta cgatgtgttt gtggtgggcg    420
agattgtgac cccaagcatt cgcaaaggcg atttgctgat tgttattagt ggcagtgggg    480
agaccgagac catgttagcg tttaccaaga aggcgaaaga acagggcgcg agtattgcgt    540
taattagtac ccgcgatagc agtagtttag gcgatttagc ggatagtgtg tttcgcattg    600
gcagtcccga attatttgga aaggtggtgg gcatgccaat gggcaccgtg tttgaattaa    660
gtaccttatt attttttagaa gcgaccattt cacatattat tcatgaaaag gcattccag    720 aggaggagat gaggactcgg catgcgaacc tggagtaagc cacacgcgct ctccccctc    780 cggtgtaatc gggggagagc gcgtgtccgc tgcagtccgg caaaaaaggg caaggtgtca    840
```

```
ccaccctgcc cttttttcttt aaaaccgaaa agattacttc gcgttatgca ggcttcctcg      900
ctcactgact cgctgcgctc ggtcgttcgg ctgcggcgag cggtatcagc tcactcaaag      960
gcggtaatac ggttatccac agaatcaggg gataacgcag gaaagaacat gtgagcaaaa     1020
ggccagcaaa aggccaggaa ccgtaaaaag gccgcgttgc tggcgttttt ccacaggctc     1080
cgcccccctg acgagcatca caaaaatcga cgctcaagtc agaggtggcg aaacccgaca     1140
ggactataaa gataccaggc gtttccccct ggaagctccc tcgtgcgctc tcctgttccg     1200
accctgccgc ttaccggata cctgtccgcc tttctccctt cgggaagcgt ggcgctttct     1260
catagctcac gctgtaggta tctcagttcg gtgtaggtcg ttcgctccaa gctgggctgt     1320
gtgcacgaac cccccgttca gcccgaccgc tgcgccttat ccggtaacta tcgtcttgag     1380
tccaacccgg taagacacga cttatcgcca ctggcagcag ccactggtaa caggattagc     1440
agagcgaggt atgtaggcgg tgctacagag ttcttgaagt ggtggcctaa ctacggctac     1500
actagaagaa cagtatttgg tatctgcgct ctgctgaagc cagttacctt cggaaaaaga     1560
gttggtagct cttgatccgg caaacaaacc accgctggta gcggtggttt ttttgtttgc     1620
aagcagcaga ttacgcgcag aaaaaaagga tctcaagaag atcctttgat cttttctacg     1680
gggtctgacg ctcagtggaa cgaaaactca cgttaaggga ttttggtcat gagattatca     1740
aaaaggatct tcacctagat ccttttaaat taaaaatgaa gttttaaatc aatctaaagt     1800
atatatgagt aaacttggtc tgacagtcg aggcttggat tctcaccaat aaaaaacgcc     1860
cggcggcaac cgagcgttct gaacaaatcc agatggagtt ctgaggtcat tactggatct     1920
atcaacagga gtccaagcga gctcgatatc aaattacgcc ccgccctgcc actcatcgca     1980
gtactgttgt aattcattaa gcattctgcc gacatggaag ccatcacaaa cggcatgatg     2040
aacctgaatc gccagcggca tcagcacctt gtcgccttgc gtataatatt tgcccatggt     2100
gaaaacgggg gcgaagaagt tgtccatatt ggccacgttt aaatcaaaac tggtgaaact     2160
cacccaggga ttggctgaga cgaaaaacat attctcaata aaccctttag ggaaataggc     2220
caggttttca ccgtaacacg ccacatcttg cgaatatatg tgtagaaact gccggaaatc     2280
gtcgtggtat tcactccaga gcgatgaaaa cgtttcagtt tgctcatgga aacggtgta      2340
acaagggtga acactatccc atatcaccag ctcaccgtct ttcattgcca tacgaaattc     2400
cggatgagca ttcatcaggc gggcaagaat gtgaataaag gccggataaa acttgtgctt     2460
atttttcttt acggtcttta aaaaggccgt aatatccagc tgaacggtct ggttataggt     2520
acattgagca actgactgaa atgcctcaaa atgttcttta cgatgccatt gggatatatc     2580
aacggtggta tatccagtga tttttttctc cattttagct tccttagctc ctgaaaatct     2640
cgataactca aaaaatacgc ccggtagtga tcttatttca ttatggtgaa agttggaacc     2700
tcttacgtgc ccgatcaact cgagtgccac ttgacgtcta agaaaccatt attatcatga     2760
cattaaccta taaaaatagg cgtatcacga ggcagaattt cagat                    2805
```

<210> SEQ ID NO 65
<211> LENGTH: 7393
<212> TYPE: DNA
<213> ORGANISM: Artificial Sequence
<220> FEATURE:
<223> OTHER INFORMATION: Synthetic DNA

<400> SEQUENCE: 65

```
acacgcgctc tccccccgtca cgtacgtcgc agtacgtgct cttcgcggga tcgtacgtta       60
gagttagcgc gcgtgacggc cccttacgtg gatattttg aaaattggcac gccatgtatt      120
```

```
aagtataacg gcattgagat tgtgcgcgaa ttaaaacgcc gtcatccgga ccgtttagtg    180
ctggtggatt taaaaaccat ggacgcgggc gagtatgaag cggccccgtt ctacgcggcg    240
ggcgctgata tttgcaccgt tttaggtgtt tcgggtccgg ccaccattgc gggtgtggtc    300
aaggccgcgc aggcccataa tgcggagtg caggttgacc tgattaacgt tccggataaa    360
gctgcgtgcg cccgcgaagc cgcgcgttta ggcgcgcaga ttattggggt tcataccggg    420
ctggacgcgc aggcgcaggg gcagacgccg tttgcggact tagagagcat tgcgcgcctg    480
aaactgccgg tgagaatttc tgttgctggt ggtattaacc agaacaccgc gtctcgtgtg    540
gcgaaagccg gtgcggatat tgtggtggtg ggggccgcca tttatggcgc ccatgtcca    600 gcgaccgccg cgcgcacgat ccgcgaactg ctggagggtg ctcaccataa atttattgtt    660
agtaaaattg gcggcgttct tgcggcgact gataaaagct atgaagcccg gctgaccggg    720
ttattagagc gggcgcgccg gatctttgtg gcgggcgcgg gtcggagtgg cctggtgggc    780
cgcttctttg cgatgcgtct gatgcatggc ggctaccagg cttacatcgt tggcgaaatt    840
gttacgccaa gcattcggca aggcgacctc ctgattgtta tcagtgggtc gggcgagacc    900
gagaccatga ttgcttatgc gaaaaaggcg aaagagcagg gtgcgagcat tgccctgatt    960
accacccgcg ataaaagtac gattgggat atggcagatg ttgttttcg tattggcact    1020 ccagaacagt atggcaaagt tgtggggatg ccgatgggca ccacctttga actgagtacc    1080
ctggttctgt tagaggcgac gatcagtcat attattcaca ccaaaaaaat tccagaagaa    1140
cagatgcgta cccgccatgc gaatctggag taagcccaca gctaacacca cgtcgtccct    1200
atctgctgcc ctaggtctat gagtggttgc tggataactt tacgggcatg cataaggctc    1260
gtatgatata ttcagggaga ccacaacggt ttccctctac aaataatttt gtttaacttt    1320
aaagaggaga aatactagat gtcgcaaatt cacaaacaca ccattcctgc caacatcgca    1380
gaccgttgcc tgataaaccc tcagcagtac gaggcgatgt atcaacaatc tattaacgta    1440
cctgatacct tctgggcga acagggaaaa attcttgact ggatcaaacc ttaccagaag    1500
gtgaaaaaca cctcctttgc ccccggtaat gtgtccatta aatggtacga ggacggcacg    1560
ctgaatctgg cggcaaactg ccttgaccgc catctgcaag aaaacggcga tcgtaccgcc    1620
atcatctggg aaggcgacga cgccagccag agcaaacata tcagctataa agagctgcac    1680
cgcgacgtct gccgcttcgc caatacccctg ctcgagctgg cattaaaaa aggtgatgtg    1740 gtggcgattt atatgccgat ggtgccggaa gccgcggttg cgatgctggc ctgcgcccgc    1800 attggcgcg tgcattcggt gattttcggc ggcttctcgc cggaagccgt tgccgggcgc    1860
attattgatt ccaactcacg actggtgatc acttccgacg aaggtgtgcg tgccgggcgc    1920
tccattccgc tgaagaaaaa cgttgatgac gcgctgaaaa acccgaacgt caccagcgta    1980
gagcatgtgg tggtactgaa gcgtactggc gggaaaattg actggcagga agggcgcgac    2040
ctgtggtggc acgacctggt tgagcaagcg agcgatcagc caccaggcgga ggagatgaac    2100 gccgaagatc cgctgtttat tctctacacc tccggttcta ccggtaagcc aaaaggtgtg    2160
ctgcatacta ccggcggtta tctggtgtac gcggcgctga cctttaaata tgtctttgat    2220
tatcatccgg gtgatatcta ctggtgcacc gccgatgtgg gctgggtgac cggacacagt    2280
tacttgctgt acggcccgct ggcctgcggt gcgaccacgc tgatgtttga aggcgtaccc    2340
aactggccga cgcctgcccg tatggcgcag gtggtggaca agcatcaggt caatattctc    2400
tataccgcac ccacggcgat ccgcgcgctg atggcggaag gcgataaagc gatcgaaggc    2460
```

```
accgaccgtt cgtcgctgcg cattctcggt tccgtgggcg agccaattaa cccggaagcg    2520
tgggagtggt actggaaaaa aatcggcaac gagaaatgtc cggtggtcga tacctggtgg    2580
cagaccgaaa ccggcggttt catgatcacc ccgctgcctg gcgctaccga gctgaaagcc    2640
ggtagtgcaa cacgtccgtt cttcggcgtg caaccggcgc tggtcgataa cgaaggtaac    2700
ccgctggagg gggccaccga aggtagcctg gtaatcaccg acagttggcc gggtcaggcg    2760
cgtacgctgt ttggcgatca cgaacgtttt gaacagacct acttctccac cttcaaaaat    2820
atgtatttca gcggcgacgg cgcgcgtcgc gatgaagatg gctattactg gataaccggg    2880
cgtgtggacg acgtgctgaa cgtctccggt caccgtctgg ggacggcaga gattgagtcg    2940
gcgctggtgg cgcatccgaa gattgccgaa gccgccgtag taggtattcc gcacaatatt    3000
aaaggtcagg cgatctacgc ctacgtcacg cttaatcacg gggaggaacc gtcaccagaa    3060
ctgtacgcag aagtccgcaa ctgggtgcgt aaagagattg gcccgctggc gacgccagac    3120
gtgctgcact ggaccgactc cctgcctaaa acccgctccg gcaaaattat gcgccgtatt    3180
ctgcgcaaaa ttgcggcggg cgataccagc aacctgggcg atacctcgac gcttgccgat    3240
cctggcgtag tcgagaagct gcttgaggag aagcaggcta tcgcgatgcc atcgtgagcc    3300
cgaagagcac gtactgctaa gctgactgcg ggggagagcg cgtgtgccgg ccagtctaca    3360
tgtactcttt ttgataaaaa attggagatt cctttacaaa tatgctctta cgtgctatta    3420
tttaagtgac tatttaaaag gagttaataa atatgcggca aggtattctt aaataaactg    3480
tcaatttgat agcgggaaca ataattaga tgtccttttt taggagggct tagttttttg    3540
tacccagttt aagaatacct ttatcatgtg attctaaagt atccagagaa tatctgtatg    3600
ctttgtatac ctatggttat gcataaaaat cccggtgata aaagtattta tcactgggat    3660
ttttatgccc ttttgggttt ttgaatggag gaatactaga tgaaaatcat aaatatcggt    3720
gtattagctc acgttgatgc aggaaaaaca acattaactg aatcacttt atataactct    3780 ggtgcaatta ctgaacttgg ttcagtagat aaaggtacta ctcgtactga taatacatta    3840
ttagaacgtc aacgtggaat cacaattcaa acaggtatca catctttca atgggaaaat    3900 acaaaagtaa atattataga tacacctgga cacatggatt ccttgcaga agtataccgt    3960 agtctttcag tattagatgg tgctatttta cttatcagcg ctaaagatgg agttcaagct    4020
caaactcgta tcttatttca cgcattacgt aaaatgggta ttccaacaat tttcttata    4080 aacaaaattg accaaaacgg aattgattta agtacagttt atcaagatat caagaaaaaa    4140
ctttctgctg aaatcgttat taaacaaaaa gttgaattat acccaaacgt ttgcgtaaca    4200
aattttactg aatcagaaca atgggataca gttatagaag gtaatgatga tttattagaa    4260
aaatacatgt caggtaaatc attagaagca ttagaattag aacaagaaga agtattcgt    4320 ttccaaaact gttctttatt ccctttatac catggaagcg ctaaaagtaa cataggtatt    4380
gataacttaa ttgaagttat tactaacaaa ttttattctt caactcatcg tgggccttct    4440
gaattatgcg gtaacgtttt caaaattgaa tatacaaaaa aacgtcaacg tttagcttat    4500
atacgtcttt atagtggtgt tttacattta cgtgatagtg ttcgtgttag tgaaaaagaa    4560
aagattaaag ttcagaaaat gtatacttct attaacggtg aattatgcaa aattgaccgt    4620
gcatattcag gtgaaattgt aatttttacaa aacgaattc ttaaacttaa tagtgtactt    4680
ggtgacacaa aactttttacc acaacgtaag aaaattgaaa atccacaccc attacttcaa    4740
acaacagtag aaccaagcaa acctgaacaa cgtgaaatgc ttttagatgc tcttttgaa    4800 attagtgact ctgacccact tttacgttac tatgtagatt ctactactca tgaaattatt    4860
```

```
ctttctttcc ttggtaaagt tcaaatggaa gttatttctg cattattaca agaaaaatat    4920
catgttgaaa tcgaattaaa agaacctact gtaatttata tggaacgtcc attaaaaaat    4980
gctgaatata caattcatat tgaagttcca ccaaatccat tttgggcttc tattggtctt    5040
tctgtttctc cacttccact tggtagcgga atgcaatatg aaagtagcgt aagtttaggt    5100
tatcttaatc aaagtttcca aaacgcagtt atggaaggta ttcgttacgg ttgcgaacaa    5160
ggtttatacg gttggaatgt tacagactgc aaaatctgtt ttaagtatgg actttactat    5220
tcacctgtat caacacctgc tgactttcgt atgcttgcac caattgtttt agaacaagtt    5280
ttaaagaaag ctggaactga acttttagaa ccatacctt  cttttaaaat ctatgcacca    5340
caagaatact aagtcgtgc  ttataacgat gcacctaaat actgtgctaa tattgttgat    5400
actcaattaa agaacaacga agtaatttta agcggagaaa ttcctgcacg ttgtattcaa    5460
gaatatcgta gtgatttaac attttcact  aatggacgtt ctgtttgctt aactgaatta    5520
aaaggttatc atgttactac tggtgaacct gtatgccaac cacgtcgtcc taatagtcgt    5580
attgataaag ttcgttatat gttcaacaaa atcacataat aaaaaaaaaa accccgcccc    5640
tgacagggcg ggttttttt  tttagttagt tagagatgtg tataagagac agctggccat    5700
ggaatagact ggatggaggc ggataaagtt gcaggaccac ttctgcgctc ggcccttccg    5760
gctggctggt ttattgctga taaatctgga gccggtgagc gtgggtctcg cggtatcatt    5820
gcagcactgg ggccagatgg taagccctcc cgtatcgtag ttatctacac gacggggagt    5880
caggcaacta tggatgaacg aaatagacag atcgctgaga taggtgcctc actgattaag    5940
cattggtaac tgtcagacca agtttactca tatatacttt agattgattt aaaacttcat    6000
ttttaattta aaaggatcta ggtgaagatc ctttttgata atctcatgac caaaatccct    6060
taacgtgagt tttcgttcca ctgagcgtca gaccccttaa taagatgatc ttcttgagat    6120
cgttttggtc tgcgcgtaat ctcttgctct gaaaacgaaa aaaccgcctt gcagggcggt    6180
ttttcgaagg ttctctgagc taccaactct ttgaaccgag gtaactggct tggaggagcg    6240
cagtcaccaa aacttgtcct ttcagtttag ccttaaccgg cgcatgactt caagactaac    6300
tcctctaaat caattaccag tggctgctgc cagtggtgct tttgcatgtc tttccgggtt    6360
ggactcaaga cgatagttac cggataaggc gcagcggtcg gactgaacgg ggggttcgtg    6420
catacagtcc agcttggagc gaactgccta cccggaactg agtgtcaggc gtggaatgag    6480
acaaacgcgg ccataacagc ggaatgacac cggtaaaccg aaaggcagga acaggagagc    6540
gcacgaggga gccgccaggg gaaacgcctg gtatctttat agtcctgtcg ggtttcgcca    6600
ccactgattt gagcgtcaga tttcgtgatg cttgtcaggg gggcggagcc tatggaaaaa    6660
cggctttgcc gcggccctct cacttccctg ttaagtatct tcctggcatc ttccaggaaa    6720
tctccgcccc gttcgtaagc catttccgct cgccgcagtc gaacgaccga gcgtagcgag    6780
tcagtgagcg aggaagcgga atatatcctg tatcacatat tctgctgacg caccggtgca    6840
gccttttttc tcctgccaca tgaagcactt cactgacacc ctcatcagtg ccaacatagt    6900
aagccagtat acactccgct agcgctgagg tctgcctcgt gaagaaggtg ttgctgactc    6960
ataccaggcc tgaatcgccc catcatccag ccagaaagtg agggagccac ggttgatgag    7020
agctttgttg taggtggacc agttggtgat tttgaacttt tgctttgcca cggaacggtc    7080
tgcgttgtcg ggaagatgcg tgatctgatc cttcaactca gcaaaagttc gatttattca    7140
acaaagccac gttgtgtctc aaaatctctg atgttacatt gcacaagata aaaatatatc    7200
```

| atcatgaaca | ataaaactgt | ctgcttacat | aaacagtaat | acaaggggtg | ttgcccagct | 7260 |

| gtctcttata | cacatctccg | gcttatcggt | cagtttcacc | tgatttacgt | aaaaacccgc | 7320 |

| ttcggcgggt | ttttgctttt | ggaggggcag | aaagatgaat | gactgtccac | gacgctatac | 7380 |

| ccaaaagaaa | gcc | | | | | 7393 |

<210> SEQ ID NO 66
<211> LENGTH: 4269
<212> TYPE: DNA
<213> ORGANISM: Artificial Sequence
<220> FEATURE:
<223> OTHER INFORMATION: Synthetic DNA

<400> SEQUENCE: 66

| gaattcgcgg | ccgcttctag | aggccgatct | cgatcccgcg | aaattaatac | gactcactat | 60 |
| agggggaattg | tgagcggata | acaattcccc | tctagaaata | attttgttta | actttaagaa | 120 |
| ggagactctt | ctatggccct | tgaggacaaa | gacctgcgga | gcatccaaga | ggtaaggaac | 180 |
| ttaatagaga | gcgcgaacaa | agcccaaaaa | gagctcgcgg | ccatgagtca | acaacaaata | 240 |
| gacactatag | tcaaagctat | agcggacgca | gggtatgggg | cgagggagaa | attagccaaa | 300 |
| atggcccacg | aggagacagg | gttcggcata | tggcaagata | aagtcataaa | aaacgttttt | 360 |
| gcgtccaagc | atgtttacaa | ttacatcaaa | gacatgaaaa | cgatagggat | gctgaaagag | 420 |
| gacaacgaga | agaaagtcat | ggaagtagcc | gtaccgcttg | gggtcgtagc | cggcctgata | 480 |
| ccatcgacta | acccaacttc | cacagtaata | tacaaaactc | ttatatctat | aaaagccggc | 540 |
| aattcaatcg | tcttctcgcc | gcacccgaac | gcccttaaag | ccatactcga | gactgtccgt | 600 |
| ataatatcag | aggcggccga | gaaagcggga | tgtccgaaag | gtgcgatcag | ttgtatgaca | 660 |
| gtaccgacta | tccaaggcac | tgaccaattg | atgaaaacata | aagacactgc | cgtaatcctc | 720 |
| gccactggag | ggtcggccat | ggtcaaagct | gcgtatagct | cggggacacc | ggccataggc | 780 |
| gtaggtccgg | ggaatggtcc | ggccttcatc | gagcggtcag | caaacatacc | acgggccgtg | 840 |
| aaacacatac | tcgactccaa | aacttttgac | aacggcacta | tatgcgcctc | ggaacaatcg | 900 |
| gttgtagtag | agagggtgaa | taagaggcg | gttatagcgg | agttccgtaa | acaaggcgcc | 960 |
| cattttctga | gcgacgccga | ggcggtacaa | ctcgggaaat | ttatcctgag | gccgaatggg | 1020 |
| agcatgaatc | cggccatcgt | cgggaaaagt | gtgcaacaca | tcgcgaacct | cgcgggcgtt | 1080 |
| actgtaccgg | cggatgcccg | tgtcctcatc | gcggaggaga | ctaaagtagg | ggcgaaaatc | 1140 |
| ccatatagcc | gtgagaaact | ggcgccgatc | ctagcgtttt | atactgccga | gacatggcaa | 1200 |
| gaggcgtgcg | agctcagtat | ggacatactc | tatcacgagg | gcgcgggcca | cactgatc | 1260 |
| atccattcgg | aggacaaaga | gatcatccgg | gagtttgcct | tgaaaaaacc | ggtatccagg | 1320 |
| ctcctggtaa | atactccggg | gcgctctcgg | tggcataggtg | ccactactaa | tctcgtccca | 1380 |
| gcgctgactc | tcgggtgtgg | agccgtaggc | ggctcaagca | gctcggacaa | tatcggccca | 1440 |
| gagaatctct | ttaacatacg | gcggatcgcg | actggcgtac | tggaactgga | ggacataagg | 1500 |
| aaagaggaga | accaagccac | ttcggagctc | cctgtagacg | ccgatgcctt | gatccaatca | 1560 |
| ctggtcgaga | aagtactggc | cgagctgaag | taagcccgaa | gagctactag | tagcggccgc | 1620 |
| tgcagcgtca | aaagggcgac | acaaaattta | ttctaaatgc | ataataaata | ctgataacat | 1680 |
| cttatagttt | gtattatatt | ttgtattatc | gttgacatgt | ataattttga | tatcaaaaac | 1740 |
| tgattttccc | tttattattt | tcgagattta | ttttcttaat | tctctttaac | aaactagaaa | 1800 |
| tattgtatat | acaaaaaatc | ataaataata | gatgaatagt | ttaattatag | gtgttcatca | 1860 |

```
atcgaaaaag caacgtatct tatttaaagt gcgttgcttt tttctcattt ataaggttaa    1920
ataattctca tatatcaagc aaagtgacag gcgcccttaa atattctgac aaatgctctt    1980
tccctaaact cccccataa aaaaaccgc cgaagcgggt ttttacgtta tttgcggatt     2040
aacgattact cgttatcaga accgcccagg gggcccgagc ttaagactgg ccgtcgtttt    2100
acaacacaga aagagtttgt agaaacgcaa aaaggccatc cgtcaggggc cttctgctta    2160
gtttgatgcc tggcagttcc ctactctcgc cttccgcttc ctcgctcact gactcgctgc    2220
gctcggtcgt tcggctgcgg cgagcggtat cagctcactc aaaggcggta atacggttat    2280
ccacagaatc aggggataac gcaggaaaga acatgtgagc aaaaggccag caaaaggcca    2340
ggaaccgtaa aaaggccgcg ttgctggcgt ttttccatag gctccgcccc cctgacgagc    2400
atcacaaaaa tcgacgctca agtcagaggt ggcgaaaccc gacaggacta taaagatacc    2460
aggcgtttcc ccctggaagc tccctcgtgc gctctcctgt tccgaccctg ccgcttaccg    2520
gatacctgtc cgcctttctc ccttcgggaa gcgtggcgct ttctcatagc tcacgctgta    2580
ggtatctcag ttcggtgtag gtcgttcgct ccaagctggg ctgtgtgcac gaaccccccg    2640
ttcagcccga ccgctgcgcc ttatccggta actatcgtct tgagtccaac ccggtaagac    2700
acgacttatc gccactggca gcagccactg gtaacaggat tagcagagcg aggtatgtag    2760
gcggtgctac agagttcttg aagtggtggg ctaactacgg ctacactaga agaacagtat    2820
ttggtatctg cgctctgctg aagccagtta ccttcggaaa aagagttggt agctcttgat    2880
ccggcaaaca aaccaccgct ggtagcggtg gttttttgt ttgcaagcag cagattacgc    2940
gcagaaaaaa aggatctcaa gaagatcctt tgatcttttc tacggggtct gacgctcagt    3000
ggaacgacgc gcgcgtaact cacgttaagg gattttggtc atgagcttgc gccgtcccgt    3060
caagtcagcg taatgctctg cttttagaaa aactcatcga gcatcaaatg aaactgcaat    3120
ttattcatat caggattatc aataccatat ttttgaaaaa gccgtttctg taatgaagga    3180
gaaaactcac cgaggcagtt ccataggatg caagatcct ggtatcggtc tgcgattccg    3240
actcgtccaa catcaataca acctattaat ttccctcgt caaaaataag gttatcaagt    3300
gagaaatcac catgagtgac gactgaatcc ggtgagaatg gcaaaagttt atgcatttct    3360
ttccagactt gttcaacagg ccagccatta cgctcgtcat caaaatcact cgcatcaacc    3420
aaaccgttat tcattcgtga ttgcgcctga gcgaggcgaa atacgcgatc gctgttaaaa    3480
ggacaattac aaacaggaat cgagtgcaac cggcgcagga acactgccag cgcatcaaca    3540
atattttcac ctgaatcagg atattcttct aatacctgga acgctgtttt tccggggatc    3600
gcagtggtga gtaaccatgc atcatcagga gtacggataa aatgcttgat ggtcggaagt    3660
ggcataaatt ccgtcagcca gtttagtctg accatctcat ctgtaacatc attggcaacg    3720
ctacctttgc catgtttcag aaacaactct ggcgcatcgg gcttcccata caagcgatag    3780
attgtcgcac ctgattgccc gacattatcg cgagcccatt tatacccata taatcagca    3840 tccatgttgg aatttaatcg cggcctcgac gtttcccgtt gaatatggct catattcttc    3900 cttttcaat attattgaag catttatcag ggttattgtc tcatgagcgg atacatattt    3960
gaatgtattt agaaaaataa acaaataggg gtcagtgtta caaccaatta accaattctg    4020
aacattatcg cgagcccatt tatacctgaa tatggctcat aacacccctt gtttgctgg    4080 cggcagtagc gcggtggtcc cacctgaccc catgccgaac tcagaagtga aacgccgtag    4140
```

-continued

```
cgccgatggt agtgtgggga ctccccatgc gagagtaggg aactgccagg catcaaataa    4200
aacgaaaggc tcagtcgaaa gactgggcct ttcgcccggg ctaattaggg ggtgtcgccc    4260
ttcgctgaa                                                            4269
```

METHODS FOR MAKING CHEMOAUTOTROPHIC CELLS BY ENGINEERING AN ENERGY CONVERSION PATHWAY AND A CARBON FIXATION PATHWAY

CROSS REFERENCE TO RELATED APPLICATIONS

This application is a continuation application of U.S. application Ser. No. 14/354,354, which is a national stage application of International Application No. PCT/US2012/062540, filed Oct. 30, 2012, which claims priority to and the benefit of U.S. patent application Ser. No. 13/285,919, filed on Oct. 31, 2011, each of which is incorporated herein by reference in its entirety.

STATEMENT REGARDING GOVERNMENT LICENSE RIGHTS

This invention was made with government support under contract number DE-AR0000091 awarded by U.S. Department of Energy, Office of ARPA-E. The government has certain rights in the invention.

SEQUENCE LISTING

The instant application contains a sequence listing (.txt file named Sequence Listing, generated on May 27, 2014 and is 180,540 bytes in size) which has been submitted in ASCII format via EFS-Web and is incoprorated by reference herein.

TECHNICAL FIELD

The invention relates to systems, mechanisms and methods to confer chemoautotrophic production of carbon-based products to a heterotrophic organism to efficiently convert inorganic carbon into various carbon-based products using chemical energy, and in particular the use of such organism for the commercial production of various carbon-based products of interest. The invention also relats to systems, mechanisms and methods to confer additional and/or alternative pathways for chemoautotrophic producion of carbon-based products to an organism that is already autotrophic or mixotrophic.

BACKGROUND

Heterotrophs are biological organisms that utilize energy from organic compounds for growth and reproduction. Commercial production of various carbon-based products of interest generally relies on heterotrophic organisms that ferment sugar from crop biomass such as corn or sugarcane as their energy and carbon source [Bai, 2008]. An alternative to fermentation-based bio-production is the production of carbon-based products of interest from photosynthetic organisms, such as plants, algae and cyanobacteria, that derive their energy from sunlight and their carbon from carbon dioxide to support growth [U.S. Pat. No. 7,981,647]. However, the algae-based production of carbon-based products of interest relies on the relatively inefficient process of photosynthesis to supply the reducing power needed for production of organic compounds from carbon dioxide [Larkum, 2010]. Moreover, commercial production of carbon-based products of interest using photosynthetic organisms relies on reliable and consistent exposure to light to achieve the high productivities needed for economic feasibility; hence, photobioreactor design remains a significant technical challenge [Morweiser, 2010].

Chemoautotrophs are biological organisms that utilize energy from inorganic energy sources such as molecular hydrogen, hydrogen sulfide, ammonia or ferrous iron, and carbon dioxide to produce all organic compounds necessary for growth and reproduction. Existing, naturally-occuring chemoautotrophs are poorly suited for industrial bio-processing and have therefore not demonstrated commercial viability for this purpose. Such organisms have long doubling times (minimum of approximately one hour for Thiomicrospira crunogena but generally much longer) relative to industrialized heterotrophic organisms such as *Escherichia coli* (twenty minutes), reflective of low total productivities. In addition, techniques for genetic manipulation (homologous recombination, transformation or transfection of nucleic acid molecules, and recombinant gene expression) are inefficient, time-consuming, laborious or non-existent.

Accordingly, the ability to endow an otherwise heterotrophic organism with chemoautotrophic capability would significantly enable more energy- and carbon-efficient production of carbon-based products of interest. Alternatively, the ability to add one or more additional or alternative pathways for chemoautotrophic capability to an autotrophic or mixotrophic organism would enhance its ability to produce carbon-based products on interest.

SUMMARY

Systems and methods of the present invention provide for efficient production of renewable energy and other carbon-based products of interest (e.g., fuels, sugars, chemicals) from inorganic carbon (e.g., greenhouse gas) using inorganic energy. As such, the present invention materially contributes to the development of renewable energy and/or energy conservation, as well as greenhouse gas emission reduction. Furthermore, systems and methods of the present invention can be used in the place of traditional methods of producing chemicals such as olefins (e.g., ethylene, propylene), which are traditionally derived from petroleum in a process that generates toxic by-products that are recognized as hazardous waste pollutants and harmful to the environment. As such, the present invention can additionally avoid the use of petroleum and the generation of such toxic by-products, and thus materially enhances the quality of the environment by contributing to the maintenance of basic life-sustaining natural elements such as air, water and/or soil by avoiding the generation of hazardous waste pollutants in the form of petroleum-derived by-products in the production of various chemicals.

In certain aspect, the invention described herein provides an organism engineered to confer chemoautotrophic production of various carbon-based products of interest from inorganic carbon and inorganic energy. The engineered organism comprises a modular metabolic architecture encompassing three metabolic modules. The first module comprises one or more energy conversion pathways that use energy from an inorganic energy source, such as formate, formic acid, methane, carbon monoxide, carbonyl sulfide, carbon disulfide, hydrogen sulfide, bisulfide anion, thiosulfate, elemental sulfur, molecular hydrogen, ferrous iron, ammonia, cyanide ion, and/or hydrocyanic acid, to produce reduced cofactors inside the cell, such as NADH, NADPH, ubiquinol, menaquinol, cytochromes, flavins and/or ferredoxin. The second module comprises one or more carbon fixation pathways that use energy from reduced cofactors to convert inorganic carbon, such as carbon dioxide, carbon monoxide, formate, formic acid, carbonic acid, bicarbonate, carbon monoxide, carbonyl sulfide, carbon disulfide, cyanide ion and/or hydrocyanic acid, to central metabolites, such as acetyl-coA, pyruvate, pyruvic acid, 3-hydropropionate, 3-hydroxypropionic acid, glycolate, glycolic acid, glyoxylate, glyoxylic acid, dihydroxyacetone phosphate, glyceraldehyde-3-phosphate, malate, malic acid, lactate, lactic acid, acetate, acetic acid, citrate and/or citric acid. Optionally, the third module comprises one or more carbon product biosynthetic pathways that convert central metabolites into desired products, such as carbon-based products of interest. Carbon-based products of interest include but are not limited to alcohols, fatty acids, fatty acid derivatives, fatty alcohols, fatty acid esters, wax esters, hydrocarbons, alkanes, polymers, fuels, commodity chemicals, specialty chemicals, carotenoids, isoprenoids, sugars, sugar phosphates, central metabolites, pharmaceuticals and pharmaceutical intermediates.

The resulting engineered chemoautotroph of the invention is capable of efficiently synthesizing carbon-based products of interest from inorganic carbon using inorganic energy. The invention also provides energy conversion pathways, carbon fixation pathways and carbon product biosynthetic pathways for conferring chemoautotrophic production of the carbon-based product of interest upon the host organism where the organism lacks the ability to efficiently produce carbon-based products of interest from inorganic carbon using inorganic energy. The invention also provides methods for culturing the engineered chemoautotroph to support efficient chemoautotrophic production of carbon-based products of interest.

In one aspect, the present invention provides an engineered cell for producing a carbon-based product of interest. The engineeted cell includes an at least partially engineered energy conversion pathway having at least one of a recombinant formate dehydrogenase and a recombinant sulfide-quinone oxidoreductase introduced into a host cell, wherein said energy conversion pathway is capable of using energy from oxidation to produce a reduced cofactor. The engineeted cell also includes a carbon fixation pathway that is capable of converting inorganic carbon to a central metabolite using energy from the reduced cofactor. The engineeted cell further includes, optionally, a carbon product biosynthetic pathway that is capable of converting the central metabolite into a carbon-based product of interest.

In certain embodiments, the recombinant formate dehydrogenase reduces NADP$^+$. For example, the recombinant formate dehydrogenase can be encoded by SEQ ID NO:1, or a homolog thereof having at least 80% sequence identity thereto. In some embodiments, the recombinant formate dehydrogenase reduces NAD$^+$. In an example, the recombinant formate dehydrogenase can be encoded by any one of SEQ ID NOs:2-4, or a homolog thereof having at least 80% sequence identity thereto. In other embodiments, the recombinant formate dehydrogenase reduces ferredoxin. As an example, the recombinant formate dehydrogenase can be encoded by one or more of SEQ ID NOs:5-8, or a homolog thereof having at least 80% sequence identity thereto.

In certain embodiments, the recombinant sulfide-quinone oxidoreductase reduces quinone. For example, the recombinant sulfide-quinone oxidoreductase can be encoded by any one of SEQ ID NOs:9-16, or a homolog thereof having at least 80% sequence identity thereto.

In some embodiments, the energy conversion pathway includes the recombinant formate dehydrogenase and the energy from oxidation is from formate oxidation. The energy conversion pathway can also include the recombinant sulfide-quinone oxidoreductase and the energy from oxidation can be from hydrogen sulfide oxidation.

In various embodiments, the inorganic carbon is one or more of formate and carbon dioxide.

In certain embodiments, the carbon fixation pathway can be at least partially engineered and can be derived from the 3-hydroxypropionate (3-HPA) bicycle. The carbon fixation pathway can include one or more of: acetyl-CoA carboxylase, malonyl-CoA reductase, propionyl-CoA synthase, propionyl-CoA carboxylase, methylmalonyl-CoA epimerase, methylmalonyl-CoA mutase, succinyl-CoA:(S)-malate CoA transferase, succinate dehydrogenase, fumarate hydratase, (S)-malyl-CoA/β-methylmalyl-CoA/(S)-citramalyl-CoA lyase, mesaconyl-C1-CoA hydratase or β-methylmalyl-CoA dehyratase, mesaconyl-CoA C1-C4 CoA transferase and mesaconyl-C4-CoA hydratase.

In some embodiments, the carbon fixation pathway can be at least partially engineered and can be derived from the ribulose monophosphate (RuMP) cycle. In one embodiment, said carbon fixation pathway can include one or more of: hexulose-6-phosphate synthase, 6-phospho-3-hexuloisomerase, hexulose-6-phosphate synthase/6-phospho-3-hexuloisomerase fusion enzyme, phosphofructokinase, fructose bisphosphate aldolase, transketolase, transaldolase, transketolase, ribose 5-phosphate isomerase and ribulose-5-phosphate-3-epimerase.

In some embodiments, said carbon fixation pathway can be at least partially engineered and can be derived from the Calvin-Benson-Bassham cycle or the reductive pentose phosphate (RPP) cycle. For example, the carbon fixation pathway can include one or more of: ribulose bisphosphate carboxylase, phosphoglycerate kinase, glyceraldehyde-3P dehydrogenase (phosphorylating), triose-phosphate isomerase, fructose-bisphosphate aldolase, fructose-bisphosphatase, transketolase, sedoheptulose-1,7-bisphosphate aldolase, sedoheptulose bisphosphatase, transketolase, ribose-5-phosphate isomerase, ribulose-5-phosphate-3-epimerase and phosphoribulokinase.

In certain embodiments, said carbon fixation pathway can be at least partially engineered and can be derived from the reductive tricarboxylic acid (rTCA) cycle. In some embodiments, the carbon fixation pathway can include one or more of: ATP citrate lyase, citryl-CoA synthetase, citryl-CoA lyase, malate dehydrogenase, fumarate dehydratase, fumarate reductase, succinyl-CoA synthetase, 2-oxoglutarate:ferredoxin oxidoreductase, isocitrate dehydrogenase, 2-oxoglutarate carboxylase, oxalosuccinate reductase, aconitate hydratrase, pyruvate:ferredoxin oxidoreductase, phosphoenolpyruvate synthetase and phosphoenolpyruvate carboxylase.

DETAILED DESCRIPTION

Figure 1:
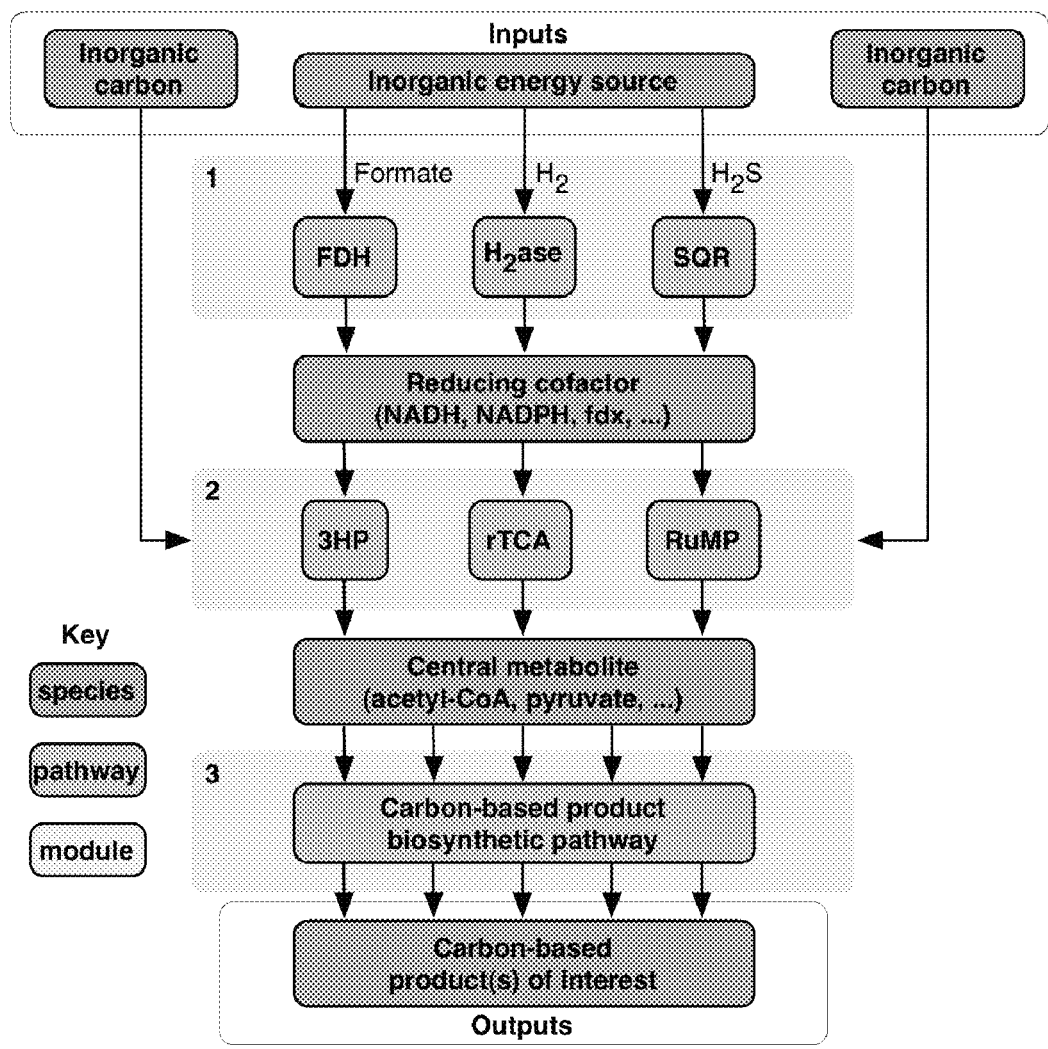
FIG. 1 is an overview of modular architecture of an engineered chemoautotroph. An engineered chemoautotroph comprises three metabolic modules. (1) In Module 1, one or more energy conversion pathways that use energy from an extracellular inorganic energy source, such as formate, hydrogen sulfide, molecular hydrogen, or ferrous iron, to produce reduced cofactors inside the cell, such as NADH, NADPH, reduced ferredoxin and/or reduced quinones or cytochromes. Depicted examples of energy conversion pathways include formate dehydrogenase (FDH), hydrogenase (H$_2$ase), and sulfide-quinone oxidoreductase (SQR). (2) In Module 2, one or more carbon fixation pathways that use energy from reduced cofactors to reduce and convert inorganic carbon, such as carbon dioxide, formate and formaldehyde, to central metabolites, such as acetyl-coA, pyruvate, glycolate, glyoxylate, and dihydroxyacetone phosphate. Depicted examples of carbon fixation pathways include the 3-hydroxypropionate cycle (3-HPA), the reverse or reductive tricarboxylic acid cycle (rTCA), and the ribulose monophosphate pathway (RuMP). (3) Optionally, in Module 3, one or more carbon product biosynthetic pathways that convert central metabolites into desired products, such as carbon-based products of interest. Since there are many possible carbon-based products of interest, no individual pathways are depicted.

The present invention relates to developing and using engineered chemoautotrophs capable of utilizing energy from inorganic energy sources and inorganic carbon to produce a desired product. The invention provides for the engineering of a heterotrophic organism, for example, *Escherichia coli* or other organism suitable for commercial large-scale production of fuels and chemicals, that can efficiently utilize inorganic energy sources and inorganic carbon as a substrate for growth (a chemoautotroph) and for chemical production provides cost-advantaged processes for manufacturing of carbon based products of interest. The organisms can be optimized and tested rapidly and at reasonable costs. The invention further provides for the engineering of an autotrophic organism to include one or more additional or alternative pathways for utilization of inorganic energy sources and inorganic carbon to produce central metabolites for growth and/or other desired products.

Inorganic energy sources together with inorganic carbon represent an alternative feedstock to sugar or light plus carbon dioxide for the production of carbon-based products of interest. There exist non-biological routes to convert inorganic energy sources and inorganic carbon to chemicals and fuels of interest. For example, the Fischer-Tropsch process consumes carbon monoxide and hydrogen gas generated from gasification of coal or biomass to produce methanol or mixed hydrocarbons as fuels [U.S. Pat. No. 1,746,464]. The drawbacks of Fischer-Tropsch processes are: 1) a lack of product selectivity, which results in difficulties separating desired products; 2) catalyst sensitivity to poisoning; 3) high energy costs due to high temperatures and pressures required; and 4) the limited range of products available at commercially competitive costs. Without the advent of carbon sequestration technologies that can operate at scale, the Fischer-Tropsch process is widely considered to be an environmentally costly method for generating liquid fuels. Alternatively, processes that rely on naturally occurring microbes that convert synthesis gas or syngas, a mixture of primarily molecular hydrogen and carbon monoxide that can be obtained via gasification of any organic feedstock, such as coal, coal oil, natural gas, biomass, or waste organic matter, to products such as ethanol, acetate, methane, or molecular hydrogen are available [Henstra, 2007]. However, these naturally occurring microbes can produce only a very restricted set of products, are limited in their efficiencies, lack established tools for genetic manipulation, and are sensitive to their end products at high concentrations. Finally, there is some work to introduce syngas utilization into industrial microbial hosts [U.S. Pat. No. 7,803,589]; however, these processes have yet to be demonstrated at commercial scale and are limited to using syngas as the feedstock.

In some embodiments, the invention provides for the use of an inorganic energy source, such as molecular hydrogen or formate, derived from electrolysis. There is tremendous commercial activity towards the goal of renewable and/or carbon-neutral energy from solar voltaic, geothermal, wind, nuclear, hydroelectric and more. However, most of these technologies produce electricity and are thus limited in use to the electrical grid [Whipple, 2010]. Furthermore, at least some of these renewable energy sources such as solar and wind suffer from being intermittent and unreliable. The lack of practical, large scale electricity storage technologies limits how much of the electricity demand can be shifted to renewable sources. The ability to store electrical energy in chemical form, such as in carbon-based products of interest, would both offer a means for large-scale electricity storage and allow renewable electricity to meet energy demand from the transportation sector. Renewable electricity combined with electrolysis, such as the electrochemical production of hydrogen from water [for example, WO/2009/154753, WO/2010/042197, WO/2010/028262 and WO/2011/028264] or formate/formic acid from carbon dioxide [for example, WO/2007/041872], opens the possibility of a sustainable, renewable supply of the inorganic energy source as one aspect of the present invention.

In some embodiments, the invention provides for the use of an inorganic energy source, such as hydrogen sulfide or molecular hydrogen, derived from waste streams. For example, hydrogen sulfide is present in waste streams arising from both hydrodesulfurization processes used during oil recovery and desulfurization of natural gas. Indeed, currently many oil companies stockpile elemental sulfur (the oxidation product of hydrogen sulfide) since worldwide production exceeds demand [Ober, 2010]. As lower quality oil deposits with higher sulfur contents (5% w/w) open up to drilling, the expectation is that global sulfur supply will continue to grow. As a second example, hydrogen and carbon dioxide are off-gas by-products of clostridial acetone-butanol-ethanol fermentations.

In some embodiments, the invention provides for the use of an inorganic carbon source, such as carbon dioxide, derived from waste streams. For example, carbon dioxide is a component of synthesis gas, the major product of gasification of coal, coal oil, natural gas, and of carbonaceous materials such as biomass materials, including agricultural crops and residues, and waste organic matter. Additional sources include, but are not limited to, production of carbon dioxide as a byproduct in ammonia and hydrogen plants, where methane is converted to carbon dioxide; combustion of wood and fossil fuels; production of carbon dioxide as a byproduct of fermentation of sugar in the brewing of beer, whisky and other alcoholic beverages, or other fermentative processes; thermal decomposition of limestone, $CaCO_3$, in the manufacture of lime, CaO; production of carbon dioxide as byproduct of sodium phosphate manufacture; and directly from natural carbon dioxide springs, where it is produced by the action of acidified water on limestone or dolomite. As a second example, formaldehyde is an oxidation product of methanol or methane. Methanol can be prepared from synthesis gas or reductive conversion of carbon dioxide and hydrogen by chemical synthetic processes. Methane is a major component of natural gas and can also be obtained from renewable biomass.

In one embodiment, the invention provides for the inorganic energy source and the inorganic carbon coming from the same chemical species, such as formate or formic acid. Formate is oxidized by an energy conversion pathway to generate reduced cofactor and carbon dioxide. The carbon dioxide can then be used as the inorganic carbon source.

The invention provides for the expression of one or more exogenous proteins or enzymes in the host cell, thereby conferring biosynthetic pathway(s) to utilize inorganic energy sources and inorganic carbon to produce reduced organic compounds. In a preferred embodiment, the present invention provides for a modular architecture for the metabolism of the engineered chemoautotroph comprising the following three metabolic modules (FIG. 1).

In Module 1, one or more energy conversion pathways that use energy from an extracellular inorganic energy source, such as formate, hydrogen sulfide, molecular hydrogen, or ferrous iron, to produce reduced cofactors inside the cell, such as NADH, NADPH, reduced ferredoxin and/or reduced quinones or cytochromes.

In Module 2, one or more carbon fixation pathways that use energy from reduced cofactors to reduce and convert inorganic carbon, such as carbon dioxide or formate, to central metabolites, such as acetyl-coA, pyruvate, glycolate, glyoxylate, and dihydroxyacetone phosphate.

Optionally, in Module 3, one or more carbon product biosynthetic pathways that convert central metabolites into desired products, such as carbon-based products of interest.

A key advantage of a modular architecture for the metabolism of an engineered chemoautotroph is that each module may be instantiated via one or more possible biosynthetic pathways. For example, in Module 1, there are several possible energy conversion pathways, such as those based on formate dehydrogenase (e.g., E.C. 1.2.1.2, E.C. 1.2.1.43, E.C. 1.1.5.6, E.C. 1.2.2.1 or E.C. 1.2.2.3), ferredoxin-dependent formate dehydrogenase, hydrogenase (e.g., E.C. 1.12.1.2, E.C. 1.12.1.3, or E.C. 1.12.7.2), sulfide-quinone oxidoreductase (e.g., E.C. 1.8.5.4), flavocytochrome c sulfide dehydrogenase (e.g., E.C. 1.8.2.3), ferredoxin-NADP+ reductase (e.g., E.C. 1.18.1.2), ferredoxin-NAD+ reductase (e.g., E.C. 1.18.1.3), NAD(P)+ transhydrogenase (e.g., E.C. 1.6.1.1 or E.C. 1.6.1.2), NADH:ubiquinone oxidoreductase I (e.g., E.C. 1.6.5.3). As a second example, in Module 2, there are several possible naturally occurring carbon fixation pathways, such as the Calvin-Benson-Bassham cycle or reductive pentose phosphate cycle, the reductive tricarboxylic acid cycle, the Wood-Ljungdhal or reductive acetyl-coA pathway, the 3-hydroxypropionate bicycle or 3-hydroxypropionate/malyl-CoA cycle, 3-hydroxypropionate/4-hydroxybutyrate cycle and the dicarboxylate/4-hydroxybutyrate cycle [Hügler, 2011] as well as many possible synthetic carbon fixation pathways [Bar-Even, 2010]. As a final example, in Module 3, there are numerous possible carbon-based products of interest, each of which has one or more corresponding biosynthetic pathways. Every combination of energy conversion pathway, carbon fixation pathway and, optionally, carbon product biosynthetic pathway, when expressed in a heterotrophic or autotrophic host cell or organism, represents a different embodiment of the present invention. It should be noted, however, that only certain embodiments of Module 1 may be paired with a particular embodiment of Module 2. For example, the reductive tricarboxlic acid cycle likely requires a low potential ferredoxin for particular carbon dioxide fixation steps in the pathway. Thus, the energy conversion pathway paired with the reductive tricarboxylic acid cycle must be capable of generating reduced low potential ferredoxin, such as using a ferredoxin-reducing formate dehydrogenase or a ferredoxin-reducing hydrogenase (E.C. 1.12.7.2). Similarly, only certain embodiments of carbon fixation pathways produce the necessary precursors for a particular carbon product biosynthetic pathway. For example, fatty acid biosynthetic pathways require acetyl-coA and malonyl-coA to be generated products from the carbon fixation pathway.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art would understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well-known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

Definitions

As used herein, the terms "nucleic acids," "nucleic acid molecule" and "polynucleotide" may be used interchangeably and include both single-stranded (ss) and double-stranded (ds) RNA, DNA and RNA:DNA hybrids. As used herein the terms "nucleic acid", "nucleic acid molecule", "polynucleotide", "oligonucleotide", "oligomer" and "oligo" are used interchangeably and are intended to include, but are not limited to, a polymeric form of nucleotides that may have various lengths, including either deoxyribonucleotides or ribonucleotides, or analogs thereof. For example, oligos may be from 5 to about 200 nucleotides, from 10 to about 100 nucleotides, or from 30 to about 50 nucleotides long. However, shorter or longer oligonucleotides may be used. Oligos for use in the present invention can be fully designed. A nucleic acid molecule may encode a full-length polypeptide or a fragment of any length thereof, or may be non-coding.

Nucleic acids can refer to naturally-occurring or synthetic polymeric forms of nucleotides. The oligos and nucleic acid molecules of the present invention may be formed from naturally-occurring nucleotides, for example forming deoxyribonucleic acid (DNA) or ribonucleic acid (RNA) molecules. Alternatively, the naturally-occurring oligonucleotides may include structural modifications to alter their properties, such as in peptide nucleic acids (PNA) or in locked nucleic acids (LNA). The terms should be understood to include equivalents, analogs of either RNA or DNA made from nucleotide analogs and as applicable to the embodiment being described, single-stranded or double-stranded polynucleotides. Nucleotides useful in the invention include, for example, naturally-occurring nucleotides (for example, ribonucleotides or deoxyribonucleotides), or natural or synthetic modifications of nucleotides, or artificial bases. Modifications can also include phosphorothioated bases for increased stability.

Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the nucleotide comparison methods and algorithms set forth below, or as defined as being capable of hybridizing to the polynucleotides that encode the protein sequences.

As used herein, the term "gene" refers to a nucleic acid that contains information necessary for expression of a polypeptide, protein, or untranslated RNA (e.g., rRNA, tRNA, anti-sense RNA). When the gene encodes a protein, it includes the promoter and the structural gene open reading frame sequence (ORF), as well as other sequences involved in expression of the protein. When the gene encodes an untranslated RNA, it includes the promoter and the nucleic acid that encodes the untranslated RNA.

The term "gene of interest" (GOI) refers to any nucleotide sequence (e.g., RNA or DNA), the manipulation of which may be deemed desirable for any reason (e.g., has the relevant activity for a biosynthetic pathway, confer improved qualities and/or yields, expression of a protein of interest in a host cell, expression of a ribozyme, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding sequences which do not encode an mRNA or protein product (e.g., promoter sequence, polyadenylation sequence, termination sequence, enhancer sequence, etc.). For example, genes involved in the cis,cis-muconic acid biosynthesis pathway can be genes of interest. It should be noted that non-coding regions are generally untranslated but can be involved in the regulation of transcription and/or translation.

As used herein, the term "genome" refers to the whole hereditary information of an organism that is encoded in the DNA (or RNA for certain viral species) including both coding and non-coding sequences. In various embodiments, the term may include the chromosomal DNA of an organism and/or DNA that is contained in an organelle such as, for example, the mitochondria or chloroplasts and/or extrachromosomal plasmid and/or artificial chromosome. A "native gene" or "endogenous gene" refers to a gene that is native to the host cell with its own regulatory sequences whereas an "exogenous gene" or "heterologous gene" refers to any gene that is not a native gene, comprising regulatory and/or coding sequences that are not native to the host cell. In some embodiments, a heterologous gene may comprise mutated sequences or part of regulatory and/or coding sequences. In some embodiments, the regulatory sequences may be heterologous or homologous to a gene of interest. A heterologous regulatory sequence does not function in nature to regulate the same gene(s) it is regulating in the transformed host cell. "Coding sequence" refers to a DNA sequence coding for a specific amino acid sequence. As used herein, "regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, ribosome binding sites, translation leader sequences, RNA processing site, effector (e.g., activator, repressor) binding sites, stem-loop structures, and so on.

As described herein, a genetic element may be any coding or non-coding nucleic acid sequence. In some embodiments, a genetic element is a nucleic acid that codes for an amino acid, a peptide or a protein. Genetic elements may be operons, genes, gene fragments, promoters, exons, introns, regulatory sequences, or any combination thereof. Genetic elements can be as short as one or a few codons or may be longer including functional components (e.g. encoding proteins) and/or regulatory components. In some embodiments, a genetic element includes an entire open reading frame of a protein, or the entire open reading frame and one or more (or all) regulatory sequences associated therewith. One skilled in the art would appreciate that the genetic elements can be viewed as modular genetic elements or genetic modules. For example, a genetic module can comprise a regulatory sequence or a promoter or a coding sequence or any combination thereof. In some embodiments, the genetic element includes at least two different genetic modules and at least two recombination sites. In eukaryotes, the genetic element can comprise at least three modules. For example, a genetic module can be a regulator sequence or a promoter, a coding sequence, and a polyadenlylation tail or any combination thereof. In addition to the promoter and the coding sequences, the nucleic acid sequence may comprises control modules including, but not limited to a leader, a signal sequence and a transcription terminator. The leader sequence is a non-translated region operably linked to the 5' terminus of the coding nucleic acid sequence. The signal peptide sequence codes for an amino acid sequence linked to the amino terminus of the polypeptide which directs the polypeptide into the cell's secretion pathway.

As generally understood, a codon is a series of three nucleotides (triplets) that encodes a specific amino acid residue in a polypeptide chain or for the termination of translation (stop codons). There are 64 different codons (61 codons encoding for amino acids plus 3 stop codons) but only 20 different translated amino acids. The overabundance in the number of codons allows many amino acids to be encoded by more than one codon. Different organisms (and organelles) often show particular preferences or biases for one of the several codons that encode the same amino acid. The relative frequency of codon usage thus varies depending on the organism and organelle. In some instances, when expressing a heterologous gene in a host organism, it is desirable to modify the gene sequence so as to adapt to the codons used and codon usage frequency in the host. In particular, for reliable expression of heterologous genes it may be preferred to use codons that correlate with the host's tRNA level, especially the tRNA's that remain charged during starvation. In addition, codons having rare cognate tRNA's may affect protein folding and translation rate, and thus, may also be used. Genes designed in accordance with codon usage bias and relative tRNA abundance of the host are often referred to as being "optimized" for codon usage, which has been shown to increase expression level. Optimal codons also help to achieve faster translation rates and high accuracy. In general, codon optimization involves silent mutations that do not result in a change to the amino acid sequence of a protein.

Genetic elements or genetic modules may derive from the genome of natural organisms or from synthetic polynucleotides or from a combination thereof. In some embodiments, the genetic elements modules derive from different organisms. Genetic elements or modules useful for the methods described herein may be obtained from a variety of sources such as, for example, DNA libraries, BAC (bacterial artificial chromosome) libraries, de novo chemical synthesis, or excision and modification of a genomic segment. The sequences obtained from such sources may then be modified using standard molecular biology and/or recombinant DNA technology to produce polynucleotide constructs having desired modifications for reintroduction into, or construction of, a large product nucleic acid, including a modified, partially synthetic or fully synthetic genome. Exemplary methods for modification of polynucleotide sequences obtained from a genome or library include, for example, site directed mutagenesis; PCR mutagenesis; inserting, deleting or swapping portions of a sequence using restriction enzymes optionally in combination with ligation; in vitro or in vivo homologous recombination; and site-specific recombination; or various combinations thereof. In other embodiments, the genetic sequences useful in accordance with the methods described herein may be synthetic oligonucleotides or polynucleotides. Synthetic oligonucleotides or polynucleotides may be produced using a variety of methods known in the art.

In some embodiments, genetic elements share less than 99%, less than 95%, less than 90%, less than 80%, less than 70% sequence identity with a native or natural nucleic acid sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences. Other techniques for alignment are described [Doolittle, 1996]. Preferably, an alignment program that permits gaps in the sequence is utilized to align the sequences. The Smith-Waterman is one type of algorithm that permits gaps in sequence alignments [Shpaer, 1997]. Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer.

As used herein, an "ortholog" is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor. Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art would understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and *Drosophila* DNA polymerase III activity. The DNA polymerase from the first species can be considered an ortholog to either or both of the exonuclease or the polymerase from the second species and vice versa.

In contrast, as used herein, "paralogs" are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

As used herein, a "nonorthologous gene displacement" is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement may be identifiable as structurally related to a known gene encoding the referenced function, less structurally related but functionally similar genes and their corresponding gene products nevertheless still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Orthologs, paralogs and nonorthologous gene displacements can be determined by methods well known to those skilled in the art. For example, inspection of nucleic acid or amino acid sequences for two polypeptides can reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences. Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art would know what modifications can be made to the above parameters to either increase or decrease the stringency of the comparison, for example, and determine the relatedness of two or more sequences.

As used herein, the term "homolog" refers to any ortholog, paralog, nonorthologous gene, or similar gene encoding an enzyme catalyzing a similar or substantially similar metabolic reaction, whether from the same or different species.

As used herein, the phrase "homologous recombination" refers to the process in which nucleic acid molecules with similar nucleotide sequences associate and exchange nucleotide strands. A nucleotide sequence of a first nucleic acid molecule that is effective for engaging in homologous recombination at a predefined position of a second nucleic acid molecule can therefore have a nucleotide sequence that facilitates the exchange of nucleotide strands between the first nucleic acid molecule and a defined position of the second nucleic acid molecule. Thus, the first nucleic acid can generally have a nucleotide sequence that is sufficiently complementary to a portion of the second nucleic acid molecule to promote nucleotide base pairing. Homologous recombination requires homologous sequences in the two recombining partner nucleic acids but does not require any specific sequences. Homologous recombination can be used to introduce a heterologous nucleic acid and/or mutations into the host genome. Such systems typically rely on sequence flanking the heterologous nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

It should be appreciated that the nucleic acid sequence of interest or the gene of interest may be derived from the genome of natural organisms. In some embodiments, genes of interest may be excised from the genome of a natural organism or from the host genome, for example E. coli. It has been shown that it is possible to excise large genomic fragments by in vitro enzymatic excision and in vivo excision and amplification. For example, the FLP/FRT site specific recombination system and the Cre/loxP site specific recombination systems have been efficiently used for excision large genomic fragments for the purpose of sequencing [Yoon, 1998]. In some embodiments, excision and amplification techniques can be used to facilitate artificial genome or chromosome assembly. Genomic fragments may be excised from the chromosome of a chemoautotrophic organism and altered before being inserted into the host cell artificial genome or chromosome. In some embodiments, the excised genomic fragments can be assembled with engineered promoters and/or other gene expression elements and inserted into the genome of the host cell.

As used herein, the term "polypeptide" refers to a sequence of contiguous amino acids of any length. The terms "peptide," "oligopeptide," "protein" or "enzyme" may be used interchangeably herein with the term "polypeptide". In certain instances, "enzyme" refers to a protein having catalytic activities. As used herein, the terms "protein of interest," "POI," and "desired protein" refer to a polypeptide under study, or whose expression is desired by one practicing the methods disclosed herein. A protein of interest is encoded by its cognate gene of interest (GOI). The identity of a POI can be known or not known. A POI can be a polypeptide encoded by an open reading frame.

A "proteome" is the entire set of proteins expressed by a genome, cell, tissue or organism. More specifically, it is the set of expressed proteins in a given type of cells or an organism at a given time under defined conditions. Transcriptome is the set of all RNA molecules, including mRNA, rRNA, tRNA, and other non-coding RNA produced in one or a population of cells. Metabolome refers to the complete set of small-molecule metabolites (such as metabolic intermediates, hormones and other signaling molecules, and secondary metabolites) to be found within a biological sample, such as a single organism.

The term "fuse," "fused" or "link" refers to the covalent linkage between two polypeptides in a fusion protein. The polypeptides are typically joined via a peptide bond, either directly to each other or via an amino acid linker. Optionally, the peptides can be joined via non-peptide covalent linkages known to those of skill in the art.

As used herein, unless otherwise stated, the term "transcription" refers to the synthesis of RNA from a DNA template; the term "translation" refers to the synthesis of a polypeptide from an mRNA template. Translation in general is regulated by the sequence and structure of the 5' untranslated region (5'-UTR) of the mRNA transcript. One regulatory sequence is the ribosome binding site (RB S), which promotes efficient and accurate translation of mRNA. The prokaryotic RBS is the Shine-Dalgarno sequence, a purine-rich sequence of 5'-UTR that is complementary to the UCCU core sequence of the 3'-end of 16S rRNA (located within the 30S small ribosomal subunit). Various Shine-Dalgarno sequences have been found in prokaryotic mRNAs and generally lie about 10 nucleotides upstream from the AUG start codon. Activity of a RBS can be influenced by the length and nucleotide composition of the spacer separating the RBS and the initiator AUG. In eukaryotes, the Kozak sequence A/GCCACCAUGG, which lies within a short 5' untranslated region, directs translation of mRNA. An mRNA lacking the Kozak consensus sequence may also be translated efficiently in an in vitro systems if it possesses a moderately long 5'-UTR that lacks stable secondary structure. While E. coli ribosome preferentially recognizes the Shine-Dalgarno sequence, eukaryotic ribosomes (such as those found in retic lysate) can efficiently use either the Shine-Dalgarno or the Kozak ribosomal binding sites.

As used herein, the terms "promoter," "promoter element," or "promoter sequence" refer to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription.

One should appreciate that promoters have modular architecture and that the modular architecture may be altered. Bacterial promoters typically include a core promoter element and additional promoter elements. The core promoter refers to the minimal portion of the promoter required to initiate transcription. A core promoter includes a Transcription Start Site, a binding site for RNA polymerases and general transcription factor binding sites. The "transcription start site" refers to the first nucleotide to be transcribed and is designated +1. Nucleotides downstream the start site are numbered +1, +2, etc., and nucleotides upstream the start site are numbered −1, −2, etc. Additional promoter elements are located 5' (i.e., typically 30-250 bp upstream of the start site) of the core promoter and regulate the frequency of the transcription. The proximal promoter elements and the distal promoter elements constitute specific transcription factor site. In prokaryotes, a core promoter usually includes two consensus sequences, a −10 sequence or a −35 sequence, which are recognized by sigma factors (see, for example, [Hawley, 1983]). The −10 sequence (10 bp upstream from the first transcribed nucleotide) is typically about 6 nucleotides in length and is typically made up of the nucleotides adenosine and thymidine (also known as the Pribnow box). In some embodiments, the nucleotide sequence of the −10 sequence is 5'-TATAAT or may comprise 3 to 6 bases pairs of the consensus sequence. The presence of this box is essential to the start of the transcription. The −35 sequence of a core promoter is typically about 6 nucleotides in length. The nucleotide sequence of the −35 sequence is typically made up of the each of the four nucleosides. The presence of this sequence allows a very high transcription rate. In some embodiments, the nucleotide sequence of the −35 sequence is 5'-TTGACA or may comprise 3 to 6 bases pairs of the consensus sequence. In some embodiments, the −10 and the −35 sequences are spaced by about 17 nucleotides. Eukaryotic promoters are more diverse than prokaryotic promoters and may be located several kilobases upstream of the transcription starting site. Some eukaryotic promoters contain a TATA box (e.g. containing the consensus sequence TATAAA or part thereof), which is located typically within 40 to 120 bases of the transcriptional start site. One or more upstream activation sequences (UAS), which are recognized by specific binding proteins can act as activators of the transcription. Theses UAS sequences are typically found upstream of the transcription initiation site. The distance between the UAS sequences and the TATA box is highly variable and may be up to 1 kb.

As used herein, the term "vector" refers to any genetic element, such as a plasmid, phage, transposon, cosmid, chromosome, artificial chromosome, episome, virus, virion, etc., capable of replication when associated with the proper control elements and which can transfer gene sequences into or between cells. The vector may contain a marker suitable for use in the identification of transformed or transfected cells. For example, markers may provide antibiotic resistant, fluorescent, enzymatic, as well as other traits. As a second example, markers may complement auxotrophic deficiencies or supply critical nutrients not in the culture media. Types of vectors include cloning and expression vectors. As used herein, the term "cloning vector" refers to a plasmid or phage DNA or other DNA sequence which is able to replicate autonomously in a host cell and which is characterized by one or a small number of restriction endonuclease recognition sites and/or sites for site-specific recombination. A foreign DNA fragment may be spliced into the vector at these sites in order to bring about the replication and cloning of the fragment. The term "expression vector" refers to a vector which is capable of expressing of a gene that has been cloned into it. Such expression can occur after transformation into a host cell, or in IVPS systems. The cloned DNA is usually operably linked to one or more regulatory sequences, such as promoters, activator/repressor binding sites, terminators, enhancers and the like. The promoter sequences can be constitutive, inducible and/or repressible.

As used herein, the term "host" refers to any prokaryotic or eukaryotic (e.g., mammalian, insect, yeast, plant, bacterial, archaeal, avian, animal, etc.) cell or organism. The host cell can be a recipient of a replicable expression vector, cloning vector or any heterologous nucleic acid molecule. Host cells may be prokaryotic cells such as M. forum and E. coli, or eukaryotic cells such as yeast, insect, amphibian, or mammalian cells or cell lines. Cell lines refer to specific cells that can grow indefinitely given the appropriate medium and conditions. Cell lines can be mammalian cell lines, insect cell lines or plant cell lines. Exemplary cell lines can include tumor cell lines and stem cell lines. The heterologous nucleic acid molecule may contain, but is not limited to, a sequence of interest, a transcriptional regulatory sequence (such as a promoter, enhancer, repressor, and the like) and/or an origin of replication. As used herein, the terms "host," "host cell," "recombinant host" and "recombinant host cell" may be used interchangeably. For examples of such hosts, see [Sambrook, 2001].

One or more nucleic acid sequences can be targeted for delivery to target prokaryotic or eukaryotic cells via conventional transformation or transfection techniques. As used herein, the terms "transformation" and "transfection" are intended to refer to a variety of art-recognized techniques for introducing an exogenous nucleic acid sequence (e.g., DNA) into a target cell, including calcium phosphate or calcium chloride co-precipitation, DEAE-dextran-mediated transfection, lipofection, electroporation, optoporation, injection and the like. Suitable transformation or transfection media include, but are not limited to, water, $CaCl_2$, cationic polymers, lipids, and the like. Suitable materials and methods for transforming or transfecting target cells can be found in [Sambrook, 2001], and other laboratory manuals. In certain instances, oligo concentrations of about 0.1 to about 0.5 micromolar (per oligo) can be used for transformation or transfection.

As used herein, the term "marker" or "reporter" refers to a gene or protein that can be attached to a regulatory sequence of another gene or protein of interest, so that upon expression in a host cell or organism, the reporter can confer certain characteristics that can be relatively easily selected, identified and/or measured. Reporter genes are often used as an indication of whether a certain gene has been introduced into or expressed in the host cell or organism. Examples of commonly used reporters include: antibiotic resistance genes, auxotropic markers, β-galactosidase (encoded by the bacterial gene lacZ), luciferase (from lightning bugs), chloramphenicol acetyltransferase (CAT; from bacteria), GUS (β-glucuronidase; commonly used in plants) and green fluorescent protein (GFP; from jelly fish). Reporters or markers can be selectable or screenable. A selectable marker (e.g., antibiotic resistance gene, auxotropic marker) is a gene confers a trait suitable for artificial selection; typically host cells expressing the selectable marker is protected from a selective agent that is toxic or inhibitory to cell growth. A screenable marker (e.g., gfp, lacZ) generally allows researchers to distinguish between wanted cells (expressing the marker) and unwanted cells (not expressing the marker or expressing at insufficient level).

As used herein, the term "chemotroph" or "chemotrophic organism" refers to organisms that obtain energy from the oxidation of electron donors in their environment. As used herein, the term "chemoautotroph" or "chemoautotrophic organism" refers to organisms that produce complex organic compounds from simple inorganic carbon molecules using oxidation of inorganic compounds as an external source of energy. In contrast, "heterotrophs" or "heterotrophic organisms" refers to organisms that must use organic carbon for growth because they cannot convert inorganic carbon into organic carbon. Instead, heterotrophs obtain energy by breaking down the organic molecules they consume. Organisms that can use a mix of different sources of energy and carbon are mixotrophs or mixotrophic organisms which can alternate, e.g., between autotrophy and heterotrophy, between phototrophy and chemotrophy, between lithotrophy and organotrophy, or a combination thereof, depending on environmental conditions.

As used herein, the term "inorganic energy source", "electron donor", "source of reducing power" or "source of reducing equivalents" refers to chemical species, such as formate, formic acid, methane, carbon monoxide, carbonyl sulfide, carbon disulfide, hydrogen sulfide, bisulfide anion, thiosulfate, elemental sulfur, molecular hydrogen, ferrous iron, ammonia, cyanide ion, and/or hydrocyanic acid, with high potential electron(s) that can be donated to another chemical species with a concomitant release of energy (a process by which the electron donor undergoes "oxidation" and the other, recipient chemical species or "electron acceptor" undergoes "reduction"). Inorganic energy sources are generally but not always present external to the cell or biological organism. The term "reducing cofactor" refers to intracellular redox and energy carriers, such as NADH, NADPH, ubiquinol, menaquinol, cytochromes, flavins and/or ferredoxin, that can donate high energy electrons in reduction-oxidation reactions. The terms "reducing cofacor", "reduced cofactor" and "redox cofactor" can be used interchangeably.

As used herein, the term "inorganic carbon" or "inorganic carbon compound" refers to chemical species, such as carbon dioxide, carbon monoxide, formate, formic acid, carbonic acid, bicarbonate, carbon monoxide, carbonyl sulfide, carbon disulfide, cyanide ion and/or hydrocyanic acid, that contains carbon but lacks the carbon-carbon bounds characteristic of organic carbon compounds. Inorganic carbon may be present in a gaseous form, such as carbon monoxide or carbon dioxide, or may be present in a liquid form, such as formate.

As used herein, the term "central metabolite" refers to organic carbon compounds, such as acetyl-coA, pyruvate, pyruvic acid, 3-hydropropionate, 3-hydroxypropionic acid, glycolate, glycolic acid, glyoxylate, glyoxylic acid, dihydroxyacetone phosphate, glyceraldehyde-3-phosphate, malate, malic acid, lactate, lactic acid, acetate, acetic acid, citrate and/or citric acid, that can be converted into carbon-based products of interest by a host cell or organism. Central metabolites are generally restricted to those reduced organic compounds from which all or most cell mass components can be derived in a given host cell or organism. In some embodiments, the central metabolite is also the carbon product of interest in which case no additional chemical conversion is necessary.

Reference to a particular chemical species includes not only that species but also water-solvated forms of the species, unless otherwise stated. For example, carbon dioxide includes not only the gaseous form ($CO_2$) but also water-solvated forms, such as bicarbonate ion.

As used herein, the term "biosynthetic pathway" or "metabolic pathway" refers to a set of anabolic or catabolic biochemical reactions for converting (transmuting) one chemical species into another. Anabolic pathways involve constructing a larger molecule from smaller molecules, a process requiring energy. Catabolic pathways involve breaking down of larger molecules, often releasing energy. As used herein, the term "energy conversion pathway" refers to a metabolic pathway that transfers energy from an inorganic energy source to a reducing cofactor. The term "carbon fixation pathway" refers to a biosynthetic pathway that converts inorganic carbon, such as carbon dioxide, bicarbonate or formate, to reduced organic carbon, such as one or more carbon product precursors. The term "carbon product biosynthetic pathway" refers to a biosynthetic pathway that converts one or more carbon product precursors to one or more carbon based products of interest.

As used herein, the term "engineered chemoautotroph" or "engineered chemoautotrophic organism" refers to organisms that have been genetically engineered to convert inorganic carbon compounds, such as carbon dioxide or formate, to organic carbon compounds using energy derived from inorganic energy sources. The genetic modifications necessary to produce an engineered chemoautotroph comprise the introduction of heterologous energy conversion pathway(s) and/or carbon fixation pathway(s) into the host organism. The host organism can be originally heterotrophic organism. As used herein, an engineered chemoautotroph need not derive its organic carbon compounds solely from inorganic carbon and need not derive its energy solely from inorganic energy sources. The term engineered chemoautotroph may also be used to refer to originally autotrophic or mixotrophic organisms that have been genetically engineered to include one or more energy conversion, carbon fixation and/or carbon product biosynthetic pathways in addition or instead of its endogenous autotrophic capability. The term "engineer," "engineering" or "engineered," as used herein, refers to genetic manipulation or modification of biomolecules such as DNA, RNA and/or protein, or like technique commonly known in the biotechnology art.

As used herein, the term "carbon based products of interest" refers to include alcohols such as ethanol, propanol, isopropanol, butanol, octanol, fatty alcohols, fatty acid esters, wax esters; hydrocarbons and alkanes such as propane, octane, diesel, Jet Propellant 8, polymers such as terephthalate, 1,3-propanediol, 1,4-butanediol, polyols, polyhydroxyalkanoates (PHAs), polyhydroxybutyrates (PHBs), acrylate, adipic acid, epsilon-caprolactone, isoprene, caprolactam, rubber; commodity chemicals such as lactate, docosahexaenoic acid (DHA), 3-hydroxypropionate, γ-valerolactone, lysine, serine, aspartate, aspartic acid, sorbitol, ascorbate, ascorbic acid, isopentenol, lanosterol, omega-3 DHA, lycopene, itaconate, 1,3-butadiene, ethylene, propylene, succinate, citrate, citric acid, glutamate, malate, 3-hydroxyprionic acid (HPA), lactic acid, THF, gamma butyrolactone, pyrrolidones, hydroxybutyrate, glutamic acid, levulinic acid, acrylic acid, malonic acid; specialty chemicals such as carotenoids, isoprenoids, itaconic acid; biological sugars such as glucose, fructose, lactose, sucrose, starch, cellulose, hemicellulose, glycogen, xylose, dextrose, galactose, uronic acid, maltose, polyketides, or glycerol; central metabolites, such as acetyl-coA, pyruvate, pyruvic acid, 3-hydropropionate, 3-hydroxypropionic acid, glycolate, glycolic acid, glyoxylate, glyoxylic acid, dihydroxyacetone phosphate, glyceraldehyde-3-phosphate, malate, malic acid, lactate, lactic acid, acetate, acetic acid, citrate and/or citric acid, from which other carbon products can be made; pharmaceuticals and pharmaceutical intermediates such as 7-aminodesacetoxycephalosporonic acid, cephalosporin, erythromycin, polyketides, statins, paclitaxel, docetaxel, terpenes, peptides, steroids, omega fatty acids and other such suitable products of interest. Such products are useful in the context of biofuels, industrial and specialty chemicals, as intermediates used to make additional products, such as nutritional supplements, neutraceuticals, polymers, paraffin replacements, personal care products and pharmaceuticals.

As used herein, the term "hydrocarbon" referes a chemical compound that consists of the elements carbon, hydrogen and optionally, oxygen. "Surfactants" are substances capable of reducing the surface tension of a liquid in which they are dissolved. They are typically composed of a water-soluble head and a hydrocarbon chain or tail. The water soluble group is hydrophilic and can either be ionic or nonionic, and the hydrocarbon chain is hydrophobic. The term "biofuel" is any fuel that derives from a biological source.

The accession numbers provided throughout this description are derived from the NCBI database (National Ceter for Biotechnology Information) maintained by the National Institute of Health, USA. The accession numbers are provided in the database on Aug. 1, 2011. The Enzyme Classification Numbers (E.C.) provided throughout this description are derived from the KEGG Ligand database, maintained by the Kyoto Encyclopedia of Genes and Genomics, sponsored in part by the University of Tokyo. The E.C. numbers are provided in the database on Aug. 1, 2011.

Other terms used in the fields of recombinant nucleic acid technology, microbiology, metabolic engineering, and molecular and cell biology as used herein will be generally understood by one of ordinary skill in the applicable arts.

Electrolytic/Electrochemical Production of Hydrogen and Formate

Hydrogen gas and formate can be produced via the electrolysis of $H_2O$ and the electrochemical conversion $CO_2$, respectively [Whipple, 2010]. Each has advantages and disadvantages as inorganic energy sources for the engineered chemoautotroph of the present invention.

Hydrogen gas mixtures with air are explosive across a wide range of hydrogen compositions. Hence, use of hydrogen gas as an inorganic energy source and oxygen gas as the terminal electron acceptor of an engineered chemoautotroph must necessarily be set up to cope with the resulting safety risk. To address this challenge, the reactor or fermentation conditions may be kept substantially anaerobic and alternative electron acceptors, such as nitrate, may be used.

Hydrogen is a gas with low water solubility which creates mass transfer limitations when using hydrogen as an inorganic energy source for engineered chemoautotrophs (biological systems are aqueous). At large reactor or fermentor scales, high rates of mass transfer from the gas to liquid phases is challenging (Example 11). There are new technologies being developed to address this issue [U.S. Pat. No. 7,923,227]. Formate, due to its higher solubility in $H_2O$, does not have this problem (Example 11).

The energy efficiency of electrolysis for production of hydrogen or electrochemical conversion of carbon dioxide impacts the overall energy efficiency of a bio-manufacturing process using an engineered chemoautotroph of the present invention. Electrolyzers achieve overall energy efficiencies of 56-73% at current densities of 110-300 mA/cm$^2$ (alkaline electrolyzers) or 800-1600 mA/cm$^2$ (PEM electrolyzers) [Whipple, 2010]. In contrast, electrochemical systems to date have achieved moderate energy efficiencies or high current densities but not at the same time. Hence, additional technology improvements are needed for electrochemical production of formate.

Organisms or Host Cells for Engineering

The host cell or organism, as disclosed herein, may be chosen from eukaryotic or prokaryotic systems, such as bacterial cells (Gram-negative or Gram-positive), archaea, yeast cells (for example, *Saccharomyces cereviseae* or *Pichia pastoris*), animal cells and cell lines (such as Chinese hamster ovary (CHO) cells), plant cells and cell lines (such as *Arabidopsis* T87 cells and Tabacco BY-2 cells), and/or insect cells and cell lines. Suitable cells and cell lines can also include those commonly used in laboratories and/or industrial applications. In some embodiments, host cells/organisms can be selected from *Escherichia coli, Glucono-* bacter oxydans, Gluconobacter Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Mesoplasmaflorum, Micrococcus sp. CCM825, Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas fluorescens, Pseudomonas Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus sp. ATCC 15592, Rhodococcus sp. ATCC 19070, Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus subtilis, Bacillus pumilus, Bacillus circulans, Bacillus thiaminolyticus, Escherichia freundii, Microbacterium ammoniaphilum, Serratia marcescens, Salmonella enterica, Salmonella typhimurium, Salmonella schottmulleri, Xanthomonas citri, Saccharomyces spp. (e.g., Saccharomyces cerevisiae, Saccharomyces bayanus, Saccharomyces boulardii, Schizosaccharomyces pombe), Arabidopsis thaliana, Nicotiana tabacum, CHO cells, 3T3 cells, COS-7 cells, DuCaP cells, HeLa cells, LNCap cells, THP1 cells, 293-T cells, Baby Hamster Kidney (BHK) cells, HKB cells, hybridoma cells, as well as bacteriophage, baculovirus, adenovirus, or any modifications and/or derivatives thereof. In certain embodiments, the genetically modified host cell is a Mesoplasma florum, E. coli, yeast, archaea, mammalian cells and cell lines, green plant cells and cell lines, or algae. Non-limiting examples of algae that can be used in this aspect of the invention include: Botryococcus braunii; Neochloris oleoabundans; Scenedesmus dimorphus; Euglena gracilis; Nannochloropsis salina; Dunaliella tertiolecta, Tetraselmis chui; Isochrysis galbana; Phaeodactylum tricornutum; Pleurochrysis carterae; Prymnesium parvum; Tetraselmis suecica; or Spirulina species. Those skilled in the art would understand that the genetic modifications, including metabolic alterations exemplified herein, are described with reference to a suitable host organism such as E. coli and their corresponding metabolic reactions or a suitable source organism for desired nucleic acids such as genes for a desired metabolic pathway. However, given the complete genome sequencing of a wide variety of organisms and the high level of skill in the area of genomics, those skilled in the art would readily be able to apply the teachings and guidance provided herein to essentially all other host cells and organisms. For example, the E. coli metabolic modifications exemplified herein can readily be applied to other species by incorporating the same or analogous encoding nucleic acid from species other than the referenced species. Such genetic modifications include, for example, genetic alterations of species homologs, in general, and in particular, orthologs, paralogs or nonorthologous gene displacements.

In certain embodiments, the host cell or organism is a microorganism which includes prokaryotic and eukaryotic microbial species from the Domains Archaea, Bacteria and Eucarya, the latter including yeast and filamentous fungi, protozoa, algae, or higher Protista. The terms "microbial organisms", "microbial cells" and "microbes" are used interchangeably with the term microorganism.

In certain embodiments, host microbial organisms can be selected from, and the engineered microbial organisms generated in, for example, bacteria, yeast, fungus or any of a variety of other microorganisms applicable to fermentation processes. Exemplary bacteria include species selected from Escherichia coli, Klebsiella oxytoca, Anaerobiospirillum succiniciproducens, Acetobacter aceti, Actinobacillus succinogenes, Mannheimia succiniciproducens, Mesoplasma florum, Rhizobium etli, Bacillus subtilis, Corynebacterium glutamicum, Gluconobacter oxydans, Zymomonas mobilis, Lactococcus lactis, Lactobacillus plantarum, Cupriavidus necator (formerly Ralstonia eutropha), Streptomyces coelicolor, Clostridium ljungdahlii, Clostridium thermocellum, Clostridium acetobutylicum, Pseudomonas fluorescens, and Pseudomonas putida. Exemplary yeasts or fungi include species selected from Saccharomyces cerevisiae, Schizosaccharomyces pombe, Kluyveromyces lactis, Kluyveromyces marxianus, Aspergillus terreus, Aspergillus niger, Penicillium chrysogenum and Pichia pastoris. E. coli is a particularly useful host organisms since it is a well characterized microbial organism suitable for genetic engineering. Other particularly useful host organisms include yeast such as Saccharomyces cerevisiae.

In various aspects of the invention, the cells are genetically engineered or metabolically evolved, for example, for the purposes of optimized energy conversion and/or carbon fixation. The terms "metabolically evolved" or "metabolic evolution" relates to growth-based selection (metabolic evolution) of host cells that demonstrate improved growth (cell yield). Yet other suitable organisms include synthetic cells or cells produced by synthetic genomes [US Patent Publication Number 2007/0264688] and cell-like systems or synthetic cells [US Patent Publication Number 2007/0269862].

Exemplary genomes and nucleic acids include full and partial genomes of a number of organisms for which genome sequences are publicly available and can be used with the disclosed methods, such as, but not limited to, Aeropyrum pernix; Agrobacterium tumefaciens; Anabaena; Anopheles gambiae; Apis mellifera; Aquifex aeolicus; Arabidopsis thaliana; Archaeoglobus fulgidus; Ashbya gossypii; Bacillus anthracis; Bacillus cereus; Bacillus halodurans; Bacillus licheniformis; Bacillus subtilis; Bacteroides fagilis; Bacteroides thetaiotaomicron; Bartonella henselae; Bartonella quintana; Bdellovibrio bacteriovirus; Bifidobacterium longum; Blochmannia floridanus; Bordetella bronchiseptica; Bordetella parapertussis; Bordetella pertussis; Borrelia burgdorferi; Bradyrhizobium japonicum; Brucella melitensis; Brucella suis; Buchnera aphidicola; Burkholderia mallei; Burkholderia pseudomallei; Caenorhabditis briggsae; Caenorhabditis elegans; Campylobacter jejuni; Candida glabrata; Canis familiaris; Caulobacter crescentus; Chlamydia muridarum; Chlamydia trachomatis; Chlamydophila caviae; Chlamydophila pneumoniae; Chlorobium tepidum; Chromobacterium violaceum; Ciona intestinalis; Clostridium acetobutylicum; Clostridium perfringens; Clostridium tetania Corynebacterium diphtheriae; Corynebacterium efficiens; Coxiella burnetii; Cryptosporidium hominis; Cryptosporidium parvum; Cyanidioschyzon merolae; Debaryomyces hansenii; Deinococcus radiodurans; Desulfotalea psychrophila; Desulfovibrio vulgaris; Drosophila melanogaster; Encephalitozoon cuniculi; Enterococcus faecalis; Erwinia carotovora; Escherichia coli; Fusobacterium nucleatum; Gallus gallus; Geobacter sulfurreducens; Gloeobacter violaceus; Guillardia theta; Haemophilus ducreyi; Haemophilus influenzae; Halobacterium; Helicobacter hepaticus; Helicobacter pylori; Homo sapiens; Kluyveromyces waltii; Lactobacillus johnsonii; Lactobacillus plantarum; Legionella pneumophila; Leifsonia xyli; Lactococcus lactis; Leptospira interrogans; Listeria innocua; Listeria monocytogenes; Magnaporthe grisea; Mannheimia succiniciproducens; Mesoplasma florum; Mesorhizobium loti; Methanobacterium thermoautotrophicum; Methanococcoides burtonii; Methanococcus jannaschii; Methanococcus maripaludis; Methanogenium frigidum; Methanopyrus kandleri; Methanosarcina acetivorans; Methanosarcina mazei; Methylococcus capsulatus; Mus musculus; Mycobacterium Bovis; Mycobacterium leprae; Mycobacterium paratuberculosis; Mycobacterium tuberculosis; Mycoplasma gallisepticum; Mycoplasma genitalium; Mycoplasma mycoides; Mycoplasma penetrans; Mycoplasma pneumoniae; Mycoplasma pulmonis; Mycoplasma mobile; Nanoarchaeum equitans; Neisseria meningitidis; Neurospora crassa; Nitrosomonas europaea; Nocardia farcinica; Oceanobacillus iheyensis; Onions yellows phytoplasma; Oryza sativa; Pan troglodytes; Pasteurella multocida; Phanerochaete chrysosporium; Photorhabdus luminescens; Picrophilus torridus; Plasmodium falciparum; Plasmodium yoelii yoelii; Populus trichocarpa; Porphyromonas gingivalis Prochlorococcus marinus; Propionibacterium acnes; Protochlamydia amoebophila; Pseudomonas aeruginosa; Pseudomonas putida; Pseudomonas syringae; Pyrobaculum aerophilum; Pyrococcus abyssi; Pyrococcus furiosus; Pyrococcus horikoshii; Pyrolobus fumarii; Ralstonia solanacearum; Rattus norvegicus; Rhodopirellula baltica; Rhodopseudomonas palustris; Rickettsia conorii; Rickettsia typhi; Rickettsia prowazekii; Rickettsia sibirica; Saccharomyces cerevisiae; Saccharomyces bayanus; Saccharomyces boulardii; Saccharopolyspora erythraea; Schizosaccharomyces pombe; Salmonella enterica; Salmonella typhimurium; Schizosaccharomyces pombe; Shewanella oneidensis; Shigella flexneria; Sinorhizobium meliloti; Staphylococcus aureus; Staphylococcus epidermidis; Streptococcus agalactiae; Streptococcus mutans; Streptococcus pneumoniae; Streptococcus pyogenes; Streptococcus thermophilus; Streptomyces avermitilis; Streptomyces coelicolor; Sulfolobus solfataricus; Sulfolobus tokodaii; Synechococcus; Synechoccous elongates, Synechocystis; Takifugu rubripes; Tetraodon nigroviridis; Thalassiosira pseudonana; Thermoanaerobacter tengcongensis; Thermoplasma acidophilum; Thermoplasma volcanium; Thermosynechococcus elongatus; Thermotagoa maritima; Thermus thermophilus; Treponema denticola; Treponemapallidum; Tropheryma whipplei; Ureaplasma urealyticum; Vibrio cholerae; Vibrio parahaemolyticus; Vibrio vulnificus; Wigglesworthia glossinidia; Wolbachia pipientis; Wolinella succinogenes; Xanthomonas axonopodis; Xanthomonas campestris; Xylella fastidiosa; Yarrowia lipolytica; Yersinia pseudotuberculosis; and Yersinia pestis nucleic acids.

In certain embodiments, sources of encoding nucleic acids for enzymes for an energy conversion pathway, carbon fixation pathway or carbon product biosynthetic pathway can include, for example, any species where the encoded gene product is capable of catalyzing the referenced reaction. Exemplary species for such sources include, for example, Aeropyrum pernix; Aquifex aeolicus; Aquifex pyrophilus; Candidatus Arcobacter sulfidicus; Candidatus Endoriftia persephone; Candidatus Nitrospira defluvii; Chlorobium limicola; Chlorobium tepidum; Clostridium pasteurianum; Desulfobacter hydrogenophilus; Desulfurobacterium thermolithotrophum; Geobacter metallireducens; Halobacterium sp. NRC-1; Hydrogenimonas thermophila; Hydrogenivirga strain 128-5-R1; Hydrogenobacter thermophilus; Hydrogenobaculum sp. Y04AAS1; Lebetimonas acidiphila Pd55$^T$; Leptospirillum ferriphilum; Leptospirillum ferrodiazotrophum; Leptospirillum rubarum; Magnetococcus marinus; Magnetospirillum magneticum; Mycobacterium bovis; Mycobacterium tuberculosis; Methylobacterium nodulans; Nautilia lithotrophica; Nautilia profundicola; Nautilia sp. strain AmN; Nitratifractor salsuginis; Nitratiruptor sp. strain SB155-2; Persephonella marina; Rimcaris exoculata episymbiont; Streptomyces avermitilis; Streptomyces coelicolor; Sulfolobus avermitilis; Sulfolobus solfataricus; Sulfolobus tokodaii; Sulfurihydrogenibium azorense; Sulfurihydrogenibium sp. Y03AOP1; Sulfurihydrogenibium yellowstonense; Sulfurihydrogenibium subterraneum; Sulfurimonas autotrophica; Sulfurimonas denitrificans; Sulfurimonas paralvinella; Sulfurovum lithotrophicum; Sulfurovum sp. strain NBC37-1; Thermocrinis ruber; Thermovibrio ammonificans; Thermovibrio ruber; Thioreductor micatisoli; Nostoc sp. PCC 7120; Acidithiobacillus ferrooxidans; Allochromatium vinosum; Aphanothece halophytica; Oscillatoria limnetica; Rhodobacter capsulatus; Thiobacillus denitrificans; Cupriavidus necator (formerly Ralstonia eutropha), Methanosarcina barkeri; Methanosarcia mazei; Methanococcus maripaludis; Mycobacterium smegmatis; Burkholderia stabilis; Candida boidinii; Candida methylica; Pseudomonas sp. 101; Methylcoccus capsulatus; Mycobacterium gastri; Cenarchaeum symbiosum; Chloroflexus aurantiacus; Erythrobacter sp. NAP 1; Metallosphaera sedula; gamma proteobacterium NOR51-B; marine gamma proteobacterium HTCC2080; Nitrosopumilus maritimus; Roseiflexus castenholzii; Synechococcus elongatus; and the like, as well as other exemplary species disclosed herein or available as source organisms for corresponding genes. However, with the complete genome sequence publicly available for now more than 4400 species (including viruses), including 1701 microbial genomes and a variety of yeast, fungi, plant, and mammalian genomes, the identification of genes encoding the requisite energy conversion, carbon fixation or carbon product biosynthetic activity for one or more genes in related or distant species, including for example, homologs, orthologs, paralogs and nonorthologous gene displacements of known genes, and the replacement of gene homolog either within an particular engineered chemoautotroph or between different host cells for the engineered chemoautotroph is routine and well known in the art. Accordingly, the metabolic modifications enabling chemoautotrophic growth and production of carbon-based products described herein with reference to a particular organism such as E. coli can be readily applied to other microorganisms, including prokaryotic and eukaryotic organisms alike. Given the teachings and guidance provided herein, those skilled in the art would know that a metabolic modification exemplified in one organism can be applied equally to other organisms.

In some instances, such as when an alternative energy conversion, carbon fixation or carbon product biosynthetic pathway exists in an unrelated species, chemoautotrophic growth and production of carbon-based products can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art would understand that the actual gene usage between different organisms may differ. However, given the teachings and guidance provided herein, those skilled in the art also would understand that the teachings and methods of the invention can be applied to all microbial organisms using the cognate metabolic modifications to those exemplified herein to construct a microbial organism in a species of interest that would produce carbon-based products of interest from inorganic energy and inorganic carbon.

It should be noted that various engineered strains and/or mutations of the organisms or cell lines discussed herein can also be used.

Methods for Identification and Selection of Candidate Enzymes for a Metabolic Activity of Interest In one aspect, the present invention provides a method for identifying candidate proteins or enzymes of interest capable of performing a desired metabolic activity. Leveraging the exponential growth of gene and genome sequence databases and the availability of commercial gene synthesis at reasonable cost, Bayer and colleagues adopted a synthetic metagenomics approach to bioinformatically search sequence databases for homologous or similar enzymes, computationally optimize their encoding gene sequences for heterologous expression, synthesize the designed gene sequence, clone the synthetic gene into an expression vector and screen the resulting enzyme for a desired function in E. coli or yeast [Bayer, 2009]. However, depending on the metabolic activity or protein of interest, there can be thousands of putative homologs in the publicly available sequence databases. Thus, it can be experimentally challenging or in some cases infeasible to synthesize and screen all possible homologs at reasonable cost and within a reasonable timeframe. To address this challenge, in one aspect, this invention provides an alternate method for identifying and selecting candidate protein sequences for a metabolic activity of interest. The method comprises the following steps. First, for a desired metabolic activity, such as an enzyme-catalyzed step in an energy conversion, carbon fixation or carbon product biosynthetic pathway, one or more enzymes of interest are identified. Typically, the enzyme(s) of interest have been previously experimentally validated to perform the desired activity, for example in the published scientific literature. In some embodiments, one or more of the enzymes of interest has been heterologously expressed and experimentally demonstrated to be functional. Second, a bioinformatic search is performed on protein classification or grouping databases, such as Clusters of Orthologous Groups (COGs) [Tatusov, 1997; Tatusov, 2003], Entrez Protein Clusters (ProtClustDB) [Klimke, 2009] and/or InterPro [Zdobnov, 2001], to identify protein groupings that contain one or more of the enzyme(s) of interest (or closely related enzymes). If the enzyme(s) of interest contain multiple subunits, then the protein corresponding to a single subunit, for example the catalytic subunit or the largest subunit, is selected as being representative of the enzyme(s) of interest for the purposes of bioinformatic analysis. Third, a systematic, expert-guided search is then performed to identify which database groupings are likely to contain a majority of members whose metabolic activity is the same or similar as the protein(s) of interest. Fourth, the list of NCBI Protein accession numbers corresponding to every members of each selected database grouping is then compiled and the corresponding protein sequences are downloaded from the sequence databases. Protein sequences available from sources other than the public sequence databases may be added to this set. Fifth, optionally, one or more outgroup protein sequences are identified and added to the set. Outgroup proteins are proteins which may share some functional, structural, or sequence similarities to the model enzyme(s) but lack an essential feature of the enzyme(s) of interest or desired metabolic activity. For example, the enzyme flavocytochrome c (E.C. 1.8.2.3) is similar to sulfide-quinone oxidoreductase (E.C. 1.8.5.4) in that it oxidizes hydrogen sulfide but it reduces cytochrome c instead of ubiquinone and thus offers a useful outgroup during bioinformatic analysis of sulfide-quinone oxidoreductases. Sixth, the complete set of protein sequences are aligned with an sequence alignment program capable of aligning large numbers of sequences, such as MUSCLE [Edgar, 2004a; Edgar, 2004b]. Seventh, a tree is drawn based on the resulting MUSCLE alignment via methods known to those skilled in the art, such as neighbor joining [Saitou, 1987] or UPGMA [Sokal, 1958; Murtagh, 1984]. Eighth, different clades are selected from the tree so that the number of clades equals the desired number of proteins for screening. Finally, one protein from each clade is selected for gene synthesis and functional screening based on the following heuristics Preference is given to proteins that have been heterologously expressed and experimentally demonstrated to have the desired metabolic activity.

Preference is given to proteins that have been biochemically characterized to have the desired metabolic activity previously.

Preference is given to proteins from source organisms for which there is strong experimental or genomic evidence that the organism has the desired metabolic activity.

Preference is given to proteins in which the key catalytic, binding and/or other signature residues are conserved with respect to the protein(s) of interest.

Preference is given to protein from source organisms whose optimal growth temperature is similar to that of the host cell or organism. For example, if the host cell is a mesophile, then the source organism is also a mesophile.

Therefore, in constructing the engineered chemoautotroph of the invention, those skilled in the art would understand that by applying the teaching and guidance provided herein, it is possible to replace or augment particular genes within a metabolic pathway, such as an energy conversion pathway, a carbon fixation pathway, and/or a carbon product biosynthetic pathway, with homologs identified using the methods described here, whose gene products catalyze a similar or substantially similar metabolic reaction. Such modifications can be done, for example, to increase flux through a metabolic pathway (for example, flux of energy or carbon), to reduce accumulation of toxic intermediates, to improve the kinetic properties of the pathway, and/or to otherwise optimize the engineered chemoautotroph. Indeed, gene homologs for a particular metabolic activity may be preferable when conferring chemoautotrophic capability on a different host cell or organism.

Methods for Design of Nucleic Acids Encoding Enzymes for Heterologous Expression In one aspect, the present invention provides a computer program product for designing a nucleic acid that encodes a protein or enzyme of interest that is codon optimized for the host cell or organism (the target species). The program can reside on a hardware computer readable storage medium and having a plurality of instructions which, when executed by a processor, cause the processor to perform operations. The program comprises the following operations. At each amino acid position of the protein of interest, the codon is selected in which the rank order codon usage frequency of that codon in the target species is the same as the rank order codon usage frequency of the codon that occurs at that position in the source species gene. To select the desired codon at each amino acid position, both the genetic code (the mapping of codons to amino acids [Jukes, 1993]) and codon frequency table (the frequency with which each synonymous codon occurs in a genome or genome [Grantham, 1980]) for both the source and target species are needed. For source species for which a complete genome sequence is available, the usage frequency for each codon may be calculate simply by summing the number of instances of that codon in all annotated coding sequences, dividing by the total number of codons in that genome, and then multiplying by 1000. For source species for which no complete genome is available, the usage frequency can be computed based on any available coding sequences or by using the codon frequency table of a closely related organism. The program then preferably standardizes the start codon to ATG, the stop codon to TAA, and the second and second last codons to one of twenty possible codons (one per amino acid). The program then subjects the codon optimized nucleic acid sequence to a series of checks to improve the likelihood that the sequence can be synthesized via commercial gene synthesis and subsequently manipulated via molecular biology [Sambrook, 2001] and DNA assembly methods [Knight, 2003; Knight, 2007; WO/2010/070295]. These checks comprise identifying if key restriction enzyme recognition sites used in a DNA assembly standard or DNA assembly method are present; if hairpins whose GC content exceeds a threshold percentage, such as 60%, and whose length exceeds a threshold number of base pairs, such as 10, are present; if sequence repeats are present; if any subsequence between 100 and 150 nucleotides in length exceeds a threshold GC content, such as 65%; if G or C homopolymers greater than 5 nucleotides in length are present; and, optionally, if any sequence motifs are present that might give rise to spurious transposon insertion sites, transcriptional or translational initiation or termination, mRNA secondary structure, RNase cleavage, and/or transcription factor binding. If the codon optimized nucleic acid sequence fails any of these checks, the program then iterates through all possible synonymous mutations and designs a new nucleic acid sequence that both passes all checks and minimizes the difference in codon frequencies between the original and new nucleic acid sequence.

Various implementations of the systems and techniques described here can be realized in digital electronic circuitry, integrated circuitry, specially designed ASICs (application-specific integrated circuits), computer hardware, firmware, software, and/or combinations thereof. These various implementations can include one or more computer programs that are executable and/or interpretable on a programmable system including at least one programmable processor, which may be special or general purpose, coupled to receive data and instructions from, and to transmit data and instructions to, a storage system, at least one input device, and at least one output device. Such computer programs (also known as programs, software, software applications or code) may include machine instructions for a programmable processor, and may be implemented in any form of programming language, including high-level procedural and/or object-oriented programming languages, and/or in assembly/machine languages. A computer program may be deployed in any form, including as a stand-alone program, or as a module, component, subroutine, or other unit suitable for use in a computing environment. A computer program may be deployed to be executed or interpreted on one computer or on multiple computers at one site, or distributed across multiple sites and interconnected by a communication network.

A computer program may, in an embodiment, be stored on a computer readable storage medium. A computer readable storage medium stores computer data, which data can include computer program code that is executed and/or interpreted by a computer system or processor. By way of example, and not limitation, a computer readable medium may comprise computer readable storage media, for tangible or fixed storage of data, or communication media for transient interpretation of code-containing signals. Computer readable storage media, may refer to physical or tangible storage (as opposed to signals) and may include without limitation volatile and non-volatile, removable and non-removable media implemented in any method or technology for the tangible storage of information such as computer-readable instructions, data structures, program modules or other data. Computer readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer or processor.

Figure 2:
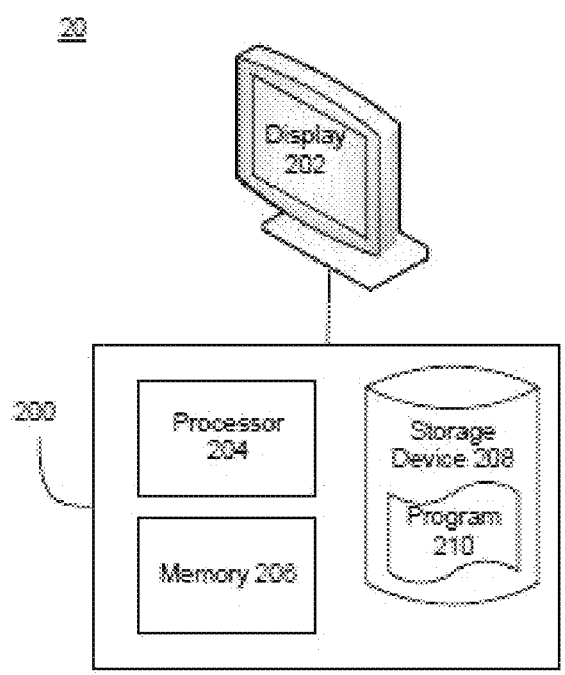
FIG. 2 is a block diagram of a computing architecture.

FIG. 2 shows a block diagram of a generic processing architecture, which may execute software applications and processes. Computer processing device 200 may be coupled to display 202 for graphical output. Processor 204 may be a computer processor capable of executing software. Typical examples of processor 204 are general-purpose computer processors (such as Intel® or AMD® processors), ASICs, microprocessors, any other type of processor, or the like. Processor 204 may be coupled to memory 206, which may be a volatile memory (e.g. RAM) storage medium for storing instructions and/or data while processor 204 executes. Processor 204 may also be coupled to storage device 208, which may be a non-volatile storage medium such as a hard drive, FLASH drive, tape drive, DVDROM, or similar device. Program 210 may be a computer program containing instructions and/or data, and may be stored on storage device 208 and/or in memory 206, for example. In a typical scenario, processor 204 may load some or all of the instructions and/or data of program 210 into memory 206 for execution.

Program 210 may be a computer program capable of performing the processes and functions described above. Program 210 may include various instructions and subroutines, which, when loaded into memory 206 and executed by processor 204 cause processor 204 to perform various operations, some or all of which may effectuate the methods, processes, and/or functions associated with the presently disclosed embodiments.

Although not shown, computer processing device 200 may include various forms of input and output. The I/O may include network adapters, USB adapters, Bluetooth radios, mice, keyboards, touchpads, displays, touch screens, LEDs, vibration devices, speakers, microphones, sensors, or any other input or output device for use with computer processing device 200.

Methods for Expression of Heterologous Enzymes

Composite nucleic acids can be constructed to include one or more energy conversion, carbon fixation and optionally carbon product biosynthetic pathway encoding nucleic acids as exemplified herein. The composite nucleic acids can subsequently be transformed or transfected into a suitable host organism for expression of one or more proteins of interest. Composite nucleic acids can be constructed by operably linking nucleic acids encoding one or more standardized genetic parts with protein(s) of interest encoding nucleic acids that have also been standardized. Standardized genetic parts are nucleic acid sequences that have been refined to conform to one or more defined technical standards, such as an assembly standard [Knight, 2003; Shetty, 2008; Shetty, 2011]. Standardized genetic parts can encode transcriptional initiation elements, transcriptional termination elements, translational initiation elements, translational termination elements, protein affinity tags, protein degradation tags, protein localization tags, selectable markers, replication elements, recombination sites for integration onto the genome, and more. Standardized genetic parts have the advantage that their function can be independently validated and characterized [Kelly, 2009] and then readily combined with other standardized parts to produce functional nucleic acids [Canton, 2008]. By mixing and matching standardized genetic parts encoding different expression control elements with nucleic acids encoding proteins of interest, transforming the resulting nucleic acid into a suitable host cell and functionally screening the resulting engineered cell, the process of both achieving soluble expression of proteins of interest and validating the function of those proteins is made dramatically faster. For example, the set of standardized parts might comprise constitutive promoters of varying strengths [Davis, 2011], ribosome binding sites of varying strengths [Anderson, 2007] and protein degradation of tags of varying strengths [Andersen, 1998].

For exogenous expression in *E. coli* or other prokaryotic cells, some nucleic acids encoding proteins of interest can be modified to introduce solubility tags onto the protein of interest to ensure soluble expression of the protein of interest. For example, addition of the maltose binding protein to a protein of interest has been shown to enhance soluble expression in *E. coli* [Sachdev, 1998; Kapust, 1999; Sachdev, 2000]. Either alternatively or in addition, chaperone proteins, such as DnaK, DnaJ, GroES and GroEL may be either co-expressed or overexpressed with the proteins of interest, such as RuBisCO [Greene, 2007], to promote correct folding and assembly [Martinez-Alonso, 2009; Martinez-Alonso, 2010].

For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* [Hoffmeister, 2005]. For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties.

Energy Conversion from Inorganic Energy Sources to Reduced Cofactors

In certain aspects, the engineered chemoautotroph of the present invention comprises one or more energy conversion pathways to convert energy from one or more inorganic energy sources, such as formate, formic acid, carbon monoxide, methane, molecular hydrogen, hydrogen sulfide, bisulfide anion, thiosulfate, elemental sulfur, ferrous iron, and/or ammonia, to one or more reduced cofactors, such as NADH, NADPH, reduced ferredoxins, quinols, reduced flavins, and reduced cytochromes. An energy conversion pathway comprises the following enzymes (only some of which may be exogenous depending on the host organism). Together, the enzymes confer an energy conversion capability on the host cell or organism that the natural organism lacks.

- one or more redox enzymes to oxidize the inorganic energy source and transfer the electrons to a reducing cofactor
- optionally, one or more proteins that serve as a reducing cofactor and/or enzymes that can alter intracellular pools of reducing cofactors
- optionally, one or more oxidoreductases or transhydrogenases that can transfer electrons from high to lower energy redox cofactors (or between redox cofactors with similar redox potentials)
- optionally, one or more transporters or channels to facilitate uptake of extracellular inorganic energy sources by the engineered chemoautotroph.

In certain embodiments, the nucleic acids encoding the proteins and enzymes of a energy conversion pathway are introduced into a host cell or organism that does not naturally contain all the energy conversion pathway enzymes. A particularly useful organism for genetically engineering energy conversion pathways is *E. coli*, which is well characterized in terms of available genetic manipulation tools as well as fermentation conditions. Following the teaching and guidance provided herein for introducing a sufficient number of encoding nucleic acids to generate a particular energy conversion pathway, those skilled in the art would understand that the same engineering design also can be performed with respect to introducing at least the nucleic acids encoding the energy conversion pathway enzymes or proteins absent in the host organism. Therefore, the introduction of one or more encoding nucleic acids into the host organisms of the invention such that the modified organism contains an energy conversion pathway can confer the ability to use inorganic energy to make reducing cofactors, provided the modified organism has a suitable inorganic energy source.

In certain embodiments, the invention provides an engineered chemoautroph that can utilize formate and/or formic acid as an inorganic energy source. To engineer a host cell for the utilization of formate and/or formic acid as the inorganic energy source, one or more formate dehydrogenases (FDH) can be expressed. In a preferred embodiment, the formate dehydrogenase reduces $NADP^+$. Some naturally occuring carbon fixation pathways use NADPH as the redox cofactor rather than NADH, such as the reductive pentose phosphate pathway and several variants of the 3-hydroxypropionate cycle. Accordingly, in certain aspects of the invention, the engineered chemoautotroph expresses a *Burkholderia stabilis* NADP+-dependent formate dehydrogenase (E.C. 1.2.1.43, ACF35003) or a homolog thereof. The homologs can be selected by any suitable methods known in the art or by the methods described herein. This enzyme has been previously shown to preferentially use NADP+ as a cofactor [Hatrongjit, 2010]. SEQ ID NO: 1 represents the *E. coli* codon optimized coding sequence for the fdh gene of the present invention. In one aspect, the invention provides a nucleic acid molecule and homologs, variants and derivatives of SEQ ID NO:1. The nucleic acid sequence can have preferably 70%, 71%, 72%, 73%, 74%, 75%, 76%, 77%, 78%, 79%, 80%, 81-85%, 90-95%, 96-98%, 99%, 99.9% or even higher identity to SEQ ID NO: 1. The present invention also provides nucleic acids comprising or consisting of a sequence which is a codon optimized version of the wild-type fdh gene. In another embodiment, the invention provides a nucleic acid encoding a polypeptide having the amino acid sequence of Genbank accession ACF35003, or homologs thereof having 70%, 71%, 72%, 73%, 74%, 75%, 76%, 77%, 78%, 79%, 80%, 81-85%, 90-95%, 96-98%, 99%, 99.9% or even higher identity thereto. Alternatively, enzymes that naturally use NAD+ can be engineered using established protein engineering techniques to require NADP+ instead of NAD+ [Serov, 2002; Gul-Karaguler, 2001].

In another embodiment, the formate dehydrogenase reduces NAD+. For example, formate dehydrogenase (E.C. 1.2.1.2) can couple the oxidation of formate to carbon dioxide with the reduction of NAD+ to NADH. Exemplary FDH enzymes include Genbank accession numbers CAA57036, AAC49766 and NP_015033 or homologs thereof. SEQ ID NO:2, SEQ ID NO:3 and SEQ ID NO:4 represent *E. coli* codon optimized coding sequence for each of these three FDHs, respectively, of the present invention. In one aspect, the invention provides nucleic acid molecules and homologs, variants and derivatives of SEQ ID NO:2, SEQ ID NO:3 and SEQ ID NO:4. The nucleic acid sequences can have preferably 70%, 71%, 72%, 73%, 74%, 75%, 76%, 77%, 78%, 79%, 80%, 81-85%, 90-95%, 96-98%, 99%, 99.9% or even higher identity to SEQ ID NO:2, SEQ ID NO:3 and SEQ ID NO:4. The present invention also provides nucleic acids each comprising or consisting of a sequence which is a codon optimized version of one of the wild-type fdh genes. In another embodiment, the invention provides nucleic acids each encoding a polypeptide having the amino acid sequence of one of Genbank accession numbers CAA57036, AAC49766 and NP_015033, or homologs thereof having 70%, 71%, 72%, 73%, 74%, 75%, 76%, 77%, 78%, 79%, 80%, 81-85%, 90-95%, 96-98%, 99%, 99.9% or even higher identity thereto.

In certain embodiments, the invention provides an engineered chemoautroph that can utilize formate and/or formic acid as an inorganic energy source and produce reduced, low potential ferredoxin as the reducing cofactor. The reductive tricarboxylic acid cycle carbon fixation pathway is believed to require a low potential ferredoxin for particular carboxylation steps [Brugna-Guiral, 2003, Yoon, 1997; Ikeda, 2005]. The organisms *Nautilia* sp. strain AmN, *Nautilia profundicola, Nautilia lithotrophica* 525$^T$ and *Thermocrinis ruber* are reported to grow on formate as the sole electron donor and use the reductive tricarboxylic acid cycle as their carbon fixation pathway [Campbell, 2001; Smith, 2008; Campbell, 2009; Miroshnichenko, 2002; Hügler, 2007], thus implying that each of these organisms have an energy conversion pathway from formate to reduced ferredoxin. To engineer a host cell for the utilization of formate and/or formic acid as the inorganic energy source and production of reduced ferredoxin as the reducing cofactor, in certain embodiments the present invention provides for the expression of formate dehydrogenase capable of reducing low potential ferredoxin in the engineered chemoautotroph. Such an enzyme would facilitate the combination of an energy conversion pathway that utilizes formate with a carbon fixation pathway based on the reductive tricarboxylic acid cycle as an embodiment of the engineered chemoautotroph of the present invention. Exemplary putative ferredoxin-dependent formate dehydrogenases include (with Genbank accession numbers of the FDH subunits listed in parentheses) *Nautilia profundicola* AmH (YP_002607699, YP_002607700, YP_002607701 and YP_002607702), *Sulfurimonas denitrificans* DSM 1251 (YP_394410 and YP_394411), *Caminibacter mediatlanticus* TB-2 (ZP_01871216, ZP_01871217, ZP_01871218 and ZP_01871219) and *Methanococcus* maripaludis strain S2 (NP_988417 and NP_988418) or homologs thereof. In another embodiment, the invention provides nucleic acids each encoding a polypeptide having the amino acid sequence of one of Genbank accession numbers YP_002607699, YP_002607700, YP_002607701, YP_002607702, YP_394410, YP_394411, ZP_01871216, ZP_01871217, ZP_01871218, ZP_01871219, NP_988417 and NP_988418, or homologs thereof having 70%, 71%, 72%, 73%, 74%, 75%, 76%, 77%, 78%, 79%, 80%, 81-85%, 90-95%, 96-98%, 99%, 99.9% or even higher identity thereto.

A ferredoxin-reducing formate dehydrogenase (FDH) has been previously purified from *Clostridium pasteurianum* W5 [Liu, 1984]; however, no protein or nucleic acid sequence information is available on the enzyme nor is there a publicly available genome sequence for *Clostridium pasteurianum* as of Aug. 1, 2011. Based on the sequencing and bioinformatic analysis of the *Clostridium pasteurianum* genome, the sequence of a two putative subunits of a ferredoxin-dependent FDH (FdhF and FdhD) as well as two associated putative ferredoxin domain-containing proteins were identified (Example 7). In one aspect, the invention provides nucleic acids each encoding a polypeptide having the amino acid sequence of one of SEQ ID NO:5, SEQ ID NO:6, SEQ ID NO:7 and SEQ ID NO:8. In another embodiment, the invention provides nucleic acids each encoding a polypeptide having the amino acid sequence of one of SEQ ID NO:5, SEQ ID NO:6, SEQ ID NO:7 and SEQ ID NO:8 which have been codon optimized for the host organism, such as *E. coli*. Based on the *Clostridium pasteurianum* putative FDH subunits, additional putative ferredoxin-dependent FDH were identified. Exemplary ferredoxin-dependent FDH include (with Genbank accession numbers of the FDH subunits listed in parentheses) *Clostridium beijerincki* NCIMB 8052 (YP_001310874 and YP_001310871), *Clostridium difficile* 630 (YP_001089834 and YP_001089833), *Clostridium difficile* CD196 (YP_003216147 and YP_003216146), *Clostridium difficile* R20291 (YP_003219654 and YP_003219653) or homologs thereof. In another embodiment, the invention provides nucleic acids each encoding a polypeptide having the amino acid sequence of one of Genbank accession numbers YP_001310874, YP_001310871, YP_001089834, YP_001089833, YP_003216147, YP_003216146, YP_003219654 and YP_003219653, or homologs thereof having 70%, 71%, 72%, 73%, 74%, 75%, 76%, 77%, 78%, 79%, 80%, 81-85%, 90-95%, 96-98%, 99%, 99.9% or even higher identity thereto.

In certain embodiments, the invention provides an engineered chemoautotroph that can utilize molecular hydrogen as an inorganic energy source. To engineer a host cell for the utilization of molecular hydrogen as an inorganic energy source, one or more hydrogenases can be expressed. For example, [NiFe]-hydrogenases are typically associated with the coupling of hydrogen oxidation to cofactor reduction [Vignais, 2004]. These hydrogenases tend to be composed of at least a large and small subunit and require several accesssory genes for maturation including a peptidase [Vignais, 2004]. Recently, there have been several published examples of heterologous expression of [NiFe]-hydrogenases in *E. coli* [Sun, 2010; Wells, 2011; Kim, 2011]. Taken together, these results demonstrate that particular maturation proteins, in particular the peptidase that cleaves the C-terminal end of the large subunit, tend to be very specific for their cognate hydrogenase and can not be substituted by homologous hydrogenase maturation factors endogenous to the host cell. Hence, functional heterologous expression of a [NiFe]-hydrogenase requires expression of not only the subunit proteins, such as the large and small subunit, but also one or more of the associated maturation factors, such as the peptidase. In a preferred embodiment, the hydrogenase reduces ferredoxin (E.C. 1.12.7.2) and in particular a low potential ferredoxin capable of being used as the reducing cofactor for the carboxylation steps of the reductive tricarboxylic acid cycle [Yoon, 1997; Ikeda, 2005]. The group 2a [NiFe]-hydrogenases are associated with reducing the ferredoxin needed for the reductive tricarboxylic acid cycle [Brugna-Guiral, 2003; Vignais, 2007]. Exemplary hydrogenases include (with Genbank accession numbers of the hydrogenase subunits listed in parentheses) *Aquifex aeolicus* Hydrogenase 3 (NP_213549 and NP_213548); *Hydrogenobacter thermophilus* TK-6 Hup2 (YP_003432664 and YP_003432663); *Hydrogenobaculum* sp. Y04AAS1 HY044AAS1_1400/HY044AAS1_1399 (YP_002122063 and YP_002122062); *Magnetococcus marinus* Mmc1_2493/Mmc1_2494 (YP_866399 and YP_866400); *Magnetospirillum magneticum* AMB-1 amb1114/amb1115 (YP_420477 and YP_420478); *Methanococcus maripaludis* S2 Hydrogenase B (NP_988273 and NP_988742); *Methanosarcina barkeri* str. fusaro Ech (YP_303717, YP_303716, YP_303715, YP_303714, YP_303713 and YP_303712); *Methanosarcina mazei* Go1 Ech (NP_634344, NP_634345, NP_634346, NP_634347, NP_634348 and NP_634349); *Mycobacterium smegmatis* str. MC2 155 Hydrogenase-2 (YP_886615 and YP_886614), *Nautilia profundicola* AmH NAMH_0573/NAMH_0572 (YP_002606989 and YP_002606988), *Nitratiruptor* sp. SB155-2 Hup (YP_001356429 and YP_001356428); *Persephonella marina* EX-H1 PERMA_0914/PERMA_0915 (YP_002730701 and YP_002730702); *Sulfurihydrogenibium azorense* Az-Fu1 SULAZ_0749/SULAZ_0748 (YP_002728734 and YP_002728733); *Sulfurimonas denitrificans* DSM 1251 Suden_1437/Suden_1436 (YP_393949 and YP_393948); *Sulfurovum* sp NBC37-1 Hup (YP_001358971 and YP_001358972); *Thermocrinis albus* DSM 14484 Thal_1414/Thal_1413 (YP_003474170 and YP_003474169); and homologs thereof. In an alternate embodiment, the hydrogenase reduces NADP$^+$ (E.C. 1.12.1.3). The group 3b and 3d [NiFe]-hydrogenases are typically NAD(P)$^+$ reducing hydrogenases from bacteria [Vignais, 2007]. Exemplary hydrogenases include (with Genbank accession numbers of the hydrogenase subunits listed in parentheses) *Cupriavidus necator* SH (NP_942732, NP_942730, NP_942729, NP_942728 and NP_942727) and *Synechocystis* sp PCC6803 bidirectional hydrogenase (NP_441418, NP_441417, NP_441415, NP_441414 and NP_441411), and homologs thereof. In an alternate embodiment, the hydrogenase reduces NAD$^+$ (E.C. 1.12.1.2). Exemplary hydrogenases include (with the Genbank accession numbers of the hydrogenase subunits listed in parentheses) *Cupriavidus necator* SH without the HoxI subunit (NP_942730, NP_942729, NP_942728 and NP_942727) and homologs thereof [Burgdorf, 2005].

In certain embodiments, the invention provides an engineered chemoautotroph that can utilize hydrogen sulfide as an inorganic energy source. To engineer a host cell for the utilization of hydrogen sulfide as the inorganic energy source, one or more sulfide-quinone oxidoreductases (SQR) can be expressed. Sulfide-quinone oxidoreductase couples the oxidation of hydrogen sulfide to the reduction of a quinone to the corresponding quinol (E.C. 1.8.5.4). The *Rhodobacter capsulatus* SQR has been functionally expressed in the heterologous host *E. coli* [Schütz, 1997] and demonstrated to reduce ubiquinone [Shibata, 2001]. Exemplary SQR enzymes include NP 214500, NP 488552, NP 661023, YP_002426210, YP_003444098, YP_003576957, YP_315983, YP_866354, and homologs thereof. SEQ ID NO:9, SEQ ID NO:10, SEQ ID NO:11, SEQ ID NO:12, SEQ ID NO:13, SEQ ID NO:14, SEQ ID NO:15 and SEQ ID NO:16 represent *E. coli* codon optimized coding sequence for each of these eight SQRs, respectively, of the present invention. In one aspect, the invention provides nucleic acid molecules and homologs, variants and derivatives of SEQ ID NO:9, SEQ ID NO: 10, SEQ ID NO: 11, SEQ ID NO: 12, SEQ ID NO:13, SEQ ID NO:14, SEQ ID NO:15 and SEQ ID NO:16. The nucleic acid sequences can have preferably 70%, 71%, 72%, 73%, 74%, 75%, 76%, 77%, 78%, 79%, 80%, 81-85%, 90-95%, 96-98%, 99%, 99.9% or even higher identity to SEQ ID NO:9, SEQ ID NO: 10, SEQ ID NO: 11, SEQ ID NO:12, SEQ ID NO:13, SEQ ID NO:14, SEQ ID NO:15 and SEQ ID NO:16. The present invention provides nucleic acids each comprising or consisting of a sequence which is a codon optimized version of one of the wild-type sqr genes. In another embodiment, the invention provides nucleic acids each encoding a polypeptide having the amino acid sequence of one of Genbank accession numbers NP_214500, NP 488552, NP 661023, YP_002426210, YP_003444098, YP_003576957, YP_315983, YP_866354, or homologs thereof having 70%, 71%, 72%, 73%, 74%, 75%, 76%, 77%, 78%, 79%, 80%, 81-85%, 90-95%, 96-98%, 99%, 99.9% or even higher identity thereto. Alternatively, to engineer a host cell for the utilization of hydrogen sulfide, one or more flavocytochrome c sulfide dehydrogenases can be expressed. Flavocytochrome c sulfide dehydrogenase is similar in structure to SQR but couples the oxidation of hydrogen sulfide to the reduction of a cytochrome (E.C. 1.8.2.3) [Marcia, 2010].

In certain embodiments, the invention provides an engineered chemoautotroph that expresses a protein that can serve as a reducing cofactor, such as preferably ferredoxin or alternatively cytochrome c. In one embodiment, the ferredoxin is a low potential ferredoxin that can donate electrons to the carboxylation steps in the reductive tricarboxylic acid cycle [Yoon, 1997; Ikeda, 2005]. Exemplary ferredoxins include AAA83524, YP_003433536, YP_003433535, YP_304316, and homologs thereof. SEQ ID NO:17, SEQ ID NO:18, SEQ ID NO:19, SEQ ID NO:20 represent *E. coli* codon optimized coding sequence for each of these four ferredoxins, respectively, of the present invention. In one aspect, the invention provides nucleic acid molecules and homologs, variants and derivatives of SEQ ID NO:17, SEQ ID NO:18, SEQ ID NO:19, SEQ ID NO:20. The nucleic acid sequences can have preferably 70%, 71%, 72%, 73%, 74%, 75%, 76%, 77%, 78%, 79%, 80%, 81-85%, 90-95%, 96-98%, 99%, 99.9% or even higher identity to SEQ ID NO: 17, SEQ ID NO: 18, SEQ ID NO:19, SEQ ID NO:20. The present invention also provides nucleic acids each comprising or consisting of a sequence which is a codon optimized version of one of the wild-type ferredoxin genes. In another embodiment, the invention provides nucleic acids each encoding a polypeptide having the amino acid sequence of one of Genbank accession numbers AAA83524, YP_003433536, YP_003433535 and YP_304316, or homologs thereof having 70%, 71%, 72%, 73%, 74%, 75%, 76%, 77%, 78%, 79%, 80%, 81-85%, 90-95%, 96-98%, 99%, 99.9% or even higher identity thereto. Two additional exemplary ferredoxins for which no Genbank accession number has been assigned include SEQ ID NO:22 and SEQ ID NO:24. SEQ ID NO:21 and SEQ ID NO:23 represent *E. coli* codon optimized coding sequence for each of these two unannotated ferredoxins, respectively, of the present invention. In one aspect, the invention provides nucleic acid molecules and homologs, variants and derivatives of SEQ ID NO:21 and SEQ ID NO:23. The nucleic acid sequences can have preferably 70%, 71%, 72%, 73%, 74%, 75%, 76%, 77%, 78%, 79%, 80%, 81-85%, 90-95%, 96-98%, 99%, 99.9% or even higher identity to SEQ ID NO:21 and SEQ ID NO:23. The present invention also provides nucleic acids each comprising or consisting of a sequence which is a codon optimized version of one of these two wild-type ferredoxin genes. In another embodiment, the invention provides nucleic acids each encoding a polypeptide having the amino acid sequence of one of SEQ ID NO:22 and SEQ ID NO:24, or homologs thereof having 70%, 71%, 72%, 73%, 74%, 75%, 76%, 77%, 78%, 79%, 80%, 81-85%, 90-95%, 96-98%, 99%, 99.9% or even higher identity thereto.

In certain embodiments, the invention provides an engineered chemoautotroph that can transfer energy from one reduced cofactor to another. In one embodiment, a ferredoxin-NADP$^+$ reductase (FNR) is expressed. FNR can catalyze reversible electron transfer between the two-electron carrier NADPH and the one-electron carrier ferredoxin (E.C 1.18.1.2). Exemplary FNR enzymes include the *Hydrogenobacter thermophilus* Fpr (Genbank accession BAH29712) and homologs thereof [Ikeda, 2009]. In another embodiment, a ferredoxin-NAD$^+$ reductase (E.C. 1.18.1.3) and/or a NAD(P)$^+$ transhydrogenase (E.C. 1.6.1.1 or E.C. 1.6.1.2) is expressed.

Carbon Fixation of Inorganic Carbon to Central Metabolites

In certain aspects, the engineered chemoautotroph of the present invention comprises one or more carbon fixation pathways to use energy from one or more reduced cofactors, such as NADH, NADPH, reduced ferredoxins, quinols, reduced flavins, and reduced cytochromes, to convert inorganic carbon, such as carbon dioxide, formate, or formic acid, into central metabolites, such as acetyl-coA, pyruvate, glyoxylate, glycolate and dihydroxyacetone phosphate. One or more of the carbon fixation pathways can be derived from naturally occurring carbon fixation pathways, such as the Calvin-Benson-Bassham cycle or reductive pentose phosphate cycle, the reductive tricarboxylic acid cycle, the Wood-Ljungdhal or reductive acetyl-coA pathway, the 3-hydroxypropionate bicycle, 3-hydroxypropionate/4-hydroxybutyrate cycle and the dicarboxylate/4-hydroxybutyrate cycle [Hügler, 2011]. Alternatively, one or more of the carbon fixation pathways can be derived from synthetic metabolic pathways not found in nature, such as those enumerated by Bar-Even et al. [Bar-Even, 2010]. In certain embodiments, the nucleic acids encoding the proteins and enzymes of a carbon fixation pathway are introduced into a host cell or organism that does not naturally contain all the carbon fixation pathway enzymes. A particularly useful organism for genetically engineering carbon fixation pathways is *E. coli*, which is well characterized in terms of available genetic manipulation tools as well as fermentation conditions. Following the teaching and guidance provided herein for introducing a sufficient number of encoding nucleic acids to generate a particular carbon fixation pathway, those skilled in the art would understand that the same engineering design also can be performed with respect to introducing at least the nucleic acids encoding the carbon fixation pathway enzymes or proteins absent in the host organism. Therefore, the introduction of one or more encoding nucleic acids into the host organisms of the invention such that the modified organism contains a carbon fixation pathway can confer the ability to use inorganic carbon to make central metabolites, provided the modified organism has a suitable inorganic energy source and energy conversion pathway.

Figure 3:
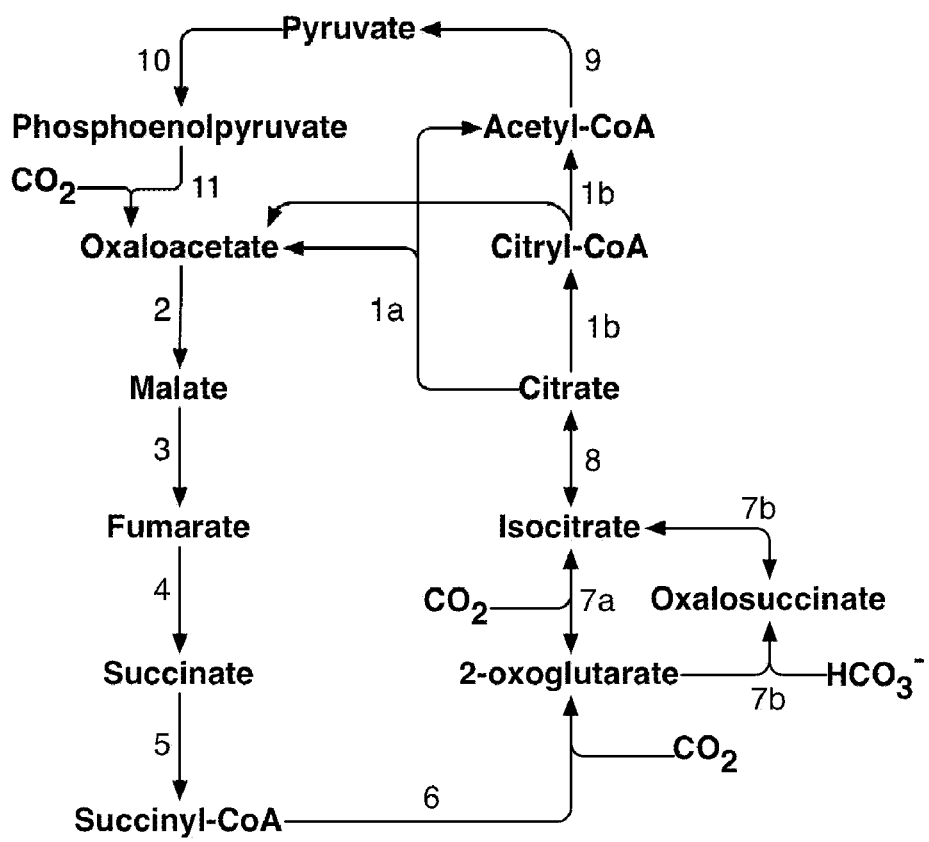
FIG. 3 depicts the metabolic reactions of the reductive tricarboxylic acid cycle [Evans, 1966; Buchanan, 1990; Hügler, 2011]. Each reaction is numbered. For certain reactions, such as reaction 1 and 7, there are two possible routes denoted by a and b, each of which is catalyzed by different enzyme(s). Enzymes catalyzing each reaction are as follows: 1a, ATP citrate lyase (E.C. 2.3.3.8); 1b, citryl-CoA synthetase (E.C. 6.2.1.18) and citryl-CoAlyase (E.C. 4.1.3.34); 2, malate dehydrogenase (E.C. 1.1.1.37); 3, fumarate dehydratase or fumarase (E.C. 4.2.1.2); 4, fumarate reductase (E.C. 1.3.99.1); 5, succinyl-CoA synthetase (E.C. 6.2.1.5); 6, 2-oxoglutarate synthase or 2-oxoglutarate:ferredoxin oxidoreductase (E.C. 1.2.7.3); 7a, isocitrate dehydrogenase (E.C. 1.1.1.41 or E.C. 1.1.1.42); 7b, 2-oxoglutarate carboxylase (E.C. 6.4.1.7) and oxalosuccinate reductase (E.C. 1.1.1.41); 8, aconitate hydratrase (E.C. 4.2.1.3); 9, pyruvate synthase or pyruvate:ferredoxin oxidoreductase (E.C. 1.2.7.1); 10, phosphoenolpyruvate synthetase (E.C. 2.7.9.2); 11, phosphoenolpyruvate carboxylase (E.C. 4.1.1.31).
Figure 4:
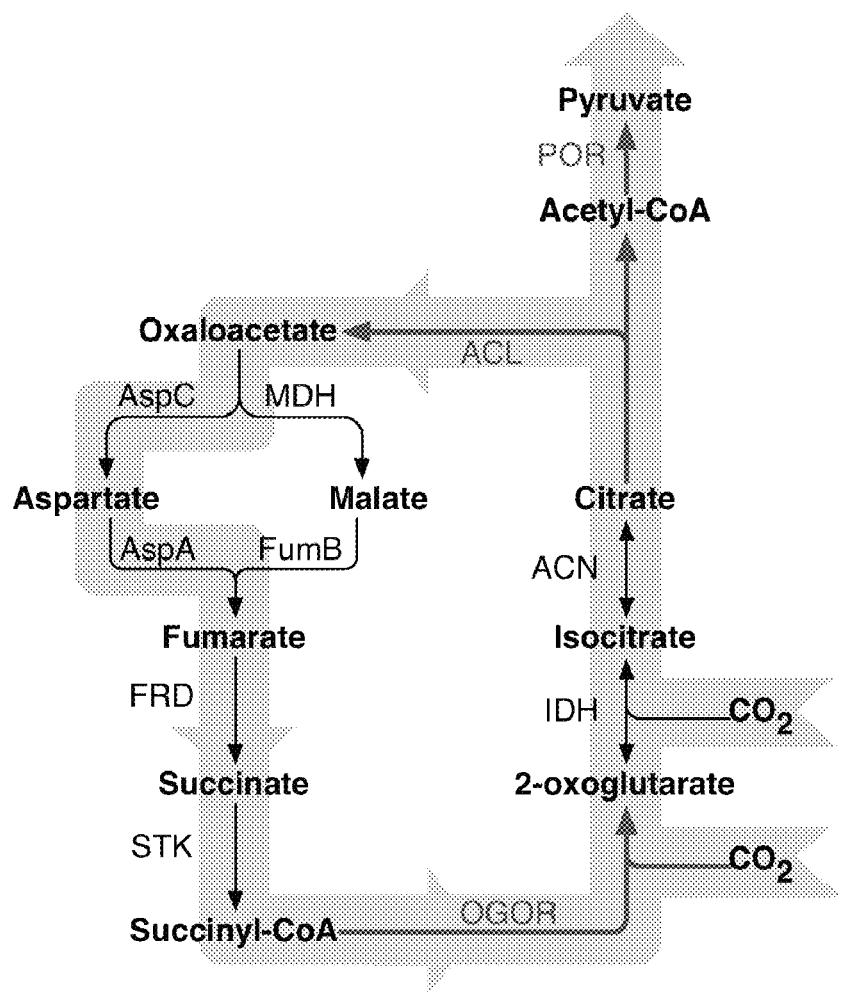
FIG. 4 depicts example metabolic reactions and enzymes needed to engineer a carbon fixation pathway derived from the reductive tricarboxylic acid (rTCA) cycle into the heterotroph Escherichia coli. Reactions in black are are known to occur in the wildtype host cell E. coli when grown in microaerobic or anaerobic conditions [Cronan, 2010]. Reactions in dark gray must be added to complete the rTCA-derived carbon fixation cycle in E. coli. The carbon input to the pathway is carbon dioxide ($CO_2$) and the carbon outputs of the pathway are acetyl-coA and/or pyruvate. The desired net flow of carbon is indicated by the wide, light gray arrow. Metabolites are shown in bold and enzyme abbreviations are as follows: AspC, aspartate aminotransferase; MDH, malate dehydrogenase; AspA, aspartate ammonia-lyase; FumB, fumarase B; FRD, fumarate reductase; STK, succinate thiokinase; OGOR, 2-oxoglutarate:ferredoxin oxidoreductase; IDH, isocitrate dehydrogenase; ACN, aconitase; ACL, ATP-citrate lyase; POR, pyruvate:ferredoxin oxidoreductase.

In certain embodiments, the invention provides an engineered chemoautotroph with a carbon fixation pathway derived from the reductive tricarboxylic acid (rTCA) cycle. The rTCA cycle is well known in the art and consists of approximately 11 reactions (FIG. 3) [Evans, 1966; Buchanan, 1990]. For two of the reactions (reaction 1 and 7), there are two known routes between the substrate and product and each route is catalyzed by different enzyme(s). The reactions in the rTCA cycle are catalyzed by the following enzymes: ATP citrate lyase (E.C. 2.3.3.8) [Sintsov, 1980; Kanao, 2002b]; citryl-CoA synthetase (E.C. 6.2.1.18) [Aoshima, 2004a]; citryl-CoA lyase (E.C. 4.1.3.34) [Aoshima, 2004b]; malate dehydrogenase (E.C. 1.1.1.37); fumarate dehydratase or fumarase (E.C. 4.2.1.2); fumarate reductase (E.C. 1.3.99.1); succinyl-CoA synthetase (E.C. 6.2.1.5); 2-oxoglutarate synthase or 2-oxoglutarate: ferredoxin oxidoreductase (E.C. 1.2.7.3) [Gehring, 1972; Yamamoto, 2010]; isocitrate dehydrogenase (E.C. 1.1.1.41 or E.C. 1.1.1.42) [Kanao, 2002a]; 2-oxoglutarate carboxylase (E.C. 6.4.1.7) [Aoshima, 2004c; Aoshima, 2006]; oxalosuccinate reductase (E.C. 1.1.1.41) [Aoshima, 2004c; Aoshima, 2006]; aconitate hydratase (E.C. 4.2.1.3); pyruvate synthase or pyruvate:ferredoxin oxidoreductase (E.C. 1.2.7.1); phosphoenolpyruvate synthetase (E.C. 2.7.9.2); phosphoenolpyruvate carboxylase (E.C. 4.1.1.31). In one embodiment, the invention provides an engineered chemoautotroph comprising one or more exogenous proteins from the rTCA cycle conferring to the organism the ability to produce central metabolites from inorganic carbon, wherein the organism lacks the ability to fix carbon via the rTCA cycle (for example, see FIG. 4). For example, the one or more exogenous proteins can be selected from ATP citrate lyase, citryl-CoA synthetase, citryl-CoA lyase, malate dehydrogenase, fumarate dehydratase, fumarate reductase, succinyl-CoA synthetase, 2-oxoglutarate synthase, isocitrate dehydrogenase, 2-oxoglutarate carboxylase, oxalosuccinate reductase, aconitate hydratase, pyruvate synthase, phosphoenolpyruvate synthetase, and phosphoenolpyruvate carboxylase. The host organism can also express two or more, three or more, four or more, five or more, and the like, including up to all the protein and enzymes that confer the rTCA pathway. For example, in the host organism *E. coli*, the exogenous enzymes comprise 2-oxoglutarate synthase and ATP citrate lyase. As a second example, in the host organism *E. coli*, the exogenous enzymes comprise 2-oxoglutarate synthase, ATP citrate lyase and pyruvate synthase. Finally, as a third example, in the host organism *E. coli*, the exogenous enzymes comprise 2-oxoglutarate synthase, ATP citrate lyase, pyruvate synthase, 2-oxoglutarate carboxylase and oxalosuccinate reductase. In another embodiment, alternate enzymes can be used that result in the same overall carbon fixation pathway. For example, the enzyme malate dehydrogenase (E.C. 1.1.1.39) can substitute for malate dehydrogenase and phosphoenolpyruvate carboxylase. The enzymes 2-oxoglutarate synthase and pyruvate synthase can be difficult to distinguish from sequence data alone. Both enzymes comprise 1-5 protein subunits depending on the species. Exemplary pyruvate/2-oxoglutarate synthases include NP_213793, NP_213794, and NP_213795; NP 213818, NP_213819 and NP_213820; AAD07654, AAD07655, AAD07656 and AAD07653; ABK44257, ABK44258 and ABK44249; ACD90193 and ACD90192; YP_001942282 and YP_001942281; and homologs thereof. Exemplary 2-oxoglutarate synthases include BAI69550 and BAI69551; YP_003432753, YP_003432754, YP_003432755, YP_003432756 and YP_003432757; YP_393565, YP_393566, YP_393567 and YP_393568; BAF71539, BAF71540, BAF71541 and BAF71538; BAF69954, BAF69955, BAF69958 and BAF69953; AAM71411 and AAM71410; YP_002607621, YP_002607620, YP_002607619 and YP_002607622; CAA12243 and CAD27440; and homologs thereof. Exemplary pyruvate synthases include YP_392614, YP_392615, YP_392612 and YP_392613; YP_001357517, YP_001357518; YP_001357515 and YP_001357515; YP_001357066, YP_001357065, YP_001357068 and YP_001357067; and homologs thereof. ATP citrate lyases comprise 1-4 protein subunits depending on the species. Exemplary ATP citrate lyases include AAC06486; YP_393085 and YP_393084; BAF71501 and BAF71502; BAF69766 and BAF69767; ACX98447; AAM72322 and AAM72321; YP_002607124 and YP_002607125; BAB21376 and BAB21375; and homologs thereof. Exemplary citryl-coA synthetases include BAD 17846 and BAD 17844. Exemplary citryl-coA lyases include BAD 17841.

Figure 5:
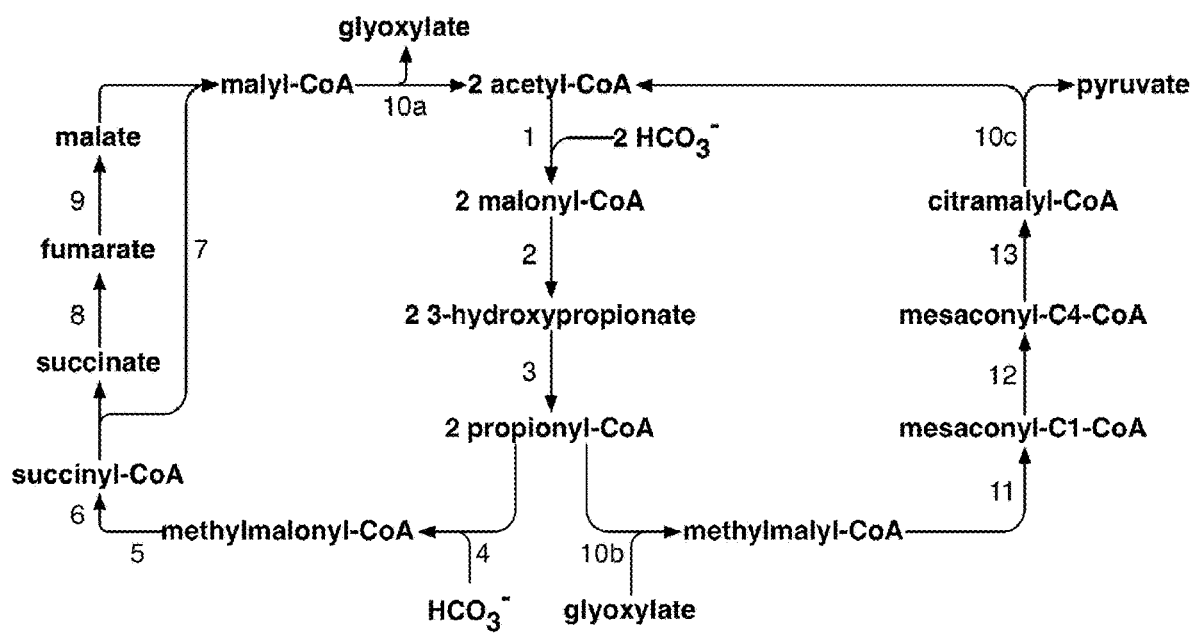
FIG. 5 depicts the metabolic reactions of the 3-hydroxypropionate bicycle [Holo, 1989; Strauss, 1993; Eisenreich, 1993; Herter, 2002a; Zarzycki, 2009; Zarzycki, 2011]. Each reaction is numbered. In some cases, multiple different reactions, such as reactions 10a, 10b and 10c, are catalyzed by the same multi-functional enzyme. Enzymes catalyzing each reaction are as follows: 1, acetyl-CoA carboxylase (E.C. 6.4.1.2); 2, malonyl-CoA reductase (E.C. 1.2.1.75 and E.C. 1.1.1.298); 3, propionyl-CoA synthase (E.C. 6.2.1.-, E.C. 4.2.1.- and E.C. 1.3.1.-); 4, propionyl-CoA carboxylase (E.C. 6.4.1.3); 5, methylmalonyl-CoA epimerase (E.C. 5.1.99.1); 6, methylmalonyl-CoA mutase (E.C. 5.4.99.2); 7, succinyl-CoA:(S)-malate CoA transferase (E.C. 2.8.3.-); 8, succinate dehydrogenase (E.C. 1.3.5.1); 9, fumarate hydratase (E.C. 4.2.1.2); 10abc, (S)-malyl-CoA/β-methylmalyl-CoA/(S)-citramalyl-CoA lyase (E.C. 4.1.3.24 and E.C. 4.1.3.25); 11, mesaconyl-C1-CoA hydratase or β-methylmalyl-CoA dehyratase (E.C. 4.2.1.-); 12, mesaconyl-CoA C1-C4 CoA transferase (E.C. 2.8.3.-); 13, mesaconyl-C4-CoA hydratase (E.C. 4.2.1.-).
Figure 6:
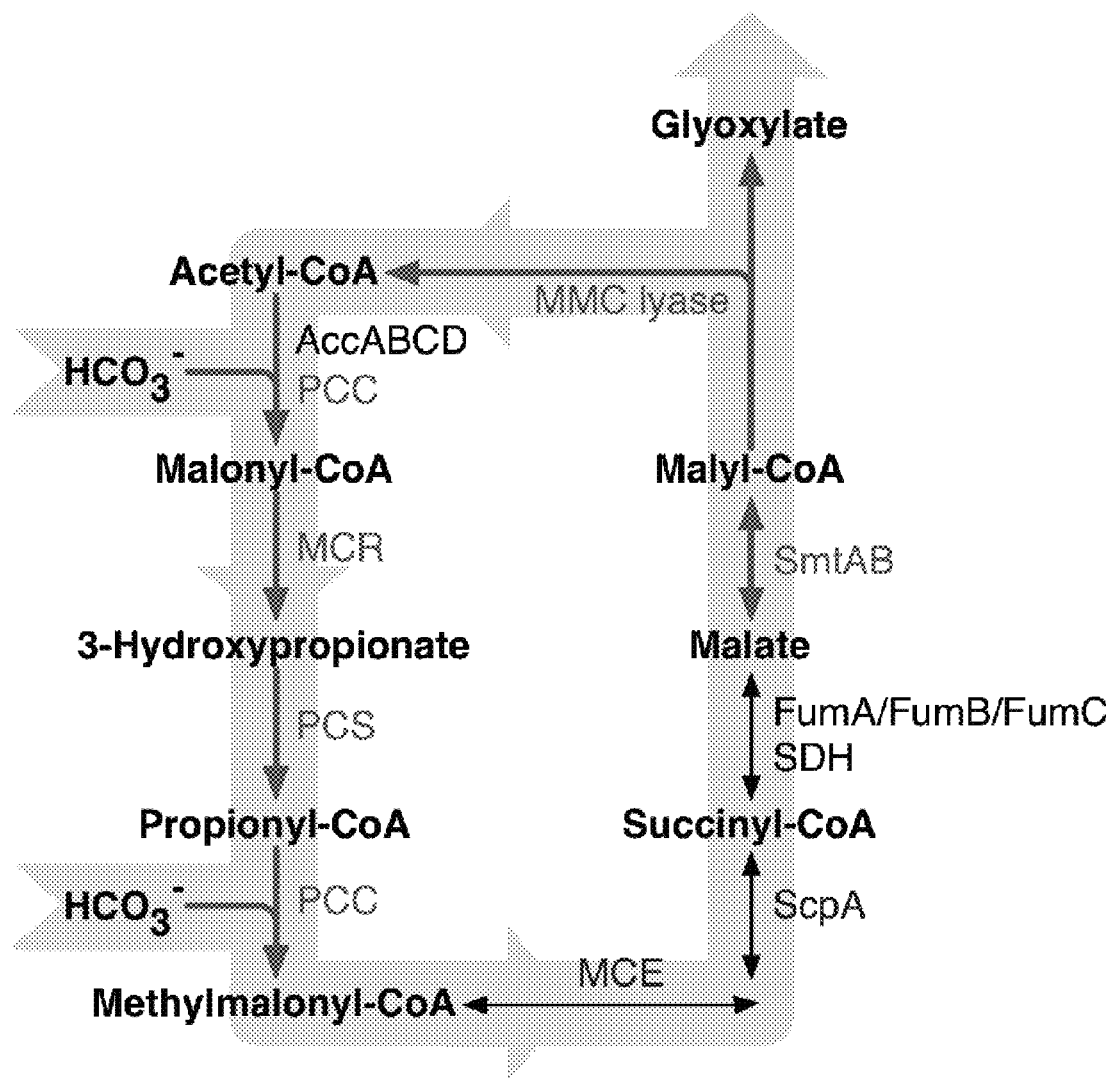
FIG. 6 depicts example metabolic reactions and enzymes needed to engineer a carbon fixation pathway derived from the 3-hydroxypropionate (3-HPA) bicycle into the heterotroph Escherichia coli. Reactions in black are reported to occur in the wildtype host cell E. coli. Reactions in dark gray must be added to complete the 3-HPA bicycle-derived carbon fixation cycle in E. coli. The carbon input to the pathway is bicarbonate ($HCO_3^-$) and the carbon output of the pathway is glyoxylate. The desired net flow of carbon is indicated by the wide, light gray arrow. Metabolites are shown in bold and enzyme abbreviations are as follows: PCC, propionyl-CoA carboxylase; MCR, malonyl-CoA reductase; PCS, propionyl-CoA synthase; MCE, methylmalonyl-CoA epimerase; ScpA, E. coli methylmalonyl-CoA mutase; SDH, E. coli succinate dehydrogenase; FumA/FumB/FumC, three E. coli fumarate hydratases; SmtAB, succinyl-CoA:(S)-malate CoA transferase; MMC lyase, (S)-malyl-CoA/β-methylmalyl-CoA/(S)-citramalyl-CoA lyase. Note that methylmalonyl-CoA epimerase activity has been reported in E. coli although no corresponding gene or gene product has been identified [Evans, 1993].

In certain embodiments, the invention provides an engineered chemoautotroph with a carbon fixation pathway derived from the 3-hydroxypropionate (3-HPA) bicycle. The 3-HPA bicycle is well known in the art and consists of 19 reactions catalyzed by 13 enzymes (FIG. 5) [Holo, 1989; Strauss, 1993; Eisenreich, 1993; Herter, 2002a; Zarzycki, 2009; Zarzycki, 2011]. The number of reactions in the metabolic pathway exceeds the number of enzymes because particular enzymes, such as malonyl-CoA reductase, propionyl-CoA synthase, and malyl-CoA/β-methylmalyl-CoA/citramalyl-CoA lyase, are multi-functional enzymes that catalyze more than one reaction. Also, in some species, such as *Metallosphaera sedula*, the same enzyme can carboxylate acetyl-CoA and propionyl-CoA. The reactions in the 3-HPA bicycle are catalyzed by the following enzymes: acetyl-CoA carboxylase (E.C. 6.4.1.2) [Menendez, 1999; Hugler, 2003]; malonyl-CoA reductase (E.C. 1.2.1.75 and E.C. 1.1.1.298) [Huigler, 2002; Alber, 2006; Rathnasingh, 2011]; propionyl-CoA synthase (E.C. 6.2.1.-, E.C. 4.2.1.- and E.C. 1.3.1.-) [Alber, 2002]; propionyl-CoA carboxylase (E.C. 6.4.1.3) [Menendez, 1999; Hiigler, 2003]; methylmalonyl-CoA epimerase (E.C. 5.1.99.1); methylmalonyl-CoA mutase (E.C. 5.4.99.2); succinyl-CoA:(S)-malate CoA transferase (E.C. 2.8.3.-) [Friedmann, 2006]; succinate dehydrogenase (E.C. 1.3.5.1); fumarate hydratase (E.C. 4.2.1.2); (S)-malyl-CoA/β-methylmalyl-CoA/(S)-citramalyl-CoA lyase (MMC lyase, E.C. 4.1.3.24 and E.C. 4.1.3.25) [Herter, 2002b; Friedmann, 2007]; mesaconyl-C1-CoA hydratase or β-methylmalyl-CoA dehyratase (E.C. 4.2.1.-) [Zarzycki, 2008]; mesaconyl-CoA C1-C4 CoA transferase (E.C. 2.8.3.-) [Zarzycki, 2009]; mesaconyl-C4-CoA hydratase (E.C. 4.2.1.-) [Zarcycki, 2009]. In one embodiment, the invention provides an engineered chemoautotroph comprising one or more exogenous proteins from the 3-HPA bicycle conferring to the organism the ability to produce central metabolites from inorganic carbon, wherein the organism lacks the ability to fix carbon via the 3-HPA bicycle (for example, see FIG. 6). Methylmalonyl-CoA epimerase activity has been reported in *E. coli* although no corresponding gene or gene product has been identified [Evans, 1993]. For *E. coli* ScpA to be active, vitamin B12 must be present in culture medium or produced intracellularly. For example, the one or more exogenous proteins can be selected from acetyl-CoA carboxylase, malonyl-CoA reductase, propionyl-CoA synthase, propionyl-CoA carboxylase, methylmalonyl-CoA epimerase, methylmalonyl-CoA mutase, succinyl-CoA:(S)-malate CoA transferase, succinate dehydrogenase, fumarate hydratase, (S)-malyl-CoA/β-methylmalyl-CoA/(S)-citramalyl-CoA lyase, mesaconyl-C1-CoA hydratase, mesaconyl-CoA C1-C4 CoA transferase, and mesaconyl-C4-CoA hydratase. The host organism can also express two or more, three or more, four or more, five or more, six or more, seven or more, and the like, including up to all the protein and enzymes that confer the 3-HPA pathway. For example, in the host organism *E. coli*, the exogenous enzymes comprise malonyl-CoA reductase, propionyl-CoA synthase, acetyl-CoA/propionyl-CoA carboxylase, succinyl-CoA:(S)-malate CoA transferase, and MMC lyase. As a second example, in the host organism *E. coli*, the exogenous enzymes comprise malonyl-CoA reductase, propionyl-CoA synthase, acetyl-CoA/propionyl-CoA carboxylase, succinyl-CoA:(S)-malate CoA transferase, MMC lyase, and methylmalonyl-CoA epimerase. Finally, as a third example, in the host organism *E. coli*, the exogenous enzymes comprise malonyl-CoA reductase, propionyl-CoA synthase, propionyl-CoA carboxylase, succinyl-CoA:(S)-malate CoA transferase, MMC lyase, methylmalonyl-CoA epimerase and methylmalonyl-CoA mutase. Exemplary malonyl-coA reductases include ZP_04957196, YP_001433009, ZP_01626393, ZP_01039179 and YP_001636209, and homologs thereof. SEQ ID NO:25, SEQ ID NO:26, SEQ ID NO:27, SEQ ID NO:28 and SEQ ID NO:29 represent *E. coli* codon optimized coding sequence for each of these five malonyl-CoA reductases, respectively, of the present invention. In one aspect, the invention provides nucleic acid molecules and homologs, variants and derivatives of SEQ ID NO:25, SEQ ID NO:26, SEQ ID NO:27, SEQ ID NO:28 and SEQ ID NO:29. The nucleic acid sequences can have preferably 70%, 71%, 72%, 73%, 74%, 75%, 76%, 77%, 78%, 79%, 80%, 81-85%, 90-95%, 96-98%, 99%, 99.9% or even higher identity to SEQ ID NO:25, SEQ ID NO:26, SEQ ID NO:27, SEQ ID NO:28 and SEQ ID NO:29. The present invention also provides nucleic acids each comprising or consisting of a sequence which is a codon optimized version of one of the wild-type malonyl-CoA reductase genes. In another embodiment, the invention provides nucleic acids each encoding a polypeptide having the amino acid sequence of one of Genbank accession numbers ZP_04957196, YP_001433009, ZP_01626393, ZP_01039179 and YP_001636209, or homologs thereof having 70%, 71%, 72%, 73%, 74%, 75%, 76%, 77%, 78%, 79%, 80%, 81-85%, 90-95%, 96-98%, 99%, 99.9% or even higher identity thereto. Exemplary propionyl-CoA synthases include AAL47820, and homologs thereof. SEQ ID NO:30 represents the *E. coli* codon optimized coding sequence for this propionyl-CoA synthase of the present invention. In one aspect, the invention provides nucleic acid molecule and homologs, variants and derivatives of SEQ ID NO:30. The nucleic acid sequence can have preferably 70%, 71%, 72%, 73%, 74%, 75%, 76%, 77%, 78%, 79%, 80%, 81-85%, 90-95%, 96-98%, 99%, 99.9% or even higher identity to SEQ ID NO:30. The present invention provides nucleic acids each comprising or consisting of a sequence which is a codon optimized version of the wild-type propionyl-CoA synthase gene. In another embodiment, the invention provides a nucleic acid encoding a polypeptide having the amino acid sequence of SEQ ID NO:31, or homologs thereof having 70%, 71%, 72%, 73%, 74%, 75%, 76%, 77%, 78%, 79%, 80%, 81-85%, 90-95%, 96-98%, 99%, 99.9% or even higher identity thereto. The enzyme acetyl-CoA/propionyl-CoA carboxylase is composed of three subunits: PccB, AccC and AccB. Exemplary acetyl-CoA/propionyl-CoA carboxylases include those from *Metallosphaera sedula* DSM 5348 (YP_001191457, YP_001190248, YP_001190249); *Nitrosopumilus maritimus* SCM1 (YP_00158606, YP_001581607, YP_001581608); *Cenarchaeum symbiosum* A (YP_876582, YP_876583, YP_876584); *Halobacterium* sp. NRC-1 (NP_280337 or NP_279647; NP_280339 or NP_280547; NP_280866), and homologs thereof. SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44 and SEQ ID NO:45 represent *E. coli* codon optimized coding sequence for each of these acetyl-CoA/propionyl-CoA carboxylase subunits, respectively, of the present invention. In one aspect, the invention provides nucleic acid molecules and homologs, variants and derivatives of SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44 and SEQ ID NO:45. The nucleic acid sequences can have preferably 70%, 71%, 72%, 73%, 74%, 75%, 76%, 77%, 78%, 79%, 80%, 81-85%, 90-95%, 96-98%, 99%, 99.9% or even higher identity to SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44 and SEQ ID NO:45. The present invention provides nucleic acids each comprising or consisting of a sequence which is a codon optimized version of one of the wild-type acetyl-CoA/propionyl-CoA carboxylase genes. In another embodiment, the invention provides nucleic acids each encoding a polypeptide having the amino acid sequence of one of Genbank accession numbers YP_001191457, YP_001190248, YP_001190249, YP_00158606, YP_001581607, YP_001581608, YP_876582, YP_876583, YP_876584, NP 280337, NP_279647, NP_280339, NP_280547 and NP_280866, or homologs thereof having 70%, 71%, 72%, 73%, 74%, 75%, 76%, 77%, 78%, 79%, 80%, 81-85%, 90-95%, 96-98%, 99%, 99.9% or even higher identity thereto. The enzyme succinyl-CoA:malate-CoA transferase is composed of two subunits, such as SmtA and SmtB in *Chloroflexus aurantiacus*. Exemplary succinyl-CoA:malate-CoA transferase subunits include ABF 14399 and ABF 14400, and homologs thereof. Exemplary MMC lyases include YP_0017633817, and homologs thereof.

Figure 7:
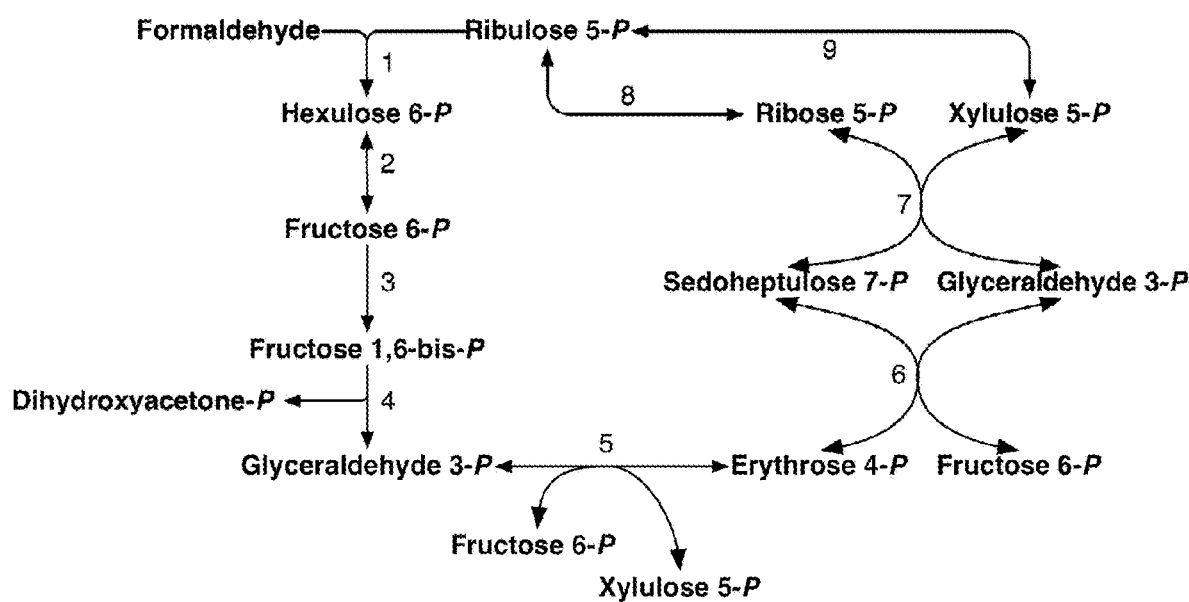
FIG. 7 depicts the metabolic reactions of the ribulose monophosphate cycle [Strom, 1974]. In metabolite names, —P denotes phosphate. Each reaction is numbered. Enzymes catalyzing each reaction are as follows: 1, hexulose-6-phosphate synthase (E.C. 4.1.2.43); 2, 6-phospho-3-hexuloisomerase (E.C. 5.3.1.27); 3, phosphofructokinase (E.C. 2.7.1.11); 4, fructose bisphosphate aldolase (E.C. 4.1.2.13); 5, transketolase (E.C. 2.2.1.1); 6, transaldolase (E.C. 2.2.1.2); 7, transketolase (E.C. 2.2.1.1); 8, ribose 5-phosphate isomerase (E.C. 5.3.1.6); 9, ribulose-5-phosphate-3-epimerase (E.C. 5.1.3.1).
Figure 8:
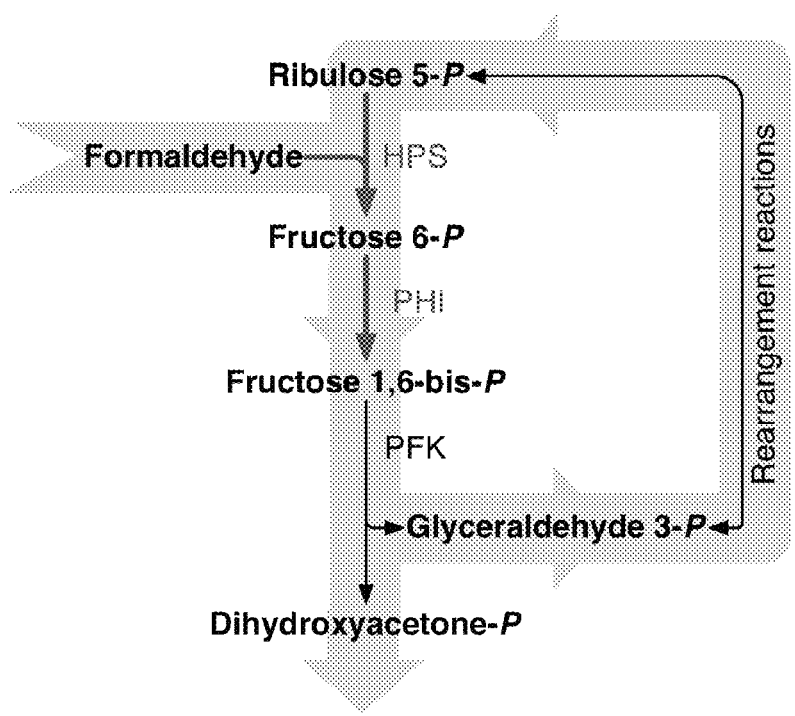
FIG. 8 depicts example metabolic reactions and enzymes needed to engineer a carbon fixation pathway derived from the ribulose monophosphate (RuMP) cycle into the heterotroph Escherichia coli. Reactions in black occur in the wildtype host cell E. coli. Reactions in dark gray must be added to complete the RuMP cycle-derived carbon fixation cycle in E. coli. The carbon input to the pathway is formaldehyde and the carbon output of the pathway is dihydroxyacetone-phosphate. The desired net flow of carbon is indicated by the wide, light gray arrow. For simplicity, a series of rearrangement reactions that regenerate ribulose-5-phosphate and all occur natively in E. coli are denoted by a single arrow. Metabolites are shown in bold with —P denoting phosphate. Enzyme abbreviations are as follows: HPS, hexulose-6-phosphate synthase; PHI, 6-phospho-3-hexuloisomerase; PFK, phosphofructokinase.

In certain embodiments, the invention provides an engineered chemoautotroph with a carbon fixation pathway derived from the ribulose monophosphate (RuMP) cycle. The RuMP cycle is well known in the art and consists of 9 reactions (FIG. 7) [Strom, 1974]. Reactions 1 and 2 (FIG. 7) are catalyzed by two separate enzymes in some organisms and by a bifunctional fusion enzyme in other organisms [Yurimoto, 2009]. The reactions in the RuMP cycle are catalyzed by the following enzymes: hexulose-6-phosphate synthase (HPS, E.C. 4.1.2.43) [Kemp, 1972; Kemp, 1974]; 6-phospho-3-hexuloisomerase (PHI, E.C. 5.3.1.27) [Strom, 1974; Ferenci, 1974]; phosphofructokinase (PFK, E.C. 2.7.1.11); fructose bisphosphate aldolase (FBA, E.C. 4.1.2.13); transketolase (TK, E.C. 2.2.1.1); transaldolase (TA, E.C. 2.2.1.2); 7, transketolase (TK, E.C. 2.2.1.1); ribose 5-phosphate isomerase (RPI, E.C. 5.3.1.6); ribulose-5-phosphate-3-epimerase (RPE, E.C. 5.1.3.1). In one embodiment, the invention provides an engineered chemoautotroph comprising one or more exogenous proteins from the RuMP cycle conferring to the organism the ability to produce central metabolites from inorganic carbon, wherein the organism lacks the ability to fix carbon via the RuMP cycle (for example, see FIG. 8). For example, the one or more exogenous proteins can be selected from hexulose-6-phosphate synthase, 6-phospho-3-hexuloisomerase, hexulose-6-phosphate synthase/6-phospho-3-hexuloisomerase fusion enzyme [Orita, 2005; Orita, 2006; Orita, 2007], phosphofructokinase, fructose bisphosphate aldolase, transketolase, transaldolase, transketolase, ribose 5-phosphate isomerase, and ribulose-5-phosphate-3-epimerase. The host organism can also express one or more, two or more, three or more, and the like, including up to all the protein and enzymes that confer the RuMP pathway. For example, in the host organism *E. coli*, the exogenous enzymes comprise hexulose-6-phosphate synthase and 6-phospho-3-hexuloisomerase. As a second example, in the host organism *E. coli*, the exogenous enzymes comprise the bifunctional fusion enzyme hexulose-6-phosphate synthase/6-phospho-3-hexuloisomerase. Exemplary HPS enzymes include YP_115138, YP_115430 and BAA90546, and homologs thereof. SEQ ID NO:46 and SEQ ID NO:47 represent *E. coli* codon optimized coding sequence for HPS enzymes YP_115138 and YP_115430, respectively, of the present invention. In one aspect, the invention provides nucleic acid molecules and homologs, variants and derivatives of SEQ ID NO:46 and SEQ ID NO:47. The nucleic acid sequences can have preferably 70%, 71%, 72%, 73%, 74%, 75%, 76%, 77%, 78%, 79%, 80%, 81-85%, 90-95%, 96-98%, 99%, 99.9% or even higher identity to SEQ ID NO:46 and SEQ ID NO:47. The present invention provides nucleic acids each comprising or consisting of a sequence which is a codon optimized version of one of the wild-type HPS genes. In another embodiment, the invention provides nucleic acids each encoding a polypeptide having the amino acid sequence of one of YP_115138 and YP_115430, or homologs thereof having 70%, 71%, 72%, 73%, 74%, 75%, 76%, 77%, 78%, 79%, 80%, 81-85%, 90-95%, 96-98%, 99%, 99.9% or even higher identity thereto. Exemplary PHI enzymes include YP_115431 and BAA90545, and homologs thereof. SEQ ID NO:48 represent *E. coli* codon optimized coding sequence for PHI enzyme YP_115431 of the present invention. In one aspect, the invention provides nucleic acid molecule and homologs, variants and derivatives of SEQ ID NO:48. The nucleic acid sequence can have preferably 78%, 79%, 80%, 81-85%, 90-95%, 96-98%, 99%, 99.9% or even higher identity to SEQ ID NO:48. The present invention provides nucleic acids each comprising or consisting of a sequence which is a codon optimized version of one of the wild-type PHI genes. In another embodiment, the invention provides nucleic acids each encoding a polypeptide having the amino acid sequence of YP_115431, or homologs thereof having 70%, 71%, 72%, 73%, 74%, 75%, 76%, 77%, 78%, 79%, 80%, 81-85%, 90-95%, 96-98%, 99%, 99.9% or even higher identity thereto. Exemplary HPS-PHI enzymes include NP_143767 and YP_182888, and homologs thereof. SEQ ID NO:49 represents an *E. coli* codon optimized coding sequence for a fusion of the *Mycobacterium gastri* MB 19 HPS enzyme (BAA90546) and PHI enzyme (BAA90545) of the present invention. In one aspect, the invention provides nucleic acid molecule and homologs, variants and derivatives of SEQ ID NO:49. The nucleic acid sequence can have preferably 70%, 71%, 72%, 73%, 74%, 75%, 76%, 77%, 78%, 79%, 80%, 81-85%, 90-95%, 96-98%, 99%, 99.9% or even higher identity to SEQ ID NO:49. The present invention provides nucleic acids each comprising or consisting of a sequence which is a codon optimized version of one of the wild-type HPS and one of the wild-type PHI genes. In another embodiment, the invention provides nucleic acids each encoding a polypeptide having the amino acid sequence of SEQ ID NO:50, or homologs thereof having 70%, 71%, 72%, 73%, 74%, 75%, 76%, 77%, 78%, 79%, 80%, 81-85%, 90-95%, 96-98%, 99%, 99.9% or even higher identity thereto.

In certain embodiments, the invention provides an engineered chemoautotroph comprising a carbon fixation pathway derived from the RuMP cycle, as described above, and in which formaldehyde is produced from formate. The conversion of formate to formyl-coenzyme A (formyl-CoA) can be catalyzed by the enzyme acetyl-CoA synthetase (ACS) operating on a non-cognate substrate [see, e.g., WO 2012/037413]. The conversion of formyl-CoA to formaldehyde can be catalyzed by the enzyme (acylating) acetaldehyde dehydrogenase (ADH), operating on a non-cognate substrate. Exemplary ACS enzymes include AAC77039, and homologs thereof. SEQ ID NO:61 represents recoded coding sequence for ACS enzyme AAC77039 of the present invention. In one aspect, the invention provides nucleic acid molecules and homologs, variants and derivatives of SEQ ID NO:61. The nucleic acid sequences can have preferably 70%, 71%, 72%, 73%, 74%, 75%, 76%, 77%, 78%, 79%, 80%, 81-85%, 90-95%, 96-98%, 99%, 99.9% or even higher identity to SEQ ID NO:61. The present invention provides nucleic acids each comprising or consisting of a sequence which is a codon optimized version of one of the wild-type ACS genes. In another embodiment, the invention provides nucleic acids each encoding a polypeptide having the amino acid sequence of AAC77039, or homologs thereof having 70%, 71%, 72%, 73%, 74%, 75%, 76%, 77%, 78%, 79%, 80%, 81-85%, 90-95%, 96-98%, 99%, 99.9% or even higher identity thereto. Exemplary ADH enzymes include NP_464704, NP_415757, AAD31841, CAA43226, and homologs thereof. SEQ ID NO:62 represents an *E. coli* codon optimized coding sequence for ADH enzyme AAC77039 of the present invention. In one aspect, the invention provides nucleic acid molecules and homologs, variants and derivatives of SEQ ID NO:62. The nucleic acid sequences can have preferably 70%, 71%, 72%, 73%, 74%, 75%, 76%, 77%, 78%, 79%, 80%, 81-85%, 90-95%, 96-98%, 99%, 99.9% or even higher identity to SEQ ID NO:62. The present invention provides nucleic acids each comprising or consisting of a sequence which is a codon optimized version of one of the wild-type ADH genes. In another embodiment, the invention provides nucleic acids each encoding a polypeptide having the amino acid sequence of NP_464704, NP_415757, AAD31841 or CAA43226, or homologs thereof having 70%, 71%, 72%, 73%, 74%, 75%, 76%, 77%, 78%, 79%, 80%, 81-85%, 90-95%, 96-98%, 99%, 99.9% or even higher identity thereto.

Figure 9:
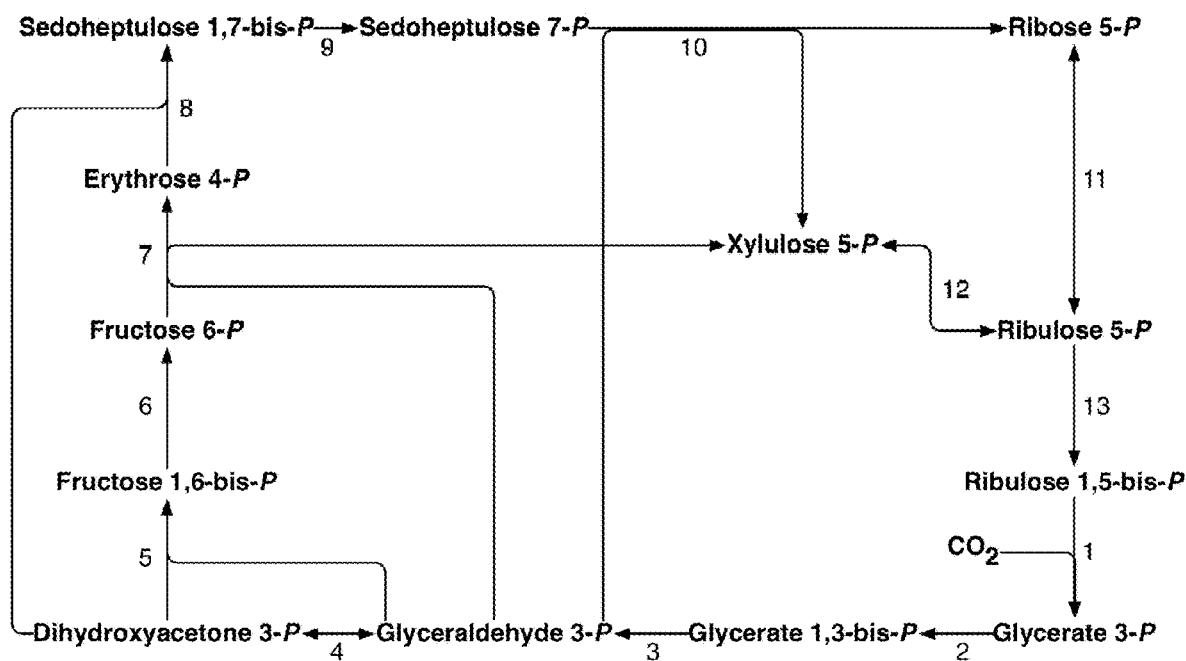
FIG. 9 depicts the metabolic reactions of the Calvin-Benson-Bassham cycle or the reductive pentose phosphate (RPP) cycle [Bassham, 1954]. In metabolite names, —P denotes phosphate. Each reaction is numbered. Enzymes catalyzing each reaction are as follows: 1, ribulose bisphosphate carboxylase (E.C. 4.1.1.39); 2, phosphoglycerate kinase (E.C. 2.7.2.3); 3, glyceraldehyde-3P dehydrogenase (phosphorylating) (E.C. 1.2.1.12 or E.C. 1.2.1.13); 4, triose-phosphate isomerase (E.C. 5.3.1.1); 5, fructose-bisphosphate aldolase (E.C. 4.1.2.13); 6, fructose-bisphosphatase (E.C. 3.1.3.11); 7, transketolase (E.C. 2.2.1.1); 8, sedoheptulose-1,7-bisphosphate aldolase (E.C. 4.1.2.-); 9, sedoheptulose bisphosphatase (E.C. 3.1.3.37); 10, transketolase (E.C. 2.2.1.1); 11, ribose-5-phosphate isomerase (E.C. 5.3.1.6); 12, ribulose-5-phosphate-3-epimerase (E.C. 5.1.3.1); 13, phosphoribulokinase (E.C. 2.7.1.19).
Figure 10:
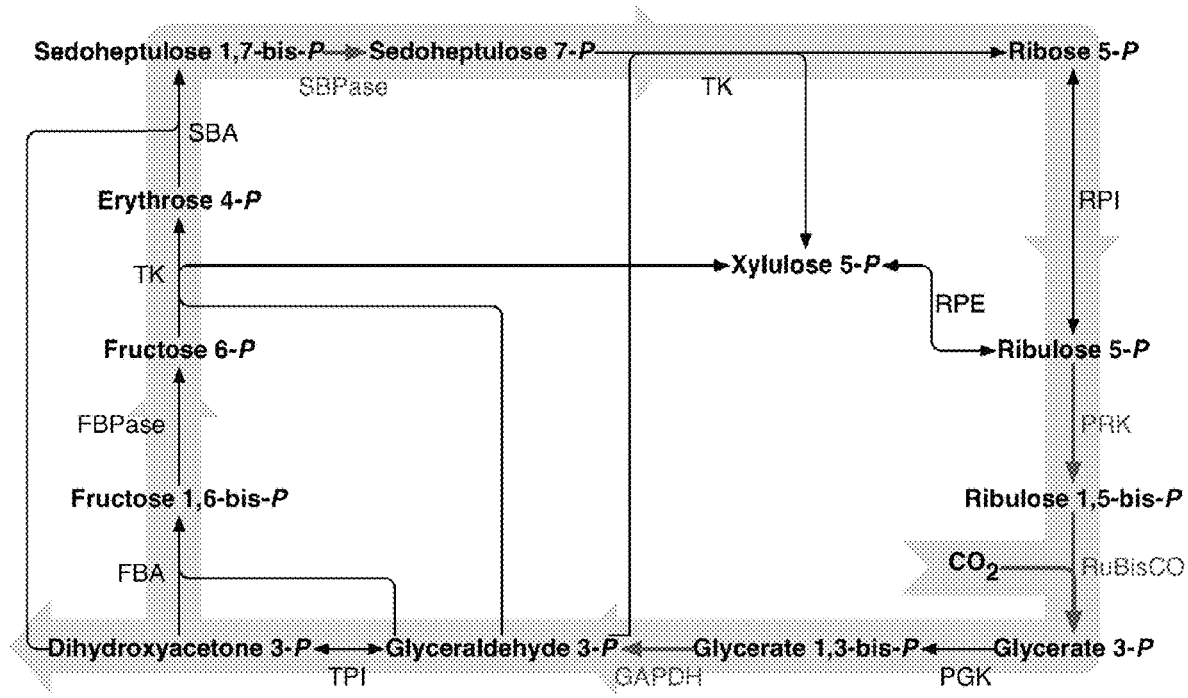
FIG. 10 depicts example metabolic reactions and enzymes needed to engineer a carbon fixation pathway derived from the Calvin-Benson-Bassham cycle or the reductive pentose phosphate (RPP) cycle into the heterotroph *Escherichia coli*. Reactions in black occur in the wildtype host cell *E. coli*. Reactions in dark gray must be added to complete the RPP cycle-derived carbon fixation cycle in *E. coli*. The carbon input to the pathway is carbon dioxide and the carbon output of the pathway is dihydroxyacetone-phosphate. The desired net flow of carbon is indicated by the wide, light gray arrow. Metabolites are shown in bold with —P denoting phosphate. Enzyme abbreviations are as follows: RuBisCO, ribulose bisphosphate carboxylase; PGK, phosphoglycerate kinase; GAPDH, NADPH-dependent glyceraldehyde-3P dehydrogenase (phosphorylating); TPI, triose-phosphate isomerase; FBA, fructose-bisphosphate aldolase; FBPase, fructose-bisphosphatase; TK, transketolase; SBA, sedoheptulose-1,7-bisphosphate aldolase; SBPase, sedoheptulose bisphosphatase; RPI, ribose-5-phosphate isomerase; RPE, ribulose-5-phosphate-3-epimerase; PRK, phosphoribulokinase.

In certain embodiments, the invention provides an engineered chemoautotroph whose carbon fixation pathway is the Calvin-Benson-Bassham cycle or reductive pentose phosphate (RPP) cycle. The Calvin cycle is well known in the art and consists of 13 reactions (FIG. 9) [Bassham, 1954]. The reactions in the RPP cycle are catalyzed by the following enzymes: ribulose bisphosphate carboxylase (RuBisCO, E.C. 4.1.1.39); phosphoglycerate kinase (PGK, E.C. 2.7.2.3); glyceraldehyde-3P dehydrogenase (phosphorylating) (GAPDH, E.C. 1.2.1.12 or E.C. 1.2.1.13); triose-phosphate isomerase (TPI, E.C. 5.3.1.1); fructose-bisphosphate aldolase (FBA, E.C. 4.1.2.13); fructose-bisphosphatase (FBPase, E.C. 3.1.3.11); transketolase (TK, E.C. 2.2.1.1); sedoheptulose-1,7-bisphosphate aldolase (SBA, E.C. 4.1.2.-); sedoheptulose bisphosphatase (SBPase, E.C. 3.1.3.37); transketolase (TK, E.C. 2.2.1.1); ribose-5-phosphate isomerase (RPI, E.C. 5.3.1.6); ribulose-5-phosphate-3-epimerase (RPE, E.C. 5.1.3.1); phosphoribulokinase (PRK, E.C. 2.7.1.19). In one embodiment, the invention provides an engineered chemoautotroph comprising one or more exogenous proteins from the RPP cycle conferring to the organism the ability to produce central metabolites from inorganic carbon, wherein the organism lacks the ability to fix carbon via the RPP cycle (for example, see FIG. 10). For example, the one or more exogenous proteins can be selected from ribulose bisphosphate carboxylase, phosphoglycerate kinase, glyceraldehyde-3P dehydrogenase (phosphorylating), triose-phosphate isomerase, fructose-bisphosphate aldolase, fructose-bisphosphatase, transketolase, sedoheptulose-1,7-bisphosphate aldolase, sedoheptulose bisphosphatase, transketolase, ribose-5-phosphate isomerase, ribulose-5-phosphate-3-epimerase and phosphoribulokinase. The host organism can also express two or more, three or more, four or more, and the like, including up to all the protein and enzymes that confer the RPP pathway. For example, in the host organism *E. coli*, the exogenous enzymes comprise ribulose bisphosphate carboxylase, sedoheptulose bisphosphatase and phosphoribulokinase. As a second example, in the host organism *E. coli*, the exogenous enzymes comprise ribulose bisphosphate carboxylase, NADPH-dependent glyceraldehyde-3P dehydrogenase, sedoheptulose bisphosphatase and phosphoribulokinase. Ribulose bisphosphate carboxylase has two distinct forms: Form I and Form II [Portis, 2007]. Form I is composed of four large subunit dimers and eight small subunits ($L_8S_8$) and has been expressed previously in heterologous hosts, such as *Escherichia coli* [Gatenby, 1985; Tabita, 1985; Gutteridge, 1986]. Exemplary RuBisCO subunits include YP_170840 and YP_170839, and homologs thereof. Extensive work has been done to attempt to optimize the function of RuBisCO [Parikh, 2006; Greene, 2007], and thus engineered RuBisCO enzymes may also be used in the present invention. Exemplary NADPH-dependent GAPDH enzymes include YP_400759, and homologs thereof. SEQ ID NO:51 represents an *E. coli* codon optimized coding sequence for this GAPDH of the present invention. In one aspect, the invention provides nucleic acid molecule and homologs, variants and derivatives of SEQ ID NO:51. The nucleic acid sequence can have preferably 70%, 71%, 72%, 73%, 74%, 75%, 76%, 77%, 78%, 79%, 80%, 81-85%, 90-95%, 96-98%, 99%, 99.9% or even higher identity to SEQ ID NO:51. The present invention provides nucleic acids each comprising or consisting of a sequence which is a codon optimized version of one of the wild-type GAPDH genes. In another embodiment, the invention provides nucleic acids each encoding a polypeptide having the amino acid sequence of YP_400759, or homologs thereof having 70%, 71%, 72%, 73%, 74%, 75%, 76%, 77%, 78%, 79%, 80%, 81-85%, 90-95%, 96-98%, 99%, 99.9% or even higher identity thereto. Exemplary SBPase enzymes include YP_399524, and homologs thereof. SEQ ID NO:52 represents an *E. coli* codon optimized coding sequence for this SBPase of the present invention. In one aspect, the invention provides nucleic acid molecule and homologs, variants and derivatives of SEQ ID NO:52. The nucleic acid sequence can have preferably 70%, 71%, 72%, 73%, 74%, 75%, 76%, 77%, 78%, 79%, 80%, 81-85%, 90-95%, 96-98%, 99%, 99.9% or even higher identity to SEQ ID NO:52. The present invention provides nucleic acids each comprising or consisting of a sequence which is a codon optimized version of one of the wild-type SBPase genes. In another embodiment, the invention provides nucleic acids each encoding a polypeptide having the amino acid sequence of YP_399524, or homologs thereof having 70%, 71%, 72%, 73%, 74%, 75%, 76%, 77%, 78%, 79%, 80%, 81-85%, 90-95%, 96-98%, 99%, 99.9% or even higher identity thereto. Exemplary PRK enzymes include YP_399994, and homologs thereof. SEQ ID NO:53 represents an *E. coli* codon optimized coding sequence for this PRK of the present invention. In one aspect, the invention provides nucleic acid molecule and homologs, variants and derivatives of SEQ ID NO:53. The nucleic acid sequence can have preferably 70%, 71%, 72%, 73%, 74%, 75%, 76%, 77%, 78%, 79%, 80%, 81-85%, 90-95%, 96-98%, 99%, 99.9% or even higher identity to SEQ ID NO:53. The present invention provides nucleic acids each comprising or consisting of a sequence which is a codon optimized version of one of the wild-type PRK genes. In another embodiment, the invention provides nucleic acids each encoding a polypeptide having the amino acid sequence of YP_399994, or homologs thereof having 70%, 71%, 72%, 73%, 74%, 75%, 76%, 77%, 78%, 79%, 80%, 81-85%, 90-95%, 96-98%, 99%, 99.9% or even higher identity thereto.

Production of Central Metabolites as the Carbon-Based Products of Interest

Figure 11:
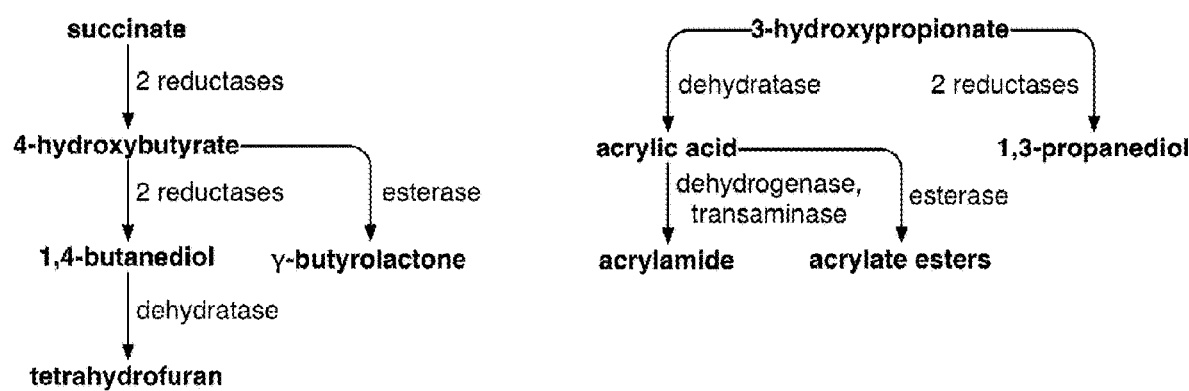
FIG. 11 provides a schematic to convert succinate or 3-hydroxypropionate to various chemicals.

In certain embodiments, the engineered chemoautotroph of the present invention produces the central metabolites, including but not limited to citrate, malate, succinate, fumarate, dihydroxyacetone, dihydroxyacetone phosphate, 3-hydroxypropionate, pyruvate, as the carbon-based products of interest. The engineered chemoautotroph produces central metabolites as an intermediate or product of the carbon fixation pathway or as a intermediate or product of host metabolism. In such cases, one or more transporters may be expressed in the engineered chemoautotroph to export the central metabolite from the cell. For example, one or more members of a family of enzymes known as C4-dicarboxylate carriers serve to export succinate from cells into the media [Janausch, 2002; Kim, 2007]. These central metabolites can be converted to other products (FIG. 11).

In some embodiments, the engineered chemoautotroph may interconvert between different central metabolites to produce alternate carbon-based products of interest. In one embodiment, the engineered chemoautotroph produces aspartate by expressing one or more aspartate aminotransferase (E.C. 2.6.1.1), such as *Escherichia coli* AspC, to convert oxaloacetate and L-glutamate to L-aspartate and 2-oxoglutarate.

In another embodiment, the engineered chemoautotroph produces dihydroxyacetone phosphate by expressing one or more dihydroxyacetone kinases (E.C. 2.7.1.29), such as *C. freundii* DhaK, to convert dihydroxyacetone and ATP to dihydroxyacetone phosphate.

In another embodiment, the engineered chemoautotroph produces serine as the carbon-based product of interest. The metabolic reactions necessary for serine biosynthesis include: phosphoglycerate dehydrogenase (E.C. 1.1.1.95), phosphoserine transaminase (E.C. 2.6.1.52), phosphoserine phosphatase (E.C. 3.1.3.3). Phosphoglycerate dehydrogenase, such as *E. coli* SerA, converts 3-phospho-D-glycerate and $NAD^+$ to 3-phosphonooxypyruvate and NADH. Phosphoserine transaminase, such as *E. coli* SerC, interconverts between 3-phosphonooxypyruvate+L-glutamate and O-phospho-L-serine+2-oxoglutarate. Phosphoserine phosphatase, such as *E. coli* SerB, converts O-phospho-L-serine to L-serine.

Figure 12:
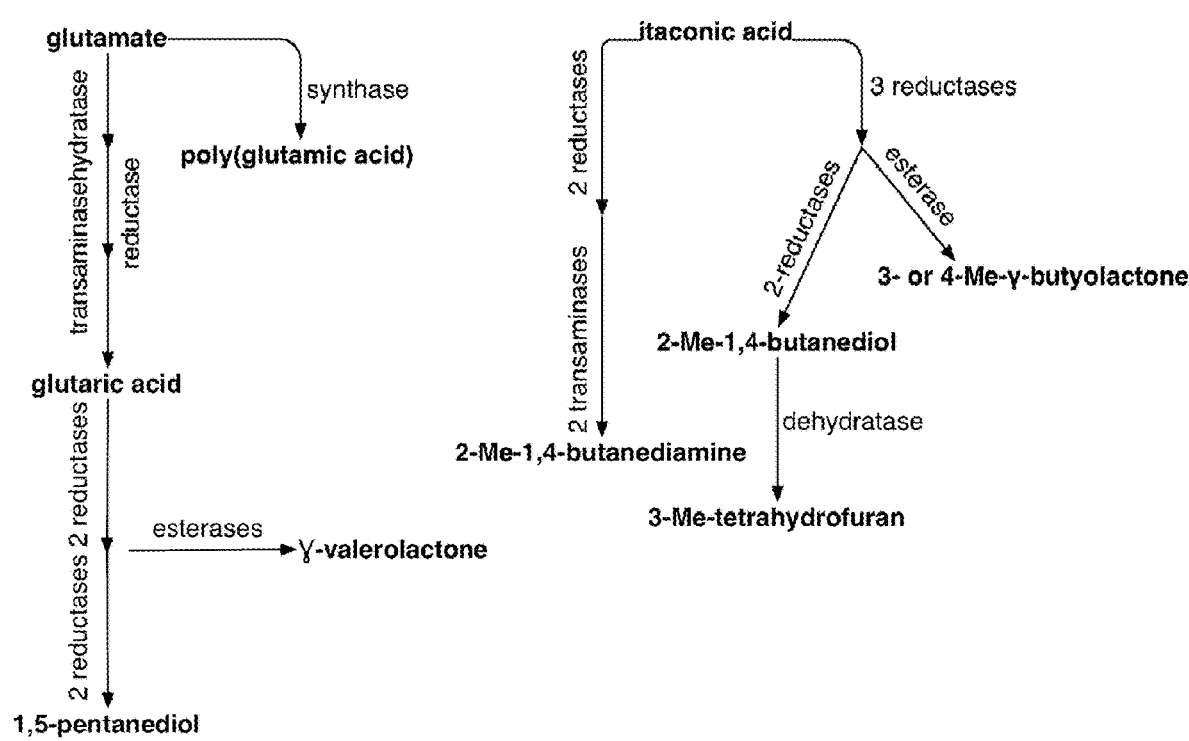
FIG. 12 provides a schematic of glutamate or itaconic acid conversion to various chemicals.

In another embodiment, the engineered chemoautotroph produces glutamate as the carbon-based product of interest. The metabolic reactions necessary for glutamate biosynthesis include glutamate dehydrogenase (E.C. 1.4.1.4; e.g., *E. coli* GdhA) which converts α-ketoglutarate, $NH_3$ and NADPH to glutamate. Glutamate can subsequently be converted to various other carbon-based products of interest, e.g., according to the scheme presented in FIG. 12.

In another embodiment, the engineered chemoautotroph produces itaconate as the carbon-based product of interest. The metabolic reactions necessary for itaconate biosynthesis include aconitate decarboxylase (E.C. 4.1.1.6; such as that from *A. terreus*) which converts cis-aconitate to itaconate and $CO_2$. Itaconate can subsequently be converted to various other carbon-based products of interest, e.g., according to the scheme presented in FIG. 12.

Production of Sugars as the Carbon-Based Products of Interest

Industrial production of chemical products from biological organisms is often accomplished using a sugar source, such as glucose or fructose, as the feedstock. Hence, in certain embodiments, the engineered chemoautotroph of the present invention produces sugars including glucose and fructose or sugar phosphates including triose phosphates (such as 3-phosphoglyceraldehyde and dihydroxyacetone-phosphate) as the carbon-based products of interest. Sugars and sugar phosphates may also be interconverted. For example, glucose-6-phosphate isomerase (E.C. 5.3.1.9; e.g., *E. coli* Pgi) may interconvert between D-fructose 6-phosphate and D-glucose-6-phosphate. Phosphoglucomutase (E.C. 5.4.2.2; e.g., *E. coli* Pgm) converts D-α-glucose-6-P to D-α-glucose-1-P. Glucose-1-phosphatase (E.C. 3.1.3.10; e.g., *E. coli* Agp) converts D-α-glucose-1-P to D-α-glucose. Aldose 1-epimerase (E.C. 5.1.3.3; e.g., *E. coli* GalM) D-β-glucose to D-α-glucose. The sugars or sugar phosphates may optionally be exported from the engineered chemoautotroph into the culture medium.

Sugar phosphates may be converted to their corresponding sugars via dephosphorylation that occurs either intra- or extracellularly. For example, phosphatases such as a glucose-6-phosphatase (E.C. 3.1.3.9) or glucose-1-phosphatase (E.C. 3.1.3.10) can be introduced into the engineered chemoautotroph of the present invention. Exemplary phosphatases include *Homo sapiens* glucose-6-phosphatase G6PC (P35575), *Escherichia coli* glucose-1-phosphatase Agp (P19926), *E. cloacae* glucose-1-phosphatase AgpE (Q6EV19) and *Escherichia coli* acid phosphatase YihX (POA8Y3).

Sugar phosphates can be exported from the engineered chemoautotroph into the culture media via transporters. Transporters for sugar phosphates generally act as antiporters with inorganic phosphate. An exemplary triose phosphate transporter includes *A. thaliana* triose-phosphate transporter APE2 (Genbank accession AT5G46110.4). Exemplary glucose-6-phosphate transporters include *E. coli* sugar phosphate transporter UhpT (NP_418122.1), *A. thaliana* glucose-6-phosphate transporter GPT1 (AT5G54800.1), *A. thaliana* glucose-6-phosphate transporter GPT2, or homologs thereof. Dephosphorylation of glucose-6-phosphate can also be coupled to glucose transport, such as Genbank accession numbers AAA16222, AAD19898, 043826.

Sugars can be diffusively effluxed from the engineered chemoautotroph into the culture media via permeases. Exemplary permeases include *H. sapiens* glucose transporter GLUT-1, -3, or -7 (P11166, P11169, Q6PXP3), *S. cerevisiae* hexose transporter HXT-1, -4, or –6 (P32465, P32467, P39003), *Z. mobilis* glucose uniporter Glf (P21906), *Synechocystis* sp. 1148 glucose/fructose:$H^+$ symporter GlcP (T.C. 2.A.1.1.32; P15729) [Zhang, 1989], *Streptomyces lividans* major glucose (or 2-deoxyglucose) uptake transporter GlcP (T.C. 2.A. 1.1.35; Q7BEC4) [van Wezel, 2005], *Plasmodium falciparum*: hexose (glucose and fructose) transporter PfHT1 (T.C. 2.A. 1.1.24; 097467), or homologs thereof. Alternatively, to enable active efflux of sugars from the engineered chemoautotroph, one or more active transporters may be introduced to the cell. Exemplary transporters include mouse glucose transporter GLUT 1 (AAB20846) or homologs thereof.

Preferably, to prevent buildup of other storage polymers from sugars or sugar phosphates, the engineered chemoautotrophs of the present invention are attenuated in their ability to build other storage polymers such as glycogen, starch, sucrose, and cellulose using one or more of the following enzymes: cellulose synthase (UDP forming) (E.C. 2.4.1.12), glycogen synthase e.g. glgA1, glgA2 (E.C. 2.4.1.21), sucrose phosphate synthase (E.C. 2.4.1.14), sucrose phosphorylase (E.C. 3.1.3.24), alpha-1,4-glucan lyase (E.C. 4.2.2.13), glycogen synthase (E.C. 2.4.1.11), 1,4-alpha-glucan branching enzyme (E.C. 2.4.1.18).

Figure 13:
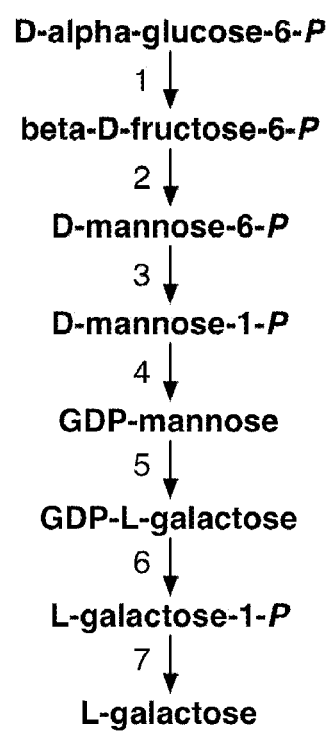
FIG. 13 depicts the metabolic reactions of a galactose biosynthetic pathway. In metabolite names, —P denotes phosphate. Each reaction is numbered. Enzymes catalyzing each reaction are as follows: 1, alpha-D-glucose-6-phosphate ketol-isomerase (E.C. 5.3.1.9); 2, D-mannose-6-phosphate ketol-isomerase (E.C. 5.3.1.8); 3, D-mannose 6-phosphate 1,6-phosphomutase (E.C. 5.4.2.8); 4, mannose-1-phosphate guanylyltransferase (E.C. 2.7.7.22); 5, GDP-mannose 3,5-epimerase (E.C. 5.1.3.18); 6, galactose-1-phosphate guanylyltransferase (E.C. 2.7.n.n); 7, L-galactose 1-phosphate phosphatase (E.C. 3.1.3.n).

The invention also provides engineered chemoautotrophs that produce other sugars such as sucrose, xylose, lactose, maltose, pentose, rhamnose, galactose and arabinose according to the same principles. A pathway for galactose biosynthesis is shown (FIG. 13). The metabolic reactions in the galactose biosynthetic pathway are catalyzed by the following enzymes: alpha-D-glucose-6-phosphate ketol-isomerase (E.C. 5.3.1.9; e.g., *Arabidopsis thaliana* PGI1), D-mannose-6-phosphate ketol-isomerase (E.C. 5.3.1.8; e.g., *Arabidopsis thaliana* DIN9), D-mannose 6-phosphate 1,6-phosphomutase (E.C. 5.4.2.8; e.g., *Arabidopsis thaliana* ATPMM), mannose-1-phosphate guanylyltransferase (E.C. 2.7.7.22; e.g., *Arabidopsis thaliana* CYT), GDP-mannose 3,5-epimerase (E.C. 5.1.3.18; e.g., *Arabidopsis thaliana* GME), galactose-1-phosphate guanylyltransferase (E.C. 2.7.n.n; e.g., *Arabidopsis thaliana* VTC2), L-galactose 1-phosphate phosphatase (E.C. 3.1.3.n; e.g., *Arabidopsis thaliana* VTC4). In one embodiment, the invention provides an engineered chemoautotroph comprising one or more exogenous proteins from the galactose biosynthetic pathway.

The invention also provides engineered chemoautotrophs that produce sugar alcohols, such as sorbitol, as the carbon-based product of interest. In certain embodiments, the engineered chemoautotroph produces D-sorbitol from D-α-glucose and NADPH via the enzyme polyol dehydrogenase (E.C. 1.1.1.21; e.g., *Saccharomyces cerevisiae* GRE3).

The invention also provides engineered chemoautotrophs that produce sugar derivatives, such as ascorbate, as the carbon-based product of interest. In certain embodiments, the engineered chemoautotroph produces ascorbate from galactose via the enzymes L-galactose dehydrogenase (E.C. 1.1.1.122; e.g., *Arabidopsis thaliana* At4G33670) and L-galactonolactone oxidase (E.C. 1.3.3.12; e.g., *Saccharomyes cerevisiae* ATGLDH). Optionally, a catalase (E.C. 1.11.1.6; e.g., *E. coli* KatE) may be included to convert the waste produce hydrogen peroxide to molecular oxygen.

The fermentation products according to the above aspect of the invention are sugars, which are exported into the media as a result of carbon fixation during chemoautotrophy. The sugars can also be reabsorbed later and fermented, directly separated, or utilized by a co-cultured organism. This approach has several advantages. First, the total amount of sugars the cell can handle is not limited by maximum intracellular concentrations because the end-product is exported to the media. Second, by removing the sugars from the cell, the equilibria of carbon fixation reactions are pushed towards creating more sugar. Third, during chemoautotrophy, there is no need to push carbon flow towards glycolysis. Fourth, the sugars are potentially less toxic than the fermentation products that would be directly produced.

Chemoautotrophic fixation of carbon dioxide may be followed by flux of carbon compounds to the creation and maintenance of biomass and to the storage of retrievable carbon in the form of glycogen, cellulose and/or sucrose. Glycogen is a polymer of glucose composed of linear alpha 1,4-linkages and branched alpha 1,6-linkages. The polymer is insoluble at degree of polymerization (DP) greater than about 60,000 and forms intracellular granules. Glycogen in synthesized in vivo via a pathway originating from glucose 1-phosphate. Its hydrolysis can proceed through phosphorylation to glucose phosphates; via the internal cleavage of polymer to maltodextrins; via the successive exo-cleavage to maltose; or via the concerted hydrolysis of polymer and maltodextrins to maltose and glucose. Hence, an alternative biosynthetic route to glucose and/or maltose is via the hydrolysis of glycogen which can optionally be exported from the cell as described above. There are a number of potential enzyme candidates for glycogen hydrolysis (Table 1).

In addition to the above, another mechanism is described to produce glucose biosynthetically. In certain embodiments, the present invention provides for cloned genes for glycogen hydrolyzing enzymes to hydrolyze glycogen to glucose and/or maltose and transport maltose and glucose from the cell. Preferred enzymes are set forth below in Table 1. Glucose is transported from the engineered chemoautotroph by a glucose/hexose transporter. This alternative allows the cell to accumulate glycogen naturally but adds enzyme activities to continuously return it to maltose or glucose units that can be collected as a carbon-based product.

TABLE 1

Enzymes for hydrolysis of glycogen

| Enzyme | E.C. number | Function |
|---|---|---|
| α-amylase | 3.2.1.1 | endohydrolysis of 1,4-α-D-glucosidic linkages in polysaccharides |
| β-amylase | 3.2.1.2 | hydrolysis of 1,4-α-D-glucosidic linkages in polysaccharides so as to remove successive maltose units from the non-reducing ends of the chains |

TABLE 1-continued

Enzymes for hydrolysis of glycogen

| Enzyme | E.C. number | Function |
|---|---|---|
| γ-amylase | 3.2.1.3 | hydrolysis of terminal 1,4-linked α-D-glucose residues successively from non-reducing ends of the chains with release of β-D-glucose |
| glucoamylase | 3.2.1.3 | hydrolysis of terminal 1,4-linked α-D-glucose residues successively from non-reducing ends of the chains with release of β-D-glucose |
| isoamylase | 3.2.1.68 | hydrolysis of (1->6)-α-D-glucosidic branch linkages in glycogen, amylopectin and their beta-limit dextrins |
| pullulanase | 3.2.1.41 | hydrolysis of (1->6)-α-D-glucosidic linkages in pullulan [a linear polymer of α-(1->6)-linked maltotriose units] and in amylopectin and glycogen, and the α- and β-limit dextrins of amylopectin and glycogen |
| amylomaltase | 2.4.1.25 | transfers a segment of a 1,4-α-D-glucan to a new position in an acceptor, which may be glucose or a 1,4-α-D-glucan (part of yeast debranching system) |
| amylo-α-1,6-glucosidase | 3.2.1.33 | debranching enzyme; hydrolysis of (1->6)-α-D-glucosidic branch linkages in glycogen phosphorylase limit dextrin |
| phosphorylase kinase | 2.7.11.19 | 2 ATP + phosphorylase b = 2 ADP + phosphorylase a |
| phosphorylase | 2.4.1.1 | (1,4-α-D-glucosyl)$_n$ + phosphate = (1,4-α-D-glucosyl)$_{n-1}$ + α-D-glucose-1-phosphate |

Production of Fermentative Products as the Carbon-Based Products of Interest

In certain embodiments, the engineered chemoautotroph of the present invention produces alcohols such as ethanol, propanol, isopropanol, butanol and fatty alcohols as the carbon-based products of interest.

Figure 14:
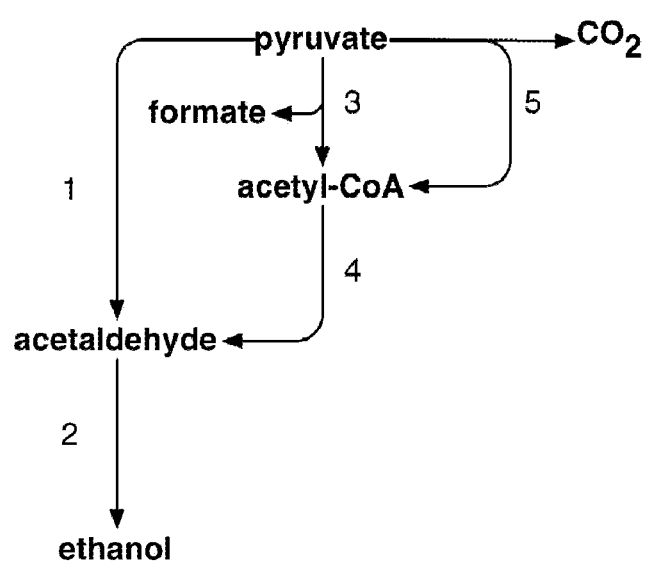
FIG. 14 depicts different fermentation pathways from pyruvate to ethanol. Each reaction is numbered. Enzymes catalyzing each reaction are as follows: 1, pyruvate decarboxylase (E.C. 4.1.1.1); 2, alcohol dehydrogenase (E.C. 1.1.1.1); 3, pyruvate-formate lyase (E.C. 2.3.1.54); 4, acetaldehyde dehydrogenase (E.C. 1.2.1.10); 5, pyruvate synthase (E.C. 1.2.7.1).

In some embodiments, the engineered chemoautotroph of the present invention is engineered to produce ethanol via pyruvate fermentation. Pyruvate fermentation to ethanol is well know to those in the art and there are several pathways including the pyruvate decarboxylase pathway, the pyruvate synthase pathway and the pyruvate formate-lyase pathway (FIG. 14). The reactions in the pyruvate decarboxylase pathway are catalyzed by the following enzymes: pyruvate decarboxylase (E.C. 4.1.1.1) and alcohol dehydrogenase (E.C. 1.1.1.1 or E.C. 1.1.1.2). The reactions in the pyruvate synthase pathway are catalyzed by the following enzymes: pyruvate synthase (E.C. 1.2.7.1), acetaldehyde dehydrogenase (E.C. 1.2.1.10 or E.C. 1.2.1.5), and alcohol dehydrogenase (E.C. 1.1.1.1 or E.C. 1.1.1.2). The reactions in the pyruvate formate-lyase pathway are catalyzed by the following enzymes: pyruvate formate-lyase (E.C. 2.3.1.54), acetaldehyde dehydrogenase (E.C. 1.2.1.10 or E.C. 1.2.1.5), and alcohol dehydrogenase (E.C. 1.1.1.1 or E.C. 1.1.1.2).

In some embodiments, the engineered chemoautotroph of the present invention is engineered to produce lactate via pyruvate fermentation. Lactate dehydrogenase (E.C. 1.1.1.28) converts NADH and pyruvate to D-lactate. Exemplary enzymes include E. coli ldhA.

Currently, fermentative products such as ethanol, butanol, lactic acid, formate, acetate produced in biological organisms employ a NADH-dependent processes. However, depending on the energy conversion pathways added to the engineered chemoautotroph, the cell may produce NADPH or reduced ferredoxin as the reducing cofactor. NADPH is used mostly for biosynthetic operations in biological organisms, e.g., cell for growth, division, and for building up chemical stores, such as glycogen, sucrose, and other macromolecules. Using natural or engineered enzymes that utilize NADPH or reduced ferredoxin as a source of reducing power instead of NADH would allow direct use of chemoautotrophic reducing power towards formation of normally fermentative byproducts. Accordingly, the present invention provides methods for producing fermentative products such as ethanol by expressing NADP$^+$-dependent or ferredoxin-dependent enzymes. NADP$^+$-dependent enzymes include alcohol dehydrogenase [NADP$^+$] (E.C. 1.1.1.2) and acetaldehyde dehydrogenase [NAD(P)$^+$] (E.C. 1.2.1.5). Exemplary NADP$^+$-dependent alcohol dehydrogenases include Moorella sp. HUC22-1 AdhA (YP_430754) [Inokuma, 2007], and homologs thereof.

In addition to providing exogenous genes or endogenous genes with novel regulation, the optimization of ethanol production in engineered chemoautotrophs preferably requires the elimination or attenuation of certain host enzyme activities. These include, but are not limited to, pyruvate oxidase (E.C. 1.2.2.2), D-lactate dehydrogenase (E.C. 1.1.1.28), acetate kinase (E.C. 2.7.2.1), phosphate acetyltransferase (E.C. 2.3.1.8), citrate synthase (E.C. 2.3.3.1), phosphoenolpyruvate carboxylase (E.C. 4.1.1.31). The extent to which these manipulations are necessary is determined by the observed byproducts found in the bioreactor or shake-flask. For instance, observation of acetate would suggest deletion of pyruvate oxidase, acetate kinase, and/or phosphotransacetylase enzyme activities. In another example, observation of D-lactate would suggest deletion of D-lactate dehydrogenase enzyme activities, whereas observation of succinate, malate, fumarate, oxaloacetate, or citrate would suggest deletion of citrate synthase and/or PEP carboxylase enzyme activities.

Production of Ethylene, Propylene, 1-Butene, 1,3-Butadiene, Acrylic Acid, Etc. as the Carbon-Based Products of Interest In certain embodiments, the engineered chemoautotroph of the present invention produces ethylene, propylene, 1-butene, 1,3-butadiene and acrylic acid as the carbon-based products of interest. Ethylene and/or propylene may be produced by either (1) the dehydration of ethanol or propanol (E.C. 4.2.1.-), respectively or (2) the decarboxylation of acrylate or crotonate (E.C. 4.1.1.-), respectively. While many dehydratases exist in nature, none has been shown to convert ethanol to ethylene (or propanol to propylene, propionic acid to acrylic acid, etc.) by dehydration. Genes encoding enzymes in the 4.2.1.x or 4.1.1.x group can be identified by searching databases such as GenBank using the methods described above, expressed in any desired host (such as Escherichia coli, for simplicity), and that host can be assayed for the appropriate enzymatic activity. A high-throughput screen is especially useful for screening many genes and variants of genes generated by mutagenesis (i.e., error-prone PCR, synthetic libraries, chemical mutagenesis, etc.).

The ethanol dehydratase gene, after development to a suitable level of activity, can then be expressed in an ethanologenic organism to enable that organism to produce ethylene. For instance, coexpress native or evolved ethanol dehydratase gene into an organism that already produces ethanol, then test a culture by GC analysis of offgas for ethylene production that is significantly higher than without the added gene or via a high-throughput assay adapted from a colorimetric test [Larue, 1973]. It may be desirable to eliminate ethanol-export proteins from the production organism to prevent ethanol from being secreted into the medium and preventing its conversion to ethylene.

Alternatively, acryloyl-CoA can be produced as described above, and acryloyl-CoA hydrolases (E.C. 3.1.2.-), such as the acuN gene from *Halomonas* sp. HTNK1, can convert acryloyl-CoA into acrylate, which can be thermally decarboxylated to yield ethylene.

Alternatively, genes encoding ethylene-forming enzyme activities (EfE, E.C. 1.14.17.4) from various sources are expressed. Exemplary enzymes include *Pseudomonas syringae* pv. *Phaseolicola* (BAA02477), *P. syringae* pv. *Pisi* (AAD16443), *Ralstonia solanacearum* (CAD18680). Optimizing production may require further metabolic engineering (improving production of alpha-ketogluterate, recycling succinate as two examples).

In some embodiments, the engineered chemoautotroph of the present invention is engineered to produce ethylene from methionine. The reactions in the ethylene biosynthesis pathway are catalyzed by the following enzymes: methionine adenosyltransferase (E.C. 2.5.1.6), 1-aminocyclopropane-1-carboxylate synthase (E.C. 4.4.1.14) and 1-aminocyclopropane-1-carboxylate oxidase (E.C. 1.14.17.4).

In some embodiments, the engineered chemoautotroph of the present invention is engineered to produce propylene as the carbon-based product of interest. In one embodiment, the engineered chemoautotroph is engineered to express one or more of the following enzymes: propionyl-CoA synthase (E.C. 6.2.1.-, E.C. 4.2.1.- and E.C. 1.3.1.-), propionyl-CoA transferase (E.C. 2.8.3.1), aldehyde dehydrogenase (E.C. 1.2.1.3 or E.C. 1.2.1.4), alcohol dehydrogenase (E.C. 1.1.1.1 or E.C. 1.1.1.2), and alcohol dehydratase (E.C. 4.2.1.-). Propionyl-CoA synthase is a multi-functional enzyme that converts 3-hydroxypropionate, ATP and NADPH to propionyl-CoA. Exemplary propionyl-CoA synthases include AAL47820, and homologs thereof. SEQ ID NO:30 represents the *E. coli* codon optimized coding sequence for this propionyl-CoA synthase of the present invention. In one aspect, the invention provides nucleic acid molecule and homologs, variants and derivatives of SEQ ID NO:30. The nucleic acid sequence can have preferably 70%, 71%, 72%, 73%, 74%, 75%, 76%, 77%, 78%, 79%, 80%, 81-85%, 90-95%, 96-98%, 99%, 99.9% or even higher identity to SEQ ID NO:30. The present invention provides nucleic acids each comprising or consisting of a sequence which is a codon optimized version of the wild-type propionyl-CoA synthase gene. In another embodiment, the invention provides a nucleic acid encoding a polypeptide having the amino acid sequence of SEQ ID NO:31. Propionyl-CoA transferase converts propionyl-CoA and acetate to acetyl-CoA and propionate. Exemplary enzymes include *Ralstonia eutropha* pct and homologs thereof. Aldehyde dehydrogenase converts propionate and NADPH to propanal. Alcohol dehydrogenase converts propanal and NADPH to 1-propanol. Alcohol dehydratase converts 1-propanol to propylene.

In another embodiment, *E. coli* thiolase atoB (E.C. 2.3.1.9) converts 2 acetyl-CoA into acetoacetyl-CoA, and *C. acetobutylicum* hbd (E.C. 1.1.1.157) converts acetoacetyl-CoA and NADH into 3-hydroxybutyryl-CoA. *E. coli* tesB (EC 3.1.2.20) or *C. acetobutylicum* ptb and buk (E.C. 2.3.1.19 and 2.7.2.7 respectively) convert 3-hydroxybutyryl-CoA into 3-hydroxybutyrate, which can be simultaneously decarboxylated and dehydrated to yield propylene. Optionally, the 3-hydroxybutyryl-CoA is polymerized to form poly(3-hydroxybutyrate), a solid compound which can be extracted from the fermentation medium and simultaneously depolymerizied, hydrolyzed, dehydrated, and decarboxyated to yield propylene (U.S. patent application Ser. No. 12/527, 714, 2008).

Production of Fatty Acids, their Intermediates and Derivatives as the Carbon-Based Products of Interest In certain embodiments, the engineered chemoautotroph of the present invention produces fatty acids, their intermediates and their derivatives as the carbon-based products of interest. The engineered chemoautotrophs of the present invention can be modified to increase the production of acyl-ACP or acyl-CoA, to reduce the catabolism of fatty acid derivatives and intermediates, or to reduce feedback inhibition at specific points in the biosynthetic pathway used for fatty acid products. In addition to modifying the genes described herein, additional cellular resources can be diverted to over-produce fatty acids. For example the lactate, succinate and/or acetate pathways can be attenuated and the fatty acid biosynthetic pathway precursors acetyl-CoA and/or malonyl-CoA can be overproduced.

In one embodiment, the engineered chemoautotrophs of the present invention can be engineered to express certain fatty acid synthase activities (FAS), which is a group of peptides that catalyze the initiation and elongation of acyl chains [Marrakchi, 2002a]. The acyl carrier protein (ACP) and the enzymes in the FAS pathway control the length, degree of saturation and branching of the fatty acids produced, which can be attenuated or over-expressed. Such enzymes include accABCD, FabD, FabH, FabG, FabA, FabZ, FabI, FabK, FabL, FabM, FabB, FabF, and homologs thereof.

In another embodiment, the engineered chemoautotrophs of the present invention form fatty acid byproducts through ACP-independent pathways, for example, the pathway described recently by [Dellomonaco, 2011] involving reversal of beta oxidation. Enzymes involved in these pathways include such genes as atoB, fadA, fadB, fadD, fadE, fadI, fadK, fad, paaZ, ydiO, yfcY, yfcZ, ydiD, and homologs thereof.

In one aspect, the fatty acid biosynthetic pathway precursors acetyl-CoA and malonyl-CoA can be overproduced in the engineered chemoautotroph of the present invention. Several different modifications can be made, either in combination or individually, to the host cell to obtain increased acetyl CoA/malonyl CoA/fatty acid and fatty acid derivative production. To modify acetyl-CoA and/or malonyl-CoA production, the expression of acetyl-CoA carboxylase (E.C. 6.4.1.2) can be modulated. Exemplary genes include accABCD (AAC73296) or homologs thereof. To increase acetyl CoA production, the expression of several genes may be altered including pdh, panK, aceEF, (encoding the Elp dehydrogenase component and the E2p dihydrolipoamide acyltransferase component of the pyruvate and 2-oxoglutarate dehydrogenase complexes), fabH/fabD/fabG/acpP/fabF, and in some examples additional nucleic acid encoding fatty-acyl-CoA reductases and aldehyde decarbonylases. Exemplary enzymes include pdh (BAB34380, AAC73227, AAC73226), panK (also known as coaA, AAC76952), aceEF (AAC73227, AAC73226), fabH (AAC74175), fabD (AAC74176), fabG (AAC74177), acpP (AAC74178), fabF (AAC74179).

Genes to be knocked-out or attenuated include fadE, gpsA, ldhA, pflb, adhE, pta, poxB, ackA, and/or ackB. Exemplary enzymes include fadE (AAC73325), gspA (AAC76632), ldhA (AAC74462), pflb (AAC73989), adhE (AAC74323), pta (AAC75357), poxB (AAC73958), ackA (AAC75356), ackB (BAB81430), and homologs thereof.

Additional potential modifications include the following. To achieve fatty acid overproduction, lipase (E.C. 3.1.1.3) which produce triacylglyerides from fatty acids and glycerol and in some cases serves as a suppressor of fabA can be included in the engineered chemoautotroph of the present invention. Exemplary enzymes include *Saccharomyces cerevisiae* LipA (CAA89087), *Saccharomyces cerevisiae* TGL2 CAA98876, and homologs thereof. To remove limitations on the pool of acyl-CoA, the D311E mutation in plsB (AAC77011) can be introduced.

To engineer an engineered chemoautotroph for the production of a population of fatty acid derivatives with homogeneous chain length, one or more endogenous genes can be attenuated or functionally deleted and one or more thioesterases can be expressed. Thioesterases (E.C. 3.1.2.14) generate acyl-ACP from fatty acid and ACP. For example, C10 fatty acids can be produced by attenuating endogenous C18 thioesterases (for example, *E. coli* tesA AAC73596 and P0ADA1, and homologs thereof), which uses C18:1-ACP, and expressing a C10 thioesterase, which uses C10-ACP, thus, resulting in a relatively homogeneous population of fatty acids that have a carbon chain length of 10. In another example, C14 fatty acid derivatives can be produced by attenuating endogenous thioesterases that produce non-C14 fatty acids and expressing the C14 thioesterase, which uses C14-ACP. In yet another example, C12 fatty acid derivatives can be produced by expressing thioesterases that use C12-ACP and attenuating thioesterases that produce non-C12 fatty acids. Exemplary C8:0 to C10:0 thioesterases include *Cuphea hookeriana* fatB2 (AAC49269) and homologs thereof. Exemplary C12:0 thioesterases include *Umbellularia california* fatB (Q41635) and homologs thereof. Exemplary C14:0 thioesterases include *Cinnamonum camphorum* fatB (Q39473). Exemplary C14:0 to C16:0 thioesterases include *Cuphea hookeriana* fatB3 (AAC49269). Exemplary C16:0 thioesterases include *Arabidopsis thaliana* fatB (CAA85388), *Cuphea hookeriana* fatB1 (Q39513) and homologs thereof. Exemplary C18:1 thioesterases include *Arabidopsis thaliana* fatA (NP_189147, NP_193041), *Arabidopsis thaliana* fatB (CAA85388), *Bradyrhizobium japonicum* fatA (CAC39106), *Cuphea hookeriana* fatA (AAC72883), *Escherichia coli* tesA (NP_415027) and homologs thereof. Acetyl CoA, malonyl CoA, and fatty acid overproduction can be verified using methods known in the art, for example by using radioactive precursors, HPLC, and GC-MS subsequent to cell lysis.

In yet another aspect, fatty acids of various lengths can be produced in the engineered chemoautotroph by expressing or overexpressing acyl-CoA synthase peptides (E.C. 2.3.1.86), which catalyzes the conversion of fatty acids to acyl-CoA. Some acyl-CoA synthase peptides, which are non-specific, accept other substrates in addition to fatty acids.

In yet another aspect, branched chain fatty acids, their intermediates and their derivatives can be produced in the engineered chemoautotroph as the carbon-based products of interest. By controlling the expression of endogenous and heterologous enzymes associated with branched chain fatty acid biosynthesis, the production of branched chain fatty acid intermediates including branched chain fatty acids can be enhanced. Branched chain fatty acid production can be achieved through the expression of one or more of the following enzymes [Kaneda, 1991]: branched chain amino acid aminotransferase to produce α-ketoacids from branched chain amino acids such as isoleucine, leucine and valine (E.C. 2.6.1.42), branched chain α-ketoacid dehydrogenase complexes which catalyzes the oxidative decarboxylation of α-ketoacids to branched chain acyl-CoA (bkd, E.C. 1.2.4.4) [Denoya, 1995], dihydrolipoyl dehydrogenase (E.C. 1.8.1.4), beta-ketoacyl-ACP synthase with branched chain acyl CoA specificity (E.C. 2.3.1.41) [Li, 2005], crotonyl-CoA reductase (E.C. 1.3.1.8, 1.3.1.85 or 1.3.1.86) [Han, 1997], and isobutyryl-CoA mutase (large subunit E.C. 5.4.99.2 and small subunit E.C. 5.4.99.13). Exemplary branched chain amino acid aminotransferases include *E. coli* ilvE (YP_026247), *Lactococcus lactis* ilvE (AAF34406), *Pseudomonas putida* ilvE (NP_745648), *Streptomyces coelicolor* ilvE (NP_629657), and homologs thereof. Branched chain α-ketoacid dehydrogenase complexes consist of E1α/β (decarboxylase), E2 (dihydrolipoyl transacylase) and E3 (dihydrolipoyl dehydrogenase) subunits. The industrial host *E. coli* has only the E3 component as a part of its pyruvate dehydrogenase complex (lpd, E.C. 1.8.1.4, NP_414658) and so it requires the E1α/β and E2 bkd proteins. Exemplary α-ketoacid dehydrogenase complexes include *Streptomyces coelicolor* bkdA1 (NP_628006) E1α (decarboxylase component), *S. coelicolor* bkdB2 (NP_628005) E1β (decarboxylase component), *S. coelicolor* bkdA3 (NP_638004) E2 (dihydrolipoyl transacylase); or *S. coelicolor* bkdA2 (NP_733618) E1α (decarboxylase component), *S. coelicolor* bkdB2 (NP_628019) E1β (decarboxylase component), *S. coelicolor* bkdC2 (NP_628018) E2 (dihydrolipoyl transacylase); or *S. avermitilis* bkdA (BAC72074) E1α (decarboxylase component), *S. avermitilis* bkdB (BAC72075) E1β (decarboxylase component), *S. avermitilis* bkdC (BAC72076) E2 (dihydrolipoyl transacylase); *S. avermitilis* bkdF (E.C.1.2.4.4, BAC72088) E1α (decarboxylase component), *S. avermitilis* bkdG (BAC72089) E1β (decarboxylase component), *S. avermitilis* bkdH (BAC72090) E2 (dihydrolipoyl transacylase); *B. subtilis* bkdAA (NP_390288) E1α (decarboxylase component), *B. subtilis* bkdAB (NP_390288) E13 (decarboxylase component), *B. subtilis* bkdB (NP_390288) E2 (dihydrolipoyl transacylase); or *P. putida* bkdA1 (AAA65614) E1α (decarboxylase component), *P. putida* bkdA2 (AAA65615) E1β (decarboxylase component), *P. putida* bkdC (AAA65617) E2 (dihydrolipoyl transacylase); and homologs thereof. An exemplary dihydrolipoyl dehydrogenase is *E. coli* lpd (NP_414658) E3 and homologs thereof. Exemplary beta-ketoacyl-ACP synthases with branched chain acyl CoA specificity include *Streptomyces coelicolor* fabH1 (NP_626634), ACP (NP_626635) and fabF (NP_626636); *Streptomyces avermitilis* fabH3 (NP_823466), fabC3 (NP_823467), fabF (NP_823468); *Bacillus subtilis* fabH_A (NP_389015), fabH_B (NP_388898), ACP (NP_389474), fabF (NP_389016); *Stenotrophomonas maltophilia* SmalDRAFT_0818 (ZP_01643059), SmalDRAFT_0821 (ZP_01643063), SmalDRAFT_0822 (ZP_01643064); *Legionella pneumophila* fabH (YP_123672), ACP (YP_123675), fabF (YP_123676); and homologs thereof. Exemplary crotonyl-CoA reductases include *Streptomyces coelicolor* ccr (NP_630556), *Streptomyces cinnamonensis* ccr (AAD53915), and homologs thereof. Exemplary isobutyryl-CoA mutases include *Streptomyces coelicolor* icmA & icmB (NP_629554 and NP_630904), *Streptomyces cinnamonensis* icmA and icmB (AAC08713 and AJ246005), and homologs thereof. Additionally or alternatively, endogenous genes that normally lead to straight chain fatty acids, their intermediates, and derivatives may be attenuated or deleted to eliminate competing pathways. Enzymes that interfere with production of branched chain fatty acids include β-ketoacyl-ACP synthase II (E.C. 2.3.1.41) and 3-ketoacyl-ACP synthase III (E.C. 2.3.1.41) with straight chain acyl CoA specificity. Exemplary enzymes for deletion include *E. coli* fabF (NP_415613) and fabH (NP_415609).

In yet another aspect, fatty acids, their intermediates and their derivatives with varying degrees of saturation can be produced in the engineered chemoautotroph as the carbon-based products of interest. In one aspect, hosts are engineered to produce unsaturated fatty acids by over-expressing β-ketoacyl-ACP synthase I (E.C. 2.3.1.41), or by growing the host at low temperatures (for example less than 37° C.). FabB has preference to cis-$6^3$ decenoyl-ACP and results in unsaturated fatty acid production in *E. coli*. Over-expression of FabB results in the production of a significant percentage of unsaturated fatty acids [de Mendoza, 1983]. These unsaturated fatty acids can then be used as intermediates in hosts that are engineered to produce fatty acids derivatives, such as fatty alcohols, esters, waxes, olefins, alkanes, and the like. Alternatively, the repressor of fatty acid biosynthesis, *E. coli* FabR (NP_418398), can be deleted, which can also result in increased unsaturated fatty acid production in *E. coli* [Zhang, 2002]. Further increase in unsaturated fatty acids is achieved by over-expression of heterologous trans-2, cis-3-decenoyl-ACP isomerase and controlled expression of trans-2-enoyl-ACP reductase II [Marrakchi, 2002b], while deleting *E. coli* FabI (trans-2-enoyl-ACP reductase, E.C. 1.3.1.9, NP_415804) or homologs thereof in the host organism. Exemplary β-ketoacyl-ACP synthase I include *Escherichia coli* fabB (BAA16180) and homologs thereof. Exemplary trans-2, cis-3-decenoyl-ACP isomerase include *Streptococcus mutans* UA159 FabM (DAA05501) and homologs thereof. Exemplary trans-2-enoyl-ACP reductase II include *Streptococcus pneumoniae* R6 FabK (NP_357969) and homologs thereof. To increase production of monounsaturated fatty acids, the sfa gene, suppressor of FabA, can be over-expressed [Rock, 1996]. Exemplary proteins include AAN79592 and homologs thereof. One of ordinary skill in the art would appreciate that by attenuating fabA, or over-expressing fabB and expressing specific thioesterases (described above), unsaturated fatty acids, their derivatives, and products having a desired carbon chain length can be produced.

In some examples the fatty acid or intermediate is produced in the cytoplasm of the cell. The cytoplasmic concentration can be increased in a number of ways, including, but not limited to, binding of the fatty acid to coenzyme A to form an acyl-CoA thioester. Additionally, the concentration of acyl-CoAs can be increased by increasing the biosynthesis of CoA in the cell, such as by over-expressing genes associated with pantothenate biosynthesis (panD) or knocking out the genes associated with glutathione biosynthesis (glutathione synthase).

Production of Fatty Alcohols as the Carbon-Based Products of Interest

In yet further aspects, hosts cells are engineered to convert acyl-CoA to fatty alcohols by expressing or overexpressing a fatty alcohol forming acyl-CoA reductase (FAR, E.C. 1.1.1.*), or an acyl-CoA reductases (E.C. 1.2.1.50) and alcohol dehydrogenase (E.C. 1.1.1.1) or a combination of the foregoing to produce fatty alcohols from acyl-CoA. Hereinafter fatty alcohol forming acyl-CoA reductase (FAR, E.C. 1.1.1.*), acyl-CoA reductases (E.C. 1.2.1.50) and alcohol dehydrogenase (E.C. 1.1.1.1) are collectively referred to as fatty alcohol forming peptides. Some fatty alcohol forming peptides are non-specific and catalyze other reactions as well: for example, some acyl-CoA reductase peptides accept other substrates in addition to fatty acids. Exemplary fatty alcohol forming acyl-CoA reductases include *Acinetobacter baylyi* ADP1 acr1 (AAC45217), *Simmondsia chinensis* jjfar (AAD38039), *Mus musculus* mfar1 (AAH07178), *Mus musculus* mfar2 (AAH55759), *Acinetobacter* sp. M1 acrM1, *Homo sapiens* hfar (AAT42129), and homologs thereof. Fatty alcohols can be used as surfactants.

Many fatty alcohols are derived from the products of fatty acid biosynthesis. Hence, the production of fatty alcohols can be controlled by engineering fatty acid biosynthesis in the engineered chemoautotroph. The chain length, branching and degree of saturation of fatty acids and their intermediates can be altered using the methods described herein, thereby affecting the nature of the resulting fatty alcohols.

As mentioned above, through the combination of expressing genes that support brFA synthesis and alcohol synthesis, branched chain alcohols can be produced. For example, when an alcohol reductase such as Acr1 from *Acinetobacter baylyi* ADP1 is coexpressed with a bkd operon, *E. coli* can synthesize isopentanol, isobutanol or 2-methyl butanol. Similarly, when Acr1 is coexpressed with ccr/icm genes, *E. coli* can synthesize isobutanol.

Production of Fatty Esters as the Carbon-Based Products of Interest

In another aspect, engineered chemoautotrophs produce various lengths of fatty esters (biodiesel and waxes) as the carbon-based products of interest. Fatty esters can be produced from acyl-CoAs and alcohols. The alcohols can be provided in the fermentation media, produced by the engineered chemoautotroph itself or produced by a co-cultured organism.

In some embodiments, one or more alcohol O-acetyltransferases is expressed in the engineered chemoautotroph to produce fatty esters as the carbon-based product of interest. Alcohol O-acetyltransferase (E.C. 2.3.1.84) catalyzes the reaction of acetyl-CoA and an alcohol to produce CoA and an acetic ester. In some embodiments, the alcohol O-acetyltransferase peptides are co-expressed with selected thioesterase peptides, FAS peptides and fatty alcohol forming peptides to allow the carbon chain length, saturation and degree of branching to be controlled. In other embodiments, the bkd operon can be co-expressed to enable branched fatty acid precursors to be produced.

Alcohol O-acetyltransferase peptides catalyze other reactions such that the peptides accept other substrates in addition to fatty alcohols or acetyl-CoA thioester. Other substrates include other alcohols and other acyl-CoA thioesters. Modification of such enzymes and the development of assays for characterizing the activity of a particular alcohol O-acetyltransferase peptides are within the scope of a skilled artisan. Engineered O-acetyltransferases and O-acyltransferases can be created that have new activities and specificities for the donor acyl group or acceptor alcohol moiety.

Alcohol acetyl transferases (AATs, E.C. 2.3.1.84), which are responsible for acyl acetate production in various plants, can be used to produce medium chain length waxes, such as octyl octanoate, decyl octanoate, decyl decanoate, and the like. Fatty esters, synthesized from medium chain alcohol (such as C6, C8) and medium chain acyl-CoA (or fatty acids, such as C6 or C8) have a relative low melting point. For example, hexyl hexanoate has a melting point of −55° C. and octyl octanoate has a melting point of −18 to −17° C. The low melting points of these compounds make them good candidates for use as biofuels. Exemplary alcohol acetyl-transferases include *Fragaria×ananassa* SAAT (AAG13130) [Aharoni, 2000], *Saccharomyces cerevisiae* Atfp1 (NP_015022), and homologs thereof.

In some embodiments, one or more wax synthases (E.C. 2.3.1.75) is expressed in the engineered chemoautotroph to produce fatty esters including waxes from acyl-CoA and alcohols as the carbon-based product of interest. Wax synthase peptides are capable of catalyzing the conversion of an acyl-thioester to fatty esters. Some wax synthase peptides can catalyze other reactions, such as converting short chain acyl-CoAs and short chain alcohols to produce fatty esters. Methods to identify wax synthase activity are provided in U.S. Pat. No. 7,118,896, which is herein incorporated by reference. Medium-chain waxes that have low melting points, such as octyl octanoate and octyl decanoate, are good candidates for biofuel to replace triglyceride-based biodiesel. Exemplary wax synthases include *Acinetobacter baylyi* ADP1 wsadp1, *Acinetobacter baylyi* ADP1 waxdgaT (AAO17391) [Kalscheuer, 2003], *Saccharomyces cerevisiae* Eeb1 (NP_015230), *Saccharomyces cerevisiae* YMR210w (NP_013937), *Simmondsia chinensis* acyltransferase (AAD38041), *Mus musculus* Dgat214 (Q6E1M8), and homologs thereof.

In other aspects, the engineered chemoautotrophs are modified to produce a fatty ester-based biofuel by expressing nucleic acids encoding one or more wax ester synthases in order to confer the ability to synthesize a saturated, unsaturated, or branched fatty ester. In some embodiments, the wax ester synthesis proteins include, but are not limited to: fatty acid elongases, acyl-CoA reductases, acyltransferases or wax synthases, fatty acyl transferases, diacylglycerol acyltransferases, acyl-coA wax alcohol acyltransferases, bifunctional wax ester synthase/acyl-CoA: diacylglycerol acyltransferase selected from a multienzyme complex from *Simmondsia chinensis, Acinetobacter* sp. strain ADP1 (formerly *Acinetobacter calcoaceticus* ADP1), *Pseudomonas aeruginosa, Fundibacter jadensis, Arabidopsis thaliana*, or *Alkaligenes eutrophus*. In one embodiment, the fatty acid elongases, acyl-CoA reductases or wax synthases are from a multienzyme complex from *Alkaligenes eutrophus* and other organisms known in the literature to produce wax and fatty acid esters.

Many fatty esters are derived from the intermediates and products of fatty acid biosynthesis. Hence, the production of fatty esters can be controlled by engineering fatty acid biosynthesis in the engineered chemoautotroph. The chain length, branching and degree of saturation of fatty acids and their intermediates can be altered using the methods described herein, thereby affecting the nature of the resulting fatty esters.

Additionally, to increase the percentage of unsaturated fatty acid esters, the engineered chemoautotroph can also overexpress Sfa which encodes a suppressor of fabA (AAN79592, AAC44390), β-ketoacyl-ACP synthase I (E.C. 2.3.1.41, BAA16180), and secG null mutant suppressors (cold shock proteins) gnsA and gnsB (ABD18647 and AAC74076). In some examples, the endogenous fabF gene can be attenuated, thus, increasing the percentage of palmitoleate (C16:1) produced.

Optionally a wax ester exporter such as a member of the FATP family is used to facilitate the release of waxes or esters into the extracellular environment from the engineered chemoautotroph. An exemplary wax ester exporter that can be used is fatty acid (long chain) transport protein CG7400-PA, isoform A from *D. melanogaster* (NP_524723), or homologs thereof.

The centane number (CN), viscosity, melting point, and heat of combustion for various fatty acid esters have been characterized in for example, [Knothe, 2005]. Using the teachings provided herein the engineered chemoautotroph can be engineered to produce any one of the fatty acid esters described in [Knothe, 2005].

Production of Alkanes as the Carbon-Based Products of Interest

In another aspect, engineered chemoautotrophs produce alkanes of various chain lengths (hydrocarbons) as the carbon-based products of interest. Many alkanes are derived from the products of fatty acid biosynthesis. Hence, the production of alkanes can be controlled by engineering fatty acid biosynthesis in the engineered chemoautotroph. The chain length, branching and degree of saturation of fatty acids and their intermediates can be altered using the methods described herein. The chain length, branching and degree of saturation of alkanes can be controlled through their fatty acid biosynthesis precursors.

In certain aspects, fatty aldehydes can be converted to alkanes and CO in the engineered chemoautotroph via the expression of decarbonylases [Cheesbrough, 1984; Dennis, 1991]. Exemplary enzymes include *Arabidopsis thaliana* cer1 (NP_171723), *Oryza sativa*cer1 CER1 (AAD29719) and homologs thereof.

In another aspect, fatty alcohols can be converted to alkanes in the engineered chemoautotroph via the expression of terminal alcohol oxidoreductases as in *Vibrio furnissii* M1 [Park, 2005].

Production of Olefins as the Carbon-Based Products of Interest

In another aspect, engineered chemoautotrophs produce olefins (hydrocarbons) as the carbon-based products of interest. Olefins are derived from the intermediates and products of fatty acid biosynthesis. Hence, the production of olefins can be controlled by engineering fatty acid biosynthesis in the engineered chemoautotroph. Introduction of genes affecting the production of unsaturated fatty acids, as described above, can result in the production of olefins. Similarly, the chain length of olefins can be controlled by expressing, overexpressing or attenuating the expression of endogenous and heterologous thioesterases which control the chain length of the fatty acids that are precursors to olefin biosynthesis. Also, by controlling the expression of endogenous and heterologous enzymes associated with branched chain fatty acid biosynthesis, the production of branched chain olefins can be enhanced. Methods for controlling the chain length and branching of fatty acid biosynthesis intermediates and products are described above.

Production of ω-Cyclic Fatty Acids and their Derivatives as the Carbon-Based Products of Interest In another aspect, the engineered chemoautotroph of the present invention produces co-cyclic fatty acids (cyFAs) as the carbon-based product of interest. To synthesize co-cyclic fatty acids (cyFAs), several genes need to be introduced and expressed that provide the cyclic precursor cyclohexylcarbonyl-CoA [Cropp, 2000]. The genes (fabH, ACP and fabF) can then be expressed to allow initiation and elongation of ω-cyclic fatty acids. Alternatively, the homologous genes can be isolated from microorganisms that make cyFAs and expressed in *E. coli*. Relevant genes include bkdC, lpd, fabH, ACP, fabF, fabH1, ACP, fabF, fabH3, fabC3, fabF, fabH_A, fabH_B, ACP.

Expression of the following genes are sufficient to provide cyclohexylcarbonyl-CoA in *E. coli*: ansJ, ansK, ansL, chcA (1-cyclohexenylcarbonyl CoA reductase) and ansM from the ansatrienin gene cluster of *Streptomyces collinus* [Chen, 1999] or plmJK (5-enolpyruvylshikimate-3-phosphate synthase), plmL (acyl-CoA dehydrogenase), chcA (enoyl-(ACP) reductase) and plmM (2,4-dienoyl-CoA reductase) from the phoslactomycin B gene cluster of *Streptomyces* sp. HK803 [Palaniappan, 2003] together with the acyl-CoA isomerase (chcB gene) [Patton, 2000] from *S. collinus, S. avermitilis* or *S. coelicolor*. Exemplary ansatrienin gene cluster enzymes include AAC44655, AAF73478 and homologs thereof. Exemplary phoslactomycin B gene cluster enzymes include AAQ84158, AAQ84159, AAQ84160, AAQ84161 and homologs thereof. Exemplary chcB enzymes include NP_629292, AAF73478 and homologs thereof.

The genes (fabH, ACP and fabF) are sufficient to allow initiation and elongation of co-cyclic fatty acids, because they can have broad substrate specificity. In the event that coexpression of any of these genes with the ansJKLM/chcAB or pmlJKLM/chcAB genes does not yield cyFAs, fabH, ACP and/or fabF homologs from microorganisms that make cyFAs can be isolated (e.g., by using degenerate PCR primers or heterologous DNA probes) and coexpressed.

Production of Halogenated Derivatives of Fatty Acids

Genes are known that can produce fluoroacetyl-CoA from fluoride ion. In one embodiment, the present invention allows for production of fluorinated fatty acids by combining expression of fluoroacetate-involved genes (e.g., fluorinase, nucleotide phosphorylase, fluorometabolite-specific aldolases, fluoroacetaldehyde dehydrogenase, and fluoroacetyl-CoA synthase).

Transport/Efflux/Release of Fatty Acids and their Derivatives

Also disclosed herein is a system for continuously producing and exporting hydrocarbons out of recombinant host microorganisms via a transport protein. Many transport and efflux proteins serve to excrete a large variety of compounds and can be evolved to be selective for a particular type of fatty acid. Thus, in some embodiments an ABC transporter can be functionally expressed by the engineered chemoautotroph, so that the organism exports the fatty acid into the culture medium. In one example, the ABC transporter is an ABC transporter from *Caenorhabditis elegans, Arabidopsis thalania, Alkaligenes eutrophus* or *Rhodococcus erythropolis* or homologs thereof. Exemplary transporters include AAU44368, NP_188746, NP_175557, AAN73268 or homologs thereof.

The transport protein, for example, can also be an efflux protein selected from: AcrAB (NP_414996.1, NP_414995.1), TolC (NP_417507.2) and AcrEF (NP_417731.1, NP_417732.1) from *E. coli*, or t111618 (NP_682408), t111619 (NP_682409), t110139 (NP_680930), H11619 and U10139 from *Thermosynechococcus elongatus* BP-I or homologs thereof.

In addition, the transport protein can be, for example, a fatty acid transport protein (FATP) selected from *Drosophila melanogaster, Caenorhabditis elegans, Mycobacterium tuberculosis* or *Saccharomyces cerevisiae, Acinetobacter* sp. H01-N, any one of the mammalian FATPs or homologs thereof. The FATPs can additionally be resynthesized with the membranous regions reversed in order to invert the direction of substrate flow. Specifically, the sequences of amino acids composing the hydrophilic domains (or membrane domains) of the protein can be inverted while maintaining the same codons for each particular amino acid. The identification of these regions is well known in the art.

Production of Isoprenoids as the Carbon-Based Products of Interest

Figure 15:
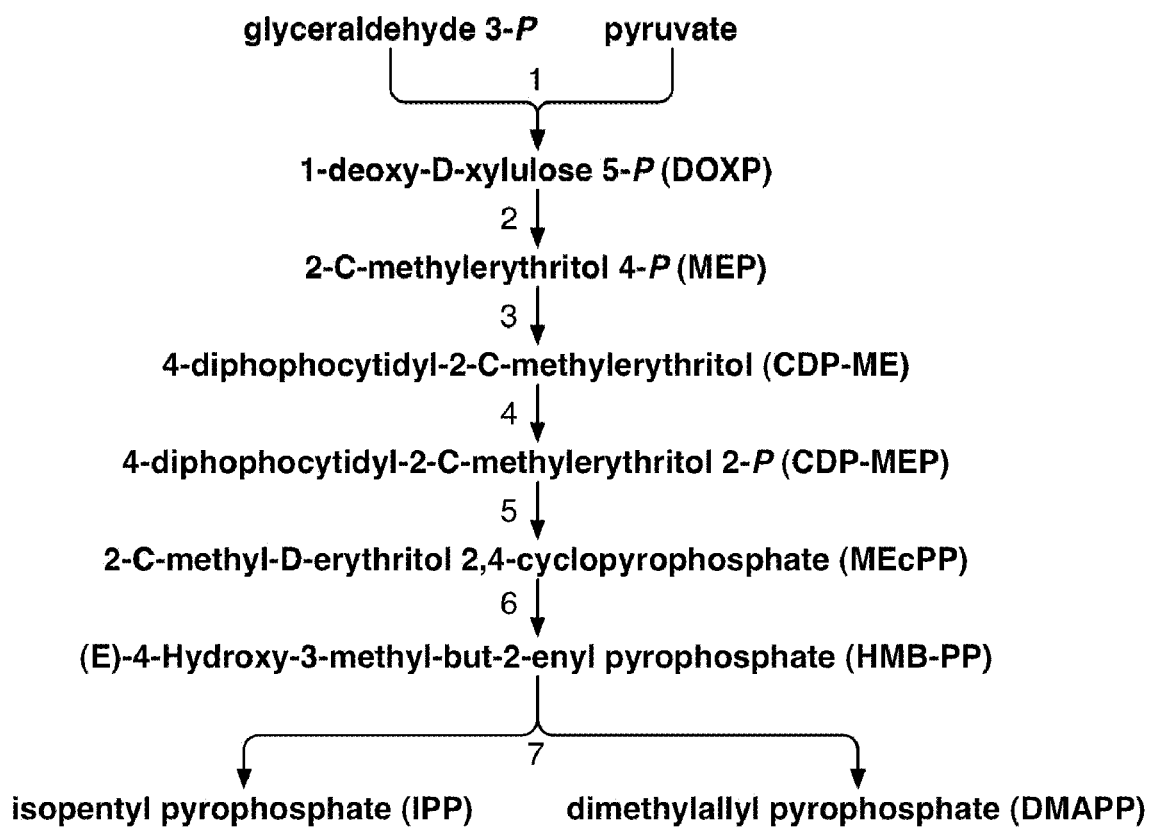
FIG. 15 depicts the metabolic reactions of the mevalonate-independent pathway (also known as the non-mevalonate pathway or deoxyxylulose 5-phosphate (DXP) pathway) for production of isopentenyl pyrophosphate (IPP) and its isomer dimethylallyl pyrophosphate (DMAPP). In metabolite names, —P denotes phosphate. Each reaction is numbered. Enzymes catalyzing each reaction are as follows: 1, 1-deoxy-D-xylulose-5-phosphate synthase (E.C. 2.2.1.7); 2, 1-deoxy-D-xylulose-5-phosphate reductoisomerase (E.C. 1.1.1.267); 3, 4-diphosphocytidyl-2C-methyl-D-erythritol synthase (E.C. 2.7.7.60); 4, 4-diphosphocytidyl-2C-methyl-D-erythritol kinase (E.C. 2.7.1.148); 5, 2C-methyl-D-erythritol 2,4-cyclodiphosphate synthase (E.C. 4.6.1.12); 6, (E)-4-hydroxy-3-methylbut-2-enyl diphosphate synthase (E.C. 1.17.7.1); 7, isopentyl/dimethylallyl diphosphate synthase or 4-hydroxy-3-methylbut-2-enyl diphosphate reductase (E.C. 1.17.1.2).
Figure 16:
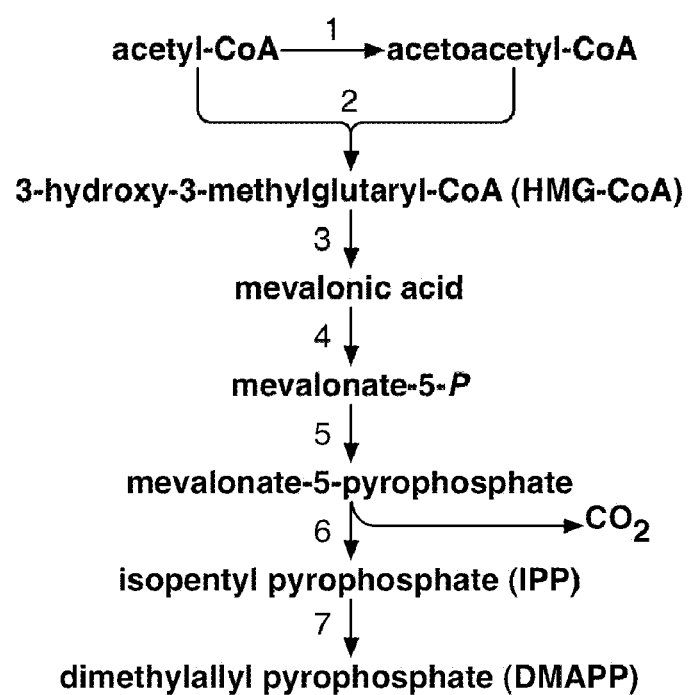
FIG. 16 depicts the metabolic reactions of the mevalonate pathway (also known as the HMG-CoA reductase pathway) for production of isopentenyl pyrophosphate (IPP) and its isomer dimethylallyl pyrophosphate (DMAPP). In metabolite names, —P denotes phosphate. Each reaction is numbered. Enzymes catalyzing each reaction are as follows: 1, acetyl-CoAthiolase; 2, HMG-CoA synthase (E.C. 2.3.3.10); 3, HMG-CoA reductase (E.C. 1.1.1.34); 4, mevalonate kinase (E.C. 2.7.1.36); 5, phosphomevalonate kinase (E.C. 2.7.4.2); 6, mevalonate pyrophosphate decarboxylase (E.C. 4.1.1.33); 7, isopentenyl pyrophosphate isomerase (E.C. 5.3.3.2).

In one aspect, the engineered chemoautotroph of the present invention produces isoprenoids or their precursors isopentenyl pyrophosphate (IPP) and its isomer, dimethylallyl pyrophosphate (DMAPP) as the carbon-based products of interest. There are two known biosynthetic pathways that synthesize IPP and DMAPP. Prokaryotes, with some exceptions, use the mevalonate-independent or deoxyxylulose 5-phosphate (DXP) pathway to produce IPP and DMAPP separately through a branch point (FIG. 15). Eukaryotes other than plants use the mevalonate-dependent (MEV) isoprenoid pathway exclusively to convert acetyl-coenzyme A (acetyl-CoA) to IPP, which is subsequently isomerized to DMAPP (FIG. 16). In general, plants use both the MEV and DXP pathways for IPP synthesis.

The reactions in the DXP pathway are catalyzed by the following enzymes: 1-deoxy-D-xylulose-5-phosphate synthase (E.C. 2.2.1.7), 1-deoxy-D-xylulose-5-phosphate reductoisomerase (E.C. 1.1.1.267), 4-diphosphocytidyl-2C-methyl-D-erythritol synthase (E.C. 2.7.7.60), 4-diphosphocytidyl-2C-methyl-D-erythritol kinase (E.C. 2.7.1.148), 2C-methyl-D-erythritol 2,4-cyclodiphosphate synthase (E.C. 4.6.1.12), (E)-4-hydroxy-3-methylbut-2-enyl diphosphate synthase (E.C. 1.17.7.1), isopentyl/dimethylallyl diphosphate synthase or 4-hydroxy-3-methylbut-2-enyl diphosphate reductase (E.C. 1.17.1.2). In one embodiment, the engineered chemoautotroph of the present invention expresses one or more enzymes from the DXP pathway. For example, one or more exogenous proteins can be selected from 1-deoxy-D-xylulose-5-phosphate reductoisomerase, 4-diphosphocytidyl-2C-methyl-D-erythritol synthase, 4-diphosphocytidyl-2C-methyl-D-erythritol kinase, 2C-methyl-D-erythritol 2,4-cyclodiphosphate synthase, (E)-4-hydroxy-3-methylbut-2-enyl diphosphate synthase, and 4-hydroxy-3-methylbut-2-enyl diphosphate reductase. The host organism can also express two or more, three or more, four or more, and the like, including up to all the protein and enzymes that confer the DXP pathway. Exemplary 1-deoxy-D-xylulose-5-phosphate synthases include *E. coli* Dxs (AAC46162); *P. putida* KT2440 Dxs (AAN66154); *Salmonella enterica Paratyphi*, see ATCC 9150 Dxs (AAV78186); *Rhodobacter sphaeroides* 2.4.1 Dxs (YP_353327); *Rhodopseudomonas palustris* CGA009 Dxs (NP_946305); *Xylella fastidiosa* Temecula1 Dxs (NP_779493); *Arabidopsis thaliana* Dxs (NP_001078570 and/or NP_196699); and homologs thereof. Exemplary 1-deoxy-D-xylulose-5-phosphate reductoisomerases include *E. coli* Dxr (BAA32426); *Arabidopsis thaliana* DXR (AAF73140); *Pseudomonas putida* KT2440 Dxr (NP_743754 and/or Q88MH4); *Streptomyces coelicolor* A3(2) Dxr (NP_629822); *Rhodobacter sphaeroides* 2.4.1 Dxr (YP_352764); *Pseudomonas fluorescens* PfO-1 Dxr (YP_346389); and homologs thereof. Exemplary 4-diphosphocytidyl-2C-methyl-D-erythritol synthases include *E. coli* IspD (AAF43207); *Rhodobacter sphaeroides* 2.4.1 IspD (YP_352876); *Arabidopsis thaliana* ISPD (NP_565286); *P. putida* KT2440 IspD (NP_743771); and homologs thereof. Exemplary 4-diphosphocytidyl-2C-methyl-D-erythritol kinases include *E. coli* IspE (AAF29530); *Rhodobacter sphaeroides* 2.4.1 IspE (YP_351828); and homologs thereof. Exemplary 2C-methyl-D-erythritol 2,4-cyclodiphosphate synthases include *E. coli* IspF (AAF44656); *Rhodobacter sphaeroides* 2.4.1 IspF (YP_352877); *P. putida* KT2440 IspF (NP_743775); and homologs thereof. Exemplary (E)-4-hydroxy-3-methylbut-2-enyl diphosphate synthase include *E. coli* IspG (AAK53460); *P. putida* KT2440 IspG (NP_743014); *Rhodobacter sphaeroides* 2.4.1 IspG (YP_353044); and homologs thereof. Exemplary 4-hydroxy-3-methylbut-2-enyl diphosphate reductases include *E. coli* IspH (AAL38655); *P. putida* KT2440 IspH (NP_742768); and homologs thereof.

The reactions in the MEV pathway are catalyzed by the following enzymes: acetyl-CoA thiolase, HMG-CoA synthase (E.C. 2.3.3.10), HMG-CoA reductase (E.C. 1.1.1.34), mevalonate kinase (E.C. 2.7.1.36), phosphomevalonate kinase (E.C. 2.7.4.2), mevalonate pyrophosphate decarboxylase (E.C. 4.1.1.33), isopentenyl pyrophosphate isomerase (E.C. 5.3.3.2). In one embodiment, the engineered chemoautotroph of the present invention expresses one or more enzymes from the MEV pathway. For example, one or more exogenous proteins can be selected from acetyl-CoA thiolase, HMG-CoA synthase, HMG-CoA reductase, mevalonate kinase, phosphomevalonate kinase, mevalonate pyrophosphate decarboxylase and isopentenyl pyrophosphate isomerase. The host organism can also express two or more, three or more, four or more, and the like, including up to all the protein and enzymes that confer the MEV pathway. Exemplary acetyl-CoA thiolases include NC_000913 REGION: 232413 L. 2325315, *E. coli*; D49362, *Paracoccus denitrificans*; L20428, *S. cerevisiae*; and homologs thereof. Exemplary HMG-CoA synthases include NC_001145 complement 19061 . . . 20536, *S. cerevisiae*; X96617, *S. cerevisiae*; X83882, *A. thaliana*; AB037907, *Kitasatospora griseola*; BT007302, *H. sapiens*; NC_002758, Locus tag SAV2546, GeneID 1 122571, *S. aureus*; and homologs thereof. Exemplary HMG-CoA reductases include NM_206548, *D. melanogaster*; NC_002758, Locus tag SAV2545, GeneID 1122570, *S. aureus*; NM_204485, *Gallus gallus*; AB015627, *Streptomyces* sp. KO 3988; AF542543, *Nicotiana attenuata*; AB037907, *Kitasatospora griseola*; AX128213, providing the sequence encoding a truncated HMGR, *S. cerevisiae*; NC_001145: complement 115734 . . . 1 18898, *S. cerevisiae*; and homologs thereof. Exemplary mevalonate kinases include L77688, *A. thaliana*; X55875, *S. cerevisiae*; and homologs thereof. Exemplary phosphomevalonate kinases include AF429385, *Hevea brasiliensis*; NM_006556, *H. sapiens*; NC_001145 complement 712315 . . . 713670, *S. cerevisiae*; and homologs thereof. Exemplary mevalonate pyrophosphate decarboxylase include include X97557, *S. cerevisiae*; AF290095, *E. faecium*; U49260, *H. sapiens*; and homologs thereof. Exemplary isopentenyl pyrophosphate isomerases include NC_000913, 3031087 . . . 3031635, *E. coli*; AF082326, *Haematococcus pluvialis*; and homologs thereof.

In some embodiments, the host cell produces IPP via the MEV pathway, either exclusively or in combination with the DXP pathway. In other embodiments, a host cell's DXP pathway is functionally disabled so that the host cell produces IPP exclusively through a heterologously introduced MEV pathway. The DXP pathway can be functionally disabled by disabling gene expression or inactivating the function of one or more of the DXP pathway enzymes.

In some embodiments, the host cell produces IPP via the DXP pathway, either exclusively or in combination with the MEV pathway. In other embodiments, a host cell's MEV pathway is functionally disabled so that the host cell produces IPP exclusively through a heterologously introduced DXP pathway. The MEV pathway can be functionally disabled by disabling gene expression or inactivating the function of one or more of the MEV pathway enzymes.

Provided herein is a method to produce isoprenoids in engineered chemoautotrophs engineered with the isopentenyl pyrophosphate pathway enzymes. Some examples of isoprenoids include: hemiterpenes (derived from 1 isoprene unit) such as isoprene; monoterpenes (derived from 2 isoprene units) such as myrcene or limonene; sesquiterpenes (derived from 3 isoprene units) such as amorpha-4,11-diene, bisabolene or farnesene; diterpenes (derived from four isoprene units) such as taxadiene; sesterterpenes (derived from 5 isoprene units); triterpenes (derived from 6 isoprene units) such as squalene; sesquarterpenes (derived from 7 isoprene units); tetraterpenes (derived from 8 isoprene units) such as β-carotene or lycopene; and polyterpenes (derived from more than 8 isoprene units) such as polyisoprene. The production of isoprenoids is also described in some detail in the published PCT applications WO2007/139925 and WO/2007/140339.

In another embodiment, the engineered chemoautotroph of the present invention produces rubber as the carbon-based product of interest via the isopentenyl pyrophosphate pathway enzymes and cis-polyprenylcistransferase (E.C. 2.5.1.20) which converts isopentenyl pyrophosphate to rubber. The enzyme cis-polyprenylcistransferase may come from, for example, *Hevea brasiliensis*.

In another embodiment, the engineered chemoautotroph of the present invention produce isopentanol as the carbon-based product of interest via the isopentenyl pyrophosphate pathway enzymes and isopentanol dikinase.

In another embodiment, the engineered chemoautotroph produces squalene as the carbon-based product of interest via the isopentenyl pyrophosphate pathway enzymes, geranyl diphosphate synthase (E.C. 2.5.1.1), farnesyl diphosphate synthase (E.C. 2.5.1.10) and squalene synthase (E.C. 2.5.1.21). Geranyl diphosphate synthase converts dimethylallyl pyrophosphate and isopentenyl pyrophosphate to geranyl diphosphate. Farnesyl diphosphate synthase converts geranyl diphosphate and isopentenyl diphosphate to farnesyl diphosphate. A bifunctional enzyme carries out the conversion of dimethylallyl pyrophosphate and two isopentenyl pyrophosphate to farnesyl pyrophosphate. Exemplary enzymes include *Escherichia coli* IspA (NP_414955) and homologs thereof. Squalene synthase converts two farnesyl pyrophosphate and NADPH to squalene. In another embodiment, the engineered chemoautotroph produces lanosterol as the carbon-based product of interest via the above enzymes, squalene monooxygenase (E.C. 1.14.99.7) and lanosterol synthase (E.C. 5.4.99.7). Squalene monooxygenase converts squalene, NADPH and $O_2$ to (S)-squalene-2,3-epoxide. Exemplary enzymes include *Saccharomyces cerevisiae* Erg1 (NP_011691) and homologs thereof. Lanosterol synthase converts (S)-squalene-2,3-epoxide to lanosterol. Exemplary enzymes include *Saccharomyces cerevisiae* Erg7 (NP_011939) and homologs thereof.

In another embodiment, the engineered chemoautotroph of the present invention produces lycopene as the carbon-based product of interest via the isopentenyl pyrophosphate pathway enzymes, geranyl diphosphate synthase (E.C. 2.5.1.21, described above), farnesyl diphosphate synthase (E.C. 2.5.1.10, described above), geranylgeranyl pyrophosphate synthase (E.C. 2.5.1.29), phytoene synthase (E.C. 2.5.1.32), phytoene oxidoreductase (E.C. 1.14.99.n) and ζ-carotene oxidoreductase (E.C. 1.14.99.30). Geranylgeranyl pyrophosphate synthase converts isopentenyl pyrophosphate and farnesyl pyrophosphate to (all trans)-geranylgeranyl pyrophosphate. Exemplary geranylgeranyl pyrophosphate synthases include *Synechocystis* sp. PCC6803 crtE (NP_440010) and homologs thereof. Phytoene synthase converts 2 geranylgeranyl-PP to phytoene. Exemplary enzymes include *Synechocystis* sp. PCC6803 crtB (P37294). Phytoene oxidoreductase converts phytoene, 2 NADPH and 2 $O_2$ to ζ-carotene. Exemplary enzymes include *Synechocystis* sp. PCC6803 crtI and *Synechocystis* sp. PCC6714 crtI (P21134). ζ-carotene oxidoreductase converts ζ-carotene, 2 NADPH and 2 $O_2$ to lycopene. Exemplary enzymes include *Synechocystis* sp. PCC6803 crtQ-2 (NP_441720).

In another embodiment, the engineered chemoautotroph of the present invention produces limonene as the carbon-based product of interest via the isopentenyl pyrophosphate pathway enzymes, geranyl diphosphate synthase (E.C. 2.5.1.21, described above) and one of (R)-limonene synthase (E.C. 4.2.3.20) and (4S)-limonene synthase (E.C. 4.2.3.16) which convert geranyl diphosphate to a limonene enantiomer. Exemplary (R)-limonene synthases include that from *Citrus limon* (AAM53946) and homologs thereof. Exemplary (4S)-limonene synthases include that from *Mentha spicata* (AAC37366) and homologs thereof.

Figure 17:
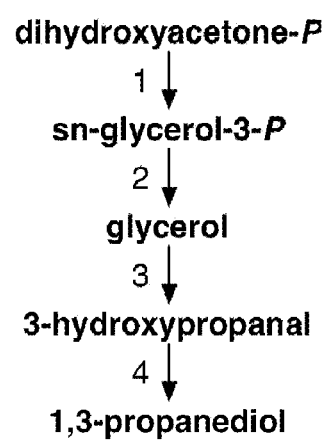
FIG. 17 depicts the metabolic reactions of the glycerol/1,3-propanediol biosynthetic pathway for production of glycerol or 1,3-propanediol. In metabolite names, —P denotes phosphate. Each reaction is numbered. Enzymes catalyzing each reaction are as follows: 1, sn-glycerol-3-P dehydrogenase (E.C. 1.1.1.8 or 1.1.1.94); 2, sn-glycerol-3-phosphatase (E.C. 3.1.3.21); 3, sn-glycerol-3-P. glycerol dehydratase (E.C. 4.2.1.30); 4, 1,3-propanediol oxidoreductase (E.C. 1.1.1.202).

Production of Glycerol or 1,3-Propanediol as the Carbon-Based Products of Interest In one aspect, the engineered chemoautotroph of the present invention produces glycerol or 1,3-propanediol as the carbon-based products of interest (FIG. 17). The reactions in the glycerol pathway are catalyzed by the following enzymes: sn-glycerol-3-P dehydrogenase (E.C. 1.1.1.8 or E.C. 1.1.1.94) and sn-glycerol-3-phosphatase (E.C. 3.1.3.21). To produce 1,3-propanediol, the following enzymes are also included: sn-glycerol-3-P. glycerol dehydratase (E.C. 4.2.1.30) and 1,3-propanediol oxidoreductase (E.C. 1.1.1.202). Exemplary sn-glycerol-3-P dehydrogenases include *Saccharomyces cerevisiae* dar1 and homologs thereof. Exemplary sn-glycerol-3-phosphatases include *Saccharomyces cerevisiae* gpp2 and homologs thereof. Exemplary sn-glycerol-3-P. glycerol dehydratases include *K. pneumoniae* dhaB1-3. Exemplary 1,3-propanediol oxidoreductase include *K. pneumoniae* dhaT.

Production of 1,4-Butanediol or 1,3-Butadiene as the Carbon-Based Products of Interest In one aspect, the engineered chemoautotroph of the present invention produces 1,4-butanediol or 1,3-butanediene as the carbon-based products of interest. The metabolic reactions in the 1,4-butanediol or 1,3-butadiene pathway are catalyzed by the following enzymes: succinyl-CoA dehydrogenase (E.C. 1.2.1.n; e.g., *C. kluyveri* SucD), 4-hydroxybutyrate dehydrogenase (E.C. 1.1.1.2; e.g., *Arabidopsis thaliana* GHBDH), aldehyde dehydrogenase (E.C. 1.1.1.n; e.g., *E. coli* AldH), 1,3-propanediol oxidoreductase (E.C. 1.1.1.202; e.g., *K. pneumoniae* DhaT), and optionally alcohol dehydratase (E.C. 4.2.1.-). Succinyl-CoA dehydrogenase converts succinyl-CoA and NADPH to succinic semialdehyde and CoA. 4-hydroxybutyrate dehydrogenase converts succinic semialdehyde and NADPH to 4-hydroxybutyrate. Aldehyde dehydrogenase converts 4-hydroxybutyrate and NADH to 4-hydroxybutanal. 1,3-propanediol oxidoreductase converts 4-hydroxybutanal and NADH to 1,4-butanediol. Alcohol dehydratase converts 1,4-butanediol to 1,3-butadiene.

Production of Polyhydroxybutyrate as the Carbon-Based Products of Interest

Figure 18:
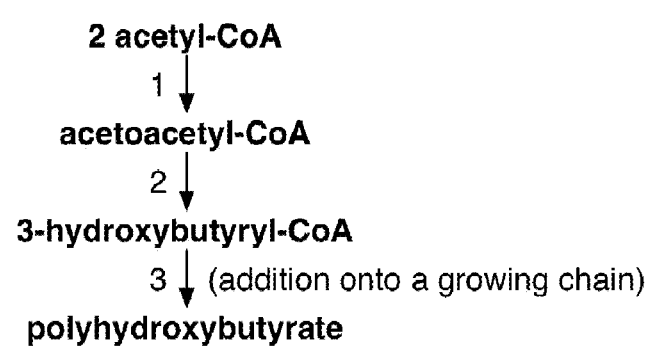
FIG. 18 depicts the metabolic reactions of the polyhydroxybutyrate biosynthetic pathway. Each reaction is numbered. Enzymes catalyzing each reaction are as follows: 1, acetyl-CoA:acetyl-CoA C-acetyltransferase (E.C. 2.3.1.9); 2, (R)-3-hydroxyacyl-CoA:NADP+ oxidoreductase (E.C. 1.1.1.36); 3, polyhydroxyalkanoate synthase (E.C. 2.3.1.-).

In one aspect, the engineered chemoautotroph of the present invention produces polyhydroxybutyrate as the carbon-based products of interest (FIG. 18). The reactions in the polyhydroxybutyrate pathway are catalyzed by the following enzymes: acetyl-CoA:acetyl-CoA C-acetyltransferase (E.C. 2.3.1.9), (R)-3-hydroxyacyl-CoA:NADP+ oxidoreductase (E.C. 1.1.1.36) and polyhydroxyalkanoate synthase (E.C. 2.3.1.-). Exemplary acetyl-CoA:acetyl-CoA C-acetyltransferases include *Ralstonia eutropha* phaA. Exemplary (R)-3-hydroxyacyl-CoA:NADP+ oxidoreductases include *Ralstonia eutropha* phaB. Exemplary polyhydroxyalkanoate synthase include *Ralstonia eutropha* phaC. In the event that the host organism also has the capacity to degrade polyhydroxybutyrate, the corresponding degradation enzymes, such as poly[(R)-3-hydroxybutanoate] hydrolase (E.C. 3.1.1.75), may be inactivated. Hosts that lack the ability to naturally synthesize polyhydroxybutyrate generally also lack the capacity to degrade it, thus leading to irreversible accumulation of polyhydroxybutyrate if the biosynthetic pathway is introduced.

Intracellular polyhydroxybutyrate can be measured by solvent extraction and esterification of the polymer from whole cells. Typically, lyophilized biomass is extracted with methanol-chloroform with 10% HCl as a catalyst. The chloroform dissolves the polymer, and the methanol esterifies it in the presence of HCl. The resulting mixture is extracted with water to remove hydrophilic substances and the organic phase is analyzed by GC.

Production of Lysine as the Carbon-Based Products of Interest

Figure 19:
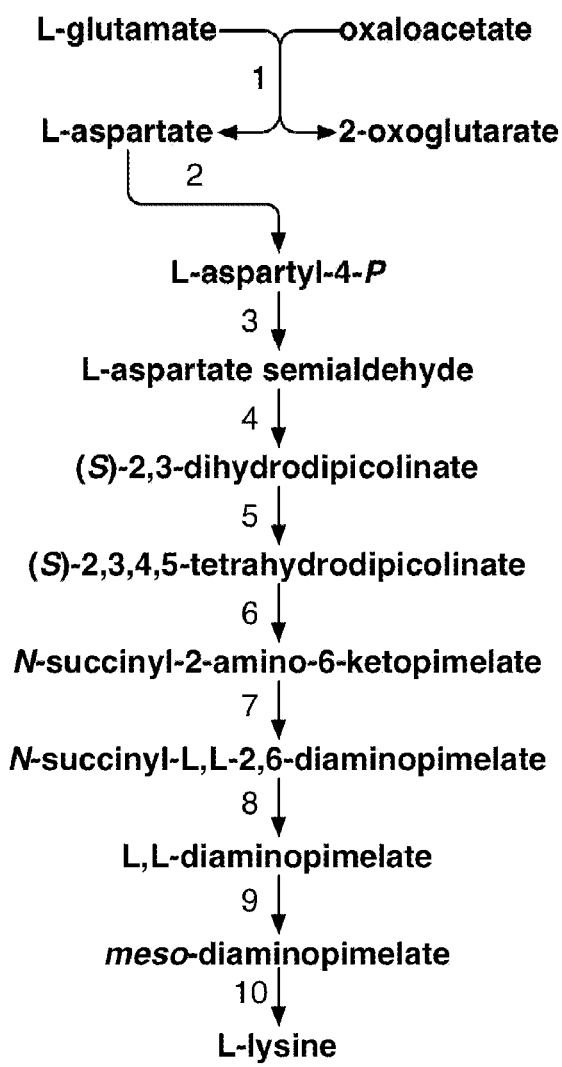
FIG. 19 depicts the metabolic reactions of one lysine biosynthesis pathway. In metabolite names, —P denotes phosphate. Each reaction is numbered. Enzymes catalyzing each reaction are as follows: 1, aspartate aminotransferase (E.C. 2.6.1.1); 2, aspartate kinase (E.C. 2.7.2.4); 3, aspartate semialdehyde dehydrogenase (E.C. 1.2.1.11); 4, dihydrodipicolinate synthase (E.C. 4.2.1.52); 5, dihydrodipicolinate reductase (E.C. 1.3.1.26); 6, tetrahydrodipicolinate succinylase (E.C. 2.3.1.117); 7, N-succinyldiaminopimelate-aminotransferase (E.C. 2.6.1.17); 8, N-succinyl-L-diaminopimelate desuccinylase (E.C. 3.5.1.18); 9, diaminopimelate epimerase (E.C. 5.1.1.7); 10, diaminopimelate decarboxylase (E.C. 4.1.1.20).

In one aspect, the engineered chemoautotroph of the present invention produces lysine as the carbon-based product of interest. There are several known lysine biosynthetic pathways. One lysine biosynthesis pathway is depicted in FIG. 19. The reactions in one lysine biosynthetic pathway are catalyzed by the following enzymes: aspartate aminotransferase (E.C. 2.6.1.1; e.g. *E. coli* AspC), aspartate kinase (E.C. 2.7.2.4; e.g., *E. coli* LysC), aspartate semialdehyde dehydrogenase (E.C. 1.2.1.11; e.g., *E. coli* Asd), dihydrodipicolinate synthase (E.C. 4.2.1.52; e.g., *E. coli* DapA), dihydrodipicolinate reductase (E.C. 1.3.1.26; e.g., *E. coli* DapB), tetrahydrodipicolinate succinylase (E.C. 2.3.1.117; e.g., *E. coli* DapD), N-succinyldiaminopimelate-aminotransferase (E.C. 2.6.1.17; e.g., *E. coli* ArgD), N-succinyl-L-diaminopimelate desuccinylase (E.C. 3.5.1.18; e.g., *E. coli* DapE), diaminopimelate epimerase (E.C. 5.1.1.7; *E. coli* DapF), diaminopimelate decarboxylase (E.C. 4.1.1.20; e.g., *E. coli* LysA). In one embodiment, the engineered chemoautotroph of the present invention expresses one or more enzymes from a lysine biosynthetic pathway. For example, one or more exogenous proteins can be selected from aspartate aminotransferase, aspartate kinase, aspartate semialdehyde dehydrogenase, dihydrodipicolinate synthase, dihydrodipicolinate reductase, tetrahydrodipicolinate succinylase, N-succinyldiaminopimelate-aminotransferase, N-succinyl-L-diaminopimelate desuccinylase, diaminopimelate epimerase, diaminopimelate decarboxylase, L,L-diaminopimelate aminotransferase (E.C. 2.6.1.83; e.g., *Arabidopsis thaliana* At4g33680), homocitrate synthase (E.C. 2.3.3.14; e.g., *Saccharomyces cerevisiae* LYS21), homoaconitase (E.C. 4.2.1.36; e.g., *Saccharomyces cerevisiae* LYS4, LYS3), homoisocitrate dehydrogenase (E.C. 1.1.1.87; e.g., *Saccharomyces cerevisiae* LYS12, LYS11, LYS10), 2-aminoadipate transaminase (E.C. 2.6.1.39; e.g., *Saccharomyces cerevisiae* ARO8), 2-aminoadipate reductase (E.C. 1.2.1.31; e.g., *Saccharomyces cerevisiae* LYS2, LYS5), aminoadipate semialdehyde-glutamate reductase (E.C. 1.5.1.10; e.g., *Saccharomyces cerevisiae* LYS9, LYS13), lysine-2-oxoglutarate reductase (E.C. 1.5.1.7; e.g., *Saccharomyces cerevisiae* LYS1). The host organism can also express two or more, three or more, four or more, and the like, including up to all the protein and enzymes that confer lysine biosynthesis.

Production of γ-Valerolactone as the Carbon-Based Product of Interest

Figure 20:
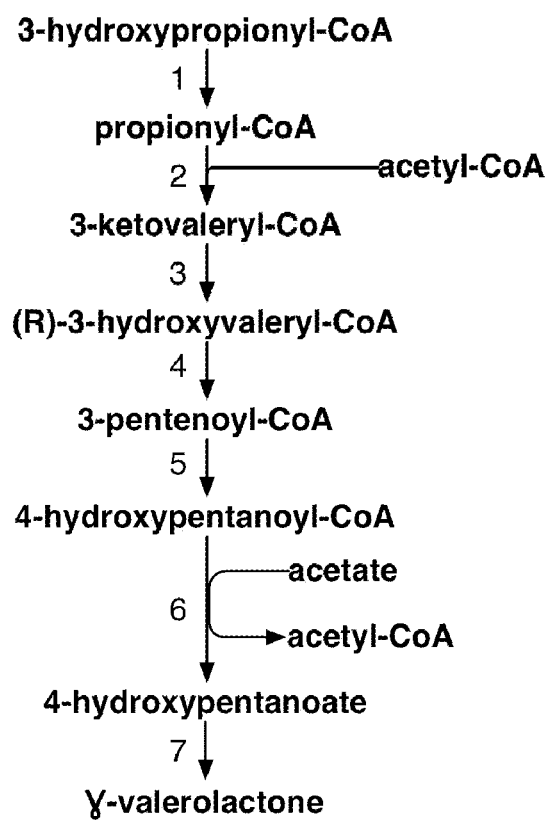
FIG. 20 depicts the metabolic reactions of the γ-valerolactone biosynthetic pathway. Each reaction is numbered. Enzymes catalyzing each reaction are as follows: 1, propionyl-CoA synthase (E.C. 6.2.1.-, E.C. 4.2.1.- and E.C. 1.3.1.-); 2, beta-ketothiolase (E.C. 2.3.1.16); 3, acetoacetyl-CoA reductase (E.C. 1.1.1.36); 4, 3-hydroxybutyryl-CoA dehydratase (E.C. 4.2.1.55); 5, vinylacetyl-CoA Δ-isomerase (E.C. 5.3.3.3); 6, 4-hydroxybutyryl-CoA transferase (E.C. 2.8.3.-); 7, 1,4-lactonase (E.C. 3.1.1.25).

In some embodiments, the engineered chemoautotroph of the present invention is engineered to produce γ-valerolactone as the carbon-based product of interest. One example γ-valerolactone biosynthetic pathway is shown in FIG. 20. In one embodiment, the engineered chemoautotroph is engineered to express one or more of the following enzymes: propionyl-CoA synthase (E.C. 6.2.1.-, E.C. 4.2.1.- and E.C. 1.3.1.-), beta-ketothiolase (E.C. 2.3.1.16; e.g., *Ralstonia eutropha* BktB), acetoacetyl-CoA reductase (E.C. 1.1.1.36; e.g., *Ralstonia eutropha* PhaB), 3-hydroxybutyryl-CoA dehydratase (E.C. 4.2.1.55; e.g., *X. axonopodis* Crt), vinylacetyl-CoA Δ-isomerase (E.C. 5.3.3.3; e.g., *C. difficile*

AbfD), 4-hydroxybutyryl-CoA transferase (E.C. 2.8.3.-; e.g., *C. kluyveri* OrfZ), 1,4-lactonase (E.C. 3.1.1.25; e.g., that from *R. norvegicus*). Propionyl-CoA synthase is a multi-functional enzyme that converts 3-hydroxypropionate, ATP and NADPH to propionyl-CoA. Exemplary propionyl-CoA synthases include AAL47820, and homologs thereof. SEQ ID NO:30 represents the *E. coli* codon optimized coding sequence for this propionyl-CoA synthase of the present invention. In one aspect, the invention provides nucleic acid molecule and homologs, variants and derivatives of SEQ ID NO:30. The nucleic acid sequence can have preferably 70%, 71%, 72%, 73%, 74%, 75%, 76%, 77%, 78%, 79%, 80%, 81-85%, 90-95%, 96-98%, 99%, 99.9% or even higher identity to SEQ ID NO:30. The present invention provides nucleic acids each comprising or consisting of a sequence which is a codon optimized version of the wild-type propionyl-CoA synthase gene. In another embodiment, the invention provides a nucleic acid encoding a polypeptide having the amino acid sequence of SEQ ID NO:31.

Integration of Metabolic Pathways into Host Metabolism

The engineered chemoautotrophs of the invention can be produced by introducing expressible nucleic acids encoding one or more of the enzymes or proteins participating in one or more energy conversion, carbon fixation and, optionally, carbon product biosynthetic pathways. Depending on the host organism chosen for conferring a chemoautotrophic capability, nucleic acids for some or all of particular metabolic pathways can be expressed. For example, if a chosen host is deficient in one or more enzymes or proteins for desired metabolic pathways, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve production of desired carbon products from inorganic energy and inorganic carbon. Thus, an engineered chemoautotroph of the invention can be produced by introducing exogenous enzyme or protein activities to obtain desired metabolic pathways or desired metabolic pathways can be obtained by introducing one or more exogenous enzyme or protein activities that, together with one or more endogenous enzymes or proteins, produces a desired product such as reduced cofactors, central metabolites and/or carbon-based products of interest.

Depending on the metabolic pathway constituents of a selected host microbial organism, the engineered chemoautotrophs of the invention can include at least one exogenously expressed metabolic pathway-encoding nucleic acid and up to all encoding nucleic acids for one or more energy conversion, carbon fixation and, optionally, carbon-based product pathways. For example, a RuMP-derived carbon fixation pathway can be established in a host deficient in a pathway enzyme or protein through exogenous expression of the corresponding encoding nucleic acid. In a host deficient in all enzymes or proteins of a metabolic pathway, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a carbon fixation pathway derived from the 3-HPA bicycle can be included, such as the acetyl-CoA carboxylase, malonyl-CoA reductase, propionyl-CoA synthase, propionyl-CoA carboxylase, methylmalonyl-CoA epimerase, methylmalonyl-CoA mutase, succinyl-CoA:(S)-malate CoA transferase, succinate dehydrogenase, fumarate hydratase, (S)-malyl-CoA/β-methylmalyl-CoA/(S)-citramalyl-CoA lyase, mesaconyl-C1-CoA hydratase, mesaconyl-CoA C1-C4 CoA transferase, and mesaconyl-C4-CoA hydratase. Given the teachings and guidance provided herein, those skilled in the art would understand that the number of encoding nucleic acids to introduce in an expressible form can, at least, parallel the metabolic pathway deficiencies of the selected host microbial organism.

Genetic Engineering Methods for Optimization of Metabolic Pathways

In some embodiments, the engineered chemoautotrophs of the invention also can include other genetic modifications that facilitate or optimize production of a carbon-based product from an inorganic energy source and inorganic carbon or that confer other useful functions onto the host organism.

In one aspect, the expression levels of the proteins of interest of the energy conversion pathways, carbon fixation pathways and, optionally, carbon product biosynthetic pathways can be either increased or decreased by, for example, replacing or altering the expression control sequences with alternate expression control sequences encoded by standardized genetic parts. The exogenous standardized genetic parts can regulate the expression of either heterologous or endogenous genes of the metabolic pathway. Altered expression of the enzyme or enzymes and/or protein or proteins of a metabolic pathway can occur, for example, through changing gene position or gene order [Smolke, 2002b], altered gene copy number [Smolke, 2002a], replacement of a endogenous, naturally occurring regulated promoters with constitutive or inducible synthetic promoters, mutation of the ribosome binding sites [Wang, 2009], or introduction of RNA secondary structural elements and/or cleavage sites [Smolke, 2000; Smolke, 2001].

In another aspect, some engineered chemoautotrophs of the present invention may require specific transporters to facilitate uptake of inorganic energy sources and/or inorganic carbon sources. In some embodiments, the engineered chemoautotrophs use formate as an inorganic energy source, inorganic carbon source or both. If formate uptake is limiting for either growth or production of carbon-based products of interest, then expression of one or more formate transporters in the engineered chemoautotroph of the present invention can alleviate this bottleneck. The formate transporters may be heterologous or endogenous to the host organism. Exemplary formate transporters include NP_415424 and NP_416987, and homologs thereof. SEQ ID NO:54 and SEQ ID NO:55 represent *E. coli* codon optimized coding sequence each of these two formate transporters, respectively, of the present invention. The present invention provides nucleic acids each comprising or consisting of a sequence which is a codon optimized version of one of the wild-type malonyl-CoA reductase genes. In another embodiment, the invention provides nucleic acids each encoding a polypeptide having the amino acid sequence of one of NP_415424 and NP_416987.

In addition, the invention provides an engineered chemoautotroph comprising a genetic modification conferring to the engineered chemoautotrophic microorganism an increased efficiency of using inorganic energy and inorganic carbon to produce carbon-based products of interest relative to the microorganism in the absence of the genetic modification. The genetic modification comprises one or more gene disruptions, whereby the one or more gene disruptions increase the efficiency of producing carbon-based products of interest from inorganic energy and inorganic carbon. In one aspect, the one or more gene disruptions target genes encoding competing reactions for inorganic energy, reduced cofactors, inorganic carbon, and/or central metabolites. In another aspect, the one or more gene disruptions target genes encoding competing reactions for intermediates or products of the energy conversion, carbon fixation, and/or carbon product biosynthetic pathways of interest. The competing reactions usually, but not exclusively, arise from metabolism endogenous to the host cell or organism.

A combination of different approaches may be used to identify candidate genetic modifications. Such approaches include, for example, metabolomics (which may be used to identify undesirable products and metabolic intermediates that accumulate inside the cell), metabolic modeling and isotopic labeling (for determining the flux through metabolic reactions contributing to hydrocarbon production), and conventional genetic techniques (for eliminating or substantially disabling unwanted metabolic reactions). For example, metabolic modeling provides a means to quantify fluxes through the cell's metabolic pathways and determine the effect of elimination of key metabolic steps. In addition, metabolomics and metabolic modeling enable better understanding of the effect of eliminating key metabolic steps on production of desired products.

To predict how a particular manipulation of metabolism affects cellular metabolism and synthesis of the desired product, a theoretical framework was developed to describe the molar fluxes through all of the known metabolic pathways of the cell. Several important aspects of this theoretical framework include: (i) a relatively complete database of known pathways, (ii) incorporation of the growth-rate dependence of cell composition and energy requirements, (iii) experimental measurements of the amino acid composition of proteins and the fatty acid composition of membranes at different growth rates and dilution rates and (iv) experimental measurements of side reactions which are known to occur as a result of metabolism manipulation. These new developments allow significantly more accurate prediction of fluxes in key metabolic pathways and regulation of enzyme activity [Keasling, 1999a; Keasling, 1999b; Martin, 2002; Henry, 2006].

Such types of models have been applied, for example, to analyze metabolic fluxes in organisms responsible for enhanced biological phosphorus removal in wastewater treatment reactors and in filamentous fungi producing polyketides [Pramanik, 1997; Pramanik, 1998a; Pramanik, 1998b; Pramanik, 1998c].

In some embodiments, the host organism may have native formate dehydrogenases or other enzymes that consume formate thereby competing with either energy conversion pathways that use formate as an inorganic energy source or carbon fixation pathways that use formate as an inorganic carbon source; hence, these competing formate consumption reactions may be disrupted to increase the efficiency of energy conversion and/or carbon fixation in the engineered chemoautotroph of the present invention. For example, in the host organism E. coli, there are three native formate dehydrogenases. Exemplary E. coli formate dehydrogenase genes for disruption include fdnG, fdnH, fdnI, fdoI, fdoH, fdoG and/or fdhF. Alternatively, since all three native formate dehydrogenases in E. coli require selenium and only those three enzymes require selenium, in a preferred embodiment, genes for selenium uptake and/or biosynthesis of selenocysteine, such as selA, selB, selC, and/or selD, are disrupted.

In other embodiments, the host organism may have native hydrogenases or other enzymes that consume molecular hydrogen thereby competing with energy conversion pathways that use hydrogen as an inorganic energy source. For example, in the host organism E. coli, there are four native hydrogenases although the fourth is not expressed to significant levels [Self, 2004]. Exemplary E. coli formate hydrogenase genes for disruption include hyaB, hybC, hycE, hyfG and fhlA. In another embodiment, a particular strain of the host organism can be selected that specifically lacks the competing reactions typical found in the species. For example, E. coli B strain BL21(DE3) lacks formate and hydrogenase metabolism unlike E. coli K strains [Pinske, 2011].

In some embodiments, the host organism may have metabolic reactions that compete with reactions of the carbon fixation pathways in the engineered chemoautotroph of the present invention. For example, in the host organism E. coli, the tricarboxylic acid cycle generally runs in the oxidative direction during aerobic growth and as a split reductive and oxidative branches during anaerobic growth. Hence, E. coli has several endogenous reactions that may compete with desired reactions of an rTCA-derived carbon fixation pathway. Exemplary E. coli enzymes whose function are candidates for disruption include citrate synthase (competes with reaction 1 in FIG. 3), 2-oxoglutarate dehydrogenase (competes with reaction 6), isocitrate dehydrogenase (may compete with desired flux for reaction 7), isocitrate dehydrogenase phosphatase (competes with reaction 8), pyruvate dehydrogenase (competes with reaction 9).

In another aspect, some engineered chemoautotrophs of the present invention may require alterations to the pool of intracellular reducing cofactors for efficient growth and/or production of the carbon-based product of interest from inorganic energy and inorganic carbon. In some embodiments, the total pool of $NAD^+/NADH$ in the engineered chemoautotroph is increased or decreased by adjusting the expression level of nicotinic acid phosphoribosyltransferase (E.C. 2.4.2.11). Over-expression of either the E. coli or Salmonella gene pncB which encodes nicotinic acid phosphoribosyltransferase has been shown to increase total $NAD^+/NADH$ levels in E. coli [Wubbolts, 1990; Berrios-River, 2002; San, 2002]. In another embodiment, the availability of intracellular NADPH can be also altered by modifying the engineered chemoautotroph to express an NADH:NADPH transhydrogenase [Sauer, 2004; Chin, 2011]. In another embodiment, the total pool of ubiquinone in the engineered chemoautotroph is increased or decreased by adjusting the expression level of ubiquinone biosynthetic enzymes, such as p-hydroxybenzoate-polyprenyl pyrophosphate transferase and polyprenyl pyrophosphate synthetase. Overexpression of the corresponding E. coli genes ubiA and ispB increased the ubiquinone pool in E. coli [Zhu, 1995]. In another embodiment, the level of the redox cofactor ferredoxin in the engineered chemoautotroph can be increased or decreased by changing the expression control sequences that regulate its expression.

In another aspect, in addition to an inorganic energy and carbon source, some engineered chemoautotrophs may require a specific nutrients or vitamin(s) for growth and/or production of carbon-based products of interest. For example, hydroxocobalamin, a vitamer of vitamin B12, is a cofactor for particular enzymes of the present invention, such as methylmalonyl-CoA mutase (E.C. 5.4.99.2). Required nutrients are generally supplemented to the growth media during bench scale propagation of such organisms. However, such nutrients can be prohibitively expensive in the context of industrial scale bio-processing. In one embodiment of the present invention, the host cell is selected from an organism that naturally produces the required nutrient(s), such as *Salmonella enterica* or *Pseudomonas denitrificans* which naturally produces hydroxocobalamin. In an alternate embodiment, the need for a vitamin is obviated by modifying the engineered chemoautotroph to express a vitamin biosynthesis pathway [Roessner, 1995]. An exemplary biosynthesis pathway for hydroxocobalamin comprises the following enzymes: uroporphyrin-III C-methyltransferase (E.C. 2.1.1.107), precorrin-2 cobaltochelatase (E.C. 4.99.1.3), cobalt-precorrin-2 ($C^{20}$)-methyltransferase (E.C. 2.1.1.151), cobalt-precorrin-3 ($C^{17}$)-methyltransferase (E.C. 2.1.1.131), cobalt precorrin-4 ($C^{11}$)-methyltransferase (E.C. 2.1.1.133), cobalt-precorrin 5A hydrolase (E.C. 3.7.1.12), cobalt-precorrin-5B ($C^1$)-methyltransferase (E.C. 2.1.1.195), cobalt-precorrin-6A reductase, cobalt-precorrin-6V ($C^5$)-methyltransferase (E.C. 2.1.1.-), cobalt-precorrin-7 ($C^{15}$)-methyltransferase (decarboxylating) (E.C. 2.1.1.196), cobalt-precorrin-8× methylmutase, cobyrinate A,C-diamide synthase (E.C. 6.3.5.11), cob(II)yrinate a,c-diamide reductase (E.C. 1.16.8.1), cob(I)yrinic acid a,c-diamide adenosyltransferase (E.C. 2.5.1.17), adenosyl-cobyrate synthase (E.C. 6.3.5.10), adenosylcobinamide phosphate synthase (E.C. 6.3.1.10), GTP:adenosylcobinamide-phosphate guanylyltransferase (E.C. 2.7.7.62), nicotinate-nucleotide dimethylbenzimidazole phosphoribosyltransferase (E.C. 2.4.2.21), adenosylcobinamide-GDP:α-ribazole-5-phosphate ribazoletransferase (E.C. 2.7.8.26) and adenosylcobalamine-5'-phosphate phosphatase (E.C. 3.1.3.73). In addition, to allow for cobalt uptake and incorporation into vitamin B12, the genes encoding the cobalt transporter are overexpressed. The exemplary cobalt transporter protein found in *Salmonella enterica* is overexpressed and is encoded by proteins ABC-type $Co^{2+}$ transport system, permease component (CbiM, NP_460968), ABC-type cobalt transport system, periplasmic component (CbiN, NP_460967), and ABC-type cobalt transport system, permease component (CbiQ, NP_461989).

In some embodiments, the intracellular concentration (e.g., the concentration of the intermediate in the engineered chemoautotroph) of the metabolic pathway intermediate can be increased to further boost the yield of the final product. For example, by increasing the intracellular amount of a substrate (e.g., a primary substrate) for an enzyme that is active in the metabolic pathway, and the like.

In another aspect, the carbon-based products of interest are or are derived from the intermediates or products of fatty acid biosynthesis. To increase the production of waxes/fatty acid esters, and fatty alcohols, one or more of the enzymes of fatty acid biosynthesis can be over expressed or mutated to reduce feedback inhibition. Additionally, enzymes that metabolize the intermediates to make nonfatty-acid based products (side reactions) can be functionally deleted or attenuated to increase the flux of carbon through the fatty acid biosynthetic pathway thereby enhancing the production of carbon-based products of interest.

Growth-Based Selection Methods for Optimization of Engineered Carbon-Fixing Strains Selective pressure provides a valuable means for testing and optimizing the engineered chemoautotrophs of the present invention. In some embodiments, the engineered chemoautotrophs of the invention can be evolved under selective pressure to optimize production of a carbon-based product from an inorganic energy source and inorganic carbon or that confer other useful functions onto the host organism. The ability of an optimized engineered chemoautotroph to replicate more rapidly than unmodified counterparts confirms the utility of the optimization. Similarly, the ability to survive and replicate in media lacking a required nutrient, such as vitamin B12, confirms the successful implementation of a nutrient biosynthetic module. In some embodiments, the engineered chemoautotrophs can be cultured in the presence of inorganic energy source(s), inorganic carbon and a limiting amount of organic carbon. Over time, the amount of organic carbon present in the culture media is decreased in order to select for evolved strains that more efficiently utilize the inorganic energy and carbon.

Evolution can occur as a result of either spontaneous, natural mutation or by addition of mutagenic agents or conditions to live cells. If desired, additional genetic variation can be introduced prior to or during selective pressure by treatment with mutagens, such as ultra-violet light, alkylators [e.g., ethyl methanesulfonate (EMS), methyl methane sulfonate (MMS), diethylsulfate (DES), and nitrosoguanidine (NTG, NG, MMG)], DNA intercalcators (e.g., ethidium bromide), nitrous acid, base analogs, bromouracil, transposonsm and the like. The engineered chemoautotrophs can be propagated either in serial batch culture or in a turbidostat as a controlled growth rate.

Alternately or in addition to selective pressure, pathway activity can be monitored following growth under permissive (i.e., non-selective) conditions by measuring specific product output via various metabolic labeling studies (including radioactivity), biochemical analyses (Michaelis-Menten), gas chromatography-mass spectrometry (GC/MS), mass spectrometry, matrix assisted laser desorption ionization time-of-flight mass spectrometry (MALDI-TOF), capillary electrophoresis (CE), and high pressure liquid chromatography (HPLC).

To generate engineered chemoautrophs with improved yield of central metabolites and/or carbon-based products of interest, metabolic modeling can be utilized to guide strain optimization. Modeling analysis allows reliable predictions of the effects on cell growth of shifting the metabolism towards more efficient production of central metabolites or products derived from central metabolites. Modeling can also be used to design gene knockouts that additionally optimize utilization of the energy conversion, carbon fixation and carbon product biosynthetic pathways. In some embodiments, modeling is used to select growth conditions that create selective pressure towards uptake and utilization of inorganic energy and inorganic carbon. An in silico stoichiometric model of host organism metabolism and the metabolic pathway(s) of interest can be constructed (see, for example, a model of the *E. coli* metabolic network [Edwards, 2002]). The resulting model can be used to compute phenotypic phase planes for the engineered chemoautotrophs of the present invention. A phenotypic phase plane is a portrait of the accessible growth states of an engineered chemoautotroph as a function of imposed substrate uptake rates. A particular engineered chemoautotroph, at particular uptake rates for limiting nutrients, may not grow as well as the phenotypic phase plane predicts, but no strain should be able to grow better than indicated by the phenotypic phase plane. Under a variety of circumstances, it has been shown the modified *E. coli* strains evolve towards, and then along, the phenotypic phase plane, always in the direction of increasing growth rates [Fong, 2004]. Thus, a phenotypic phase plane can be viewed as a landscape of selective pressure. Strains in an environment where a given nutrient uptake is positively correlated with growth rate are predicted to evolve towards increased nutrient uptake. Conversely, strains in an environment where nutrient uptake are inversely correlated with growth rate are predicted to evolve away from nutrient uptake.

Fermentation Conditions

The engineered chemoautotrophs of the present invention are cultured in a medium comprising inorganic energy source(s), inorganic carbon source(s) and any required nutrients. The culture conditions can include, for example, liquid culture procedures as well as fermentation and other large scale culture procedures.

The production and isolation of carbon-based products of interest can be enhanced by employing specific fermentation techniques. One method for maximizing production while reducing costs is increasing the percentage of the carbon that is converted to carbon-based products of interest. During normal cellular lifecycles carbon is used in cellular functions including producing lipids, saccharides, proteins, organic acids, and nucleic acids. Reducing the amount of carbon necessary for growth-related activities can increase the efficiency of carbon source conversion to output. This can be achieved by first growing engineered chemoautotrophs to a desired density, such as a density achieved at the peak of the log phase of growth. At such a point, replication checkpoint genes can be harnessed to stop the growth of cells. Specifically, quorum sensing mechanisms [Camilli, 2006; Venturi, 2006; Reading, 2006] can be used to activate genes such as p53, p21, or other checkpoint genes. Genes that can be activated to stop cell replication and growth in E. coli include umuDC genes, the over-expression of which stops the progression from stationary phase to exponential growth [Murli, 2000]. UmuC is a DNA polymerase that can carry out translesion synthesis over non-coding lesions—the mechanistic basis of most UV and chemical mutagenesis. The umuDC gene products are used for the process of translesion synthesis and also serve as a DNA damage checkpoint. UmuDC gene products include UmuC, UmuD, umuD', UmuD'$_2$C, UmuD'$_2$ and UmUD$_2$. Simultaneously, the carbon product biosynthetic pathway genes are activated, thus minimizing the need for replication and maintenance pathways to be used while the carbon-based product of interest is being made.

Alternatively, cell growth and product production can be achieved simultaneously. In this method, cells are grown in bioreactors with a continuous supply of inputs and continuous removal of product. Batch, fed-batch, and continuous fermentations are common and well known in the art and examples can be found in [Brock, 1989; Deshpande, 1992].

In a preferred embodiment, the engineered chemoautotroph is engineered such that the final product is released from the cell. In embodiments where the final product is released from the cell, a continuous process can be employed. In this approach, a reactor with organisms producing desirable products can be assembled in multiple ways. In one embodiment, the reactor is operated in bulk continuously, with a portion of media removed and held in a less agitated environment such that an aqueous product can self-separate out with the product removed and the remainder returned to the fermentation chamber. In embodiments where the product does not separate into an aqueous phase, media is removed and appropriate separation techniques (e.g., chromatography, distillation, etc.) are employed.

In an alternate embodiment, the product is not secreted by the engineered chemoautotrophs. In this embodiment, a batch-fed fermentation approach is employed. In such cases, cells are grown under continued exposure to inputs (inorganic energy and inorganic carbon) as specified above until the reaction chamber is saturated with cells and product. A significant portion to the entirety of the culture is removed, the cells are lysed, and the products are isolated by appropriate separation techniques (e.g., chromatography, distillation, filtration, centrifugation, etc.).

In certain embodiments, the engineered chemoautotrophs of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. It is highly desirable to maintain anaerobic conditions in the fermenter to reduce the cost of the overall process.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

In another embodiment, the engineered chemoautotrophs can be cultured in the presence of an electron acceptor, for example, nitrate, in particular under substantially anaerobic conditions. It is understood that an appropriate amount of nitrate can be added to a culture to achieve a desired increase in biomass, for example, 1 mM to 100 mM nitrate, or lower or higher concentrations, as desired, so long as the amount added provides a sufficient amount of electron acceptor for the desired increase in biomass. Such amounts include, but are not limited to, 5 mM, 10 mM, 15 mM, 20 mM, 25 mM, 30 mM, 40 mM, 50 mM, as appropriate to achieve a desired increase in biomass.

In some embodiments, the engineered chemoautotrophs of the present invention are initially grown in culture conditions with a limiting amount of organic carbon to facilitate growth. Then, once the supply of organic carbon is exhausted, the engineered chemoautotrophs transition from heterotrophic to autotrophic growth relying on energy from an inorganic energy sources to fix inorganic carbon in order to produce carbon-based products of interest. The organic carbon can be, for example, a carbohydrate source. Such sources include, for example, sugars such as glucose, xylose, arabinose, galactose, mannose, fructose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art would understand that renewable feedstocks and biomass other than those exemplified above also can be used for culturing the engineered chemoautotrophs of the invention. In some embodiments, the engineered chemoautotrophs are optimized for a two stage fermentation by regulating the expression of the carbon product biosynthetic pathway.

In one aspect, the percentage of input carbon atoms converted to hydrocarbon products is an efficient and inexpensive process. Typical efficiencies in the literature are ~<5%. Engineered chemoautotrophs which produce hydrocarbon products can have greater than 1, 3, 5, 10, 15, 20, 25, and 30% efficiency. In one example engineered chemoautotrophs can exhibit an efficiency of about 10% to about 25%. In other examples, such microorganisms can exhibit an efficiency of about 25% to about 30%, and in other examples such engineered chemoautotrophs can exhibit >30% efficiency.

In some examples where the final product is released from the cell, a continuous process can be employed. In this approach, a reactor with engineered chemoautrophs producing for example, fatty acid derivatives, can be assembled in multiple ways. In one example, a portion of the media is removed and allowed to separate. Fatty acid derivatives are separated from the aqueous layer, which can in turn, be returned to the fermentation chamber.

In another example, the fermentation chamber can enclose a fermentation that is undergoing a continuous reduction. In this instance, a stable reductive environment can be created. The electron balance would be maintained by the release of oxygen. Efforts to augment the NAD/H and NADP/H balance can also facilitate in stabilizing the electron balance.

Consolidated Chemoautotrophic Fermentation

The above aspect of the invention is an alternative to directly producing final carbon-based product of interest as a result of chemoautotrophic metabolism. In this approach, carbon-based products of interest would be produced by leveraging other organisms that are more amenable to making any one particular product while culturing the engineered chemoautotroph for its carbon source. Consequently, fermentation and production of carbon-based products of interest can occur separately from carbon source production in a bioreactor.

In one aspect, the methods of producing such carbon-based products of interest include two steps. The first-step includes using engineered chemoautotrophs to convert inorganic carbon to central metabolites or sugars such as glucose. The second-step is to use the central metabolites or sugars as a carbon source for cells that produce carbon-based products of interest. In one embodiment, the two-stage approach comprises a bioreactor comprising engineered chemoautotrophs; a second reactor comprising cells capable of fermentation; wherein the engineered chemoautotrophs provides a carbon source such as glucose for cells capable of fermentation to produce a carbon-based product of interest. The second reactor may comprise more than one type of microorganism. The resulting carbon-based products of interest are subsequently separated and/or collected.

Preferably, the two steps are combined into a single-step process whereby the engineered chemoautotrophs convert inorganic energy and inorganic carbon and directly into central metabolites or sugars such as glucose and such organisms are capable of producing a variety of carbon-based products of interest.

The present invention also provides methods and compositions for sustained glucose production in engineered chemoautotrophs wherein these or other organisms that use the sugars are cultured using inorganic energy and inorganic carbon for use as a carbon source to produce carbon-based products of interest. In such embodiments, the host cells are capable of secreting the sugars, such as glucose from within the cell to the culture media in continuous or fed-batch in a bioreactor.

Certain changes in culture conditions of engineered chemoautrophs for the production of sugars can be optimized for growth. For example, conditions are optimized for inorganic energy source(s) and their concentration(s), inorganic carbon source(s) and their concentration(s), electron acceptor(s) and their concentrations, addition of supplements and nutrients. As would be apparent to those skilled in the art, the conditions sufficient to achieve optimum growth can vary depending upon location, climate, and other environmental factors, such as the temperature, oxygen concentration and humidity. Other adjustments may be required, for example, an organism's ability for carbon uptake. Increased inorganic carbon, such as in the form of carbon dioxide, may be introduced into a bioreactor by a gas sparger or aeration devices.

Advantages of consolidated chemoautotrophic fermentation include a process where there is separation of chemical end products, e.g., glucose, spatial separation between end products (membranes) and time. Additionally, unlike traditional or cellulosic biomass to biofuels production, pretreatment, saccharification and crop plowing are obviated.

The consolidated chemoautrophic fermentation process produces continuous products. In preferred embodiments, the process involves direct conversion of inorganic energy and inorganic carbon to product from engineered front-end organisms to produce various products without the need to lyse the organisms. For instance, the organisms can utilize 3PGAL to make a desired fermentation product, e.g., ethanol. Such end products can be readily secreted as opposed to intracellular products such as oil and cellulose. In yet other embodiments, organisms produce sugars, which are secreted into the media and such sugars are used during fermentation with the same or different organisms or a combination of both.

Processing and Separation of Carbon-Based Products of Interest

The carbon-based products produced by the engineered chemoautotrophs during fermentation can be separated from the fermentation media. Known techniques for separating fatty acid derivatives from aqueous media can be employed. One exemplary separation process provided herein is a two-phase (bi-phasic) separation process. This process involves fermenting the genetically-engineered production hosts under conditions sufficient to produce for example, a fatty acid, allowing the fatty acid to collect in an organic phase and separating the organic phase from the aqueous fermentation media. This method can be practiced in both a batch and continuous fermentation setting.

Bi-phasic separation uses the relative immisciblity of fatty acid to facilitate separation. A skilled artisan would appreciate that by choosing a fermentation media and the organic phase such that the fatty acid derivative being produced has a high log P value, even at very low concentrations the fatty acid can separate into the organic phase in the fermentation vessel.

When producing fatty acids by the methods described herein, such products can be relatively immiscible in the fermentation media, as well as in the cytoplasm. Therefore, the fatty acid can collect in an organic phase either intracellularly or extracellularly. The collection of the products in an organic phase can lessen the impact of the fatty acid derivative on cellular function and allows the production host to produce more product.

The fatty alcohols, fatty acid esters, waxes, and hydrocarbons produced as described herein allow for the production of homogeneous compounds with respect to other compounds wherein at least 50%, 60%, 70%, 80%, 90%, or 95% of the fatty alcohols, fatty acid esters, waxes and hydrocarbons produced have carbon chain lengths that vary by less than 4 carbons, or less than 2 carbons. These compounds can also be produced so that they have a relatively uniform degree of saturation with respect to other compounds, for example at least 50%, 60%, 70%, 80%, 90%, or 95% of the fatty alcohols, fatty acid esters, hydrocarbons and waxes are mono-, di-, or tri-unsaturated.

Detection and Analysis

Generally, the carbon-based products of interest produced using the engineered chemoautotrophs described herein can be analyzed by any of the standard analytical methods, e.g., gas chromatography (GC), mass spectrometry (MS) gas chromatography-mass spectrometry (GCMS), and liquid chromatography-mass spectrometry (LCMS), high performance liquid chromatography (HPLC), capillary electrophoresis, Matrix-Assisted Laser Desorption Ionization time-of-flight mass spectrometry (MALDI-TOF MS), nuclear magnetic resonance (NMR), near-infrared (NIR) spectroscopy, viscometry [Knothe, 1997; Knothe, 1999], titration for determining free fatty acids [Komers, 1997], enzymatic methods [Bailer, 1991], physical property-based methods, wet chemical methods, etc.

Carbon Fingerprinting

Biologically-produced carbon-based products, e.g., ethanol, fatty acids, alkanes, isoprenoids, represent a new commodity for fuels, such as alcohols, diesel and gasoline. Such biofuels have not been produced using biomass but use carbon dioxide as its carbon source. These new fuels may be distinguishable from fuels derived form petrochemical carbon on the basis of carbon-isotopic fingerprinting. Such products, derivatives, and mixtures thereof may be completely distinguished from their petrochemical derived counterparts on the basis of $^{14}C$ (fM) and carbon-isotopic fingerprinting, indicating new compositions of matter.

There are three naturally occurring isotopes of carbon: $^{12}C$, $^{13}C$, and $^{14}C$. These isotopes occur in above-ground total carbon at fractions of 0.989, 0.011, and $10^{-12}$, respectively. The isotopes $^{12}C$ and $^{13}C$ are stable, while $^{14}C$ decays naturally with a half-life of 5730 years to $^{14}N$, a beta particle, and an anti-neutrino. The isotope $^{14}C$ originates in the atmosphere, due primarily to neutron bombardment of $^{14}N$ caused ultimately by cosmic radiation. Because of its relatively short half-life (in geologic terms), $^{14}C$ occurs at extremely low levels in fossil carbon. Over the course of 1 million years without exposure to the atmosphere, just 1 part in $10^{50}$ will remain $^{14}C$.

The $^{13}C:^{12}C$ ratio varies slightly but measurably among natural carbon sources. Generally these differences are expressed as deviations from the $^{13}C:^{12}C$ ratio in a standard material. The international standard for carbon is Pee Dee Belemnite, a form of limestone found in South Carolina, with a $^{13}C$ fraction of 0.0112372. For a carbon source a, the deviation of the $^{13}C:^{12}C$ ratio from that of Pee Dee Belemnite is expressed as:

$\delta_a = (R_a/R_s) - 1$, where $R_a = {}^{13}C:^{12}C$ ratio in the natural source, and $R_s = {}^{13}C:^{12}C$ ratio in Pee Dee Belemnite, the standard.

For convenience, $\delta_a$ is expressed in parts per thousand, or ‰. A negative value of $\delta_a$ shows a bias toward $^{12}C$ over $^{13}C$ as compared to Pee Dee Belemnite. Table 2 shows $\delta_a$ and $^{14}C$ fraction for several natural sources of carbon.

TABLE 2

$^{13}C:^{12}C$ variations in natural carbon sources

| Source | -$\delta_a$ (‰) | References |
|---|---|---|
| Underground coal | 32.5 | [Farquhar, 1989] |
| Fossil fuels | 26 | [Farquhar, 1989] |
| Ocean DIC* | 0-1.5 | [Goericke, 1994; Ivlev, 2010] |
| Atmospheric $CO_2$ | 6-8 | [Ivlev, 2010; Farquhar, 1989] |
| Freshwater DIC* | 6-14 | [Dettman, 1999] |
| Pee Dee Belemnite | 0 | [Ivlev, 2010] |

*DIC = dissolved inorganic carbon.

Biological processes often discriminate among carbon isotopes. The natural abundance of $^{14}C$ is very small, and hence discrimination for or against $^{14}C$ is difficult to measure. Biological discrimination between $^{13}C$ and $^{12}C$, however, is well-documented. For a biological product p, we can define similar quantities to those above:

$\delta_p = (R_p/R_s) - 1$, where $R_p = {}^{13}C:^{12}C$ ratio in the biological product, and $R_s = {}^{13}C:^{12}C$ ratio in Pee Dee Belemnite, the standard.

Table 3 shows measured deviations in the $^{13}C:^{12}C$ ratio for some biological products that arise from carbon fixation by the Calvin cycle. Other carbon fixation pathways provide different "fingerprint" $^{13}C:^{12}C$ ratios.

TABLE 3

$^{13}C:^{12}C$ variations in selected biological products.

| Product | -$\delta_p$ (‰) | -epsilon (‰)* | References |
|---|---|---|---|
| Plant sugar/starch from atmospheric $CO_2$ | 18-28 | 10-20 | [Ivlev, 2010] |
| Cyanobacterial biomass from marine DIC | 18-31 | 16.5-31 | [Goericke, 1994; Sakata, 1997] |
| Cyanobacterial lipid from marine DIC | 39-40 | 37.5-40 | [Sakata, 1997] |
| Algal lipid from marine DIC | 17-28 | 15.5-28 | [Goericke, 1994; Abelseon, 1961] |
| Algal biomass from freshwater DIC | 17-36 | 3-30 | [Marty, 2008] |
| E. coli lipid from plant sugar | 15-27 | near 0 | [Monson, 1980] |
| Cyanobacterial lipid from fossil carbon | 63.5-6 | 37.5-40 | — |
| Cyanobacterial biomass from fossil carbon | 42.5-57 | 16.5-31 | — |

*epsilon = fractionation by a biological process in its utilization of $^{12}C$ versus $^{13}C$ (see text)

Table 3 introduces a new quantity, epsilon. This is the discrimination by a biological process in its utilization of $^{12}C$ vs. $^{13}C$. We define epsilon as follows: epsilon=$(R_p/R_a)-1$.

This quantity is very similar to $\delta_a$ and $\delta_p$, except we now compare the biological product directly to the carbon source rather than to a standard. Using epsilon, we can combine the bias effects of a carbon source and a biological process to obtain the bias of the biological product as compared to the standard. Solving for $\delta_p$, we obtain: $\delta_p$=(epsilon)($\delta_a$)+epsilon+$\delta_a$, and, because (epsilon)($\delta_a$) is generally very small compared to the other terms, $\delta_p \approx \delta_a$+epsilon.

For a biological product having a production process with a known epsilon, we may therefore estimate $\delta_p$ by summing $\delta_a$ and epsilon. We assume that epsilon operates irrespective of the carbon source.

This has been done in Table 3 for cyanobacterial lipid and biomass produced from fossil carbon. As shown in the Tables above, cyanobacterial products made from fossil carbon (in the form of, for example, flue gas or other emissions) can have a higher $\delta_p$ than those of comparable biological products made from other sources, distinguishing them on the basis of composition of matter from these other biological products. In addition, any product derived solely from fossil carbon can have a negligible fraction of $^{14}C$, while products made from above-ground carbon can have a $^{14}C$ fraction of approximately $10^{-12}$.

Accordingly, in certain aspects, the invention provides various carbon-based products of interest characterized as $-\delta_p$(‰) of about 63.5 to about 66 and −epsilon(‰) of about 37.5 to about 40. For carbon-based products that are derived from engineered autotrophs that make use of carbon fixation pathways other than the Calvin cycle, epsilon, and thus δ, can vary, as previously described [Hayes, 2001].

Sequences Provided by the Invention

Table 4 provides a summary of SEQ ID NOs: 1-60 disclosed herein.

TABLE 4

| SEQ ID NO | Sequence |
|---|---|
| 1 | Codon optimized *Burkholderia stabilis* NADP+ FDH gene |
| 2 | Codon optimized *Candida* methylica NAD+ FDH gene |
| 3 | Codon optimized *Candida boidinii* NAD+ FDH gene |
| 4 | Codon optimized *Saccharomyces cerevisiae* S288c NAD+ FDH gene |
| 5 | *Clostridium pasteurianum* putative ferredoxin-FDH FdhF subunit amino acid sequence |
| 6 | *Clostridium pasteurianum* putative ferredoxin-FDH FdhD subunit amino acid sequence |
| 7 | *Clostridium pasteurianum* putative FDH-associated ferredoxin domain containing protein 1 amino acid sequence |
| 8 | *Clostridium pasteurianum* putative FDH-associated ferredoxin domain containing protein 2 amino acid sequence |
| 9 | Codon optimized *Aquifex aeolicus* VF5 SQR gene |
| 10 | Codon optimized *Nostoc* sp. PCC 7120 SQR gene |
| 11 | Codon optimized *Chlorobium tepidum* TLS SQR gene |
| 12 | Codon optimized *Acidithiobacillus ferrooxidans* ATCC 23270 SQR gene |
| 13 | Codon optimized *Allochromatium vinosum* DSM 180 SQR gene |
| 14 | Codon optimized *Rhodobacter capsulatus* SB 1003 SQR gene |
| 15 | Codon optimized *Thiobacillus denitrificans* ATCC 25259 SQR gene |
| 16 | Codon optimized *Magnetococcus* sp. MC-1 SQR gene |
| 17 | Codon optimized *Clostridium pasteurianum* ferredoxin gene |
| 18 | Codon optimized *Hydrogenobacter thermophilus* TK-6 fdx1 gene |
| 19 | Codon optimized *Hydrogenobacter thermophilus* TK-6 fdx2 gene |
| 20 | Codon optimized *Methanosarcina barkeri* str. Fusaro ferredoxin gene |
| 21 | Codon optimized *Aquifex aeolicus* fdx7 gene |
| 22 | *Aquifex aeolicus* fdx7 amino acid sequence |
| 23 | Codon optimized *Aquifex aeolicus* fdx6 gene |
| 24 | *Aquifex aeolicus* fdx6 amino acid sequence |
| 25 | Codon optimized gamma-proteobacterium NOR51-B MCR gene |
| 26 | Codon optimized *Roseiflexus castenholzii* DSM 13941 MCR gene |
| 27 | Codon optimized marine gamme proteobacterium HTCC2080 MCR gene |
| 28 | Codon optimized *Erythrobacter* sp. NAP1 MCR gene |
| 29 | Codon optimized *Chloroflexus aurantiacus* J-10-fl MCR gene |
| 30 | Codon optimized *Chloroflexus aurantiacus* PCS gene |
| 31 | *Chloroflexus aurantiacus* PCS amino acid sequence |
| 32 | Codon optimized *Metallosphaera sedula* PccB gene |
| 33 | Codon optimized *Metallosphaera sedula* AccC gene |
| 34 | Codon optimized *Metallosphaera sedula* AccB gene |
| 35 | Codon optimized *Nitrosopumilus maritimus* SCM1 PccB gene |
| 36 | Codon optimized *Nitrosopumilus maritimus* SCM1 AccC gene |
| 37 | Codon optimized *Nitrosopumilus maritimus* SCM1 AccB gene |
| 38 | Codon optimized *Cenarchaeum symbiosum* A PccB gene |
| 39 | Codon optimized *Cenarchaeum symbiosum* A AccC gene |
| 40 | Codon optimized *Cenarchaeum symbiosum* A AccB gene |
| 41 | Codon optimized *Halobacterium* sp. NRC-1 PccB gene 1 |
| 42 | Codon optimized *Halobacterium* sp. NRC-1 PccB gene 2 |
| 43 | Codon optimized *Halobacterium* sp. NRC-1 AccB gene 1 |
| 44 | Codon optimized *Halobacterium* sp. NRC-1 AccC gene 2 |
| 45 | Codon optimized *Halobacterium* sp. NRC-1 AccB gene |
| 46 | Codon optimized *Methylcoccus capsulatus* str. Bath HPS gene 1 |
| 47 | Codon optimized *Methylcoccus capsulatus* str. Bath HPS gene 2 |
| 48 | Codon optimized *Methylcoccus capsulatus* str. Bath PHI gene |
| 49 | Codon optimized *Mycobacterium gastri* MB19 HPS-PHI fusion gene |
| 50 | *Mycobacterium gastri* MB19 HPS-PHI fusion amino acid sequence |
| 51 | Codon optimized *Synechococcus elongatus* PCC 7942 GAPDH gene |
| 52 | Codon optimized *Synechococcus elongatus* PCC 7942 SBPase gene |
| 53 | Codon optimized *Synechococcus elongatus* PCC 7942 PRK gene |
| 54 | Codon optimized *Escherichia coli* FocA gene |
| 55 | Codon optimized *Escherichia coli* FocB gene |
| 56 | Plasmid 2430 |
| 57 | Plasmid 2429 |
| 58 | Plasmid 4767 |
| 59 | Plasmid 4768 |
| 60 | Plasmid 4986 |
| 61 | Codon optimized *Escherichia coli* ACS gene |
| 62 | Codon optimized *Listeria monocytogenes* ADH gene |
| 63 | Plasmid 9463 |
| 64 | Plasmid 9462 |
| 65 | Plasmid 20566 |
| 66 | Plasmid 27439 |

EXAMPLES

The examples below are provided herein for illustrative purposes and are not intended to be restrictive.

Example 1: Identification and Selection of Candidate Sulfide:Quinone Oxidoreductase Enzymes To identify candidate sulfide-quinone oxidoreductases (SQR) for the energy conversion pathway that uses hydrogen sulfide as an inorganic energy source, the *Rhodobacter capsulatus* SQR was selected as the model enzyme. The *R. capsulatus* SQR has been functionally expressed in the heterologous host *E. coli* [Schütz, 1997] and demonstrated to reduce ubiquinone [Shibata, 2001]. A search of the NCBI Protein Clusters database was performed using the search term "sulfide quinone reductase" and 17 different protein clusters were identified as of Feb. 1, 2011 (CLSK2755575, CLSK2397089, CLSK2336986, CLSK2302249, CLSK2299965, CLSK943035, CLSK940594, CLSK917086, CLSK903971, CLSK892907, CLSK884384, CLSK871744, CLSK871685, CLSK870501, CLSK785404, CLSK767599, CLSK724710). The 17 protein clusters comprised 203 putative SQRs which were subsequently aligned using MUSCLE 3.8.31 using sequence YP_003443063 as an outgroup. The resulting alignment was imported into Geneious Pro 5.3.6 and a tree was made using a neighbor-joining method. Based on the alignment, any sequences containing less than four of six conserved residues were eliminated from the set. The six conserved residues were three conserved cysteines, two conserved histidines thought to be involved n quinone binding and the absence of a conserved aspartate that is characteristic of all glutathion reductase family of flavoproteins with the exception of SQRs [Griesbeck, 2000]. The resulting sequences were realigned using MUSCLE and a new tree was made. Representative sequences from each clade were selected as candidate SQRs.

Example 2: Engineered E. coli that Transfer Electrons from Formate to NADH or NADPH Plasmids comprising a high copy number replication origin, chloramphenicol resistance marker and each of two different codon-optimized formate dehydrogenase (fdh) genes under the control of an rrnB-derived constitutive promoter were constructed using DNA assembly methods described in WO/2010/070295. The resulting plasmids 2430 (SEQ ID NO:56) and 2429 (SEQ ID NO:57) and transformed into E. coli using standard plasmid transformation techniques. As a negative control, an expression plasmid without any fdh gene was also constructed. As a positive control, purified NAD$^+$-dependent FDH enzyme obtained from commercial sources was used.

Figure 21:
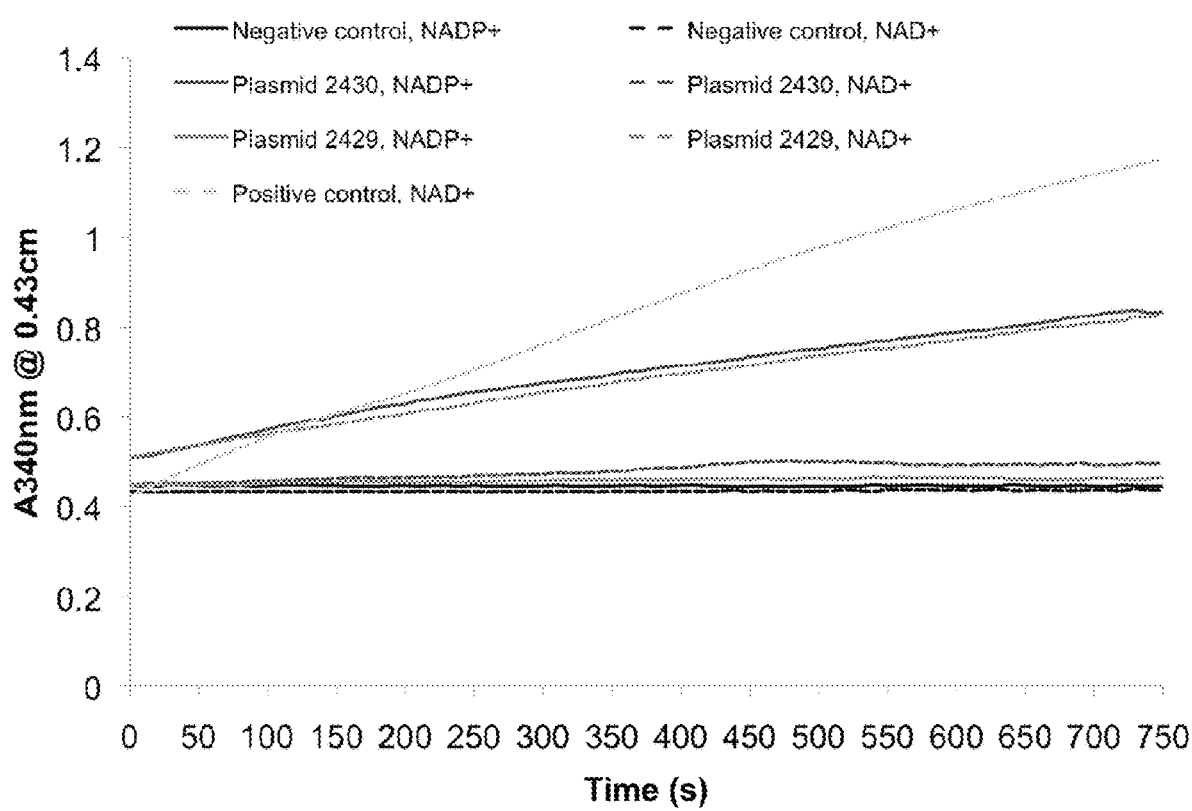
FIG. 21 depicts the spectrophotometric assay results of in vitro formate dehydrogenase (FDH) assays for strains propagating plasmid 2430, plasmid 2429 as well as positive and negative control. The positive control is commercially available purified $NAD^+$-dependent FDH enzyme. The negative control is a strain propagating a plasmid without an FDH-encoding gene. For each strain, assay results are shown with for both $NADP^+$ and $NAD^+$ as the cofactor, as indicated. The reduction of either $NADP^+$ or $NAD^+$ is monitored by measuring the absorbance at 340 nm.

Cultures propagating each of the plasmids were inoculated from glycerol stocks and grown overnight in a 24-well plate with fresh LB media supplemented with 34 µg/ml chloramphenicol at 37° C. The grown cultures were then diluted into 1 ml fresh media in a 96-well plate. Cells were pelleted by centrifugation for 10 minutes at 3000×g and the supernatant decanted. The cell pellets were resuspended in 100 µl complete B-PER (contains DNaseI and lysozyme). The assay reactions were prepared in a 96-well assay plate and contained the following: 100 µl of 200 mM potassium phosphate buffer, pH 7.0 (made by titering 200 mM dipotassium hydrogen phosphate into 200 mM potassium dihydrogen phosphate until the solution pH reached 7.0), 15 µl of 10 mM NAD(P)$^+$ as appropriate, 20 µl cell lysate, and 30 µl 0.5 M sodium formate. The absorbance at 340 nm of each sample was measured every 20 seconds in a Spectramax Gemini Plus plate reader in order to monitor the reduction of NAD(P)$^+$. The assay plate was maintained at a temperature of 37° C. The measured rates of NAD(P)$^+$ reduction were normalized to the number of cells used to prepare the cell lysates. The assay results are shown in FIG. 21. From the assay data, the quantitative activities of each FDH can be computed as well as their cofactor preference (Table 5).

TABLE 5

| Quantitative, measured activities of FDH | | | |
|---|---|---|---|
| Plasmid | amol NADP$^+$ min$^{-1}$ CFU$^{-1}$ | amol NADP$^+$ min$^{-1}$ CFU$^{-1}$ | ln (NADP$^+$/NAD$^+$) |
| negative control | −0.05 | 0.18 | — |
| 2430 | 21.37 | 3.06 | 1.9 |
| 2429 | 0.12 | 9.79 | −4.4 |

Example 3: Engineered E. coli that Oxidizes Hydrogen Sulfide

Plasmids comprising a high copy number replication origin, chloramphenicol resistance marker and a codon-optimized sulfide-quinone oxidoreductase from *Rhodobacter capsulatus* (sqr) gene under the control of two different rrnB-derived constitutive promoters were constructed using DNA assembly methods described in WO/2010/070295. The resulting plasmids 4767 (SEQ ID NO:58) and 4768 (SEQ ID NO:59) were transformed into E. coli using standard plasmid transformation techniques. As a negative control, an expression plasmid without a constitutive promoter but including the sqr gene was also constructed.

Figure 22:
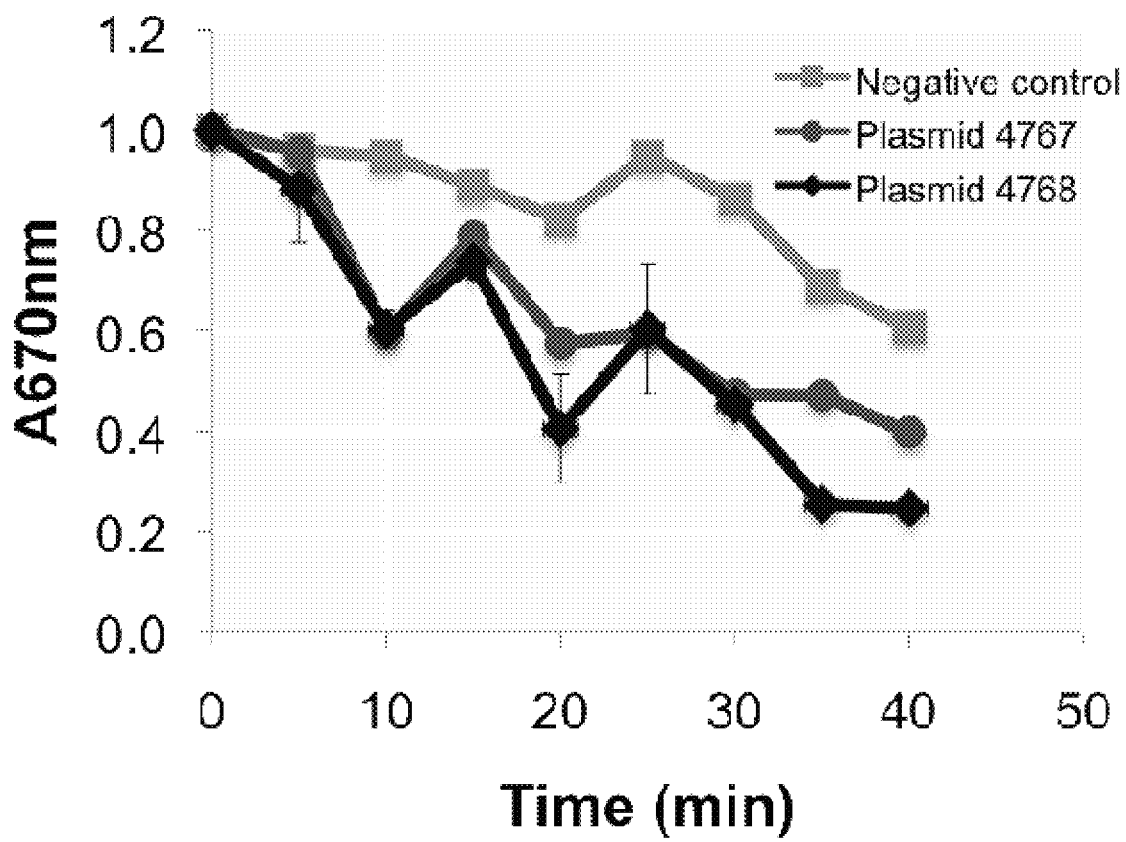
FIG. 22 depicts the spectrophotometric assay results of sulfide oxidation assays for strain propagating plasmid 4767, plasmid 4768 and a negative control plasmid (a plasmid without a constitutive promoter upstream of the sqr gene). Depletion of sulfide over time is monitored by measuring the absorbance at 670 nm after treatment of the samples with Cline reagent [Cline, 1969].

Cultures propagating each of the plasmids were inoculated from glycerol stocks and grown for two days in an 8-well plate with fresh LB media supplemented with 34 µg/ml chloramphenicol at 30° C. Cells were pelleted by centrifugation for 10 minutes at 2500 rpm and the supernatant decanted. The cell pellets were resuspended in 2 ml of SQR assay buffer (5 g/L sodium chloride, 5 mM magnesium chloride hexahydrate, 1 mM calcium chloride dihydrate, 20 mM Tris-HCl, pH 7.5). The absorbance at 600 nm of a 100 µl aliquot of each resuspended culture was measured to monitor the cell density. The assay reactions were prepared in a 96-well plate containing 0, 100, 150, 200 µl of SQR assay buffer; 10 µl of 0.1M sodium sulfide; and 200, 100, 50, and 0 µl of resuspended cells. The absorbance at 600 nm of each assay reaction was measured to monitor the cell density. The sampling reactions were prepared in a 96-well assay plate and contained the following: 90 µl of Tris-HCl, pH 7.5; 8 µl aliquot from sampling plate; and 8 µl Cline reagent [Cline, 1969]. The absorbance at 670 nm of each sampling reaction was measured to monitor the sulfide concentration. The assay results are shown in FIG. 22. Based on this data, we estimate the sulfide oxidation rates in the cell resuspensions to be between 2-3.5 mM hour$^{-1}$ or roughly 0.5-2.0 mmol sulfide g DCW$^{-1}$ hour$^{-1}$.

Example 4: Engineered E. coli Producing Propionyl-coA from 3-Hydroxypropionate Plasmids comprising a high copy number replication origin, chloramphenicol resistance marker and a codon-optimized propionyl-coA synthase from *Chloroflexus aurantiacus* (pcs) gene under the control of two different rrnB-derived constitutive promoters were constructed using DNA assembly methods described in WO/2010/070295. The resulting plasmid 4986 (SEQ ID NO:60) was transformed into E. coli using standard plasmid transformation techniques. As a negative control, an expression plasmid without the pcs gene was also constructed.

Figure 23:
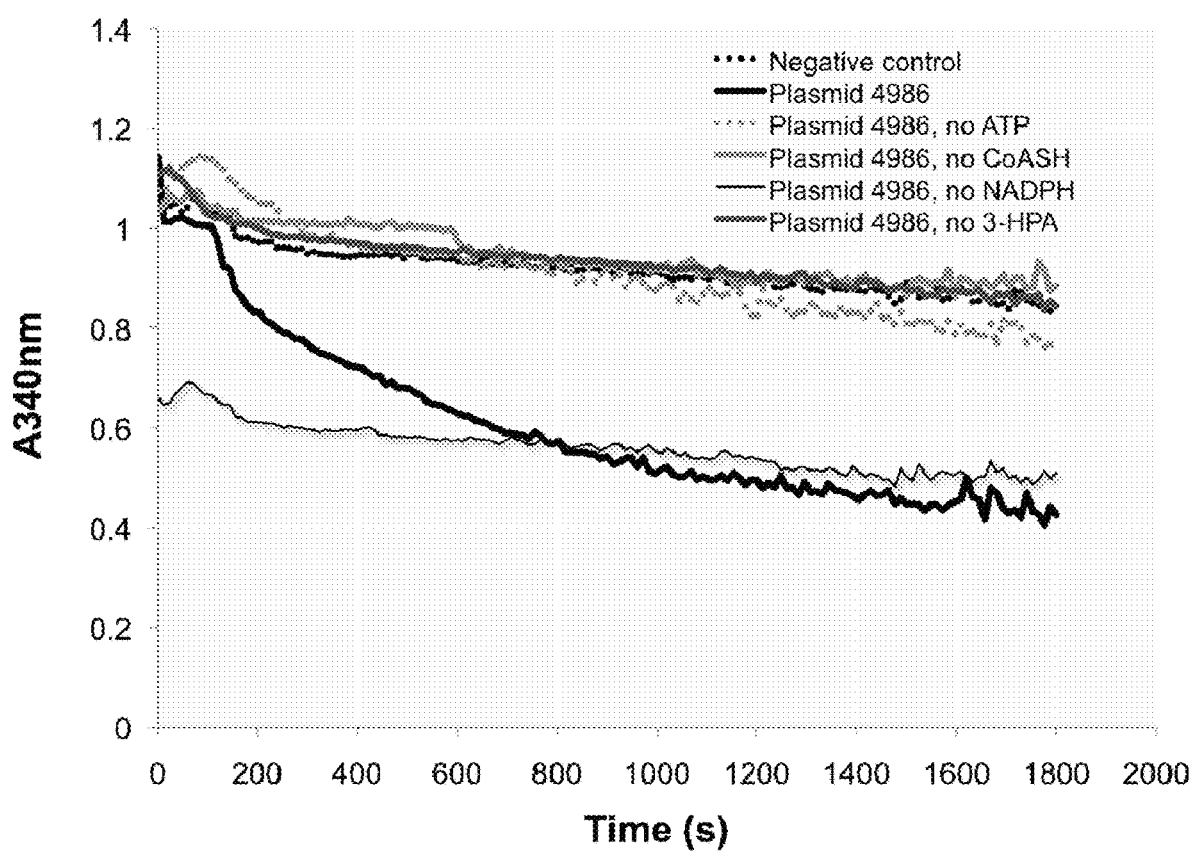
FIG. 23 depicts the spectrophotometric assay results of in vitro propionyl-CoA synthase (PCS) assays for strain propagating plasmid 4986 as well as a negative control plasmid containing no pcs gene. For the strain propagating plasmid 4986, assay results are shown with all required substrates as well as control reactions that omit one of the required substrates, as indicated. The oxidation of NADPH is monitored by measuring the absorbance at 340 nm.

Cultures propagating each of the plasmids were inoculated from glycerol stocks and grown overnight in a 24-well plate with fresh LB media supplemented with 34 µg/ml chloramphenicol at 37° C. Cells were pelleted by centrifugation and the supernatant decanted. The cell pellets were resuspended in 600 µl complete B-PER (contains DNaseI and lysozyme) and incubated for 30 minutes at 37° C. The assay reactions were prepared in a 96-well assay plate and contained the following: 71 µl of reaction buffer (3 mM ATP, 0.5 mM CoASH, 0.4 mM NADPH, 1×PCS buffer), 20 µl of cell lysate and 9 µl of a ten-fold dilution of chemically synthesized 3-hydroxypropionate (see below). The 1×PCS buffer contained 100 mM Tris-HCl, pH 7.6, 10 mM potassium chloride, 5 mM magnesium chloride hexahydrate, 2 mM 1,4-dithioerythritol. The absorbance at 340 nm of each assay reaction was measured every 12 seconds to monitor the oxidation of NADPH. As controls, the assay reaction contain lysate from a strain propagating plasmid 4986 was also assayed in the absence of each required substrate (ATP, CoASH, NADPH, 3-hydroxypropionate or 3-HPAA). The assay results are shown in FIG. 23.

The chemical 3-hydroxypropionate is used a substrate in enzymatic assays of propionyl-coA synthase (PCS). 3-hydroxypropionate can be made via chemical synthesis from β-propiolactone via the following method. A solution is prepared containing 0.3 M technical grade β-propiolactone (Sigma Aldrich catalog number P-5648) and 2 M sodium hydroxide and incubated overnight at room temperature. The solution is then neutralized with either hydrochloric acid or phosphoric acid. The presence of the reaction product 3-hydroxypropionate can be confirmed via LC-MS. LC-MS can also reveal that no other measureable side-products are formed. Since the starting material, β-propiolactone, is highly bacteriocidal, but the product, 3-hydroxypropionate, is not, growth inhibition assays can also be used to demonstrate complete conversion of the starting material.

Example 5: Engineered *E. coli* with Reduced Competing Formate Uptake Activity The formate uptake of a series of gene deletion strains of *E. coli* were analyzed as to identify genes responsible for competing, endogenous formate uptake activity in *E. coli*. All deletion strains were obtained from the Keio collection [Baba, 2006]. The negative control was the absence of cells. Cultures were grown aerobically in LB medium supplemented with 50 mM formate overnight, harvested by centrifugation, resuspended in fresh LB medium with formate, and incubated for four hours to allow the cells to reenter growth phase. The cells were then resuspended in either M9 minimal medium with 50 mM formate as the sole carbon source (results shown in Table 6) or LB medium with 50 mM formate (results shown in Table 7). Assays for formate levels (as measured in mM of formate) were performed as described in Example 8 at different timepoints.

TABLE 6

Formate uptake by various deletion strains, minimal medium

| Strain genotype | 0 | 20 | 40 | 60 | 240 |
|---|---|---|---|---|---|
| negative control | 88 | 89 | 98 | 90 | 85 |
| ΔfdhF | 89 | 91 | 85 | 66 | 46 |
| ΔfdnG | 84 | 80 | 65 | 48 | 14 |
| ΔfdoG | 84 | 77 | 93 | 54 | 54 |
| ΔselA | 84 | 130 | 93 | 88 | 77 |
| ΔselB | 89 | 124 | 95 | 86 | 59 |

TABLE 7

Formate uptake by various deletion strains, rich medium

| Strain genotype | 0 | 20 | 40 | 60 | 240 |
|---|---|---|---|---|---|
| negative control | 68 | 74 | 74 | 64 | 70 |
| ΔfdhF | 81 | 76 | 74 | 66 | 62 |
| ΔfdnG | 73 | 74 | 66 | 57 | 28 |
| ΔfdoG | 77 | 74 | 69 | 63 | 64 |
| ΔselA | 77 | 78 | 76 | 72 | 78 |
| ΔselB | 72 | 46 | 67 | 60 | 76 |

Example 6: Assay Methods to Measure Hydrogenase Activity

Figure 24:
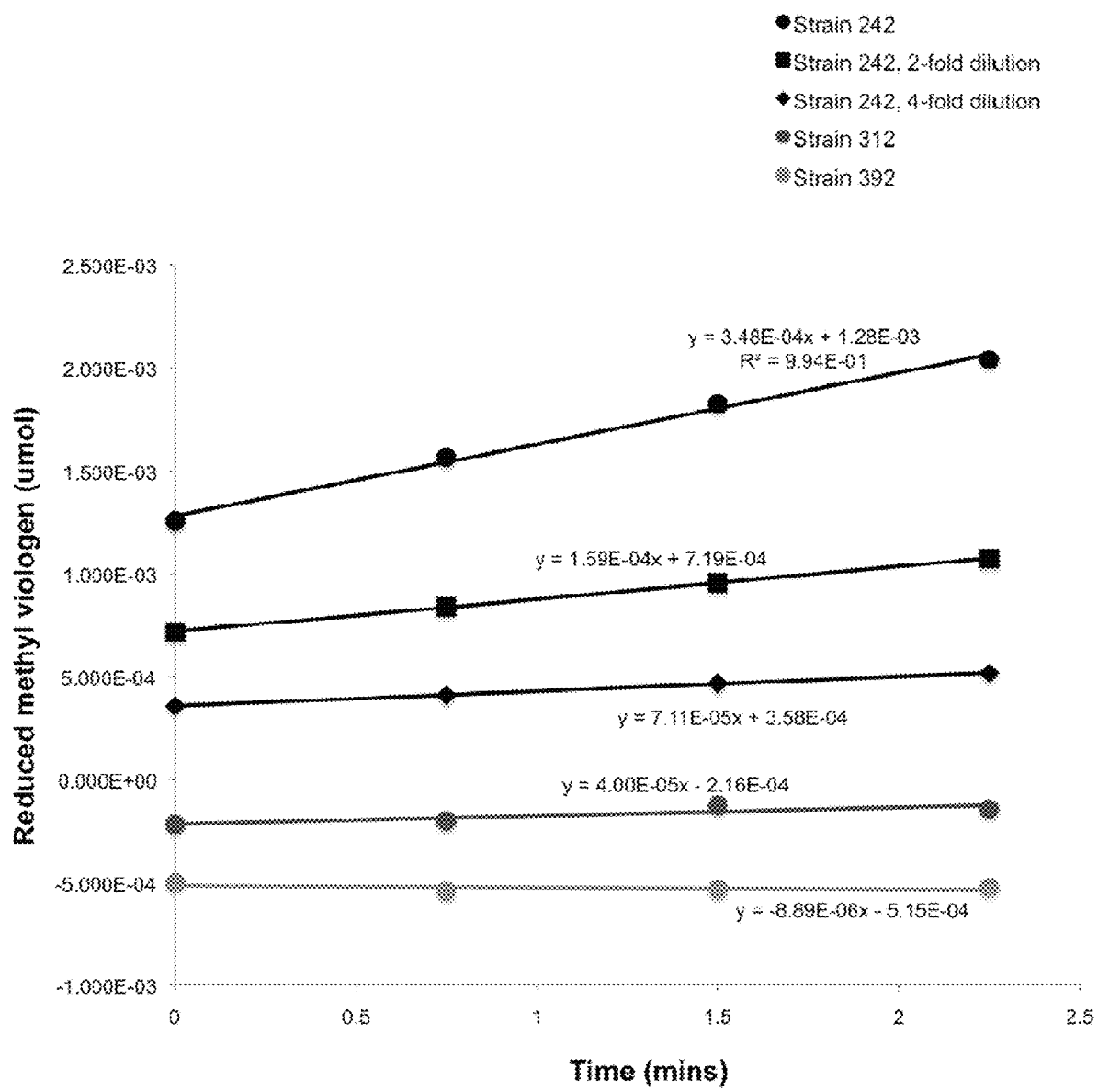
FIG. 24 depicts hydrogenase assay results for strains 242 (at three different dilutions), 312 and 392. Hydrogenase activity is measured by monitoring the reduction of the electron acceptor methyl viologen; hence, the y axis is denoted in μmol of reduced methyl viologen.

The following assay can be used to measure hydrogenase enzyme activity in intact cells. All steps are performed in a Shel-labs Bactron IV anaerobic chamber containing anaerobic mixed gas (90% nitrogen gas, 5% hydrogen gas, 5% carbon dioxide). Cultures with and without hydrogenase activity are inoculated from single colonies on LB-agar plates and grown overnight in a 24-well plate with fresh LB media. An aliquot of each culture (1-2 ml) is pelleted by centrifugation and the supernatant decanted. The cells are then resuspended in 1-2 ml 50 mM Tris-HCl, pH 7.6. A very small amount of sodium dithionite is picked up with a pipette tip and dissolved into 100 µl of 50 mM Tris-HCl, pH 7.6. The assay reactions are prepared in a 96-well plate and contain the following: 100 µl resuspended cells and 100 µl 0.8 mM methyl viologen in 50 mM Tris-HCl, pH 7.6. The 96-well plate is then loaded into a Biochrom UVM340 spectrophotometric plate reader and the absorbance at 600 nm is measured at 45 second intervals. To validate the assay, we assayed *E. coli* strain 242 (K strain MG1655), strain 312 (B strain BL21 DE3 with pLysS plasmid) and strain 393 (B strain BL21 DE2 with genes tonA, hycE, hyaB and hybC deleted). *E. coli* K strains are known to have hydrogenase activity whereas B strains do not [Pinske, 2011]. Assay results are shown in FIG. 24.

Example 7: Identification and Sequencing of a Formate-Ferredoxin Oxidoreductase from *Clostridium pasteurianum*

A culture sample of *Clostridium pasteurianum* W5 (ATCC 6013) was obtained from the ATCC (genome size is 3.9 Mbp) [Fogel, 1999]. The strain was cultured under anaerobic conditions in reinforced clostridial medium (Difco). Four aliquots of 1 ml of culture were pelleted by centrifugation at 6000×g for 5 minutes and the supernatant removed by aspiration. Genomic DNA was isolated with the Wizard genomic DNA purification kit (Promega) according to the manufacturer's instructions for Gram-positive bacteria with the following exceptions. In the lysis step, 10 mg/L lysozyme in 10 mM Tris, 0.5 mM EDTA, pH 8.2 was used without any additional lysis enzymes. Also, 10 mM Tris, 0.5 mM EDTA, pH 8.2 was used in lieu of DNA rehybridization solution. The DNA yield was approximate 26 µg of DNA from 4 ml of culture. The genomic DNA was sequenced at the Harvard/MGH sequencing facility. They prepared 160 bp inserts from the genomic DNA and obtained 300 MM 75 bp paired end reads on an Illumina HiSeq sequencer. The resulting coverage was 5000×. De novo assembly of the reads using Velvet resulting in 170 contigs greater than 5 kb in length comprising 3.9 Mbp. The resulting contigs were analyzed by Glimmer resulting in 3474 identified ORFs comprising 3.6 Mbp. A BLASTable database of amino acid sequences of all identified ORFs was produced using NCBI BLAST formatdb tool and subsequently a BLASTable contig database was generated. Based on inspection of the BLAST results, two putative FDH subunits were identified (SEQ ID NO:5 and SEQ ID NO:6) as well as two putative associated ferredoxin domain containing subunits (SEQ ID NO:7 and SEQ ID NO:8).

Example 8: Assay Methods to Measure Formate Uptake by Intact Cells

Figure 25:
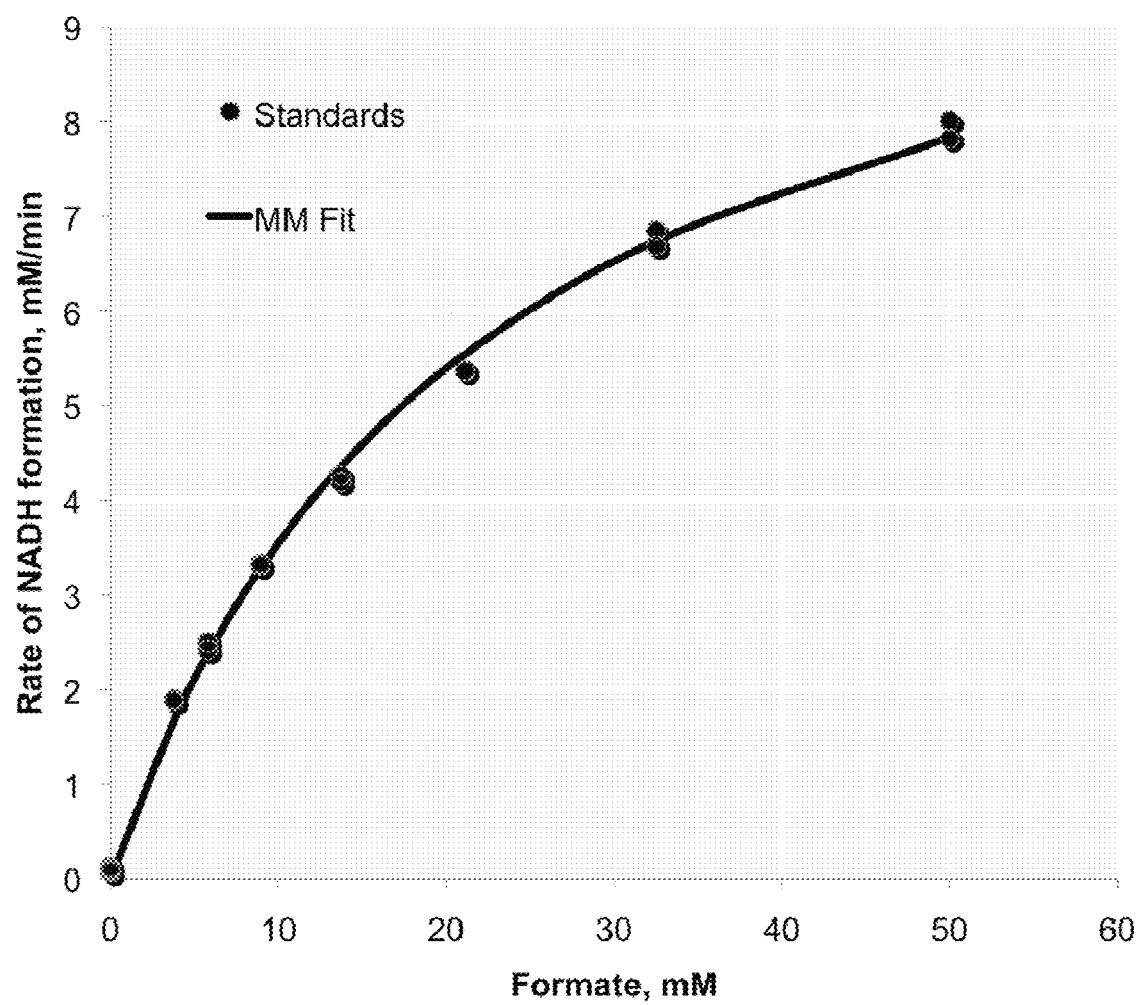
FIG. 25 depicts a standard curve correlating the rate of NADH formation by a commercially available formate dehydrogenase as a function of formate concentration in the sample.

The following assay can be used to measure formate levels in cultures thereby facilitating measurement of formate uptake by intact cells. Cultures are inoculated from glycerols and grown overnight in a 24-well plate with fresh LB media supplemented with the appropriate antibiotic as needed. The cultures are pelleted and an aliquot of the supernatant (300 µl) is saved. The assay reactions are prepared in a 96-well plate and contain the following: 80 µl of 200 mM potassium phosphate buffer pH 7.0, 15 µl of freshly prepared 100 mM $NAD^+$, 35 µl of culture supernant, 20 µl of 100× dilution of pure FDH enzyme purchased commercially. The 96-well plate is then loaded into a Spectramax spectrophotometric plate reader and the absorbance at 340 nm is measured at 12 second intervals preceded by 5 seconds of mixing. The rate of NADH formation can be calculated from the rate of change in the absorbance at 340 nm and varies with the level of formate in the sample (FIG. 25).

Example 9: Methods for Growth-Based Selections for 2-Oxoglutarate Synthase Activity To select for functional 2-oxoglutarate synthase activity in *E. coli*, the following growth-based selection can be used. A strain with the gene encoding isocitrate dehydrogenase rendered non-functional is used such that the strain cannot make 2-oxoglutarate (a precursor to glutamate synthesis in the cell). Such a strain can only grow in glucose minimal media that is supplemented with either glutamate or proline (proline degradation produces glutamate) [Helling, 1971]. Strain 149 (CGSC #4451) has the icd-3 mutation rendering isocitrate dehydrogenase non-functional. Table 8 shows the results of endpoint absorbance at 600 nm measurements of Strain 149 grown under different conditions for 36 hours at 37° C. The negative control is M9 media with glucose with no cells. All readings shown are an average of three measurement replicates of the same culture.

TABLE 8

Endpoint A 600 nm measurements of Strain 149

| Growth conditions | Average | Std Dev |
|---|---|---|
| Negative control | 0.0358 | 0.0003 |
| M9 media + glucose | 0.0363 | 0.0008 |
| M9 media + glucose + glutamate | 0.2155 | 0.0073 |
| M9 media + glucose + proline | 0.1913 | 0.0041 |
| M9 media + glucose + glutamate + proline | 0.2145 | 0.0049 |

Figure 26:
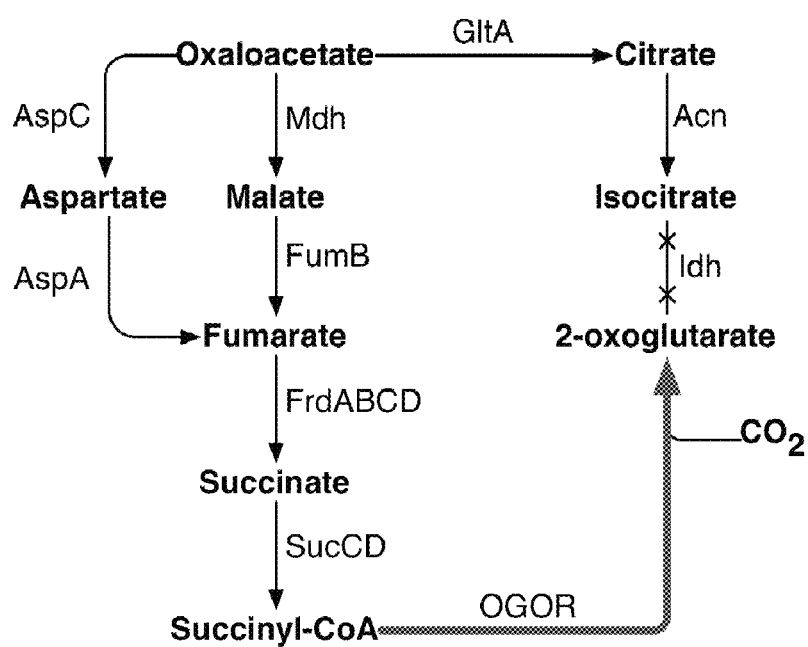
FIG. 26 depicts the branched tricarboxylic acid cycle run by *E. coli* when grown under anaerobic conditions. If the gene encoding isocitrate dehydrogenase (Icd) is rendered non-functional (denoted by Xs), then synthesis of 2-oxoglutarate is restored through introduction of a functional 2-oxoglutarate synthase (OGOR, bold gray arrow). Metabolite names are denoted in bold.

When grown under anaerobic conditions, *E. coli* runs a branched version of the tricarboxylic acid cycle. Hence, the glutamate/proline auxotrophy phenotype of strains such as Strain 149 in which the icd gene is rendered non-functional can be rescued by introduction of an exogenous, functional 2-oxoglutarate synthase (FIG. 26).

Example 10: Methods for Growth-Based Selections for Formate Utilization

Figure 27:
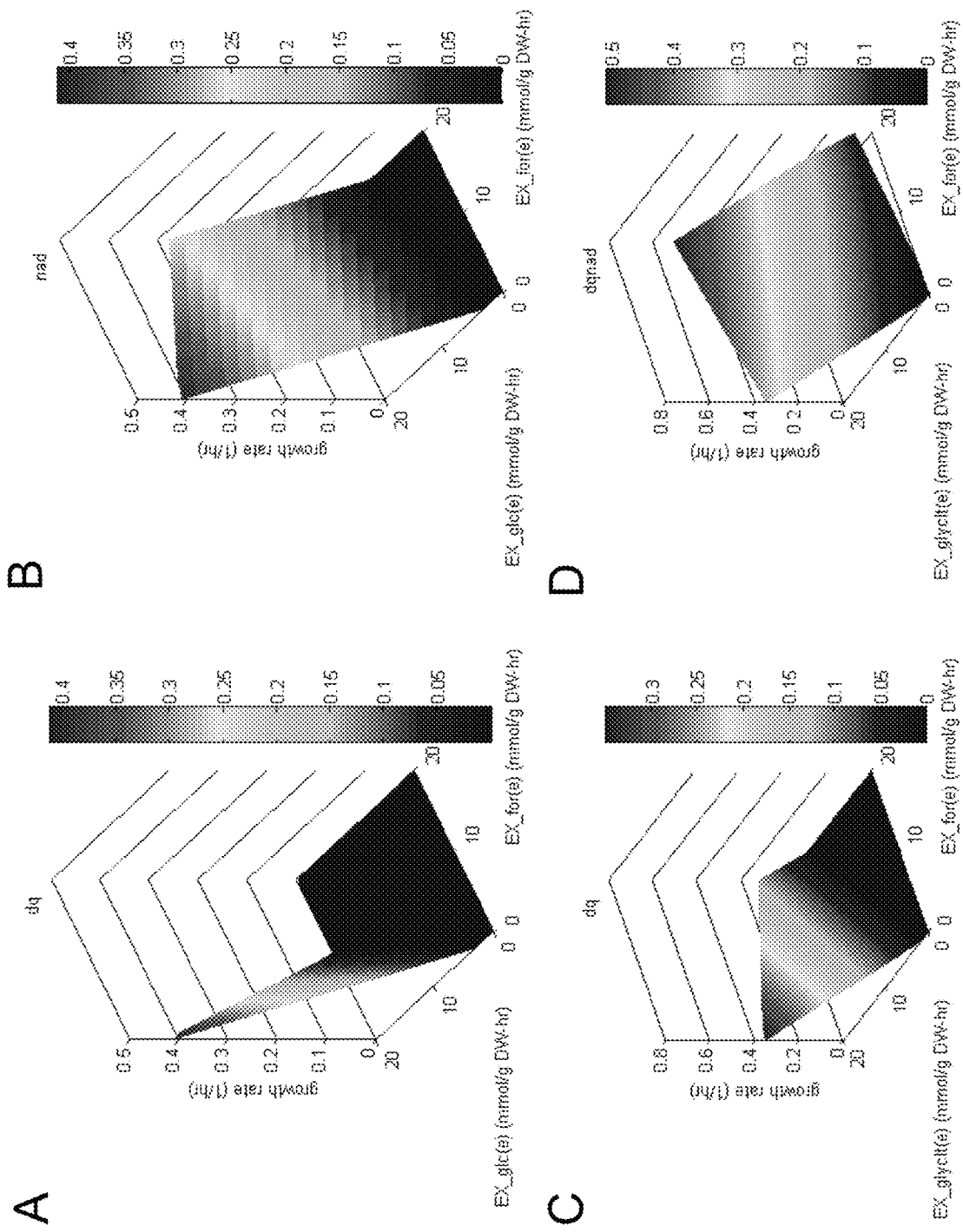
FIG. 27 depicts computed phenotypic phase planes for *E. coli* strains with the native formate dehydrogenases deleted in either the absence (A and C) or presence (B and D) of an exogenous $NAD^+$-dependent formate dehydrogenase. The growth conditions are aerobic with dual carbon sources of formate and either glucose (A and B) or glycolate (C and D).
Figure 28:
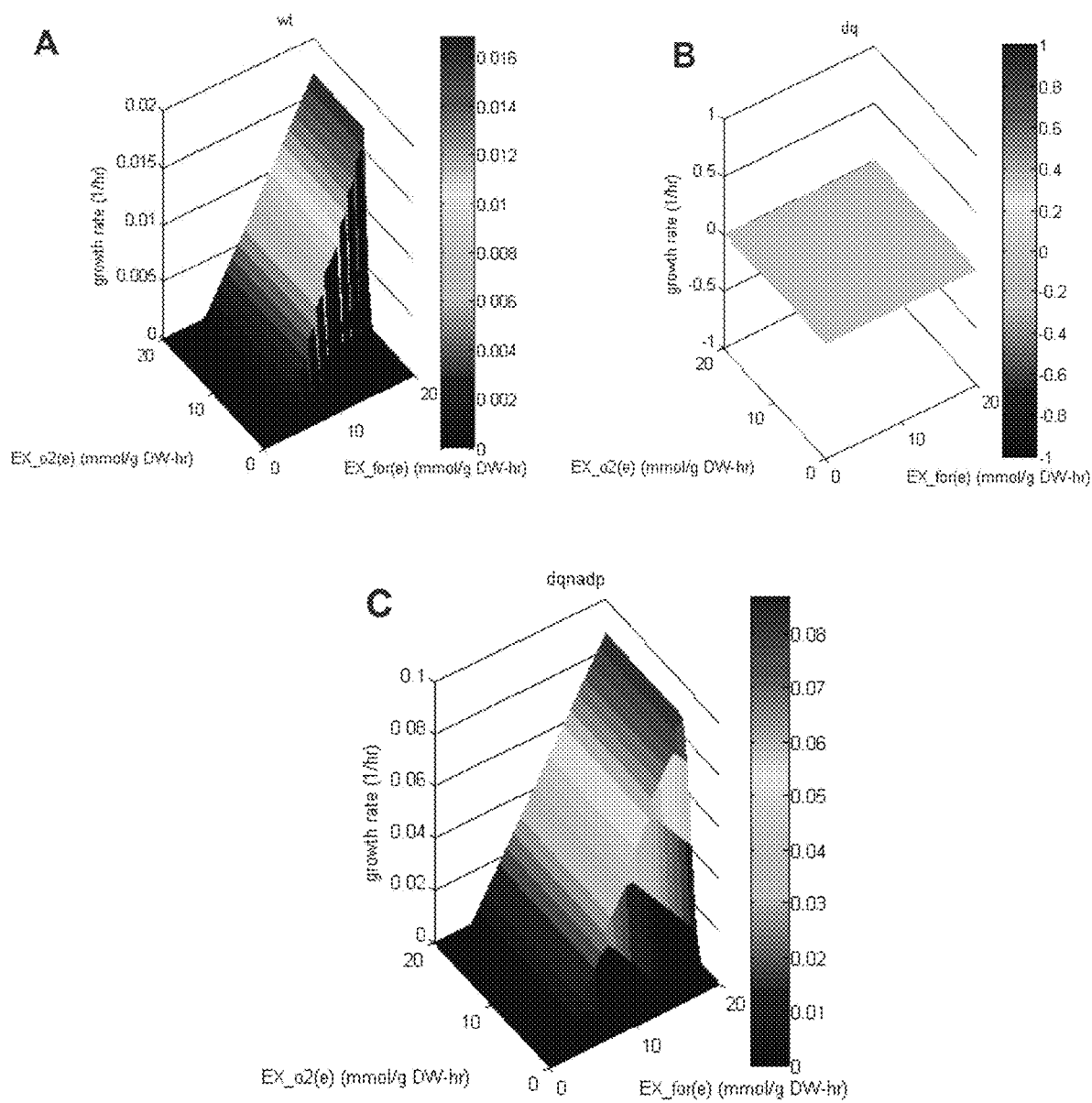
FIG. 28 depicts computed phenotypic phase planes during growth on formate as a sole carbon source for wildtype *E. coli* (A), *E. coli* with native formate dehydrogenases deleted (B) and *E. coli* with native formate dehydrogenases deleted and an exogenous $NAD^+$-dependent formate dehydrogenase added (C).

Using a model of *E. coli* metabolism [Edwards, 2002], the phenotypic phase planes for *E. coli* under a variety of growth conditions were computed. The growth conditions examined included formate co-metabolism with a second, limiting organic carbon source under both anaerobic and aerobic (i.e., unlimited oxygen uptake) conditions. The organic carbon sources examined include glucose, glycerol, malate, succinate, acetate and glycolate. For each carbon source, several in silico genotypes were evaluated including (1) wild-type *E. coli*, (2) *E. coli* with its native formate dehydrogenases (FDH) enzymes removed, (3) wild-type *E. coli* with a heterologous $NAD(P)^+$-dependent FDH and (4) *E. coli* with native FDHs removed and a heterologous $NAD(P)^+$-dependent FDH. The purpose of the analysis was to identify growth conditions that created selective pressure for increased formate uptake and utilization. Based on the computed phenotypic phase planes (FIG. 27), increased formate uptake correlated with increased growth rates under aerobic growth conditions with a non-fermentable inorganic carbon source (glycerol>succinate>malate=propionate>acetate>glycolate). Hence, this set of growth conditions is the preferred set of conditions for growth-based selections for formate utilization. The model analysis also suggests that wildtype *E. coli* is capable of growth on formate as a sole carbon source with a predicted doubling time of 1.4 days and that inclusion of an exogenous $NAD^+$-dependent FDH reduces the doubling time (FIG. 28).

*E. coli* strains can be evolved for improved formate utilization either through repeated subculturing or through continuous culturing in a chemostat or turbidostat using the above culture conditions.

Example 11: Computing Mass Transfer Limitations of Hydrogen Versus Formate as an Inorganic Energy Source The mass transfer limitations of hydrogen from the gas to liquid phase is illustrated here. For the purpose of this analysis, an ideal engineered chemoautotroph that has an unlimited capacity to (i) metabolize dissolved aqueous-phase hydrogen and (ii) convert it and carbon dioxide to a desired fuel at 100% of the theoretical yield is assumed. Under these conditions, the rate of fuel production per unit of reactor volume can depend solely on the rate at which hydrogen can be transferred from the gas phase to the liquid phase.

Fuel productivity P in units of $g \cdot L^{-1} \cdot h^{-1}$ can be expressed as the product of fuel molecular weight $m_F$, fuel molar yield on hydrogen $Y_{F/H}$, the biomass concentration in a bioreactor X, and the specific cellular uptake rate of hydrogen $q_H$, as shown in the equation below.

$$P = m_F Y_{F/H} X q_H$$

At steady state, the bulk hydrogen uptake rate $Xq_H$ is equal to the rate of hydrogen transfer from gas to liquid, meaning the productivity can be expressed as in the equation below, where C* is the liquid-phase solubility of hydrogen, $C_L$ is the liquid-phase concentration of hydrogen, and $K_L a$ is the mass transfer coefficient for hydrogen transport from the gas phase (e.g., as bubbles sparged into the reactor) to the liquid. $K_L a$ is a complex function of reactor geometry, bubble size, superficial gas velocity, impeller speed, etc. and is best regarded as an empirical parameter that needs to be determined for a given bioreactor setup.

$$P = m_F Y_{F/H} K_L a (C^* - C_L)$$

Again, as a best-case scenario, an ideal engineered chemoautotroph capable of maintaining rapid hydrogen uptake rates even at vanishingly low hydrogen concentrations (i.e. that $q_H$ is not a function of $C_L$ even as $C_L$ tends to zero) is assumed. This assumption maximizes the fuel productivity at $P = m_F Y_{F/H} K_L a C^*$.

For a fixed production target t, say 0.5 t d$^{-1}$ (equivalent to 20800 g h$^{-1}$), the productivity P determines the required reactor volume V because V t/β. Thus, both fuel productivity and reactor volumes, even assuming "perfect" organisms, are bounded by achieveable $K_L a$ values, as shown in the equations below.

$$P = (m_F Y_{F/H} C^*) K_L a$$
$$V = \frac{t}{(m_F Y_{F/H} C^*) K_L a}$$

Figure 29:
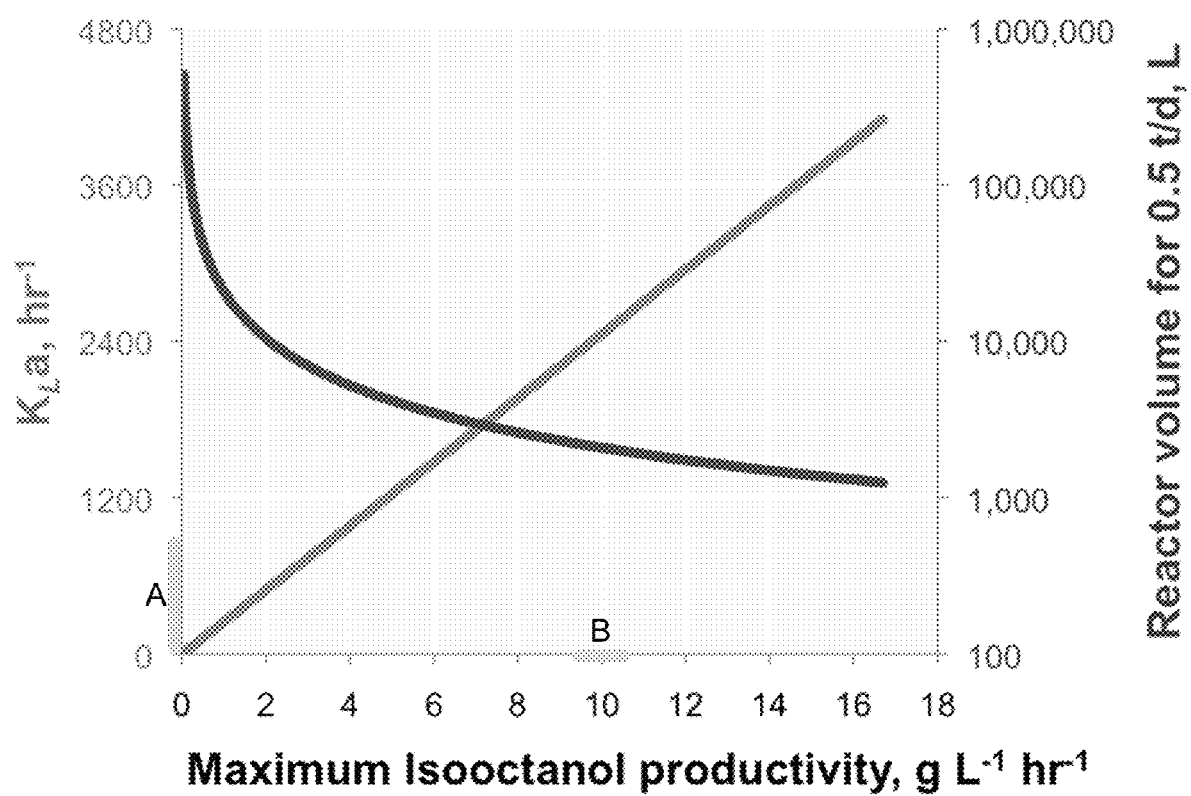
FIG. 29 depicts the required mass transfer coefficient ($K_L a$) and required reactor volume for 0.5 t/d of fuel production, as a function of maximum fuel productivity for isooctanol, assuming fuel production from inorganic energy source $H_2$ and inorganic carbon source $CO_2$ for an ideal engineered chemoautotroph. On the y axis, the typical range of $K_L a$ in large-scale stirred-tank bioreactors is denoted (A). On the x axis, reported natural formate uptake rates at industrially relevant culture densities is denoted (B).

Maximal productivity corresponds to minimal reaction volumes, and occurs at maximal values of $m_F Y_{F/H} C^* K_L a$. The fuel yield cannot exceed the stoichiometric maximal yield. For the fuel isooctanol, the stoichiometric maximal yield is determined from the balanced chemical equation 8 $CO_2 + 24\ H_2 \rightarrow C_8H_{18}O + 15\ H_2O$, which shows that 24 moles of $H_2$ are required for each mole of isooctanol produced. At atmospheric pressure, $C^*$ is unlikely to greatly exceed 0.75 mM, the solubility of $H_2$ in pure water. Using these representative values for representative values for $m_F$, $Y_{F/H}$, $C^*$ and t, the relationships between $K_L a$ and P as well as between $K_L a$ and t are shown (FIG. 29).

Alternative electron donors have the potential to solve both the safety problem and the mass transfer problem presented by hydrogen. An ideal non-hydrogen vector for carrying electrical energy would share hydrogen's attractive characteristics, which include (a) a highly negative standard reduction potential, and (b) established high-efficiency technology to for converting electricity into the vector. Unlike hydrogen, however, it would (c) have a low propensity to explode when mixed with air, and (d) have high water solubility under bio-compatible conditions. Formic acid, HCOOH, or its salts, satisfies these conditions. Formic acid is stoichiometrically equivalent to $H_2 + CO_2$, and formate has as standard reduction potential nearly identical to that of hydrogen. Since both formic acid and formate salts are highly soluble in water, the mass transfer limitations discussed above for hydrogen do not apply. However, a modified form of the fuel productivity equation, written for formic acid (A) instead of hydrogen (H), still applies, as shown below.

$$P = m_F Y_{F/A} X q_A$$

Unlike hydrogen-powered electrofuels bioproduction, limits on formate-powered fuel productivity P stem only from the attainable yield, the biomass concentration in the reactor, and the specific uptake rate. We assume $Y_{F/A}$, the molar yield of fuel on formic acid, is the stoichiometric maximum, whose value is the same as for hydrogen, 0.0467 mol isooctanol (mol HCOOH)$^{-1}$. For high-cell density cultivations of E. coli, biomass concentrations of X=50 gDCW L$^{-1}$ are attainable, although these values have not been observed for growth on formate or in minimal medium. For Thiobacillus strain A2, naturally capable of growing on formate, observed values of were 0.0368 mol formate·gDCW$^{-1}$·h$^{-1}$ [Kelly, 1979]. The representative values for $q_A$ and X imply a maximal isooctanol productivity on formate of about 10 g·L$^{-1}$·h$^{-1}$.

On the y-axis of FIG. 29, the range of reported $K_L a$ attainable in large-scale stirred-tank bioreactors is shown. Although there are many reports of higher $K_L a$ values in laboratory-scale reactors, during scale up the inevitable increase in volume-to-surface area ratios means that maintaining high $K_L a$ values is for practical purposes impossible. The maximum of the indicated range of 10-800 h$^{-1}$ translates to a best-case productivity of 4 g·L$^{-1}$·h$^{-1}$, which implies a best-case reactor volume of 6,400 L. The best-case productivity on formate is 10 g·L$^{-1}$·h$^{-1}$, implying a reactor volume less than half as large would be required to achieve the same production. Most sources that give $K_L a$ values for large scale reactors have values much closer to 100 h$^{-1}$, meaning the best-case productivity using formate as the inorganic energy source would be more than 15 times larger than on hydrogen.

Example 12: Engineered Organisms Producing Butanol

The enzyme beta-ketothiolase (R. eutropha PhaA or E. coli AtoB) (E.C. 2.3.1.16) converts 2 acetyl-CoA to acetoacetyl-CoA and CoA. Acetoacetyl-CoA reductase (R. eutropha PhaB) (E.C. 1.1.1.36) generates R-3-hydroxybutyryl-CoA from acetoacetyl-CoA and NADPH. Alternatively, 3-hydroxybutyryl-CoA dehydrogenase (C. acetobutylicum Hbd) (E.C. 1.1.1.30) generates S-3-hydroxybutyryl-CoA from acetoacetyl-CoA and NADH. Enoyl-CoA hydratase (E. coli MaoC or C. acetobutylicum Crt) (E.C. 4.2.1.17) generates crotonyl-CoA from 3-hydroxybutyryl-CoA. Butyryl-CoA dehydrogenase (C. acetobutylicum Bcd) (E.C. 1.3.99.2) generates butyryl-CoA and NAD(P)H from crotonyl-CoA. Alternatively, trans-enoyl-coenzyme A reductase (Treponema denticola Ter) (E.C. 1.3.1.86) generates butyryl-CoA from crotonyl-CoA and NADH. Butyrate CoA-transferase (R. eutropha Pct) (E.C. 2.8.3.1) generates butyrate and acetyl-CoA from butyryl-CoA and acetate. Aldehyde dehydrogenase (E. coli AdhE) (E.C. 1.2.1. {3,4}) generates butanal from butyrate and NADH. Alcohol dehydrogenase (E. coli adhE) (E.C. 1.1.1. {1,2}) generates 1-butanol from butanal and NADH, NADPH. Production of 1-butanol is conferred by the engineered host cell by expression of the above enzyme activities.

To create butanol-producing cells, host cells can be further engineered to express acetyl-CoA acetyltransferase (atoB) from E. coli K12, β-hydroxybutyryl-CoA dehydrogenase from Butyrivibrio fibrisolvens, crotonase from Clostridium beijerinckii, butyryl CoA dehydrogenase from Clostridium beijerinckii, CoA-acylating aldehyde dehydrogenase (ALDH) from Cladosporium fulvum, and adhE encoding an aldehyde-alcohol dehydrogenase of Clostridium acetobutylicum (or homologs thereof).

Example 13: Engineered Organisms Producing Acrylate

Enoyl-CoA hydratase (E. coli paaF) (E.C. 4.2.1.17) converts 3-hydroxypropionyl-CoA to acryloyl-CoA. Propionyl-CoA synthase (E.C. 6.2.1.-, E.C. 4.2.1.- and E.C. 1.3.1.-)

also converts 3-hydroxypropionyl-CoA to acryloyl-CoA (AAL47820, SEQ ID NO:30, SEQ ID NO:31). Acrylate CoA-transferase (*R. eutropha* pct) (E.C. 2.8.3.n) generates acrylate+acetyl-CoA from acryloyl-CoA and acetate.

Example 14: Conversion of Formaldehyde to Central Metabolic Intermediates by Lysates of Recombinant *E. coli* Cells The hexulose-6-phosphate isomerase (HPS) enzyme YP_115430 and 6-phospho-3-hexuloisomerase (PHI) enzyme YP_115431 were recoded for expression in *E. coli* using the algorithm described in [00110] above and/or elsewhere in the present application. Briefly, the algorithm attempts to (a) preserve codon rank order frequency in the source organism (*Methylococcus capsulatus*) and the target organism (*E. coli*); (b) eliminate undesired restriction endonuclease recognition sequences in the re-coded gene sequence; and (c) avoid undesired DNA or RNA secondary structure in the re-coded gene or its transcript. The resulting nucleotide sequences are provided as SEQ ID NO:47 and SEQ ID NO:48, respectively. The codon-optimized genes were obtained via commercial gene synthesis.

Plasmids encoding a high copy number replication origin, an antibiotic resistance marker and either a codon-optimized hexulose-6-phosphate isomerase from *M. capsulatus* under the control of a constitutive promoter or a codon-optimized 6-phospho-3-hexuloisomerase from *M. capsulatus* were constructed using DNA assembly methods described in WO/2010/07025. The resulting plasmids 9463 (SEQ ID NO:63) and 9462 (SEQ ID NO:64) were transformed into *E. coli* using standard plasmid transformation techniques.

*E. coli* NEB10β cells harboring plasmid 9463 were grown overnight with selection in Luria Broth (LB) medium containing 20 g $L^{-1}$ of xylose. In parallel, *E. coli* NEB10β cells harboring plasmid 9462 were grown overnight with selection in Luria Broth (LB) medium containing 20 g $L^{-1}$ of xylose.

Both *E. coli* cultures were harvested by centrifugation, and cell pellets were lysed by resuspension in 0.1 culture volumes of a buffer containing DNAse I (8 U $mL^{-1}$), lysozyme (>1 mg $mL^{-1}$), dithioerythritol (0.5 mM), and Tris buffer (20 mM, pH 7.5) followed by rapid freeze-thaw (3 cycles using liquid nitrogen and at warm water bath). Lysates were clarified by centrifugation for 5 min at >4000 g.

The lysates were mixed by combining 20 μL of each into the well of a standard 96-well flat-bottom assay plate. The plate was incubated at 30 C. In parallel, lysates from *E. coli* cultures expressing a metabolically inert gfp gene as a negative control were prepared in an identical fashion. "Blank" lysates made from the lysis reagent only—i.e. with no cells—were also included as a control.

A reaction mixture was added to the lysates or lysate mixtures at time zero so that the final volume in the well was 200 μL and the final concentration of (non-lysate derived) reactants was: coenzyme A, 0.5 mM; adenosine triphosphate (ATP), 10 mM; ribulose-5-phosphate (Ru5P), 1 mM; nicotine adenine dinucleotide ($NAD^+$), 1 mM; magnesium sulfate, 5 mM; potassium phosphate buffer pH 7.0, >150 mM; formaldehyde; 5 mM. The formaldehyde stock solution was previously prepared by autoclaving 240 mg of paraformaldehyde powder suspended in 8 mL of pure water at 121 C in a sealed septum vial until it was solubilized.

In parallel, a separate reaction mixture was prepared with an identical composition, except that $^{13}C$-enriched paraformaldehyde (>99% isotopic purity; Cambridge Isotope Laboratories, Massachusetts USA) was used as a formaldehyde source.

At 0 minutes, 30 minutes, and 120 minutes after the start of the enzyme reactions, 40 μL of the reaction mixture was withdrawn from the assay plate and mixed with 160 μL of a quenching solution consisting of 0.1 M formic acid in 40% v/v methanol, 40% v/v acetonitrile, and 20% v/v water. Samples were vacuum-aspirated to dryness in preparation for detection by liquid chromatography electrospray ionization mass spectrometry (LC-ESI-MS) of fructose-6-phosphate pool sizes and fructose-1,6-bisphosphate pool sizes.

LC-ESI-MS analysis was carried out on a Thermo Q-Exactive LC-ESI-MS system capable of mass determination to within 5 ppm. Metabolites were eluted from a 100-by-2.1 mm hybrid reverse-phase chromatography column with 2.6 μm beads (Accucore aQ, Thermo Scientific) with a linear gradient consisting of 15 mM acetic acid in ultrapure water as the weak solvent and methanol as the strong solvent and introduced to the mass spectrometer via a HESI-III ESI source. Elution and column reequilibration was carried out under uPLC conditions at a flow rate of 500 μL/min and total run time of 7 minutes using an Accela 1250 uPLC pump and Accela Open AS autosampler. During autosampling, samples were maintained at 4 C, while the column was kept at 30 C. ESI source and mass spectrometer acquisition settings were optimized and operated in both negative and positive polarities, using a panel of pure standards of metabolites of interest. Full MS scans were performed at a resolution of 70,000 over a mass range of 70-900 m/z, allowing for a minimum of 15-20 scans across each extracted ion chromatogram for absolute and relative quantitation under uPLC conditions. When needed, tandem MS/MS scans were also performed in both targeted and data dependent schemes to obtain additional structural information via HCD-induced fragmentation of intact precursor ions. Metabolite feature identification and full scan quantitation were performed using integration and alignment algorithms in Xcalibur (Thermo) and XCMS (Scripps Research Institute).

Fructose-6-phosphate was detected in negative mode as the $C_6H12O_9P^-$ anion at m/z=259.0224 Da+/−5 ppm. The M+1 $^{13}C$ isotopologue of fructose-6-phosphate (1-$^{13}C$-F6P) was detected at m/z=260.0258 Da+/−5 ppm. A time course showing incorporation of carbon derived from formaldehyde into fructose-6-phosphate (F6P) is shown in Table 9. The time is in units of minutes and the metabolites are in units of peak area (counts). $H^{12}CHO$ denotes formaldehyde and $H^{13}CHO$ denotes $^{13}C$-enriched paraformaldehyde. The results shows that carbon from formaldehyde is converted to the native *E. coli* metabolite fructose-6-phosphate in an HPS and PHI-dependent manner.

TABLE 9

HPS- and PHI-dependent conversion of formaldehyde ($H^{12}CHO$) to fructose-6-phosphate (F6P)

| | | with $H^{12}CHO$ | | with $H^{13}CHO$ | | with no formaldehyde | |
|---|---|---|---|---|---|---|---|
| | Time | F6P | 1-$^{13}$C-F6P | F6P | 1-$^{13}$C-F6P | F6P | 1-$^{13}$C-F6P |
| HPS/PHI mixture | 0 | 2.6E+06 | NF | 1.0E+06 | 2.0E+06 | 6.1E+05 | NF |
| | 30 | 4.9E+07 | 4.1E+06 | 4.4E+06 | 4.7E+07 | 6.0E+06 | 2.9E+05 |
| | 120 | 3.1E+07 | 2.0E+06 | 5.3E+06 | 2.7E+07 | 2.5E+07 | 3.1E+06 |
| GFP control lysate | 0 | 3.4E+05 | NF | 4.0E+05 | NF | 4.5E+05 | NF |
| | 30 | 1.1E+06 | NF | 1.1E+06 | NF | 1.7E+06 | NF |
| | 120 | 2.9E+06 | NF | 2.8E+06 | 1.2E+04 | 5.2E+06 | NF |

Example 15: Conversion of Formate to Formyl-CoA in Lysates Derived from Recombinant E. coli Cells Expressing Acetyl-CoA Synthetase The E. coli acetyl-CoA synthetase (ACS) enzyme AAC77039 was re-coded using the algorithm described in [00110] above, and/or elsewhere in the present application, to eliminate undesired restriction endonuclease recognition sequences in the re-coded gene sequence and avoid undesired DNA or RNA secondary structure in the re-coded gene or its transcript. The resulting nucleotide sequences is provided as SEQ ID NO:61. The codon-optimized gene was obtained via commercial gene synthesis.

A plasmid encoding a medium copy number replication origin, an antibiotic resistance marker and the recoded acetyl-CoA synthetase from E. coli under the control of an rrnB-derived constitutive promoter was constructed using DNA assembly methods described in WO/2010/07025. The resulting plasmid 20566 (SEQ ID NO:65) was transformed into E. coli using standard plasmid transformation techniques.

E. coli cells harboring plasmid 20566 were grown in culture and lysed by the methods described in Example 14. Lysate-based enzyme reactions were started as described in Example 14, except that sodium formate 30 mM was used in place of formaldehyde and 30 mM of sodium $^{13}$C-formate (>99 atom % isotopic purity; Cambridge Isotope Laboratories) was used in place of $^{13}$C formaldehyde.

Samples were withdrawn for LC-ESI-MS analysis as described in Example 14.

Formyl-coenzyme A (formyl-CoA) was detected in negative mode as the $C_{22}H_{35}N_7O_{17}P_3S^-$ anion at m/z=794.1028 Da. The M+1 $^{13}$C isotopologue of formyl-CoA (1-$^{13}$C-formyl-CoA) was detected at m/z=795.1062 Da. Total counts detected for the m/z=794.1028 ion increased sharply in a time in reaction mixtures to which sodium formate 30 mM ($H^{12}COO^-$) was added. Total counts detected for the m/z=795.1062 ion increased sharply in time only in reaction mixtures to which sodium 30 mM $^{13}$C-formate ($H^{13}COO^-$) was added. In control reactions using lysates from cells not expressing acs, no corresponding increases were observed. In control reactions using lysis buffer and no cellular material, no corresponding increase was observed. The data are shown in Table 10. The time is in units of minutes and the metabolites are in units of peak area (counts). Formyl-CoA is denoted by f-CoA and the M+1 $^{13}$C isotopologue of formyl-CoA is denoted by 1-$^{13}$C-f-CoA. The results demonstrate that formate was converted to formyl-CoA in a formate- and ACS-dependent manner.

TABLE 10

ACS-dependent conversion of formate to formyl-CoA

| | | with $H^{12}COO^-$ | | with $H^{13}COO^-$ | | with no formate | |
|---|---|---|---|---|---|---|---|
| | Time | f-CoA | 1-$^{13}$C-f-CoA | f-CoA | 1-$^{13}$C-f-CoA | f-CoA | 1-$^{13}$C-f-CoA |
| Plasmid 20566 lysate | 0 | 2.0E+08 | 5.9E+07 | 1.5E+08 | 4.5E+07 | 4.5E+07 | 1.0E+09 |
| | 30 | 2.6E+08 | 6.9E+07 | 5.5E+07 | 7.5E+07 | 1.7E+08 | 4.6E+07 |
| | 120 | 1.3E+09 | 3.7E+08 | 4.5E+07 | 1.0E+09 | 7.9E+07 | 2.1E+07 |
| GFP control lysate | 0 | 2.0E+08 | 5.6E+07 | 1.5E+08 | 4.4E+07 | 1.7E+08 | 4.9E+07 |
| | 30 | 2.0E+08 | 5.6E+07 | 1.5E+08 | 4.5E+07 | 1.4E+08 | 3.9E+07 |
| | 120 | 1.8E+08 | 4.8E+07 | 1.4E+08 | 4.4E+07 | 1.5E+08 | 4.2E+07 |

Example 16: Interconversion of Formyl-CoA and Formaldehyde by Lysates Derived from Recombinant E. coli Cells Expressing an Acylating Aldehyde Dehydrogenase The Listeria monocytogenes acetaldehyde dehydrogenase, acylating (ADH) enzyme NP_464704 was recoded for expression in E. coli using the algorithm described in [00110] and Example 14 above, and/or elsewhere in the present application. The resulting nucleotide sequences is provided as SEQ ID NO:62.

A plasmid encoding a high copy number replication origin, an antibiotic resistance marker and the recoded ADH under the control of an isopropyl 3-D-1-thiogalactopyranoside (IPTG)-inducible bacteriophage T7-based promoter was designed by us and synthesized via commercial gene synthesis. The resulting plasmid 27439 (SEQ ID NO:66) was transformed into E. coli using standard plasmid transformation techniques.

Cells were grown as described in Example 14, except that after 2 hr of incubation in the overnight growth medium, 1 mM of IPTG was added to induce gene expression.

Lysates were prepared and reactions were initiated as described in Example 14, except (i) that ATP and ribulose-5-phosphate were omitted from the reaction and (ii) time point samples were taken after 0, 3, and 10 minutes after starting the reactions.

Formyl-CoA was detected as described in Example 15. Total counts detected for the m/z=794.1028 ion increased sharply in time in reaction mixtures to which formaldehyde 5 mM was added. Total counts detected for the m/z=795.1062 ion increased sharply with time only in reaction mixtures to which $^{13}$C formaldehyde 5 mM was added. In control reactions using lysates from cells that were not induced to express ADH, no corresponding increases were observed. LC-ESI-MS detection of both NAD$^+$ and NADH (in negative mode using m/z=662.1018 and m/z=664.1175, respectively) confirmed that formyl-CoA formation was linked to NAD$^+$ depletion and NADH formation (data not shown). The data are shown in Table 11. The time is in units of minutes and the metabolites are in units of peak area (counts). Formyl-CoA is denoted by f-CoA, and the M+1 $^{13}$C isotopologue of formyl-CoA is denoted by 1-$^{13}$C-f-CoA. The results show that ADH expressed in *E. coli* lysates effects the interconversion of formaldehyde and NAD$^+$ with formyl-CoA and NADH.

TABLE 11

ADH-dependent interconversion of formaldehyde and formyl-CoA

|  | Time | with H$^{12}$CHO | | with H$^{13}$CHO | | with no formaldehyde | |
| --- | --- | --- | --- | --- | --- | --- | --- |
|  |  | f-CoA | 1-$^{13}$C-f-CoA | f-CoA | 1-$^{13}$C-f-CoA | f-CoA | 1-$^{13}$C-f-CoA |
| induced | 0 | 5.3E+06 | NF | NF | NF | 4.5E+05 | NF |
|  | 3 | 9.2E+07 | 2.3E+07 | NF | 4.4E+07 | 1.0E+06 | NF |
|  | 10 | 1.7E+08 | 4.4E+07 | NF | 1.1E+08 | NF | NF |
| uninduced | 0 | NF | NF |  |  |  |  |
|  | 3 | 2.9E+06 | NF |  |  |  |  |
|  | 10 | NF | NF |  |  |  |  |

Other Embodiments

The examples have focused on *E. coli*. Nevertheless, the key concept of using genetically engineering to convert a heterotroph into an engineered chemoautotroph is extensible to other, more complex organisms such as other prokaryotic or eukaryotic single cell organisms such as *E. coli* or *S. cerevisiae*, hosts suitable for scale up during fermentation, archaea, plant cells or cell lines, mammalian cells or cell lines, or insect cells or cell lines. Alternatively, the same energy conversion, carbon fixation and/or carbon product biosynthetic pathways described here may be used to enhance or augment the autotrophic capability of an organism that is natively autotrophic.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EQUIVALENTS

The present invention provides among other things novel methods and systems for synthetic biology. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

All publications, patents and patent applications referenced in this specification are incorporated herein by reference in their entirety for all purposes to the same extent as if each individual publication, patent or patent application were specifically indicated to be so incorporated by reference.

REFERENCES CITED

Abelseon P H, Hoering T C. Carbon isotope fractionation in formation of amino acids by photosynthetic organisms. Proc Natl Acad Sci. 1961; 47:623-32.

Aharoni A, Keizer L C, Bouwmeester H J, Sun Z, Alvarez-Huerta M, Verhoeven H A, Blaas J, van Houwelingen A M, De Vos R C, van der Voet H, Jansen R C, Guis M, Mol J, Davis R W, Schena M, van Tunen A J, O'Connell A P. Identification of the SAAT gene involved in strawberry flavor biogenesis by use of DNA microarrays. Plant Cell. 2000 May; 12(5):647-62.

Alber B E, Fuchs G. Propionyl-coenzyme A synthase from *Chloroflexus aurantiacus*, a key enzyme of the 3-hydroxypropionate cycle for autotrophic CO$_2$ fixation. J Biol Chem. 2002 Apr. 5; 277(14):12137-43.

Alber B, Olinger M, Rieder A, Kockelkorn D, Jobst B, Hiigler M, and Fuchs G Malonyl-coenzyme A reductase in the modified 3-hydroxypropionate cycle for autotrophic carbon fixation in archaeal *Metallosphaera* and *Sulfolobus* spp. J Bacteriol 2006 December; 188(24) 8551-9.

Andersen J B, Sternberg C, Poulsen L K, Bjorn S P, Givskov M, Molin S. New unstable variants of green fluorescent protein for studies of transient gene expression in bacteria. Appl Environ Microbiol. 1998 June; 64(6):2240-6.

Anderson J C, Voigt C A, Arkin A P. Environmental signal integration by a modular AND gate. Mol Syst Biol. 2007; 3:133.

Aoshima M, Ishii M, and Igarashi Y A novel enzyme, citryl-CoA synthetase, catalysing the first step of the citrate cleavage reaction in *Hydrogenobacter thermophilus* TK-6. Mol Microbiol 2004 May; 52(3) 751-61. (a)

Aoshima M, Ishii M, and Igarashi Y A novel enzyme, citryl-CoA lyase, catalysing the second step of the citrate cleavage reaction in *Hydrogenobacter thermophilus* TK-6. Mol Microbiol 2004 May; 52(3) 763-70. (b)

Aoshima M, Ishii M, and Igarashi Y A novel biotin protein required for reductive carboxylation of 2-oxoglutarate by isocitrate dehydrogenase in *Hydrogenobacter thermophilus* TK-6.Mol Microbiol 2004 February; 51(3) 791-8. ©

Aoshima M and Igarashi Y A novel oxalosuccinate-forming enzyme involved in the reductive carboxylation of 2-oxoglutarate in *Hydrogenobacter thermophilus* TK-6. Mol Microbiol 2006 November; 62(3) 748-59.

Baba T, Ara T, Hasegawa M, Takai Y, Okumura Y, Baba M, Datsenko K A, Tomita M, Wanner B L, Mori H. Construction of *Escherichia coli* K-12 in-frame, single-gene knockout mutants: the Keio collection. Mol Syst Biol. 2006; 2:2006.0008.

Bai F W, Anderson W A, Moo-Young M. Ethanol fermentation technologies from sugar and starch feedstocks. Biotechnol Adv. 2008 January-February; 26(1):89-105.

Bailer J, de Hueber K. Determination of saponifiable glycerol in "bio-diesel." Fresenius J Anal Chem. 1991; 340 (3):186.

Bar-Even A, Noor E, Lewis N E, Milo R. Design and analysis of synthetic carbon fixation pathways. Proc Natl Acad Sci USA. 2010 May 11; 107(19):8889-94.

Bassham J A, Benson A A, Kay L D, Harris A Z, Wilson A T, Calvin M. The path of carbon in photosynthesis. XXI. The cyclic regeneration of carbon dioxide acceptor. J Am Chem Soc. 1954; 76:1760-70.

Bayer T S, Widmaier D M, Temme K, Mirsky E A, Santi D V, Voigt C A. Synthesis of methyl halides from biomass using engineered microbes. JAm Chem Soc. 2009 May 13; 131(18):6508-15.

Berríos-Rivera S J, San K Y, Bennett G N. The effect of NAPRTase overexpression on the total levels of NAD, the NADH/NAD+ ratio, and the distribution of metabolites in *Escherichia coli*. Metab Eng. 2002 July; 4(3):238-47.

Brock T. Biotechnology: A Textbook of Industrial Microbiology. Second Edition. Sinauer Associates, Inc. Sunderland, Mass. 1989.

Brugna-Guiral M, Tron P, Nitschke W, Stetter K O, Burlat B, Guigliarelli B, Bruschi M, Giudici-Orticoni M T. [NiFe] hydrogenases from the hyperthermophilic bacterium *Aquifex aeolicus*: properties, function, and phylogenetics. Extremophiles. 2003 April; 7(2):145-57. Buchanan B B, Arnon D I. A reverse KREBS cycle in photosynthesis: consensus at last. Photosynth Res. 1990; 24:47-53.

Burgdorf T, van der Linden E, Bernhard M, Yin Q Y, Back J W, Hartog A F, Muij sers A O, de Koster C G, Albracht S P, Friedrich B. The soluble NAD+-Reducing [NiFe]-hydrogenase from *Ralstonia eutropha* H16 consists of six subunits and can be specifically activated by NADPH. J Bacteriol. 2005 May; 187(9):3122-32.

Camilli A, Bassler B L. Bacterial small-molecule signaling pathways. Science. 2006 Feb. 24; 311(5764):1113-6.

Campbell B J, Jeanthon C, Kostka J E, Luther G W 3rd, Cary S C. Growth and phylogenetic properties of novel bacteria belonging to the epsilon subdivision of the Proteobacteria enriched from Alvinella pompejana and deep-sea hydrothermal vents. Appl Environ Microbiol. 2001 October; 67(10):4566-72.

Campbell B J, Smith J L, Hanson T E, Klotz M G, Stein L Y, Lee C K, Wu D, Robinson J M, Khouri H M, Eisen J A, Cary S C. Adaptations to submarine hydrothermal environments exemplified by the genome of *Nautilia profundicola*. PLoS Genet. 2009 February; 5(2): e1000362.

Canton B, Labno A, Endy D. Refinement and standardization of synthetic biological parts and devices. Nat Biotechnol. 2008 July; 26(7):787-93.

Cheesbrough T M, Kolattukudy P E. Alkane biosynthesis by decarbonylation of aldehydes catalyzed by a particulate preparation from *Pisum sativum*. Proc Natl Acad Sci USA. 1984 November; 81(21):6613-7.

Chen S, von Bamberg D, Hale V, Breuer M, Hardt B, Muiller R, Floss H G, Reynolds K A, Leistner E. Biosynthesis of ansatrienin (mycotrienin) and naphthomycin. Identification and analysis of two separate biosynthetic gene clusters in *Streptomyces collinus* Ti 1892. Eur J Biochem. 1999 April; 261(1):98-107.

Chin J W, Cirino P C. Improved NADPH supply for xylitol production by engineered *Escherichia coli* with glycolytic mutations. Biotechnol Prog. 2011 March-April; 27(2): 333-41. doi: 10.1002/btpr.559.

Cline J D. Spectrophotometric Determination of Hydrogen Sulfide in Natural Waters. Limnol Oceanogr. 1969; 14(3): 454-8.

Cronan J E, LaPorte D. Tricarboxylic Acid Cycle and Glyoxylate Bypass. In A. Bock, R. Curtiss III, J. B. Kaper, P. D. Karp, F. C. Neidhardt, T. Nystrom, J. M. Slauch, C. L. Squires, and D. Ussery (ed.), EcoSal-*Escherichia coli* and *Salmonella*: Cellular and Molecular Biology. http://www.ecosal.org. ASM Press, Washington, D C. 2010 March 12.

Cropp T A, Wilson D J, Reynolds K A. Identification of a cyclohexylcarbonyl CoA biosynthetic gene cluster and application in the production of doramectin. Nat Biotechnol. 2000 September; 18(9):980-3.

Davis J H, Rubin A J, Sauer R T. Design, construction and characterization of a set of insulated bacterial promoters. Nucleic Acids Res. 2011 February; 39(3):1131-41.

de Mendoza D, Klages Ulrich A, Cronan J E Jr. Thermal regulation of membrane fluidity in *Escherichia coli*. Effects of overproduction of beta-ketoacyl-acyl carrier protein synthase I. J Biol Chem. 1983 Feb. 25; 258(4): 2098-101.

Dellomonaco C, Clomburg J M, Miller E N, Gonzalez R. Engineered reversal of the β-oxidation cycle for the synthesis of fuels and chemicals. Nature. 2011 Aug. 10; 476(7360):355-9.

Dennis M W, Kolattukudy P E. Alkane biosynthesis by decarbonylation of aldehyde catalyzed by a microsomal preparation from *Botryococcus braunii*. Arch Biochem Biophys. 1991 June; 287(2):268-75.

Denoya C D, Fedechko R W, Hafner E W, McArthur H A, Morgenstern M R, Skinner D D, Stutzman-Engwall K, Wax R Q Wernau W C. A second branched-chain alpha-keto acid dehydrogenase gene cluster (bkdFGH) from *Streptomyces avermitilis*: its relationship to avermectin biosynthesis and the construction of a bkdF mutant suitable for the production of novel antiparasitic avermectins. J Bacteriol. 1995 June; 177(12):3504-11.

Deshpande M V Ethanol production from cellulose by coupled saccharification/fermentation using *Saccharomyces cerevisiae* and cellulase complex from *Sclerotium rolfsii* UV-8 mutant. Appl Biochem Biotechnol. 1992 September; 36(3):227-34.

Dettman D L, Reische A K, Lohmann K C. Controls on the stable isotope composition of seasonal growth bands in aragonitic fresh-water bivalves (unionidae). Geochim Cosmochim Acta. 1999; 63:1049-57.

Doolittle, R F (Editor). Computer Methods for Macromolecular Sequence Analysis. Methods in Enzymology. 1996; 266:3-711.

Edgar R C. MUSCLE: multiple sequence alignment with high accuracy and high throughput. Nucleic Acids Res. 2004 Mar. 19; 32(5): 1792-7. (a)

Edgar R C. MUSCLE: a multiple sequence alignment method with reduced time and space complexity. BMC Bioinformatics. 2004 Aug. 19; 5:113. (b)

Edwards J S, Ramakrishna R, Palsson B O. Characterizing the metabolic phenotype: a phenotype phase plane analysis. Biotechnol Bioeng. 2002 Jan. 5; 77(1):27-36.

Eisenreich W, Strauss Q Werz U, Fuchs Q Bacher A. Retrobiosynthetic analysis of carbon fixation in the phototrophic eubacterium Chloroflexus aurantiacus. Eur J Biochem. 1993 Aug. 1; 215(3):619-32.

Evans M C, Buchanan B B, Arnon D I. A new ferredoxin-dependent carbon reduction cycle in a photosynthetic bacterium. Proc Natl Acad Sci USA. 1966 April; 55(4): 928-34.

Evans C T, Sumegi B, Srere P A, Sherry A D, Malloy C R. [13C]propionate oxidation in wild-type and citrate synthase mutant Escherichia coli: evidence for multiple pathways of propionate utilization. Biochem J. 1993 May 1; 291 (Pt 3):927-32.

Farquhar G D, Ehleringer J R, and Hubick K T. Carbon isotope discrimination and photosynthesis. Annu Rev Plant Physiol Plant Mol Biol. 1989; 40:503-37.

Ferenci T, Strom T, and Quayle J R. Purification and properties of 3-hexulose phosphate synthase and phospho-3-hexuloisomerase from Methylococcus capsulatus. Biochem J 1974 December; 144(3) 477-86.

Fogel G B, Collins C R, Li J, Brunk C F. Prokaryotic Genome Size and SSU rDNA Copy Number: Estimation of Microbial Relative Abundance from a Mixed Population. Microb Ecol. 1999 August; 38(2):93-113.

Fong S S, Palsson B O. Metabolic gene-deletion strains of Escherichia coli evolve to computationally predicted growth phenotypes. Nat Genet. 2004 October; 36(10): 1056-8.

Friedmann S, Steindorf A, Alber B E, Fuchs G. Properties of succinyl-coenzyme A:L-malate coenzyme A transferase and its role in the autotrophic 3-hydroxypropionate cycle of Chloroflexus aurantiacus. J Bacteriol. 2006 April; 188(7):2646-55.

Friedmann S, Alber B E, Fuchs G. Properties of R-citramalyl-coenzyme A lyase and its role in the autotrophic 3-hydroxypropionate cycle of Chloroflexus aurantiacus. J Bacteriol. 2007 April; 189(7):2906-14.

Gehring U and Arnon D I. Purification and properties of -ketoglutarate synthase from a photosynthetic bacterium. J Biol Chem 1972 Nov. 10; 247(21) 6963-9.

Gerhold D, Rushmore T, Caskey C T. DNA chips: promising toys have become powerful tools. Trends Biochem Sci. 1999 May; 24(5):168-73.

Goericke R, Montoya J P, Fry B. Physiology of isotopic fractionation in algae and cyanobacteria. Chapter 9 in "Stable Isotopes in Ecology and Environmental Science". Blackwell Publishing. 1994.

Grantham R, Gautier C, Gouy M, Mercier R, Pave A. Codon catalog usage and the genome hypothesis. Nucleic Acids Res. 1980 Jan. 11; 8(1):r49-r62.

Greene D N, Whitney S M, Matsumura I. Artificially evolved Synechococcus PCC6301 Rubisco variants exhibit improvements in folding and catalytic efficiency. Biochem J. 2007 Jun. 15; 404(3):517-24.

Griesbeck C, Hauska Q Schutz M. Biological Sulfide Oxidation: Sulfide-Quinone Reductase (SQR), the Primary Reaction. Recent Research Developments in Microbiology. 2000; 4:179-203. Gul-Karaguler N, Session R B, Clarke A R, Holbrook J J. A single mutation in the NAD-specific formate dehydrogenase from Candida methylica allows the enzyme to use NADP. Biotechnol Lett. 2001; 23(4):283-7.

Gutteridge S, Phillips A L, Kettleborough C A, Parry M A J. Expression of bacterial Rubisco genes in Escherichia coli. Phil Trans R Soc Lond B 313:433-45.

Han L, Reynolds K A. A novel alternate anaplerotic pathway to the glyoxylate cycle in streptomycetes. J Bacteriol. 1997 August; 179(16):5157-64.

Hatrongjit R, Packdibamrung K. A novel NADP+-dependent formate dehydrogenase from Burkholderia stabilis 15516: Screening, purification and characterization. Enzyme Microb Technol. 2010 Jun. 7; 46(7):557-61.

Hawley D K, McClure W R. Compilation and analysis of Escherichia coli promoter DNA sequences. Nucleic Acids Res. 1983 Apr. 25; 11(8):2237-55.

Hayes J M. Fractionation of Carbon and Hydrogen Isotopes in Biosynthetic Processes. Rev Mineral Geochem. 2001 January; 43(1):225-77.

Helling R B, Kukora J S. Nalidixic acd-resistant mutants of Escherichia coli deficient in isocitrate dehydrogenase. J Bacteriol. 1971 March; 105(3): 1224-6.

Henry C S, Jankowski M D, Broadbelt L J, Hatzimanikatis V. Genome-scale thermodynamic analysis of Escherichia coli metabolism. Biophys J. 2006 Feb. 15; 90(4):1453-61.

Henstra A M, Sipma J, Rinzema A, Stams A J. Microbiology of synthesis gas fermentation for biofuel production. Curr Opin Biotechnol. 2007 June; 18(3):200-6.

Herter S, Fuchs Q Bacher A, Eisenreich W. A bicyclic autotrophic $CO_2$ fixation pathway in Chloroflexus aurantiacus. J Biol Chem. 2002 Jun. 7; 277(23):20277-83. (a)

Herter S, Busch A, Fuchs G. L-Malyl-coenzyme A lyase/beta-methylmalyl-coenzyme A lyase from Chloroflexus aurantiacus, a bifunctional enzyme involved in autotrophic $CO_2$ fixation. J Bacteriol. 2002 November; 184 (21):5999-6006. (b)

Ho N W, Chen Z, Brainard A P. Genetically engineered Saccharomyces yeast capable of effective cofermentation of glucose and xylose. Appl Environ Microbiol. 1998 May; 64(5):1852-9. Hoffmeister M, Piotrowski M, Nowitzki U, Martin W. Mitochondrial trans-2-enoyl-CoAreductase of wax ester fermentation from Euglena gracilis defines a new family of enzymes involved in lipid synthesis. J Biol Chem. 2005 Feb. 11; 280(6):4329-38.

Holo H. Chloroflexus aurantiacus secretes 3-hydroxypropionate, a possible intermediate in the assimilation of $CO_2$ and acetate. Arch Microbiol. 1989; 151(3):252-6.

Hügler M, Menendez C, Schägger H, Fuchs G. Malonyl-coenzyme A reductase from Chloroflexus aurantiacus, a key enzyme of the 3-hydroxypropionate cycle for autotrophic $CO_2$ fixation. J Bacteriol. 2002 May; 184(9):2404-10.

Hügler M, Huber H, Molyneaux S J, Vetriani C, Sievert S M. Autotrophic $CO_2$ fixation via the reductive tricarboxylic acid cycle in different lineages within the phylum Aquificae: evidence for two ways of citrate cleavage. Environ Microbiol. 2007 January; 9(1):81-92.

Hügler M, Sievert S M. Beyond the Calvin cycle: autotrophic carbon fixation in the ocean. Ann Rev Mar Sci. 2011; 3:261-89.

Huisman G W, Gray D. Towards novel processes for the fine-chemical and pharmaceutical industries. Curr Opin Biotechnol. 2002 August; 13(4):352-8.

Ikeda T, Yamamoto M, Arai H, Ohmori D, Ishii M, Igarashi Y Two tandemly arranged ferredoxin genes in the *Hydrogenobacter thermophilus* genome: comparative characterization of the recombinant [4Fe-4S] ferredoxins. Biosci Biotechnol Biochem. 2005 June; 69(6):1172-7.

Inokuma K, Nakashimada Y, Akahoshi T, Nishio N. Characterization of enzymes involved in the ethanol production of *Moorella* sp. HUC22-1. Arch Microbiol. 2007 July; 188(1):37-45.

Ivlev A A. Carbon isotope effects ($^{13}C/^{12}C$) in biological systems. Separation Sci Technol. 2010; 36:1819-1914.

Janausch I G, Zientz E, Tran Q H, Kroger A, Unden G. C4-dicarboxylate carriers and sensors in bacteria. Biochim Biophys Acta. 2002 Jan. 17; 1553(1-2):39-56.

Jukes T H, Osawa S. Evolutionary changes in the genetic code. Comp Biochem Physiol B. 1993 November; 106(3):489-94.

Kalscheuer R, Steinbichel A. A novel bifunctional wax ester synthase/acyl-CoA:diacylglycerol acyltransferase mediates wax ester and triacylglycerol biosynthesis in *Acinetobacter calcoaceticus* ADP1. J Biol Chem. 2003 Mar. 7; 278(10):8075-82.

Kalscheuer R, Stolting T, Steinbichel A. Microdiesel: *Escherichia coli* engineered for fuel production. Microbiology. 2006 September; 152(Pt 9):2529-36.

Kanao T, Kawamura M, Fukui T, Atomi H, and Imanaka T. Characterization of isocitrate dehydrogenase from the green sulfur bacterium *Chlorobium limicola*. A carbon dioxide-fixing enzyme in the reductive tricarboxylic acid cycle. Eur J Biochem 2002 April; 269(7) 1926-31. (a)

Kanao T, Fukui T, Atomi H, and Imanaka T. Kinetic and biochemical analyses on the reaction mechanism of a bacterial ATP-citrate lyase. Eur J Biochem 2002 July; 269(14) 3409-16. (b)

Kaneda T. Iso- and anteiso-fatty acids in bacteria: biosynthesis, function, and taxonomic significance. Microbiol Rev. 1991 June; 55(2):288-302.

Kapust R B, Waugh D S. *Escherichia coli* maltose-binding protein is uncommonly effective at promoting the solubility of polypeptides to which it is fused. Protein Sci. 1999 August; 8(8):1668-74.

Keasling J D, Jones K L, Van Dien S J. New Tools for Metabolic Engineering of *Escherichia coli*. Chapter 5 in Metabolic Engineering. Marcel Dekker. New York, N.Y. 1999. (a)

Keasling J D. Gene-expression tools for the metabolic engineering of bacteria. Trends Biotechnol. 1999 November; 17(11):452-60. (b)

Kelly D P, Wood P, Gottschal J C, Kuenen J G. Autotrophic metabolism of formate by *Thiobacillus* strain A2. J Gen Microbiol. 1979; 114:1-13.

Kelly J R, Rubin A J, Davis J H, Ajo-Franklin C M, Cumbers J, Czar M J, de Mora K, Glieberman A L, Monie D D, Endy D. Measuring the activity of BioBrick promoters using an in vivo reference standard. J Biol Eng. 2009 Mar. 20; 3:4.

Kemp M B. The hexose phosphate synthetase of *Methylococcus capsulatus*. Biochem J. 1972 April; 127(3):64P-65P.

Kemp M B. Hexose phosphate synthase from *Methylcoccus capsulatus* makes D-arabino-3-hexulose phosphate. Biochem J. 1974 April; 139(1): 129-34.

Kim O B, Unden G. The L-tartrate/succinate antiporter TtdT (YgjE) of L-tartrate fermentation in *Escherichia coli*. J Bacteriol. 2007 March; 189(5): 1597-603.

Kim J Y, Jo B H, Cha H J. Production of biohydrogen by heterologous expression of oxygen-tolerant Hydrogenovibrio marinus [NiFe]-hydrogenase in *Escherichia coli*. J Biotechnol. 2011 Jul. 20.

Klimke W, Agarwala R, Badretdin A, Chetvernin S, Ciufo S, Fedorov B, Kiryutin B, O'Neill K, Resch W, Resenchuk S, Schafer S, Tolstoy I, Tatusova T. The National Center for Biotechnology Information's Protein Clusters Database. Nucleic Acids Res. 2009 January; 37(Database issue):D216-23.

Knight T. Idempotent Vector Design for Standard Assembly of Biobricks. DOI: 1721.1/21168.

Knight T. BBF RFC10: Draft Standard for BioBrick™ biological parts. DOI: 1721.1/45138. Larkum A W. Limitations and prospects of natural photosynthesis for bioenergy production. Curr Opin Biotechnol. 2010 June; 21(3):271-6.

Knothe G, Dunn R O, Bagby M O. Biodiesel: The use of vegetable oils and their derivatives as alternative diesel fuels. Am Chem Soc Symp Series. 1997; 666:172-208.

Knothe G. Rapid monitoring of transesterification and assessing biodiesel fuel quality by NIR spectroscopy using a fiber-optic probe. J Am Oil Chem Soc. 1999; 76(7):795-800.

Knothe G. Dependence of biodiesel fuel properties on the structure of fatty acid alkyl Esters. Fuel Process Technol. 2005; 86:1059-1070.

Kolkman J A, Stemmer W P. Directed evolution of proteins by exon shuffling. Nat Biotechnol. 2001 May; 19(5):423-8.

Komers K, Skopal F, Stloukal R. Determination of the neutralization number for biodiesel fuel production. Fett/Lipid. 1997; 99(2):52-54.

Larue T A, Kurz W G. Estimation of nitrogenase using a colorimetric determination for ethylene. Plant Physiol. 1973 June; 51(6):1074-5.

Li Y, Florova Q Reynolds K A. Alteration of the fatty acid profile of *Streptomyces coelicolor* by replacement of the initiation enzyme 3-ketoacyl acyl carrier protein synthase III (FabH). J Bacteriol. 2005 June; 187(11):3795-9.

Liu C L, Mortenson L E. Formate dehydrogenase of *Clostridium pasteurianum*. J Bacteriol. 1984 July; 159(1): 375-80.

Marcia M, Ermler U, Peng Q Michel H. A new structure-based classification of sulfide:quinone oxidoreductases. Proteins. 2010 April; 78(5):1073-83.

Marrakchi H, Zhang Y M, Rock C O. Mechanistic diversity and regulation of Type II fatty acid synthesis. Biochem Soc Trans. 2002 November; 30(Pt 6): 1050-5. (a)

Marrakchi H, Choi K H, Rock C O. A new mechanism for anaerobic unsaturated fatty acid formation in *Streptococcus pneumoniae*. J Biol Chem. 2002 Nov. 22; 277(47): 44809-16. (b)

Martin V J J, Smolke C, Keasling J D. Redesigning cells for production of complex organic molecules. ASM News. 2002; 68:336-343.

Martínez-Alonso M, Toledo-Rubio V, Noad R, Unzueta U, Ferrer-Miralles N, Roy P, Villaverde A. Rehosting of bacterial chaperones for high-quality protein production. Appl Environ Microbiol. 2009 December; 75(24):7850-4.

Martínez-Alonso M, García-Fruitós E, Ferrer-Miralles N, Rinas U, Villaverde A. Side effects of chaperone gene co-expression in recombinant protein production. Microb Cell Fact. 2010 Sep. 2; 9:64.

Marty J, Planas D. Comparison of methods to determine algal $\delta^{13}C$ in freshwater. Limnol Oceanogr: Methods. 2008; 6:51-63.

Menendez C, Bauer Z, Huber H, Gad'on N, Stetter K O, Fuchs G. Presence of acetyl coenzyme A (CoA) carboxylase and propionyl-CoA carboxylase in autotrophic Crenarchaeota and indication for operation of a 3-hydroxypropionate cycle in autotrophic carbon fixation. J Bacteriol. 1999 February; 181(4):1088-98.

Minshull J, Stemmer W P. Protein evolution by molecular breeding. Curr Opin Chem Biol. 1999 June; 3(3):284-90.

Miroshnichenko M L, Kostrikina N A, L'Haridon S, Jeanthon C, Hippe H, Stackebrandt E, Bonch-Osmolovskaya E A. *Nautilia lithotrophica* gen. nov., sp. nov., a thermophilic sulfur-reducing epsilon-proteobacterium isolated from a deep-sea hydrothermal vent. Int J Syst Evol Microbiol. 2002 July; 52(Pt 4): 1299-304.

Mitsui R, Sakai Y, Yasueda H, Kato N. A novel operon encoding formaldehyde fixation: the ribulose monophosphate pathway in the gram-positive facultative methylotrophic bacterium *Mycobacterium gastri* M B 19. J Bacteriol. 2000 February; 182(4):944-8.

Monson K D, Hayes J M. Biosynthetic control of the natural abundance of carbon 13 at specific positions within fatty acids in *Escherichia coli*. J Biol Chem. 1980; 255:11435-41.

Moriya Y, Itoh M, Okuda S, Yoshizawa A C, Kanehisa M. KAAS: an automatic genome annotation and pathway reconstruction server. Nucleic Acids Res. 2007 July; 35(Web Server issue):W182-5.

Morweiser M, Kruse O, Hankamer B, Posten C. Developments and perspectives of photobioreactors for biofuel production. Appl Microbiol Biotechnol. 2010 July; 87(4): 1291-301.

Murli S, Opperman T, Smith B T, Walker G C. A role for the umuDC gene products of *Escherichia coli* in increasing resistance to DNA damage in stationary phase by inhibiting the transition to exponential growth. J Bacteriol. 2000 February; 182(4):1127-35.

Murtagh, F. Complexities of Hierarchic Clustering Algorithms: the State of the Art. Computational Statistics Quarterly. 1984; 1:101-13.

Nature Genetics. 1999; 21(1):1-60.

Ness J E, Del Cardayre S B, Minshull J, Stemmer W P. Molecular breeding: the natural approach to protein design. Adv Protein Chem. 2000; 55:261-92.

Ober J A. Sulfur. U.S. Geological Survery Minerals Report—2008. 2010; 74:1-17.

Orita I, Yurimoto H, Hirai R, Kawarabayasi Y, Sakai Y, Kato N. The archaeon *Pyrococcus horikoshii* possesses a bifunctional enzyme for formaldehyde fixation via the ribulose monophosphate pathway. J Bacteriol. 2005 June; 187(11):3636-42.

Orita I, Sato T, Yurimoto H, Kato N, Atomi H, Imanaka T, Sakai Y The ribulose monophosphate pathway substitutes for the missing pentose phosphate pathway in the archaeon *Thermococcus kodakaraensis*. J Bacteriol. 2006 July; 188(13):4698-704.

Orita I, Sakamoto N, Kato N, Yurimoto H, and Sakai Y Bifunctional enzyme fusion of 3-hexulose-6-phosphate synthase and 6-phospho-3-hexuloisomerase. Appl Microbiol Biotechnol 2007 August; 76(2) 439-45.

Palaniappan N, Kim B S, Sekiyama Y, Osada H, Reynolds K A. Enhancement and selective production of phoslactomycin B, a protein phosphatase IIa inhibitor, through identification and engineering of the corresponding biosynthetic gene cluster. J Biol Chem. 2003 Sep. 12; 278 (37):35552-7.

Park M O. New pathway for long-chain n-alkane synthesis via 1-alcohol in *Vibrio furnissii* M1. J Bacteriol. 2005 February; 187(4):1426-9.

Parikh M R, Greene D N, Woods K K, Matsumura I. Directed evolution of RuBisCO hypermorphs through genetic selection in engineered *E. coli*. Protein Eng Des Sel. 2006 March; 19(3):113-9.

Patton S M, Cropp T A, Reynolds K A. A novel delta(3), delta(2)-enoyl-CoA isomerase involved in the biosynthesis of the cyclohexanecarboxylic acid-derived moiety of the polyketide ansatrienin A. Biochemistry. 2000 Jun. 27; 39(25):7595-604.

Pinske C, Bonn M, Kruger S, Lindenstrauß U, Sawers R G. Metabolic Deficiences Revealed in the Biotechnologically Important Model Bacterium *Escherichia coli* BL21 (DE3). PLoS One. 2011; 6(8):e22830.

Portis A R Jr, Parry M A. Discoveries in Rubisco (Ribulose 1,5-bisphosphate carboxylase/oxygenase): a historical perspective. Photosynth Res. 2007 October; 94(1):121-43.

Pramanik J, Keasling J D. Stoichiometric model of *Escherichia coli* metabolism: incorporation of growth-rate dependent biomass composition and mechanistic energy requirements. Biotechnol Bioeng. 1997 Nov. 20; 56(4): 398-421.

Pramanik J, Keasling J D. Effect of *Escherichia coli* biomass composition on central metabolic fluxes predicted by a stoichiometric model. Biotechnol Bioeng. 1998 Oct. 20; 60(2):230-8. (a)

Pramanik J, Trelstad P L, Keasling J D. A flux-based stoichiometric model of enhanced biological phosphorus removal metabolism. Wat Sci Technol. 1998; 37(4-5): 609-13. (b) Pramanik J, Trelstad P L, Schuler A J, Jenkins D, Keasling J D. Development and validation of a flux-based stoichiometric model for enhanced biological phosphorus removal metabolism. Water Res. 1998; 33(2):462-76. ©.

Rathnasingh C, Raj S M, Lee Y, Catherine C, Ashok S, and Park S. Production of 3-hydroxypropionic acid via malonyl-CoA pathway using recombinant *Escherichia coli* strains. J Biotechnol 2011 Jun. 23.

Reading N C, Sperandio V. Quorum sensing: the many languages of bacteria. FEMS Microbiol Lett. 2006 January; 254(1):1-11.

Rock C O, Tsay J T, Heath R, Jackowski S. Increased unsaturated fatty acid production associated with a suppressor of the fabA6(Ts) mutation in *Escherichia coli*. J Bacteriol. 1996 September; 178(18):5382-7.

Roessner C A, Spencer J B, Ozaki S, Min C, Atshaves B P, Nayar P, Anousis N, Stolowich N J, Holderman M T, Scott A I. Overexpression in *Escherichia coli* of 12 vitamin B 12 biosynthetic enzymes. Protein Expr Purif. 1995 April; 6(2): 155-63.

Sachdev D, Chirgwin J M. Solubility of proteins isolated from inclusion bodies is enhanced by fusion to maltose-binding protein or thioredoxin. Protein Expr Purif. 1998 February; 12(1):122-32.

Sachdev D, Chirgwin J M. Fusions to maltose-binding protein: control of folding and solubility in protein purification. Methods Enzymol. 2000; 326:312-21.

Saitou N, Nei M. The neighbor-joining method: a new method for reconstructing phylogenetic trees. Mol Biol Evol. 1987 July; 4(4):406-25.

Sakata S, Hayes J M, McTaggart A R, Evans R A, Leckrone K J, Togasaki R K. Carbon isotopic fractionation associated with lipid biosynthesis by a cyanobacterium: relevance for interpretation of biomarker records. Geochim Cosmochim Acta. 1997; 61:5379-89.

Sambrook, J, Russell, D. Molecular Cloning: A Laboratory Manual, Third Edition. CSHL Press. Cold Spring Harbor, N.Y. 2001.

San K Y, Bennett G N, Berríos-Rivera S J, Vadali R V, Yang Y T, Horton E, Rudolph F B, Sariyar B, Blackwood K. Metabolic engineering through cofactor manipulation and its effects on metabolic flux redistribution in *Escherichia coli*. Metab Eng. 2002 April; 4(2):182-92.

Sauer U, Canonaco F, Heri S, Perrenoud A, Fischer E. The soluble and membrane-bound transhydrogenases UdhA and PntAB have divergent functions in NADPH metabolism of *Escherichia coli*. J Biol Chem. 2004 Feb. 20; 279(8):6613-9.

Schena M (editor). DNA Microarrays: A Practical Approach. The Practical Approach Series, Oxford University Press, 1999.

Schena M (editor). Microarray Biochip: Tools and Technology. Eaton Publishing Company/BioTechniques Books Division. 2000.

Schütz M, Shahak Y, Padan E, and Hauska G. Sulfide-quinone reductase from *Rhodobacter capsulatus*. Purification, cloning, and expression. J Biol Chem 1997 Apr. 11; 272(15) 9890-4.

Self W T, Hasona A, Shanmugam K T. Expression and regulation of a silent operon, hyf, coding for hydrogenase 4 isoenzyme in *Escherichia coli*. J Bacteriol. 2004 January; 186(2):580-7.

Serov A E, Popova A S, Fedorchuk V V, Tishkov V I. Engineering of coenzyme specificity of formate dehydrogenase from *Saccharomyces cerevisiae*. Biochem J. 2002 Nov. 1; 367(Pt 3):841-7.

Shetty R P, Endy D, Knight T F Jr. Engineering BioBrick vectors from BioBrick parts. J Biol Eng. 2008 Apr. 14; 2:5.

Shetty R, Lizarazo M, Rettberg R, Knight T F. Assembly of BioBrick standard biological parts using three antibiotic assembly. Methods Enzymol. 2011; 498:311-26.

Shibata H and Kobayashi S. Sulfide oxidation in gram-negative bacteria by expression of the sulfide-quinone reductase gene of *Rhodobacter capsulatus* and by electron transport to ubiquinone. Can J Microbiol 2001 September; 47(9) 855-60.

Shpaer E G. GeneAssist. Smith-Waterman and other database similarity searches and identification of motifs. Methods Mol Biol. 1997; 70:173-87.

Sintsov N V, Ivanovskii R N, and Kondrat'eva E N. [ATP-dependent citrate lyase in the green phototrophic bacterium, *Chlorobium limicola*]. Mikrobiologiia 1980 July-August; 49(4) 514-6.

Smith J L, Campbell B J, Hanson T E, Zhang C L, Cary S C. *Nautilia profundicola* sp. nov., a thermophilic, sulfur-reducing epsilonproteobacterium from deep-sea hydrothermal vents. Int J Syst Evol Microbiol. 2008 July; 58(Pt 7):1598-602.

Smolke C D, Carrier T A, Keasling J D. Coordinated, differential expression of two genes through directed mRNA cleavage and stabilization by secondary structures. Appl Environ Microbiol. 2000 December; 66(12): 5399-405.

Smolke C D, Martin V J, Keasling J D. Controlling the metabolic flux through the carotenoid pathway using directed mRNA processing and stabilization. Metab Eng. 2001 October; 3(4):313-21.

Smolke C D, Keasling J D. Effect of copy number and mRNA processing and stabilization on transcript and protein levels from an engineered dual-gene operon. Biotechnol Bioeng. 2002 May 20; 78(4):412-24. (a)

Smolke C D, Keasling J D. Effect of gene location, mRNA secondary structures, and RNase sites on expression of two genes in an engineered operon. Biotechnol Bioeng. 2002 Dec. 30; 80(7):762-76. (b)

Sokal R, Michener, C. A Statistical Method for Evaluating Systematic Relationships. University of Kansas Science Bulletin. 1958; 38:1409-38.

Strauss G, Fuchs G. Enzymes of a novel autotrophic $CO_2$ fixation pathway in the phototrophic bacterium *Chloroflexus aurantiacus*, the 3-hydroxypropionate cycle. Eur J Biochem. 1993 Aug. 1; 215(3):633-43.

Strom T, Ferenci T, and Quayle J R. The carbon assimilation pathways of *Methylococcus capsulatus*, *Pseudomonas methanica* and *Methylosinus trichosporium* (OB3B) during growth on methane. Biochem J 1974 December; 144(3) 465-76.

Sun J, Hopkins R C, Jenney F E, McTernan P M, Adams M W. Heterologous expression and maturation of an NADP-dependent [NiFe]-hydrogenase: a key enzyme in biofuel production. PLoS One. 2010 May 6; 5(5):e10526.

Tabita F R, Small C L. Expression and assembly of active cyanobacterial ribulose-1,5-bisphosphate carboxylase/oxygenase in *Escherichia coli* containing stoichiometric amounts of large and small subunits. Proc Natl Acad Sci USA. 1985 September; 82(18):6100-3.

Tatusov R L, Koonin E V, Lipman D J. A genomic perspective on protein families. Science. 1997 Oct. 24; 278 (5338):631-7.

Tatusov R L, Fedorova N D, Jackson J D, Jacobs A R, Kiryutin B, Koonin E V, Krylov D M, Mazumder R, Mekhedov S L, Nikolskaya A N, Rao B S, Smirnov S, Sverdlov A V, Vasudevan S, Wolf Y I, Yin J J, Natale D A. The COG database: an updated version includes eukaryotes. BMC Bioinformatics. 2003 Sep. 11; 4:41.

van Wezel G P, Mahr K, Konig M, Traag B A, Pimentel-Schmitt E F, Willimek A, Titgemeyer F. GlcP constitutes the major glucose uptake system of *Streptomyces coelicolor* A3(2). Mol Microbiol. 2005 January; 55(2):624-36.

Venturi V Regulation of quorum sensing in *Pseudomonas*. FEMS Microbiol Rev. 2006 March; 30(2):274-91.

Vignais P M, Colbeau A. Molecular biology of microbial hydrogenases. Curr Issues Mol Biol. 2004 July; 6(2):159-88.

Vignais P M, Billoud B. Occurrence, classification, and biological function of hydrogenases: an overview. Chem Rev. 2007 October; 107(10):4206-72.

Wells M A, Mercer J, Mott R A, Pereira-Medrano A G, Burja A M, Radianingtyas H, Wright P C. Engineering a non-native hydrogen production pathway into *Escherichia coli* via a cyanobacterial [NiFe] hydrogenase. Metab Eng. 2011 July; 13(4):445-53.

Wubbolts M G, Terpstra P, van Beilen J B, Kingma J, Meesters H A, Witholt B. Variation of cofactor levels in *Escherichia coli*. Sequence analysis and expression of the pncB gene encoding nicotinic acid phosphoribosyltransferase. J Biol Chem. 1990 Oct. 15; 265(29):17665-72.

Yamamoto M, Ikeda T, Arai H, Ishii M, and Igarashi Y Carboxylation reaction catalyzed by 2-oxoglutarate:ferredoxin oxidoreductases from *Hydrogenobacter thermophilus*.Extremophiles 2010 January; 14(1) 79-85.

Yoon K S, Ishii M, Kodama T, Igarashi Y Purification and characterization of pyruvate:ferredoxin oxidoreductase from *Hydrogenobacter thermophilus* TK-6. Arch Microbiol. 1997 May; 167(5):275-9.

Yoon Y G, Cho J H, Kim S C. Cre/loxP-mediated excision and amplification of large segments of the *Escherichia coli* genome. Genet Anal. 1998 January; 14(3):89-95.

Zarzycki J, Brecht V, Müller M, Fuchs G. Identifying the missing steps of the autotrophic 3-hydroxypropionate $CO_2$ fixation cycle in *Chloroflexus aurantiacus*. Proc Natl Acad Sci USA. 2009 Dec. 15; 106(50):21317-22.

Zarzycki J, Fuchs G. Co-Assimilation of Organic Substrates via the Autotrophic 3-Hydroxypropionate Bi-Cycle in *Chloroflexus aurantiacus*. Appl Environ Microbiol. 2011 Jul. 15. Zdobnov E M, Apweiler R. InterProScan—an integration platform for the signature-recognition methods in InterPro. Bioinformatics. 2001 September; 17(9): 847-8.

Zhang C C, Durand M C, Jeanjean R, Joset F. Molecular and genetical analysis of the fructose-glucose transport system in the cyanobacterium *Synechocystis* PCC6803. Mol Microbiol. 1989 September; 3(9):1221-9.

Zhang Y M, Marrakchi H, Rock C O. The FabR (YijC) transcription factor regulates unsaturated fatty acid biosynthesis in *Escherichia coli*. J Biol Chem. 2002 May 3; 277(18):15558-65.

Zhu X, Yuasa M, Okada K, Suzuki K, Nakagawa T, Kawamukai M, Matsuda H. Production of ubiquinone in *Escherichia coli* by expression of various genes responsible for ubiquinone biosynthesis. J Ferm Bioeng. 1995; 79(5):493-5.

Zweiger G. Knowledge discovery in gene-expression-microarray data: mining the information output of the genome. Trends Biotechnol. 1999 November; 17(11): 429-36.

The invention claimed is:

1. A method of making a chemoautotrophic cell, the method comprising steps of:
   (i) engineering in a cell an energy conversion pathway comprising a recombinant formate dehydrogenase or a recombinant sulfide-quinone oxidoreductase, wherein the recombinant formate dehydrogenase is encoded by any one of SEQ ID NOs:1-4 or a homolog thereof having at least 80% sequence identity thereto, or comprises any one of SEQ ID NOs:5-8 or a homolog thereof having at least 80% sequence identity thereto, and the recombinant sulfide-quinone oxidoreductase is encoded by any one of SEQ ID NOs:9-16 or a homolog thereof having at least 80% sequence identity thereto; wherein the energy conversion pathway transfers energy from an extracellular inorganic energy source to a reducing cofactor, and
   (ii) engineering in the cell a carbon fixation pathway that utilizes the reducing cofactor to convert inorganic carbon to a reduced organic carbon molecule.

2. The method of claim 1, wherein the energy conversion pathway comprises an enzyme heterologous to the cell.

3. The method of claim 1, wherein the energy conversion pathway consists essentially of enzymes exogenous to the cell.

4. The method of claim 1, wherein the energy conversion pathway comprises an enzyme that is endogenous to the cell.

5. The method of claim 4, wherein the enzyme is modified, wherein the modification comprises addition of a solubility tag, removal of a leader sequence, or addition of a targeting sequence.

6. The method of claim 1, wherein the carbon fixation pathway comprises an enzyme exogenous to the cell.

7. The method of claim 1, wherein the carbon fixation pathway consists essentially of enzymes exogenous to the cell.

8. The method of claim 1, wherein the carbon fixation pathway comprises an enzyme that is endogenous to the cell.

9. The method of claim 8, wherein the enzyme is modified, and wherein the modification comprises addition of a solubility tag, removal of a leader sequence, or addition of a targeting sequence.

10. The method of claim 1, wherein the carbon fixation pathway is derived from a pathway comprising one or more of 3-hydroxypropionate (3-HPA) bicycle, ribulose monophosphate (RuMP) cycle, Calvin-Benson-Bassham cycle or the reductive pentose phosphate (RPP) cycle, and reductive tricarboxylic acid (rTCA) cycle.

11. The method of claim 1, wherein the extracellular inorganic energy source comprises one or more of formate, formic acid, methane, carbon monoxide, carbonyl sulfide, carbon disulfide, hydrogen sulfide, bisulfide anion, thiosulfate, elemental sulfur, molecular hydrogen, ferrous iron, ammonia, cyanide ion, and hydrocyanic acid.

12. The method of claim 1, wherein the reducing cofactor comprises one or more of NADH, NADPH, ubiquinol, menaquinol, cytochromes, flavins and ferredoxin.

13. The method of claim 1, wherein the reduced organic carbon molecule comprises one or more of acetyl-coA, pyruvate, pyruvic acid, 3-hydropropionate, 3-hydroxypropionic acid, glycolate, glycolic acid, glyoxylate, glyoxylic acid, dihydroxyacetone phosphate, glyceraldehyde-3-phosphate, malate, malic acid, lactate, lactic acid, acetate, acetic acid, citrate, and citric acid.

14. The method of claim 1, further comprising a step of engineering a carbon biosynthetic pathway that produces an organic carbon molecule derived from a reduced organic carbon molecule.

15. The method of claim 14, wherein the derived organic carbon molecule comprises one or more of alcohols, fatty acids, fatty acid derivatives, fatty alcohols, fatty acid esters, wax esters, hydrocarbons, alkanes, polymers, fuels, commodity chemicals, specialty chemicals, carotenoids, isoprenoids, sugars, sugar phosphates, central metabolites, pharmaceuticals and pharmaceutical intermediates.

* * * * *